US009751944B2

(12) United States Patent
Hiruma et al.

(10) Patent No.: US 9,751,944 B2
(45) Date of Patent: *Sep. 5, 2017

(54) ANTI-SIGLEC-15 ANTIBODY

(71) Applicant: Daiichi Sankyo Company, Limited, Tokyo (JP)

(72) Inventors: Yoshiharu Hiruma, Tokyo (JP); Eisuke Tsuda, Tokyo (JP); Takeshi Takizawa, Tokyo (JP); Makiko Nakayama, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,519

(22) Filed: Jun. 5, 2015

(65) Prior Publication Data
US 2015/0299318 A1 Oct. 22, 2015

Related U.S. Application Data

(60) Division of application No. 14/401,479, filed on Sep. 30, 2013, now Pat. No. 9,079,959, which is a continuation of application No. 13/143,253, filed as application No. PCT/JP2010/056294 on Apr. 7, 2010, now Pat. No. 8,575,316.

(30) Foreign Application Priority Data

Apr. 9, 2009 (JP) .................... 2009-094613

(51) Int. Cl.
*A61K 39/00* (2006.01)
*A61K 39/395* (2006.01)
*C07K 16/28* (2006.01)
*A61K 45/06* (2006.01)

(52) U.S. Cl.
CPC ...... *C07K 16/2803* (2013.01); *A61K 39/3955* (2013.01); *A61K 45/06* (2013.01); *A61K 2039/505* (2013.01); *A61K 2039/545* (2013.01); *C07K 2317/24* (2013.01); *C07K 2317/30* (2013.01); *C07K 2317/565* (2013.01); *C07K 2317/622* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| 6,855,808 | B2 | 2/2005 | Goto et al. | |
|---|---|---|---|---|
| 7,125,686 | B1 | 10/2006 | Goto et al. | |
| 7,205,397 | B2 | 4/2007 | Goto et al. | |
| 7,276,344 | B2 | 10/2007 | Goto et al. | |
| 7,405,037 | B2 | 7/2008 | Greenwalt | |
| 7,468,268 | B2 | 12/2008 | Goto et al. | |
| 7,608,704 | B2 | 10/2009 | Yue et al. | |
| 7,989,160 | B2 | 8/2011 | Sooknanan et al. | |
| 8,546,540 | B2 * | 10/2013 | Hiruma ................ | A61K 31/593 435/326 |
| 8,575,316 | B2 * | 11/2013 | Hiruma .............. | C07K 16/2803 435/252.3 |
| 2004/0023313 | A1 | 2/2004 | Boyle et al. | |
| 2004/0033535 | A1 * | 2/2004 | Boyle .............. | A61K 39/39541 435/7.2 |
| 2004/0076992 | A1 | 4/2004 | Nakamura et al. | |
| 2009/0298763 | A1 | 12/2009 | Sooknanan et al. | |
| 2010/0104575 | A1 | 4/2010 | Sooknanan et al. | |
| 2011/0268733 | A1 | 11/2011 | Hiruma et al. | |
| 2011/0311526 | A1 | 12/2011 | Sooknanan et al. | |
| 2013/0039915 | A1 * | 2/2013 | Tremblay .......... | A61K 31/7088 424/139.1 |

FOREIGN PATENT DOCUMENTS

| CA | 2 225 366 C | 10/2006 |
|---|---|---|
| EP | 1 580 263 A1 | 9/2005 |
| EP | 1 715 038 | 10/2006 |
| JP | 2007-020403 | 2/2007 |
| RU | 2 228 335 C2 | 8/1999 |
| RU | 2 238 948 C2 | 3/2004 |
| RU | 2238949 C2 | 10/2004 |
| WO | WO 98/46644 A1 | 10/1998 |
| WO | WO 02/38602 | 5/2002 |
| WO | WO 02/064771 | 8/2002 |
| WO | WO 03/048305 | 6/2003 |
| WO | WO 2005/113794 A1 | 12/2005 |
| WO | WO 2007/093042 | 8/2007 |
| WO | WO 2009/048072 | 4/2009 |
| WO | WO 2011/041894 A1 | 4/2011 |

OTHER PUBLICATIONS

Protest Under 37 CFR § 1.291 filed Nov. 18, 2015, against U.S. Appl. No. 14/826,515, 301 pages.
Petitioner's Reply to Corrected Patent Owner's Response filed Nov. 30, 2015, in IPR2015-00291, 47 pages.
Declaration of Dr. Paul R. Crocker dated Dec. 1, 2015, filed Dec. 2, 2015, in IPR2015-00291, 7 pages.
Corrected Patent Owner's Response, Redacted Public Version, filed Sep. 28, 2015, in IPR2015-00291, 109 pages.
Declaration of Brendan F. Boyce, MD, Ch.B.. dated Sep. 6, 2015, 71 pages, served on Petitioner in IPR2015-00291 on Sep. 14, 2015.
Declaration of Kathryn E. Stein, Ph.D., dated Sep. 13, 2015, 51 pages, served on Petitioner in IPR2015-00291 on Sep. 14, 2015.
Saldanha, Jose W., "Molecular Engineering I: Humanization," Handbook of Therapeutic Antibodies, Chapter 6, Stephan Duebel, Ed., Jan. 1, 2007, 119-144, XP007913671.
Wu et al., "Simultaneous Humanization and Affinity Optimization of Monoclonal Antibodies," Methods in Molecular Biology, Jan. 1, 2003, 207:197-212.
Abaza et al., "Effects of amino acid substitutions outside an antigenic site on protein binding to monoclonal antibodies of predeter (Continued)

*Primary Examiner* — Elizabeth C Kemmerer
(74) *Attorney, Agent, or Firm* — Foley & Lardner LLP

(57) ABSTRACT

Provided is a pharmaceutical composition for treating and/or preventing abnormal bone metabolism targeting a protein encoded by a gene strongly expressed in osteoclasts. Specifically provided is a pharmaceutical composition containing an antibody which specifically recognizes human Siglec-15 and has an activity of inhibiting osteoclast formation, and the like.

10 Claims, 57 Drawing Sheets

(56) References Cited

OTHER PUBLICATIONS mined specificity obtained by peptide immunization: demonstration with region 94-100 (antigenic site 3) of myoglobin," J. Protein Chem., Oct. 1992, 11(5):433-444.
Akatsu et al., "Osteoclastogenesis inhibitory factor suppresses osteoclast survival by interfering in the interaction of stromal cells with osteoclast," Biochemical and Biophysical Research Communications, Sep. 18, 1998, 250(2):229-234.
Angata et al., "Siglec-15: an immune system Siglec c observed throughout vertebrate evolulation," Glycobiology, Aug. 2007, 17(8):838-846.
Bird et al., "Single-chain antigen-binding proteins," Science, 1988, 242(4877):423-426.
Buckley et al., "Human Osteoclast Culture From Peripheral Blood Monocytes," Methods in Molecular Medicine, 107:55-68, Human Cell Culture Protocols, Second Edition, 2005.
Clackson et al., "Making antibody fragments using phage display libraries," 1991, Nature 352:624-628.
Collin-Osdoby et al., "RANKL-Mediated Osteoclast Formation from Murine RAW 264.7 Cells," Methods in Molecular Medicine, 80:153-166, Bone Research Protocols, 2003.
Colman, P.M., "Effects of amino acid sequence changes on antibody-antigen interactions," Res. Immunol., 1994, 145(1):33-36.
Daugherty et al., "Antibody affinity maturation using bacterial surface display," 1998, Protein Eng., 11:825-832.
Decision to Grant dated Aug. 13, 2014 in RU 2011128332, 24 pages, with English translation, 20 pages.
Duquesnoy, R.J., "Structural and functional definitions of epitopes reacting with mouse monoclonal antibodies," 2008, suppl. www/hlamatchmaker.net, 14 pages.
GenBank: BAA08453, human bone morphogenetic protein-3b (*Homo sapiens*), Dec. 27, 2006.
Harlow et al., Antibodies A Laboratory Manual, Cold Spring Harbor, New York, Cold Spring Harbor Laboratory Press, 1989, 141-155.
Hino et al., "cDNA Cloning and Genomic Structure of Human Bone Morphogenetic Protein-3b (BMP-3b)," Biochemical and Biophysical Research Communications, 1996, 223:304-310.
Hiruma et al., "Siglec-15, a member of the sialic acid-binding lectin is a novel regulator for osteoclast differentiation," Biochemical and Biophysical Research Communications, 2011, 409:424-429.
Janssens et al., "Molecular genetics of too much bone," Human Molecular Genetics, 2002, 11(20):2385-2393.
Kania et al., "CD44 antibodies inhibit osteoclast formation," J. Bone Miner. Res., 1997, 12(8):1155-1164.
Kitaura et al., "An anti-c-Fms antibody inhibits orthodontic tooth movement," J. Dent. Res., 2008, 87(4):395-400.
Kussie et al., "A Single Engineered Amino Acid Substitution changes Antibody Fine Specificity," 1994, J. Immunology, 152(1):146-152.
Lederman et al., "A single amino acid substitution in a common African allele of the CD4 molecule ablates binding of the monoclonal antibody, OKT4," Mol. Immunol., 1991, 28(11):1171-1181.
Li et al. "Beta-Endorphin omission analogs: dissociation of immunoreactivity from other biological activities," PNAS USA, 1980, 77(6):3211-3214.
Mirny et al., "Protein folding theory: From Lattice to All-Atom Models," Annu. Rev. Biophys. Biomol. Struct., 2001, 30:361-396.

Nakagavva et al., "RANK is the Essential Signaling Receptor for Osteoclast Differentiation Factor in Osteoclastogenesis," Biochemical and Biophysical Research Communications, 1998, 253:395-400.
Ngo et al., "Computational complexity, protein structure prediction, and the Levinthal paradox," The Protein Folding Problem, Birkhauser, 1994, Ch. 14:491-494.
Notice of Opposition to Grant of Patent dated Jun. 29, 2012, filed by Alethia Biotherapeutics Inc. against New Zealand Application 583397, 3 pages.
Owens et al., "The genetic engineering of monoclonal antibodies," J. Immunol. Methods, 1994, 168(2):149-165.
Presta et al., "Antibody engineering for therapeutics," Current Opinion in Structural Biology, 2003, 13:519-525.
Protest to the Grant of a Patent dated Apr. 2, 2014, filed against Canadian Patent Application No. 2698326, 11 pages.
Siegel et al., "Antibody affinity optimization using yeast cell surface display," 2009 Methods Mol. Biol., 504:351-383.
Statement of Grounds and Particulars to Each Ground dated Jun. 1, 2012, filed by Alethia Biotherapeutics Inc. against Australian Patent Application 2008311698, 10 pages.
Takahashi et al., "A new treatment for osteoporosis using fully human monoclonal antibody to RANKL, AMG 162," Clin. Calcium, 2005, 15(1):43-48, with English summary on first page.
Teitelbaum, S.L., "Osteoclasts: What Do They Do and How Do They Do It?" 2007, AJP, 170(2):427-435.
Third Party Observations dated Aug. 20, 2012, filed by Alethia Biotherapeutics Inc. against European Patent Application 08838427.6, 4 pages.
Third Party Observations dated Dec. 10, 2012, filed by Alethia Biotherapeutics Inc. against European Patent Application 08838427.6, 7 pages.
Tsuda, Eisuke, "Hone Kyushi Yokuseiyaku Koho to shite no Hakotso Saibo Keisei Yokusei Inshi OCIF/OPG, Ko-RANKL Kotai, Oyobi sono hoka no RANKL/RANK System Modulator," J. Jpn. Orthop. Assoc., 2005, 79(8):S753 (1-4-S6-3).
Tsuda, Eisuke, "Waga Kuni ni Okeru Hone Ryoki no Soyaku no Rekishi Kaihatsu Chu no Hinmoke 6. Hakotsu Saibo Keisei Yokusei Inshi (OCIF/OPG), Ko RANKL Kotai, Oyobi Sono Ta no RANKL/RANK System Modulator," Bone, Jan. 2005, 19(1):85-92.
Wada et al., "New bone density conservation agents for osteoporosis under research and development: Anti-RANKL antibody," Nihon Rinsho, 2007, 65(Suppl.9):459-462.
Woo et al., "Pharmacological Topics of Bone Metabolism: Antiresorptive Microbial Compounds That Inhibit Osteoclast Differentiation, Function, and Survival," J. Pharmacol. Sci., 2008, 106:547-554.
MacCallum et al., "Antibody-antigen Interactions: Contact Analysis and Binding Site Topography," J. Mol. Biol, 1996, 262:732-745.
Rudikoff et al., "Single amino acid substitution altering antigen-binding specificity," Proc. Natl. Acad. Sci. USA, Mar. 1982, 79:1979-1983.
Reexamination Notice dated Apr. 28, 2016, in Chinese application No. CN 201080004195.7, with English translation.
He Qiuzao et al., Cellular and Molecular Immunology, Shanghai: Shanghai Scientific and Technical Literature Publishing House, Oct. 1998, 12-15.
Wan Wenhui, Tumor Marker in Clinical Application and Research, $2^{nd}$ Edition, Peking University Medical Press, Sep. 2007, 45.
Xu Yuqin, Functional Genomics, Science Press, Jun. 2007, 328.
Wu Naihu, Genetic Engineering and Principles, vol. 2 ($2^{nd}$ Edition), Science Press, Apr. 2002, 423.
Final Written Decision dated Jun. 14, 2016, in IPR2015-00291, 26 pages.

\* cited by examiner

Figure 23
SEQ ID NO:27: Cloned Nucleotide Sequence of Rat #32A1 Heavy Chain (Variable Region + alpha)
ATGAAGTTGTGGTTGAGCTGGATATTCCTTGTTGTTCTTTTCAAAGGTGTGAGGTGTGA
GGTGCAAATTTTGGAGACTGGAGGAGGCTTGGTGAAGCCCGGTGGTTCCCTGAGACT
GTCTTGTGCAACGTCTGGATTCAATTTCAATGATTATTTCATGAACTGGGTCCGTCAGG
CTCCAGAAAAGGGGCTAGAGTGGGTTGCTCAAATAAGGAACAAAATTTATACTTATGC
CACATTTTATGCGGAGTCTTTGGAAGGCAGAGTCACAATCTCACGAGACGATTCCGAA
AGCAGTGTCTACCTGCAAGTGAGCAGTTTAAGAGCTGAAGACACTGCCATTTATTACT
GTACAAGATCCCTAACTGGGGGAGACTACTTTGATTACTGGGGCCAAGGAGTCATGG
TCACAGTCTCCTTAGCTGAAACAACAGCCCCATCTGTCTATCCACTGGCTCCTGGAAC
TGCTCTCAAAAGTAACTCCATGGTGACCCTGGGATGC
Signal Sequence (1-57), Variable Region (58-420), Partial Sequence of Constant Region (421-501)

SEQ ID NO:28: Amino Acid Sequence Encoded by Cloned rat #32A1 Heavy Chain (Variable Region + alpha)
MKLWLSWIFLVVLFKGVRCEVQILETGGGLVKPGGSLRLSCATSGFNFNDYFMNWVRQA
PEKGLEWVAQIRNKIYTYATFYAESLEGRVTISRDDSESSVYLQVSSLRAEDTAIYYCTRSL
TGGDYFDYWGQGVMVTVSLAETTAPSVYPLAPGTALKSNSMVTLGC
Signal Sequence (1-19), Variable Region (20-140), Partial Sequence of Constant Region (141-167)

Figure 24
SEQ ID NO:29: Cloned Nucleotide Sequence of Rat #32A1 Light Chain (Variable Region + alpha)
ATGGAGACAGACAGACTCCTGCTATGGGCACTGCTGCTCTGGGTTCCAGGCTCCACT
GGTGACATTGTCTTGACCCAGTCTCCTGCTTTGGCTGTGTCTCTAGGGCAGAGGGCC
ACAATCTCCTGTAGGGCCAGCCAAAGTGTCACTATTTCTGGATATAGTTTTATACACTG
GTACCAACAGAAACCAGGACAGCAACCCAGACTCCTCATCTATCGTGCATCCAACCTA
GCCTCTGGGATCCCGGCCAGGTTCAGTGGCAGTGGGTCTGGGACAGACTTCACCCTC
ACCATCAATCCTGTGCAGGCTGATGATATTGCAACCTATTTCTGTCAGCAGAGTAGGA
AATCTCCGTGGACGTTCGCTGGAGGCACCAAGCTGGAATTGAGACGGGCTGATGCTG
CACCAACTGTATCT
Signal Sequence (1-60), Variable Region (61-396), Partial Sequence of Constant Region (397-417)

SEQ ID NO:30: Amino Acid Sequence Encoded by Cloned Rat #32A1 Light Chain (Variable Region + alpha)
METDRLLLWALLLWVPGSTGDIVLTQSPALAVSLGQRATISCRASQSVTISGYSFIHWYQQ
KPGQQPRLLIYRASNLASGIPARFSGSGSGTDFTLTINPVQADDIATYFCQQSRKSPWTFA
GGTKLELRRADAAPTVS
Signal Sequence (1-20), Variable Region (21-132), Partial Sequence of Constant Region (133-139)

Figure 25

SEQ ID NO: 40: Nucleotide Sequence of #32A1 Human Chimeric Antibody Heavy Chain
ATGAAACACCTGTGGTTCTTCCTCCTGCTGGTGGCAGCTCCCAGATGGGTGCTGAGC
GAGGTGCAAATTTTGGAGACTGGAGGAGGCTTGGTGAAGCCCGGTGGTTCCCTGAGA
CTGTCTTGTGCAACGTCTGGATTCAATTTCAATGATTATTTCATGAACTGGGTCCGTCA
GGCTCCAGAAAAGGGGCTAGAGTGGGTTGCTCAAATAAGGAACAAAATTTATACTTAT
GCCACATTTTATGCGGAGTCTTTGGAAGGCAGAGTCACAATCTCACGAGACGATTCCG
AAAGCAGTGTCTACCTGCAAGTGAGCAGTTTAAGAGCTGAAGACACTGCCATTTATTA
CTGTACAAGATCCCTAACTGGGGGAGACTACTTTGATTACTGGGGCCAAGGAGTCATG
GTCACAGTCAGCTCAGCCTCCACCAAGGGCCCAAGCGTCTTCCCCCTGGCACCCTCC
TCCAAGAGCACCTCTGGCGGCACAGCCGCCCTGGGCTGCCTGGTCAAGGACTACTTC
CCCGAACCCGTGACCGTGAGCTGGAACTCAGGCGCCCTGACCAGCGGCGTGCACAC
CTTCCCCGCTGTCCTGCAGTCCTCAGGACTCTACTCCCTCAGCAGCGTGGTGACCGT
GCCCTCCAGCAGCTTGGGCACCCAGACCTACATCTGCAACGTGAATCACAAGCCCAG
CAACACCAAGGTGGACAAGAGAGTTGAGCCCAAATCTTGTGACAAAACTCACACATGC
CCACCCTGCCCAGCACCTGAACTCCTGGGGGGACCCTCAGTCTTCCTCTTCCCCCCA
AAACCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTGGA
GGTGCATAATGCCAAGACAAAGCCCCGGGAGGAGCAGTACAACAGCACGTACCGGG
TGGTCAGCGTCCTCACCGTCCTGCACCAGGACTGGCTGAATGGCAAGGAGTACAAGT
GCAAGGTCTCCAACAAAGCCCTCCCAGCCCCCATCGAGAAAACCATCTCCAAAGCCA
AAGGCCAGCCCCGGGAACCACAGGTGTACACCCTGCCCCCATCCCGGGAGGAGATG
ACCAAGAACCAGGTCAGCCTGACCTGCCTGGTCAAAGGCTTCTATCCCAGCGACATC
GCCGTGGAGTGGGAGAGCAATGGCCAGCCCGAGAACAACTACAAGACCACCCCTCC
CGTGCTGGACTCCGACGGCTCCTTCTTCCTCTACAGCAAGCTCACCGTGGACAAGAG
CAGGTGGCAGCAGGGCAACGTCTTCTCATGCTCCGTGATGCATGAGGCTCTGCACAA
CCACTACACCCAGAAGAGCCTCTCCCTGTCTCCGGCAAATGA
Signal Sequence (1-57), Variable Region (58-420), Constant Region (421-1413, including stop codon)

SEQ ID NO: 41: Amino Acid Sequence of #32A1 Human Chimeric Antibody Heavy Chain
MKHLWFFLLLVAAPRWVLSEVQILETGGGLVKPGGSLRLSCATSGFNFNDYFMNWVRQA
PEKGLEWVAQIRNKIYTYATFYAESLEGRVTISRDDSESSVYLQVSSLRAEDTAIYYCTRSL
TGGDYFDYWGQGVMVTVSSASTKGPSVFPLAPSSKSTSGGTAALGCLVKDYFPEPVTVS
WNSGALTSGVHTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGK
Signal Sequence (1-19), Variable Region (20-140), Constant Region (141-470)

Figure 26
SEQ ID NO: 42: Nucleotide Sequence of #32A1 Human Chimeric Antibody Light Chain
ATGGTGCTGCAGACCCAGGTGTTCATCTCCCTGCTGCTGTGGATCTCCGGCGCATAT
GGCGACATTGTCTTGACCCAGTCTCCTGCTTTGGCTGTGTCTCTAGGGCAGAGGGCC
ACAATCTCCTGTAGGGCCAGCCAAAGTGTCACTATTTCTGGATATAGTTTTATACACTG
GTACCAACAGAAACCAGGACAGCAACCCAGACTCCTCATCTATCGTGCATCCAACCTA
GCCTCTGGGATCCCGGCCAGGTTCAGTGGCAGTGGGTCTGGGACAGACTTCACCCTC
ACCATCAATCCTGTGCAGGCTGATGATATTGCAACCTATTTCTGTCAGCAGAGTAGGA
AATCTCCGTGGACGTTCGCTGGAGGCACCAAGCTGGAATTGAGACGTACGGTGGCCG
CCCCCTCCGTGTTCATCTTCCCCCCTCCGACGAGCAGCTGAAGTCCGGCACCGCCT
CCGTGGTGTGCCTGCTGAATAACTTCTACCCCAGAGAGGCCAAGGTGCAGTGGAAGG
TGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAG
AAGCACAAGGTGTACGCCTGCGAGGTGACCCACCAGGGCCTGAGCTCCCCCGTCAC
CAAGAGCTTCAACAGGGGGGAGTGTTAG
Signal Sequence (1-60), Variable Region (61-396), Constant Region (397-714, including stop codon )

SEQ ID NO: 43: Amino Acid Sequence of of #32A1 Human Chimeric Antibody Light Chain
MVLQTQVFISLLLWISGAYGDIVLTQSPALAVSLGQRATISCRASQSVTISGYSFIHWYQQK
PGQQPRLLIYRASNLASGIPARFSGSGSGTDFTLTINPVQADDIATYFCQQSRKSPWTFAG
GTKLELRRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC
Signal Sequence (1-20), Variable Region (21-132), Constant Region (133-237)

Figure 27

SEQ ID NO:50: Nucleotide Sequence of h#32A1-T1H
ATGAAACACCTGTGGTTCTTCCTCCTGCTGGTGGCAGCTCCCAGATGGGTGCTGAGCGAGGTGC
AACTGGTGGAGAGCGGCGGCGGACTTGTGCAACCTGGCGGCTCCCTGAGACTTAGCTGTGCCGC
CTCCGGCTTCAACTTCAACGACTACTTCATGAACTGGGTGAGACAAGCCCCTGGCAAGGGCCTG
GAGTGGGTGGCCCAAATCAGAAACAAGATCTACACCTACGCCACCTTCTACGCCGAGAGCCTTG
AGGGCAGATTCACCATCTCCAGAGACAACGCCAAGAACAGCCTGTACCTTCAAATGAACTCCCT
GAGAGCCGAGGACACCGCCGTGTACTACTGTGCCAGAAGCCTTACCGGCGGCGACTACTTCGAC
TACTGGGGCCAAGGCACCCTGGTGACCGTGAGCTCAGCCTCCACCAAGGGCCCAAGCGTCTTCC
CCCTGGCACCCTCCTCCAAGAGCACCTCTGGCGGCACAGCCGCCCTGGGCTGCCTGGTCAAGGA
CTACTTCCCCGAACCCGTGACCGTGAGCTGGAACTCAGGCGCCCTGACCAGCGGCGTGCACACC
TTCCCCGCTGTCCTGCAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTGGA
CAAGAGAGTTGAGCCCAAATCTTGTGACAAAACTCACACATGCCCACCCTGCCCAGCACCTGAA
CTCCTGGGGGGACCCTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCCCGGGAGGAGCAGTACAAC
AGCACGTACCGGGTGGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACCATCTCCAAAGCCAA
AGGCCAGCCCCGGGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGACGGCTCCTT
CTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCA
AA Signal Sequence (1-57), Variable Region (58-420), Constant Region (421-1410)

SEQ ID NO:51: Amino Acid Sequence of h#32A1-T1H
MKHLWFFLLLVAAPRWVLSEVQLVESGGGLVQPGGSLRLSCAASGFNFNDYFMNWVRQAPGKGL
EWVAQIRNKIYTYATFYAESLEGRFTISRDNAKNSLYLQMNSLRAEDTAVYYCARSLTGGDYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal Sequence (1-19), Variable Region (20-140), Constant Region (141-470)

Figure 28

SEQ ID NO:52: Nucleotide Sequence of h#32A1-T2H
ATGAAACACCTGTGGTTCTTCCTCCTGCTGGTGGCAGCTCCCAGATGGGTGCTGAGCGAGGTGC
AACTGGTGGAGAGCGGCGGCGGACTGGTGCAACCTGGCGGCTCCCTGAGACTGAGCTGTGCCGC
CTCCGGCTTCAACTTCAACGACTACTTCATGAACTGGGTGAGACAAGCCCCTGAGAAGGGCCTG
GAGTGGGTGGCCCAAATCAGAAACAAGATCTACACCTACGCCACCTTCTACGCCGAGAGCCTGG
AGGGCAGAGTGACCATCTCCAGAGACAACGCCAAGAACAGCCTGTACCTGCAAATGTCCTCCCT
GAGAGCCGAGGACACCGCCGTGTACTACTGTGCCAGAAGCCTGACCGGCGGCGACTACTTCGAC
TACTGGGGCCAAGGCACCCTGGTGACCGTGAGCTCAGCCTCCACCAAGGGCCCAAGCGTCTTCC
CCCTGGCACCCTCCTCCAAGAGCACCTCTGGCGGCACAGCCGCCCTGGGCTGCCTGGTCAAGGA
CTACTTCCCCGAACCCGTGACCGTGAGCTGGAACTCAGGCGCCCTGACCAGCGGCGTGCACACC
TTCCCCGCTGTCCTGCAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTGGA
CAAGAGAGTTGAGCCCAAATCTTGTGACAAAACTCACACATGCCCACCCTGCCCAGCACCTGAA
CTCCTGGGGGGACCCTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCCCGGGAGGAGCAGTACAAC
AGCACGTACCGGGTGGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACCATCTCCAAAGCCAA
AGGCCAGCCCCGGGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGACGGCTCCTT
CTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCA
AA Signal Sequence (1-57), Variable Region (58-420), Constant Region (421-1410)

SEQ ID NO:53: Amino Acid Sequence of h#32A1-T2H
MKHLWFFLLLVAAPRWVLSEVQLVESGGGLVQPGGSLRLSCAASGFNFNDYFMNWVRQAPEKGL
EWVAQIRNKIYTYATFYAESLEGRVTISRDNAKNSLYLQMSSLRAEDTAVYYCARSLTGGDYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal Sequence (1-19), Variable Region (20-140), Constant Region (141-470)

Figure 29

SEQ ID NO:54: Nucleotide Sequence of h#32A1-T3H
ATGAAACACCTGTGGTTCTTCCTCCTGCTGGTGGCAGCTCCCAGATGGGTGCTGAGCGAGGTGC
AGATCGTGGAGAGCGGCGGCGGACTTGTGCAGCCTGGCGGCTCCCTGAGACTTAGCTGTGCCAC
CTCCGGCTTCAACTTCAACGACTACTTCATGAACTGGGTGAGACAGGCCCCTGAGAAGGGCCTG
GAGTGGGTGGCCCAGATCAGAAACAAGATCTACACCTACGCCACCTTCTACGCCGAGAGCCTTG
AGGGCAGAGTGACCATCTCCAGAGACGACAGCGAGTCCAGCGTGTACCTTCAGATGTCCAGCCT
GAGAGCCGAGGACACCGCCGTGTACTACTGTACCAGAAGCCTTACCGGCGGCGACTACTTCGAC
TACTGGGGCCAGGGCACCCTGGTGACCGTGAGCTCAGCCTCCACCAAGGGCCCAAGCGTCTTCC
CCCTGGCACCCTCCTCCAAGAGCACCTCTGGCGGCACAGCCGCCCTGGGCTGCCTGGTCAAGGA
CTACTTCCCCGAACCCGTGACCGTGAGCTGGAACTCAGGCGCCCTGACCAGCGGCGTGCACACC
TTCCCCGCTGTCCTGCAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTGGA
CAAGAGAGTTGAGCCCAAATCTTGTGACAAAACTCACACATGCCCACCCTGCCCAGCACCTGAA
CTCCTGGGGGGACCCTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCCCGGGAGGAGCAGTACAAC
AGCACGTACCGGGTGGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACCATCTCCAAAGCCAA
AGGCCAGCCCCGGGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGACGGCTCCTT
CTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCA
AA Signal Sequence (1-57), Variable Region (58-420), Constant Region (421-1410)

SEQ ID NO:55: Amino Acid Sequence of h#32A1-T3H
MKHLWFFLLLVAAPRWVLSEVQIVESGGGLVQPGGSLRLSCATSGFNFNDYFMNWVRQAPEKGL
EWVAQIRNKIYTYATFYAESLEGRVTISRDDSESSVYLQMSSLRAEDTAVYYCTRSLTGGDYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal Sequence (1-19), Variable Region (20-140), Constant Region (141-470)

Figure 30

SEQ ID NO:56: Nucleotide Sequence of h#32A1-T5H
ATGAAACACCTGTGGTTCTTCCTCCTGCTGGTGGCAGCTCCCAGATGGGTGCTGAGCGAGGTGC
AGGTGGTGGAGAGCGGCGGCGGACTTGTGCAGCCTGGCGGCTCCCTGAGACTTAGCTGTGCCAC
CTCCGGCTTCAACTTCAACGACTACTTCATGAACTGGGTGAGACAGGCCCCTGGCAAGGGCCTG
GAGTGGGTGGCCCAGATCAGAAACAAGATCTACACCTACGCCACCTTCTACGCCGAGAGCCTTG
AGGGCAGATTCACCATCTCCAGAGACAACAGCAAGTCCACCGTGTACCTTCAGATGAACTCCCT
GAGAGCCGAGGACACCGCCGTGTACTACTGTACCAGAAGCCTTACCGGCGGCGACTACTTCGAC
TACTGGGGCCAGGGCACCCTGGTGACCGTGAGCTCAGCCTCCACCAAGGGCCCAAGCGTCTTCC
CCCTGGCACCCTCCTCCAAGAGCACCTCTGGCGGCACAGCCGCCCTGGGCTGCCTGGTCAAGGA
CTACTTCCCCGAACCCGTGACCGTGAGCTGGAACTCAGGCGCCCTGACCAGCGGCGTGCACACC
TTCCCCGCTGTCCTGCAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTGGA
CAAGAGAGTTGAGCCCAAATCTTGTGACAAAACTCACACATGCCCACCCTGCCCAGCACCTGAA
CTCCTGGGGGGACCCTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCCCGGGAGGAGCAGTACAAC
AGCACGTACCGGGTGGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACCATCTCCAAAGCCAA
AGGCCAGCCCCGGGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGACGGCTCCTT
CTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCCGGCA
AA Signal Sequence (1-57), Variable Region (58-420), Constant Region (421-1410)

SEQ ID NO:57: Amino Acid Sequence of h#32A1-T5H
MKHLWFFLLLVAAPRWVLSEVQVVESGGGLVQPGGSLRLSCATSGFNFNDYFMNWVRQAPGKGL
EWVAQIRNKIYTYATFYAESLEGRFTISRDNSKSTVYLQMNSLRAEDTAVYYCTRSLTGGDYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal Sequence (1-19), Variable Region (20-140), Constant Region (141-470)

Figure 31

SEQ ID NO:58: Nucleotide Sequence of h#32A1-T6H
ATGAAACACCTGTGGTTCTTCCTCCTGCTGGTGGCAGCTCCCAGATGGGTGCTGAGCGAGGTGC
AGGTGGTGGAGAGCGGCGGCGGACTTGTGCAGCCTGGCGGCTCCCTGAGACTTAGCTGTGCCAC
CTCCGGCTTCAACTTCAACGACTACTTCATGAACTGGGTGAGACAGGCCCCTGAGAAGGGCCTG
GAGTGGGTGGCCCAGATCAGAAACAAGATCTACACCTACGCCACCTTCTACGCCGAGAGCCTTG
AGGGCAGAGTGACCATCTCCAGAGACAACAGCAAGTCCACCGTGTACCTTCAGATGTCCAGCCT
TAGAGCCGAGGACACCGCCGTGTACTACTGTACCAGAAGCCTTACCGGCGGCGACTACTTCGAC
TACTGGGGCCAGGGCACCCTTGTGACAGTGAGCTCAGCCTCCACCAAGGGCCCAAGCGTCTTCC
CCCTGGCACCCTCCTCCAAGAGCACCTCTGGCGGCACAGCCGCCCTGGGCTGCCTGGTCAAGGA
CTACTTCCCCGAACCCGTGACCGTGAGCTGGAACTCAGGCGCCCTGACCAGCGGCGTGCACACC
TTCCCCGCTGTCCTGCAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTGGA
CAAGAGAGTTGAGCCCAAATCTTGTGACAAAACTCACACATGCCCACCCTGCCCAGCACCTGAA
CTCCTGGGGGGACCCTCAGTCTTCCTCTTCCCCCCAAAACCCAAGGACACCCTCATGATCTCCC
GGACCCCTGAGGTCACATGCGTGGTGGTGGACGTGAGCCACGAAGACCCTGAGGTCAAGTTCAA
CTGGTACGTGGACGGCGTGGAGGTGCATAATGCCAAGACAAAGCCCCGGGAGGAGCAGTACAAC
AGCACGTACCGGGTGGTCAGCGTCCTCACCGTCCTGCACCAGGACTGGCTGAATGGCAAGGAGT
ACAAGTGCAAGGTCTCCAACAAAGCCCTCCCAGCCCCCATCGAGAAAACCATCTCCAAAGCCAA
AGGCCAGCCCCGGGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGACGGCTCCTT
CTTCCTCTACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTCTCCGGCA
AA Signal Sequence (1-57), Variable Region (58-420), Constant Region (421-1410)

SEQ ID NO:59: Amino Acid Sequence of h#32A1-T6H
MKHLWFFLLLVAAPRWVLSEVQVVESGGGLVQPGGSLRLSCATSGFNFNDYFMNWVRQAPEKGL
EWVAQIRNKIYTYATFYAESLEGRVTISRDNSKSTVYLQMSSLRAEDTAVYYCTRSLTGGDYFD
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSC
SVMHEALHNHYTQKSLSLSPGK Signal Sequence (1-19), Variable Region (20-140), Constant Region (141-470)

Figure 32

SEQ ID NO:60: Nucleotide Sequence of h#32A1-T1L

ATGGTGCTGCAGACCCAGGTGTTCATCTCCCTGCTGCTGTGGATCTCCGGCGCATATGGCGACA
TCGTGATGACCCAGAGCCCTGACTCCCTTGCCGTGTCCCTGGGCGAGAGAGCCACCATCAACTG
TAGAGCCTCCCAGAGCGTGACCATCTCCGGCTACAGCTTCATCCACTGGTACCAGCAGAAGCCT
GGCCAGCCTCCTAAGCTTCTGATCTACAGAGCCTCCAACCTTGCCAGCGGCGTGCCTGCCAGAT
TCTCCGGCAGCGGCTCCGGCACCGACTTCACCCTGACCATCAGCTCCCTTCAGGCCGAGGACGT
GGCCGTGTACTACTGTCAGCAGAGCAGAAAGTCCCCTTGGACCTTCGGCGGCGGCACCAAGGTG
GAGATCAAGCGTACGGTGGCCGCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT

Signal Sequence (1-60), Variable Region (61-399), Constant Region (400-714)

SEQ ID NO:61: Amino Acid Sequence of h#32A1-T1L

MVLQTQVFISLLLWISGAYGDIVMTQSPDSLAVSLGERATINCRASQSVTISGYSFIHWYQQKP
GQPPKLLIYRASNLASGVPARFSGSGSGTDFTLTISSLQAEDVAVYYCQQSRKSPWTFGGGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

Signal Sequence (1-20), Variable Region (21-133), Constant Region (134-238)

Figure 33

SEQ ID NO:62: Nucleotide Sequence of h#32A1-T2L
ATGGTGCTGCAGACCCAGGTGTTCATCTCCCTGCTGCTGTGGATCTCCGGCGCATATGGCGACA
TCGTGATGACCCAGAGCCCTGACTCCCTTGCCGTGTCCCTGGGCGAGAGAGCCACCATCAGCTG
TAGAGCCTCCCAGAGCGTGACCATCTCCGGCTACAGCTTCATCCACTGGTACCAGCAGAAGCCT
GGCCAGCCTCCTAGACTTCTGATCTACAGAGCCTCCAACCTTGCCAGCGGCGTGCCTGCCAGAT
TCTCCGGCAGCGGCTCCGGCACCGACTTCACCCTGACCATCAGCTCCCTTCAGGCCGAGGACGT
GGCCGTGTACTTCTGTCAGCAGAGCAGAAAGTCCCCTTGGACCTTCGCCGGCGGCACCAAGGTG
GAGATCAAGCGTACGGTGGCCGCCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT Signal Sequence (1-60), Variable Region (61-399), Constant Region (400-714)

SEQ ID NO:63: Amino Acid Sequence of h#32A1-T2L
MVLQTQVFISLLLWISGAYGDIVMTQSPDSLAVSLGERATISCRASQSVTISGYSFIHWYQQKP
GQPPRLLIYRASNLASGVPARFSGSGSGTDFTLTISSLQAEDVAVYFCQQSRKSPWTFAGGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Signal Sequence (1-20), Variable Region (21-133), Constant Region (134-238)

Figure 34
SEQ ID NO:64: Nucleotide Sequence of h#32A1-T3L
ATGGTGCTGCAGACCCAGGTGTTCATCTCCCTGCTGCTGTGGATCTCCGGCGCATATGGCGACA
TCGTGCTTACCCAGAGCCCTGACTCCCTTGCCGTGTCCCTGGGCGAGAGAGCCACCATCAGCTG
TAGAGCCTCCCAGAGCGTGACCATCTCCGGCTACAGCTTCATCCACTGGTACCAGCAGAAGCCT
GGCCAGCAGCCTAGACTTCTGATCTACAGAGCCTCCAACCTTGCCAGCGGCATCCCTGCCAGAT
TCTCCGGCAGCGGCTCCGGCACCGACTTCACCCTGACCATCAGCTCCCTTCAGGCCGAGGACGT
GGCCACCTACTTCTGTCAGCAGAGCAGAAAGTCCCCTTGGACCTTCGCCGGCGGCACCAAGGTG
GAGATCAAGCGTACGGTGGCCGCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT Signal Sequence (1-60), Variable Region (61-399), Constant Region (400-714)

SEQ ID NO:65: Amino Acid Sequence of h#32A1-T3L
MVLQTQVFISLLLWISGAYGDIVLTQSPDSLAVSLGERATISCRASQSVTISGYSFIHWYQQKP
GQQPRLLIYRASNLASGIPARFSGSGSGTDFTLTISSLQAEDVATYFCQQSRKSPWTFAGGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Signal Sequence (1-20), Variable Region (21-133), Constant Region (134-238)

Figure 35

SEQ ID NO:66: Nucleotide Sequence of h#32A1-T4L
ATGGTGCTGCAGACCCAGGTGTTCATCTCCCTGCTGCTGTGGATCTCCGGCGCATATGGCGACA
TCGTGCTTACCCAGAGCCCTGCCCTTGCCGTGTCCCTGGGCGAGAGAGCCACCATCAGCTGTAG
AGCCTCCCAGAGCGTGACCATCTCCGGCTACAGCTTCATCCACTGGTACCAGCAGAAGCCTGGC
CAGCAGCCTAGACTTCTGATCTACAGAGCCTCCAACCTTGCCAGCGGCATCCCTGCCAGATTCT
CCGGCAGCGGCTCCGGCACCGACTTCACCCTGACCATCAGCTCCCTTCAGGCCGAGGACGTGGC
CACCTACTTCTGTCAGCAGAGCAGAAAGTCCCCTTGGACCTTCGCCGGCGGCACCAAGCTGGAG
ATCAAGCGTACGGTGGCCGCCCCCTCCGTGTTCATCTTCCCCCCTCCGACGAGCAGCTGAAGT
CCGGCACCGCCTCCGTGGTGTGCCTGCTGAATAACTTCTACCCCAGAGAGGCCAAGGTGCAGTG
GAAGGTGGACAACGCCCTGCAGTCCGGGAACTCCCAGGAGAGCGTGACCGAGCAGGACAGCAAG
GACAGCACCTACAGCCTGAGCAGCACCCTGACCCTGAGCAAAGCCGACTACGAGAAGCACAAGG
TGTACGCCTGCGAGGTGACCCACCAGGGCCTGAGCTCCCCCGTCACCAAGAGCTTCAACAGGGG
GGAGTGT Signal Sequence (1-60), Variable Region (61-396), Constant Region (397-711)

SEQ ID NO:67: Amino Acid Sequence of h#32A1-T4L
MVLQTQVFISLLLWISGAYGDIVLTQSPALAVSLGERATISCRASQSVTISGYSFIHWYQQKPG
QQPRLLIYRASNLASGIPARFSGSGSGTDFTLTISSLQAEDVATYFCQQSRKSPWTFAGGTKLE
IKRTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC Signal Sequence (1-20), Variable Region (21-132), Constant Region (133-237)

Figure 36
SEQ ID NO:68: Nucleotide Sequence of h#32A1-T5L
ATGGTGCTGCAGACCCAGGTGTTCATCTCCCTGCTGCTGTGGATCTCCGGCGCATATGGCGACA
TCGTGCTTACCCAGAGCCCTGACTCCCTTGCCGTGTCCCTGGGCGAGAGAGCCACCATCAACTG
TAGAGCCTCCCAGAGCGTGACCATCTCCGGCTACAGCTTCATCCACTGGTACCAGCAGAAGCCT
GGCCAGCCTCCTAAGCTTCTGATCTACAGAGCCTCCAACCTTGCCAGCGGCATCCCTGCCAGAT
TCTCCGGCAGCGGCTCCGGCACCGACTTCACCCTGACCATCAGCTCCCTTCAGGCCGAGGACGT
GGCCACCTACTACTGTCAGCAGAGCAGAAAGTCCCCTTGGACCTTCGGCCAGGGCACCAAGGTG
GAGATCAAGCGTACGGTGGCCGCCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT Signal Sequence (1-60), Variable Region (61-399), Constant Region (400-714)

SEQ ID NO:69: Amino Acid Sequence of h#32A1-T5L
MVLQTQVFISLLLWISGAYGDIVLTQSPDSLAVSLGERATINCRASQSVTISGYSFIHWYQQKP
GQPPKLLIYRASNLASGIPARFSGSGSGTDFTLTISSLQAEDVATYYCQQSRKSPWTFGQGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Signal Sequence (1-20), Variable Region (21-133), Constant Region (134-238)

Figure 37

SEQ ID NO:70: Nucleotide Sequence of h#32A1-T6L
ATGGTGCTGCAGACCCAGGTGTTCATCTCCCTGCTGCTGTGGATCTCCGGCGCATATGGCGACA
TCGTGCTTACCCAGAGCCCTGACTCCCTTGCCGTGTCCCTGGGCGAGAGAGCCACCATCAGCTG
TAGAGCCTCCCAGAGCGTGACCATCTCCGGCTACAGCTTCATCCACTGGTACCAGCAGAAGCCT
GGCCAGCCTCCTAGACTGCTGATCTACAGAGCCTCCAACCTTGCCAGCGGCATCCCTGCCAGAT
TCTCCGGCAGCGGCTCCGGCACCGACTTCACCCTGACCATCAGCTCCCTTCAGGCCGAGGACGT
GGCCACCTACTTCTGTCAGCAGAGCAGAAAGTCCCCTTGGACCTTCGCCGGCGGCACCAAGGTG
GAGATCAAGCGTACGGTGGCCGCCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT Signal Sequence (1-60), Variable Region (61-399), Constant Region (400-714)

SEQ ID NO:71: Amino Acid Sequence of h#32A1-T6L
MVLQTQVFISLLLWISGAYGDIVLTQSPDSLAVSLGERATISCRASQSVTISGYSFIHWYQQKP
GQPPRLLIYRASNLASGIPARFSGSGSGTDFTLTISSLQAEDVATYFCQQSRKSPWTFAGGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Signal Sequence (1-20), Variable Region (21-133), Constant Region (134-238)

Figure 38
SEQ ID NO:72: Amino Acid Sequence of h#32A1-T7H
EVQLVESGGGLVQPGGSLRLSCAASGFNFNDYFMNWVRQAPEKGLEWVAQIRNKIYTYATFYAE
SLEGRFTISRDNAKNSLYLQMNSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

SEQ ID NO:73: Amino Acid Sequence of h#32A1-T8H
EVQLVESGGGLVQPGGSLRLSCAASGFNFNDYFMNWVRQAPGKGLEWVAQIRNKIYTYATFYAE
SLEGRVTISRDNAKNSLYLQMNSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

SEQ ID NO:74: Amino Acid Sequence of h#32A1-T9H
EVQLVESGGGLVQPGGSLRLSCAASGFNFNDYFMNWVRQAPGKGLEWVAQIRNKIYTYATFYAE
SLEGRFTISRDNAKNSLYLQMSSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

Figure 39

SEQ ID NO:75: Amino Acid Sequence of h#32A1-T10H
EVQLVESGGGLVQPGGSLRLSCAASGFNFNDYFMNWVRQAPEKGLEWVAQIRNKIYTYATFYAE
SLEGRVTISRDNAKNSLYLQMNSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

SEQ ID NO:76: Amino Acid Sequence of h#32A1-T11H
EVQLVESGGGLVQPGGSLRLSCAASGFNFNDYFMNWVRQAPEKGLEWVAQIRNKIYTYATFYAE
SLEGRFTISRDNAKNSLYLQMSSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

SEQ ID NO:77: Amino Acid Sequence of h#32A1-T12H
EVQLVESGGGLVQPGGSLRLSCAASGFNFNDYFMNWVRQAPGKGLEWVAQIRNKIYTYATFYAE
SLEGRVTISRDNAKNSLYLQMSSLRAEDTAVYYCARSLTGGDYFDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGK
Variable Region (1-121), Constant Region (122-451)

Figure 40

SEQ ID NO:78: Amino Acid Sequence of h#32A1-T7L
DIVMTQSPDSLAVSLGERATISCRASQSVTISGYSFIHWYQQKPGQPPKLLIYRASNLASGVPA
RFSGSGSGTDFTLTISSLQAEDVAVYYCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:79: Amino Acid Sequence of h#32A1-T8L
DIVMTQSPDSLAVSLGERATINCRASQSVTISGYSFIHWYQQKPGQPPRLLIYRASNLASGVPA
RFSGSGSGTDFTLTISSLQAEDVAVYYCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:80: Amino Acid Sequence of h#32A1-T9L
DIVMTQSPDSLAVSLGERATINCRASQSVTISGYSFIHWYQQKPGQPPKLLIYRASNLASGVPA
RFSGSGSGTDFTLTISSLQAEDVAVYFCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:81: Amino Acid Sequence of h#32A1-T10L
DIVMTQSPDSLAVSLGERATINCRASQSVTISGYSFIHWYQQKPGQPPKLLIYRASNLASGVPA
RFSGSGSGTDFTLTISSLQAEDVAVYYCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:82: Amino Acid Sequence of h#32A1-11L
DIVMTQSPDSLAVSLGERATISCRASQSVTISGYSFIHWYQQKPGQPPRLLIYRASNLASGVPA
RFSGSGSGTDFTLTISSLQAEDVAVYYCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

Figure 41

SEQ ID NO:83: Amino Acid Sequence of h#32A1-T12L
DIVMTQSPDSLAVSLGERATISCRASQSVTISGYSFIHWYQQKPGQPPKLLIYRASNLASGVPA
RFSGSGSGTDFTLTISSLQAEDVAVYFCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:84: Amino Acid Sequence of h#32A1-T13L
DIVMTQSPDSLAVSLGERATISCRASQSVTISGYSFIHWYQQKPGQPPKLLIYRASNLASGVPA
RFSGSGSGTDFTLTISSLQAEDVAVYYCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:85: Amino Acid Sequence of h#32A1-T14L
DIVMTQSPDSLAVSLGERATINCRASQSVTISGYSFIHWYQQKPGQPPRLLIYRASNLASGVPA
RFSGSGSGTDFTLTISSLQAEDVAVYFCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:86: Amino Acid Sequence of h#32A1-T15L
DIVMTQSPDSLAVSLGERATINCRASQSVTISGYSFIHWYQQKPGQPPRLLIYRASNLASGVPA
RFSGSGSGTDFTLTISSLQAEDVAVYYCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:87: Amino Acid Sequence of h#32A1-T16L
DIVMTQSPDSLAVSLGERATINCRASQSVTISGYSFIHWYQQKPGQPPKLLIYRASNLASGVPA
RFSGSGSGTDFTLTISSLQAEDVAVYFCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

Figure 42

SEQ ID NO:88: Amino Acid Sequence of h#32A1-T17L
DIVMTQSPDSLAVSLGERATISCRASQSVTISGYSFIHWYQQKPGQPPRLLIYRASNLASGVPA
RFSGSGSGTDFTLTISSLQAEDVAVYFCQQSRKSPWTFGGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:89: Amino Acid Sequence of h#32A1-T18L
DIVMTQSPDSLAVSLGERATISCRASQSVTISGYSFIHWYQQKPGQPPRLLIYRASNLASGVPA
RFSGSGSGTDFTLTISSLQAEDVAVYYCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:90: Amino Acid Sequence of h#32A1-T19L
DIVMTQSPDSLAVSLGERATISCRASQSVTISGYSFIHWYQQKPGQPPKLLIYRASNLASGVPA
RFSGSGSGTDFTLTISSLQAEDVAVYFCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:91: Amino Acid Sequence of h#32A1-T20L
DIVMTQSPDSLAVSLGERATINCRASQSVTISGYSFIHWYQQKPGQPPRLLIYRASNLASGVPA
RFSGSGSGTDFTLTISSLQAEDVAVYFCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:92: Amino Acid Sequence of h#32A1-T21L
EILMTQSPATLSLSPGERATLSCRASQSVTISGYSFIHWYQQKPGQAPRLLIYRASNLASGIPA
RFSGSGSGTDFTLTISSLEPEDFALYYCQQSRKSPWTFGQGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

Figure 43
SEQ ID NO:93: Amino Acid Sequence of h#32A1-T22L
EILMTQSPATLSLSPGERATLSCRASQSVTISGYSFIHWYQQKPGQAPRLLIYRASNLASGIPA
RFSGSGSGTDFTLTISSLEPEDFALYFCQQSRKSPWTFAQGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:94: Amino Acid Sequence of h#32A1-T23L
EILLTQSPATLSLSPGERATLSCRASQSVTISGYSFIHWYQQKPGQAPRLLIYRASNLASGIPA
RFSGSGSGTDFTLTISSLEPEDFALYYCQQSRKSPWTFGQGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:95: Amino Acid Sequence of h#32A1-T24L
EILLTQSPATLSLSPGERATLSCRASQSVTISGYSFIHWYQQKPGQAPRLLIYRASNLASGIPA
RFSGSGSGTDFTLTISSLEPEDFALYYCQQSRKSPWTFGQGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

SEQ ID NO:96: Amino Acid Sequence of h#32A1-T25L
DILLTQSPATLSLSPGERATLSCRASQSVTISGYSFIHWYQQKPGQQPRLLIYRASNLASGIPA
RFSGSGSGTDFTLTISSLEPEDFATYFCQQSRKSPWTFAGGTKVEIKRTVAAPSVFIFPPSDEQ
LKSGTASVVCLLNNFYPREAKVQWKVDNALQSGNSQESVTEQDSKDSTYSLSSTLTLSKADYEK
HKVYACEVTHQGLSSPVTKSFNRGEC
Variable Region (1-113), Constant Region (114-218)

Figure 46
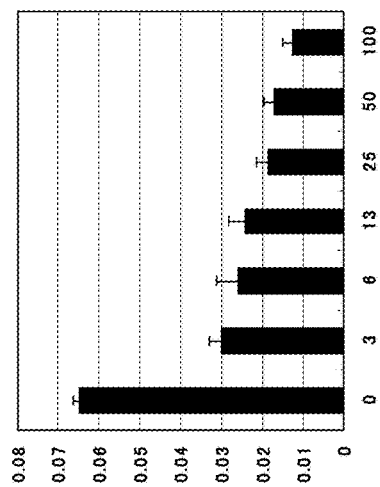
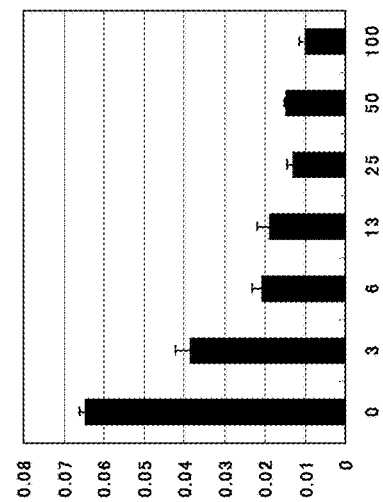
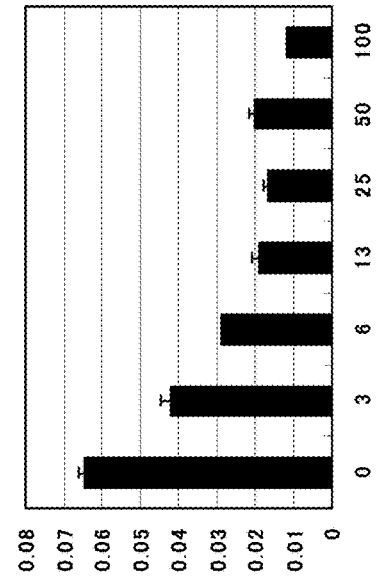

Figure 54

SEQ ID NO:98: Nucleotide Sequence of h#32A1-H1-1
ATGAAACACCTGTGGTTCTTCCTCCTGCTGGTGGCAGCTCCCAGATGGGTGCTGAGCGAAGTCC
AGCTTGTGGAAAGCGGAGGGGGACTCGTTCAGCCAGGAGGCTCTCTGCGCCTGTCATGCGCTGC
CAGCGGATTTAATTTCAATGATTATTTTATGAACTGGGTCAGGCAGGCTCCGGGAAAAGGGCTG
GAATGGGTCGCCCAGATCAGAAACAAGATCTATACTTACGCTACATTCTACGCCGCATCTGTAA
AGGGGAGGTTTACAATTAGTCGCGACAATGCAAAAAATAGTCTGTATCTCCAAATGAACTCCCT
CCGCGCAGAGGATACTGCTGTCTACTACTGCGCCAGGTCCTTGACTGGCGGCGACTATTTTGAT
TACTGGGGACAGGGCACCCTGGTGACGGTGAGCTCAGCCAGCACCAAGGGCCCTTCCGTGTTCC
CTCTGGCCCCTTGTAGCCGTTCCACCAGCGAGTCCACCGCCGCCCTTGGCTGTCTGGTGAAGGA
CTACTTCCCTGAGCCTGTGACCGTGAGCTGGAACTCCGGAGCCCTTACCAGCGGCGTGCACACC
TTCCCTGCCGTGCTGCAGTCCAGCGGCCTTTACTCCCTGAGCTCCGTGGTGACCGTGCCTAGCT
CCAACTTCGGCACCCAAACCTACACCTGTAACGTGGACCACAAGCCTAGCAACACCAAGGTGGA
CAAGACCGTGGAGCGTAAGTGTTGTGTGGAGTGTCCTCCTTGTCCTGCCCCTCCTGTGGCCGGA
CCTTCCGTGTTCCTTTTCCCTCCTAAGCCTAAGGACACCCTGATGATCAGCCGTACCCCTGAGG
TGACCTGTGTGGTGGTGGACGTGTCCCACGAGGACCCTGAGGTGCAGTTCAACTGGTACGTGGA
CGGCGTGGAGGTGCACAACGCCAAGACCAAGCCTCGTGAGGAGCAATTCAACAGCACCTTCCGT
GTGGTGTCCGTGCTTACCGTGGTGCACCAAGACTGGCTGAACGGCAAGGAGTACAAGTGTAAGG
TGAGCAACAAGGGACTTCCTGCCCCTATCGAGAAGACCATCTCCAAGACCAAGGGCCAACCTCG
TGAGCCTCAAGTGTACACCCTTCCTCCTAGCCGTGAGGAGATGACCAAGAACCAAGTGTCCCTT
ACCTGTCTGGTGAAGGGCTTCTACCCTAGCGACATCGCCGTGGAGTGGGAGTCCAACGGACAAC
CTGAGAACAACTACAAGACCACCCCTCCTATGCTTGACAGCGACGGCTCCTTCTTCCTGTACAG
CAAGCTGACCGTGGACAAGTCCCGTTGGCAACAAGGCAACGTGTTCAGCTGTTCCGTGATGCAC
GAGGCCCTGCACAACCACTACACCCAAAAGAGCCTTTCCCTGAGCCCTGGAAAG Signal Sequence (1-57), Variable Region (58-420), Constant Region (421-1398)

SEQ ID NO:99: Amino Acid Sequence of h#32A1-H1-1
MKHLWFFLLLVAAPRWVLSEVQLVESGGGLVQPGGSLRLSCAASGFNFNDYFMNWVRQAPGKGL
EWVAQIRNKIYTYATFYAASVKGRFTISRDNAKNSLYLQMNSLRAEDTAVYYCARSLTGGDYFD
YWGQGTLVTVSSASTKGPSVFPLAPCSRSTSESTAALGCLVKDYFPEPVTVSWNSGALTSGVHT
FPAVLQSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKSRWQQGNVFSCSVMH
EALHNHYTQKSLSLSPGK Signal Sequence (1-19), Variable Region (20-140), Constant Region (141-466)

Figure 55

SEQ ID NO:100: Nucleotide Sequence of h#32A1-H5
ATGAAACACCTGTGGTTCTTCCTCCTGCTGGTGGCAGCTCCCAGATGGGTGCTGAGCGAGGTGC
AGGTGGTGGAGAGCGGCGGCGGACTTGTGCAGCCTGGCGGCTCCCTGAGACTTAGCTGTGCCAC
CTCCGGCTTCAACTTCAACGACTACTTCATGAACTGGGTGAGACAGGCCCCTGGCAAGGGCCTG
GAGTGGGTGGCCCAGATCAGAAACAAGATCTACACCTACGCCACCTTCTACGCCGAGAGCCTTG
AGGGCAGATTCACCATCTCCAGAGACAACAGCAAGTCCACCGTGTACCTTCAGATGAACTCCCT
GAGAGCCGAGGACACCGCCGTGTACTACTGTACCAGAAGCCTTACCGGCGGCGACTACTTCGAC
TACTGGGGCCAGGGCACCCTGGTGACCGTGAGCTCAGCCAGCACCAAGGGCCCTTCCGTGTTCC
CTCTGGCCCCTTGTAGCCGTTCCACCAGCGAGTCCACCGCCGCCCTTGGCTGTCTGGTGAAGGA
CTACTTCCCTGAGCCTGTGACCGTGAGCTGGAACTCCGGAGCCCTTACCAGCGGCGTGCACACC
TTCCCTGCCGTGCTGCAGTCCAGCGGCCTTTACTCCCTGAGCTCCGTGGTGACCGTGCCTAGCT
CCAACTTCGGCACCCAAACCTACACCTGTAACGTGGACCACAAGCCTAGCAACACCAAGGTGGA
CAAGACCGTGGAGCGTAAGTGTTGTGTGGAGTGTCCTCCTTGTCCTGCCCCTCCTGTGGCCGGA
CCTTCCGTGTTCCTTTTCCCTCCTAAGCCTAAGGACACCCTGATGATCAGCCGTACCCCTGAGG
TGACCTGTGTGGTGGTGGACGTGTCCCACGAGGACCCTGAGGTGCAGTTCAACTGGTACGTGGA
CGGCGTGGAGGTGCACAACGCCAAGACCAAGCCTCGTGAGGAGCAATTCAACAGCACCTTCCGT
GTGGTGTCCGTGCTTACCGTGGTGCACCAAGACTGGCTGAACGGCAAGGAGTACAAGTGTAAGG
TGAGCAACAAGGGACTTCCTGCCCCTATCGAGAAGACCATCTCCAAGACCAAGGGCCAACCTCG
TGAGCCTCAAGTGTACACCCTTCCTCCTAGCCGTGAGGAGATGACCAAGAACCAAGTGTCCCTT
ACCTGTCTGGTGAAGGGCTTCTACCCTAGCGACATCGCCGTGGAGTGGGAGTCCAACGGACAAC
CTGAGAACAACTACAAGACCACCCCTCCTATGCTTGACAGCGACGGCTCCTTCTTCCTGTACAG
CAAGCTGACCGTGGACAAGTCCCGTTGGCAACAAGGCAACGTGTTCAGCTGTTCCGTGATGCAC
GAGGCCCTGCACAACCACTACACCCAAAAGAGCCTTTCCCTGAGCCCTGGAAAG Signal Sequence (1-57), Variable Region (58-420), Constant Region (421-1398)

SEQ ID NO:101: Amino Acid Sequence of h#32A1-H5
MKHLWFFLLLVAAPRWVLSEVQVVESGGGLVQPGGSLRLSCATSGFNFNDYFMNWVRQAPGKGL
EWVAQIRNKIYTYATFYAESLEGRFTISRDNSKSTVYLQMNSLRAEDTAVYYCTRSLTGGDYFD
YWGQGTLVTVSSASTKGPSVFPLAPCSRSTSESTAALGCLVKDYFPEPVTVSWNSGALTSGVHT
FPAVLQSSGLYSLSSVVTVPSSNFGTQTYTCNVDHKPSNTKVDKTVERKCCVECPPCPAPPVAG
PSVFLFPPKPKDTLMISRTPEVTCVVVDVSHEDPEVQFNWYVDGVEVHNAKTKPREEQFNSTFR
VVSVLTVVHQDWLNGKEYKCKVSNKGLPAPIEKTISKTKGQPREPQVYTLPPSREEMTKNQVSL
TCLVKGFYPSDIAVEWESNGQPENNYKTTPPMLDSDGSFFLYSKLTVDKSRWQQGNVFSCSVMH
EALHNHYTQKSLSLSPGK Signal Sequence (1-19), Variable Region (20-140), Constant Region (141-466)

Figure 56

SEQ ID NO:102: Nucleotide Sequence of h#32A1-L2-15
ATGGTGCTGCAGACCCAGGTGTTCATCTCCCTGCTGCTGTGGATCTCCGGCGCATATGGCGAAA
TTCTGATGACGCAGAGTCCTGCAACTCTTAGTCTGTCACCTGGCGAGAGAGCCACACTCAGCTG
CCGAGCGTCCCAGTCCGTGACCATTAGCGGCTATTCTTTTATTCATTGGTATCAGCAAAAGCCT
GGACAGGCGCCAAGGCTGCTCATTTACAGAGCAAGCAACCTTGCCTCTGGCATTCCAGCAAGAT
TCAGCGGGAGCGGATCAGGGACAGATTTCACCTTGACCATCTCCTCCCTGGAGCCGGAGGATTT
CGCGTTGTATTATTGTCAGCAATCTAGGAAGAGTCCATGGACATTTGGCCAGGGCACCAAAGTG
GAGATCAAGCGTACGGTGGCCGCCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT Signal Sequence (1-60), Variable Region (61-399), Constant Region (400-714)

SEQ ID NO:103: Amino Acid Sequence of h#32A1-L2-15
MVLQTQVFISLLLWISGAYGEILMTQSPATLSLSPGERATLSCRASQSVTISGYSFIHWYQQKP
GQAPRLLIYRASNLASGIPARFSGSGSGTDFTLTISSLEPEDFALYYCQQSRKSPWTFGQGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC Signal Sequence (1-20), Variable Region (21-133), Constant Region (134-238)

Figure 57

SEQ ID NO:104: Nucleotide Sequence of h#32A1-L2-16

ATGGTGCTGCAGACCCAGGTGTTCATCTCCCTGCTGCTGTGGATCTCCGGCGCATATGGCGAAA
TCCTGATGACACAGAGTCCTGCGACCCTCTCCCTCTCACCAGGCGAGAGGGCCACCCTGTCTTG
TAGAGCCAGCCAGTCAGTCACTATTAGTGGATACTCATTTATCCATTGGTATCAACAGAAACCA
GGACAGGCGCCTCGGCTTCTGATCTACCGCGCCTCAAACCTTGCCTCTGGCATCCCCGCGAGGT
TCTCTGGCTCTGGCAGCGGTACCGATTTTACACTGACTATCTCAAGCCTCGAACCTGAAGACTT
CGCACTGTACTTTTGCCAGCAGAGCAGGAAGTCCCCCTGGACTTTTGCACAGGGAACCAAAGTC
GAAATCAAGCGTACGGTGGCCGCCCCCTCCGTGTTCATCTTCCCCCCCTCCGACGAGCAGCTGA
AGTCCGGCACCGCCTCCGTGGTGTGCCTGCTGAATAACTTCTACCCCAGAGAGGCCAAGGTGCA
GTGGAAGGTGGACAACGCCCTGCAGTCCGGGAACTCCCAGGAGAGCGTGACCGAGCAGGACAGC
AAGGACAGCACCTACAGCCTGAGCAGCACCCTGACCCTGAGCAAAGCCGACTACGAGAAGCACA
AGGTGTACGCCTGCGAGGTGACCCACCAGGGCCTGAGCTCCCCCGTCACCAAGAGCTTCAACAG
GGGGGAGTGT

Signal Sequence (1-60), Variable Region (61-399), constant Region (400-714)

SEQ ID NO:105: Amino Acid Sequence of h#32A1-L2-16

MVLQTQVFISLLLWISGAYGEILMTQSPATLSLSPGERATLSCRASQSVTISGYSFIHWYQQKP
GQAPRLLIYRASNLASGIPARFSGSGSGTDFTLTISSLEPEDFALYFCQQSRKSPWTFAQGTKV
EIKRTVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC

Signal Sequence (1-20), Variable Region (21-133), constant Region (134-238)

SEQUENCE LISTING

```
<160> NUMBER OF SEQ ID NOS: 106

<210> SEQ ID NO 1
<211> LENGTH: 987
<212> TYPE: DNA
<213> ORGANISM: Homo sapiens
<220> FEATURE:
<221> NAME/KEY: CDS
<222> LOCATION: (1)..(987)

<400> SEQUENCE: 1 atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctc cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc cgc aac gac ctc tcg ctg cgc     384
Arg Phe Arg Leu Leu Gly Asn Pro Arg Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
    130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccg ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
    210                 215                 220 gaa ctg ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240
```

```
aac agc ctg ggc cgc tcc gag gcc agc gtc tac ctg ttc cgc ttc cat    768
Asn Ser Leu Gly Arg Ser Glu Ala Ser Val Tyr Leu Phe Arg Phe His
            245                 250                 255 ggc gcc agc ggg gcc tcg acg gtc gcc ctc ctg ctc ggc gct ctc ggc    816
Gly Ala Ser Gly Ala Ser Thr Val Ala Leu Leu Leu Gly Ala Leu Gly
        260                 265                 270 ttc aag gcg ctg ctg ctg ctc ggg gtc ctg gcc gcc cgc gct gcc cgc    864
Phe Lys Ala Leu Leu Leu Leu Gly Val Leu Ala Ala Arg Ala Ala Arg
    275                 280                 285 cgc cgc cca gag cat ctg gac acc ccg gac acc cca cgg tcc cag        912
Arg Arg Pro Glu His Leu Asp Thr Pro Asp Thr Pro Arg Ser Gln
290                 295                 300 gcc cag gag tcc aat tat gaa aat ttg agc cag atg aac ccc cgg agc    960
Ala Gln Glu Ser Asn Tyr Glu Asn Leu Ser Gln Met Asn Pro Arg Ser
305                 310                 315                 320 cca cca gcc acc atg tgc tca ccg tga                                987
Pro Pro Ala Thr Met Cys Ser Pro
            325

<210> SEQ ID NO 2
<211> LENGTH: 328
<212> TYPE: PRT
<213> ORGANISM: Homo sapiens

<400> SEQUENCE: 2

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
```

```
                       245                 250                 255
Gly Ala Ser Gly Ala Ser Thr Val Ala Leu Leu Leu Gly Ala Leu Gly
            260                 265                 270

Phe Lys Ala Leu Leu Leu Gly Val Leu Ala Ala Arg Ala Ala Arg
            275                 280                 285

Arg Arg Pro Glu His Leu Asp Thr Pro Asp Thr Pro Arg Ser Gln
    290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
                325
```

<210> SEQ ID NO 3
<211> LENGTH: 1026
<212> TYPE: DNA
<213> ORGANISM: Mus musculus
<220> FEATURE:
<221> NAME/KEY: CDS
<222> LOCATION: (1)..(1026)

<400> SEQUENCE: 3

```
atg gag ggg tcc ctc caa ctc ctg gcc tgc ttg gcc tgt gtg ctc cag      48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc      96
Met Gly Ser Leu Val Lys Thr Arg Arg Asp Ala Ser Gly Asp Leu Leu
                20                  25                  30 aac aca gag gcg cac agt gcc ccg gcg cag cgc tgg tcc atg cag gtg     144
Asn Thr Glu Ala His Ser Ala Pro Ala Gln Arg Trp Ser Met Gln Val
            35                  40                  45 ccc gcg gag gtg aac gcg gag gct ggc gac gcg gcg gtg ctg ccc tgc     192
Pro Ala Glu Val Asn Ala Glu Ala Gly Asp Ala Ala Val Leu Pro Cys
        50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc tcg ggc gag ccg tac gcg ggc ccg cag gtg ttc cgc tgc acc     288
Trp Arg Ser Gly Glu Pro Tyr Ala Gly Pro Gln Val Phe Arg Cys Thr
                85                  90                  95 gcg gcg ccg ggc agc gag ctg tgc cag acg gcg ctg agc ctg cac ggc     336
Ala Ala Pro Gly Ser Glu Leu Cys Gln Thr Ala Leu Ser Leu His Gly
            100                 105                 110 cgc ttc cgc ctg ctg ggc aac ccg cgc cgc aac gac ctg tcc ctg cgc     384
Arg Phe Arg Leu Leu Gly Asn Pro Arg Arg Asn Asp Leu Ser Leu Arg
        115                 120                 125 gtc gag cgc ctc gcc ctg gcg gac agc ggc cgc tac ttc tgc cgc gtg     432
Val Glu Arg Leu Ala Leu Ala Asp Ser Gly Arg Tyr Phe Cys Arg Val
    130                 135                 140 gag ttc acc ggc gac gcc cac gat cgc tat gag agt cgc cat ggg gtc     480
Glu Phe Thr Gly Asp Ala His Asp Arg Tyr Glu Ser Arg His Gly Val
145                 150                 155                 160 cgt ctg cgc gtg act gct gcg ccg cgg atc gtc aac atc tcg gtg ctg     528
Arg Leu Arg Val Thr Ala Ala Pro Arg Ile Val Asn Ile Ser Val Leu
                165                 170                 175 ccg ggc ccc gcg cac gcc ttc cgc gcg ctc tgc acc gcc gag ggg gag     576
Pro Gly Pro Ala His Ala Phe Arg Ala Leu Cys Thr Ala Glu Gly Glu
            180                 185                 190 ccc ccg ccc gcc ctc gcc tgg tcg ggt ccc gcc cca ggc aac agc tcc     624
Pro Pro Pro Ala Leu Ala Trp Ser Gly Pro Ala Pro Gly Asn Ser Ser
        195                 200                 205
```

```
gct gcc ctg cag ggc cag ggt cac ggc tac cag gtg acc gcc gag ttg    672
Ala Ala Leu Gln Gly Gln Gly His Gly Tyr Gln Val Thr Ala Glu Leu
    210                 215                 220 ccc gcg ctg acc cgc gac ggc cgc tac acg tgc acg gcg gcc aat agc    720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc    768
Leu Gly Arg Ala Glu Ala Ser Val Tyr Leu Phe Arg Phe His Gly Ala
                245                 250                 255 ccc gga acc tcg acc cta gcg ctc ctg ggc gcg ctg ggc ctc aag        816
Pro Gly Thr Ser Thr Leu Ala Leu Leu Gly Ala Leu Gly Leu Lys
            260                 265                 270 gcc ttg ctg ctg ctt ggc att ctg gga gcg cgt gcc acc cga cgc cga    864
Ala Leu Leu Leu Leu Gly Ile Leu Gly Ala Arg Ala Thr Arg Arg Arg
        275                 280                 285 cta gat cac ctg gtc ccc cag gac acc cct cca cgg tct cag gct cag    912
Leu Asp His Leu Val Pro Gln Asp Thr Pro Pro Arg Ser Gln Ala Gln
    290                 295                 300 gag tcc aat tat gaa aat ttg agc cag atg agt cct cca ggc cac cag    960
Glu Ser Asn Tyr Glu Asn Leu Ser Gln Met Ser Pro Pro Gly His Gln
305                 310                 315                 320 ctg cca cgt gtt tgc tgt gag gaa ctc ctc agc cat cac cat cta gtc   1008
Leu Pro Arg Val Cys Cys Glu Glu Leu Leu Ser His His His Leu Val
                325                 330                 335 att cac cat gag aaa taa                                           1026
Ile His His Glu Lys
            340

<210> SEQ ID NO 4
<211> LENGTH: 341
<212> TYPE: PRT
<213> ORGANISM: Mus musculus

<400> SEQUENCE: 4

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
```

```
                       180                 185                 190
Pro Pro Pro Ala Leu Ala Trp Ser Gly Pro Ala Pro Gly Asn Ser Ser
            195                 200                 205

Ala Ala Leu Gln Gly Gln Gly His Gly Tyr Gln Val Thr Ala Glu Leu
            210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
            245                 250                 255

Pro Gly Thr Ser Thr Leu Ala Leu Leu Gly Ala Leu Gly Leu Lys
            260                 265                 270

Ala Leu Leu Leu Gly Ile Leu Gly Ala Arg Ala Thr Arg Arg
            275                 280                 285

Leu Asp His Leu Val Pro Gln Asp Thr Pro Pro Arg Ser Gln Ala Gln
            290                 295                 300

Glu Ser Asn Tyr Glu Asn Leu Ser Gln Met Ser Pro Gly His Gln
305                 310                 315                 320

Leu Pro Arg Val Cys Cys Glu Leu Leu Ser His His Leu Val
            325                 330                 335

Ile His His Glu Lys
            340

<210> SEQ ID NO 5
<211> LENGTH: 774
<212> TYPE: DNA
<213> ORGANISM: Mus musculus
<220> FEATURE:
<221> NAME/KEY: CDS
<222> LOCATION: (1)..(774)

<400> SEQUENCE: 5 atg gag ggg tcc ctc caa ctc ctg gcc tgc ttg gcc tgt gtg ctc cag      48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc      96
Met Gly Ser Leu Val Lys Thr Arg Arg Asp Ala Ser Gly Asp Leu Leu
                20                  25                  30 aac aca gag gcg cac agt gcc ccg gcg cag cgc tgg tcc atg cag gtg     144
Asn Thr Glu Ala His Ser Ala Pro Ala Gln Arg Trp Ser Met Gln Val
            35                  40                  45 ccc gcg gag gtg aac gcg gag gct ggc gac gcg gcg gtg ctg ccc tgc     192
Pro Ala Glu Val Asn Ala Glu Ala Gly Asp Ala Ala Val Leu Pro Cys
        50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc tcg ggc gag ccg tac gcg ggc ccg cag gtg ttc cgc tgc acc     288
Trp Arg Ser Gly Glu Pro Tyr Ala Gly Pro Gln Val Phe Arg Cys Thr
                85                  90                  95 gcg gcg ccg ggc agc gag ctg tgc cag acg gcg ctg agc ctg cac ggc     336
Ala Ala Pro Gly Ser Glu Leu Cys Gln Thr Ala Leu Ser Leu His Gly
                100                 105                 110 cgc ttc cgc ctg ctg ggc aac ccg cgc aac gac ctg tcc ctg cgc        384
Arg Phe Arg Leu Leu Gly Asn Pro Arg Arg Asn Asp Leu Ser Leu Arg
            115                 120                 125 gtc gag cgc ctc gcc ctg gcg gac agc ggc cgc tac ttc tgc cgc gtg     432
Val Glu Arg Leu Ala Leu Ala Asp Ser Gly Arg Tyr Phe Cys Arg Val
        130                 135                 140
```

```
gag ttc acc ggc gac gcc cac gat cgc tat gag agt cgc cat ggg gtc         480
Glu Phe Thr Gly Asp Ala His Asp Arg Tyr Glu Ser Arg His Gly Val
145                 150                 155                 160 cgt ctg cgc gtg act gct gcg ccg cgg atc gtc aac atc tcg gtg ctg         528
Arg Leu Arg Val Thr Ala Ala Pro Arg Ile Val Asn Ile Ser Val Leu
                165                 170                 175 ccg ggc ccc gcg cac gcc ttc cgc gcg ctc tgc acc gcc gag ggg gag         576
Pro Gly Pro Ala His Ala Phe Arg Ala Leu Cys Thr Ala Glu Gly Glu
            180                 185                 190 ccc ccg ccc gcc ctc gcc tgg tcg ggt ccc gcc cca ggc aac agc tcc         624
Pro Pro Pro Ala Leu Ala Trp Ser Gly Pro Ala Pro Gly Asn Ser Ser
        195                 200                 205 gct gcc ctg cag ggc cag ggt cac ggc tac cag gtg acc gcc gag ttg         672
Ala Ala Leu Gln Gly Gln Gly His Gly Tyr Gln Val Thr Ala Glu Leu
    210                 215                 220 ccc gcg ctg acc cgc gac ggc cgc tac acg tgc acg gcg gcc aat agc         720
Pro Ala Leu Thr Arg Asp Gly Arg Tyr Thr Cys Thr Ala Ala Asn Ser
225                 230                 235                 240 ctg ggc cgc gcc gag gcc agc gtc tac ctg ttc cgc ttc cac ggc gcc         768
Leu Gly Arg Ala Glu Ala Ser Val Tyr Leu Phe Arg Phe His Gly Ala
                245                 250                 255 ccc gga                                                                  774
Pro Gly <210> SEQ ID NO 6
<211> LENGTH: 258
<212> TYPE: PRT
<213> ORGANISM: Mus musculus

<400> SEQUENCE: 6

Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
```

```
               210                 215                 220
Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255

Pro Gly

<210> SEQ ID NO 7
<211> LENGTH: 55
<212> TYPE: DNA
<213> ORGANISM: Artificial Sequence
<220> FEATURE:
<223> OTHER INFORMATION: PCR primer of soluble mouse Siglec-15 cDNA

<400> SEQUENCE: 7
ggggacaagt ttgtacaaaa aagcaggctt caccatggag ggtccctcc aactc         55

<210> SEQ ID NO 8
<211> LENGTH: 55
<212> TYPE: DNA
<213> ORGANISM: Artificial Sequence
<220> FEATURE:
<223> OTHER INFORMATION: PCR primer of soluble mouse Siglec-15 cDNA

<400> SEQUENCE: 8
ggggaccact ttgtacaaga aagctgggtc tccgggggcg ccgtggaagc ggaac         55

<210> SEQ ID NO 9
<211> LENGTH: 20
<212> TYPE: DNA
<213> ORGANISM: Artificial Sequence
<220> FEATURE:
<223> OTHER INFORMATION: Sequencing primer of soluble mouse Siglec-15
      cDNA

<400> SEQUENCE: 9
tgcgtgaagg tgcagggcag                                                20

<210> SEQ ID NO 10
<211> LENGTH: 17
<212> TYPE: DNA
<213> ORGANISM: Artificial Sequence
<220> FEATURE:
<223> OTHER INFORMATION: Sequencing primer of soluble mouse Siglec-15
      cDNA

<400> SEQUENCE: 10
cctcgcctgg tcgggtc                                                   17

<210> SEQ ID NO 11
<211> LENGTH: 891
<212> TYPE: DNA
<213> ORGANISM: Artificial Sequence
<220> FEATURE:
<223> OTHER INFORMATION: His-tagged mouse Siglec-15 cDNA
<220> FEATURE:
<221> NAME/KEY: CDS
<222> LOCATION: (1)..(891)

<400> SEQUENCE: 11 atg gag ggg tcc ctc caa ctc ctg gcc tgc ttg gcc tgt gtg ctc cag    48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc    96
Met Gly Ser Leu Val Lys Thr Arg Arg Asp Ala Ser Gly Asp Leu Leu
```

|  |  |  |  |  |  |  |  |  |  |  |  |  |  |  |  |
|---|---|---|---|---|---|---|---|---|---|---|---|---|---|---|---|
|  |  |  | 20 |  |  |  | 25 |  |  |  | 30 |  |  |  |  |
| aac | aca | gag | gcg | cac | agt | gcc | ccg | gcg | cag | cgc | tgg | tcc | atg | cag | gtg | 144 |
| Asn | Thr | Glu | Ala | His | Ser | Ala | Pro | Ala | Gln | Arg | Trp | Ser | Met | Gln | Val |  |
|  |  | 35 |  |  |  | 40 |  |  |  | 45 |  |  |  |  |  |
| ccc | gcg | gag | gtg | aac | gcg | gag | gct | ggc | gac | gcg | gcg | gtg | ctg | ccc | tgc | 192 |
| Pro | Ala | Glu | Val | Asn | Ala | Glu | Ala | Gly | Asp | Ala | Ala | Val | Leu | Pro | Cys |  |
|  | 50 |  |  |  |  | 55 |  |  |  |  | 60 |  |  |  |  |  |
| acc | ttc | acg | cac | ccg | cac | cgc | cac | tac | gac | ggg | ccg | ctg | acg | gcc | atc | 240 |
| Thr | Phe | Thr | His | Pro | His | Arg | His | Tyr | Asp | Gly | Pro | Leu | Thr | Ala | Ile |  |
| 65 |  |  |  |  | 70 |  |  |  |  | 75 |  |  |  |  | 80 |  |
| tgg | cgc | tcg | ggc | gag | ccg | tac | gcg | ggc | ccg | cag | gtg | ttc | cgc | tgc | acc | 288 |
| Trp | Arg | Ser | Gly | Glu | Pro | Tyr | Ala | Gly | Pro | Gln | Val | Phe | Arg | Cys | Thr |  |
|  |  |  |  | 85 |  |  |  |  | 90 |  |  |  |  | 95 |  |  |
| gcg | gcg | ccg | ggc | agc | gag | ctg | tgc | cag | acg | gcg | ctg | agc | ctg | cac | ggc | 336 |
| Ala | Ala | Pro | Gly | Ser | Glu | Leu | Cys | Gln | Thr | Ala | Leu | Ser | Leu | His | Gly |  |
|  |  |  | 100 |  |  |  |  | 105 |  |  |  |  | 110 |  |  |  |
| cgc | ttc | cgc | ctg | ctg | ggc | aac | ccg | cgc | cgc | aac | gac | ctg | tcc | ctg | cgc | 384 |
| Arg | Phe | Arg | Leu | Leu | Gly | Asn | Pro | Arg | Arg | Asn | Asp | Leu | Ser | Leu | Arg |  |
|  |  | 115 |  |  |  |  | 120 |  |  |  |  | 125 |  |  |  |  |
| gtc | gag | cgc | ctc | gcc | ctg | gcg | gac | agc | ggc | cgc | tac | ttc | tgc | cgc | gtg | 432 |
| Val | Glu | Arg | Leu | Ala | Leu | Ala | Asp | Ser | Gly | Arg | Tyr | Phe | Cys | Arg | Val |  |
| 130 |  |  |  |  | 135 |  |  |  |  | 140 |  |  |  |  |  |  |
| gag | ttc | acc | ggc | gac | gcc | cac | gat | cgc | tat | gag | agt | cgc | cat | ggg | gtc | 480 |
| Glu | Phe | Thr | Gly | Asp | Ala | His | Asp | Arg | Tyr | Glu | Ser | Arg | His | Gly | Val |  |
| 145 |  |  |  |  | 150 |  |  |  |  | 155 |  |  |  |  | 160 |  |
| cgt | ctg | cgc | gtg | act | gct | gcg | ccg | cgg | atc | gtc | aac | atc | tcg | gtg | ctg | 528 |
| Arg | Leu | Arg | Val | Thr | Ala | Ala | Pro | Arg | Ile | Val | Asn | Ile | Ser | Val | Leu |  |
|  |  |  |  | 165 |  |  |  |  | 170 |  |  |  |  | 175 |  |  |
| ccg | ggc | ccc | gcg | cac | gcc | ttc | cgc | gcg | ctc | tgc | acc | gcc | gag | ggg | gag | 576 |
| Pro | Gly | Pro | Ala | His | Ala | Phe | Arg | Ala | Leu | Cys | Thr | Ala | Glu | Gly | Glu |  |
|  |  |  | 180 |  |  |  |  | 185 |  |  |  |  | 190 |  |  |  |
| ccc | ccg | ccc | gcc | ctc | gcc | tgg | tcg | ggt | ccc | gcc | cca | ggc | aac | agc | tcc | 624 |
| Pro | Pro | Pro | Ala | Leu | Ala | Trp | Ser | Gly | Pro | Ala | Pro | Gly | Asn | Ser | Ser |  |
|  |  | 195 |  |  |  |  | 200 |  |  |  |  | 205 |  |  |  |  |
| gct | gcc | ctg | cag | ggc | cag | ggt | cac | ggc | tac | cag | gtg | acc | gcc | gag | ttg | 672 |
| Ala | Ala | Leu | Gln | Gly | Gln | Gly | His | Gly | Tyr | Gln | Val | Thr | Ala | Glu | Leu |  |
|  | 210 |  |  |  |  | 215 |  |  |  |  | 220 |  |  |  |  |  |
| ccc | gcg | ctg | acc | cgc | gac | ggc | cgc | tac | acg | tgc | acg | gcg | gcc | aat | agc | 720 |
| Pro | Ala | Leu | Thr | Arg | Asp | Gly | Arg | Tyr | Thr | Cys | Thr | Ala | Ala | Asn | Ser |  |
| 225 |  |  |  |  | 230 |  |  |  |  | 235 |  |  |  |  | 240 |  |
| ctg | ggc | cgc | gcc | gag | gcc | agc | gtc | tac | ctg | ttc | cgc | ttc | cac | ggc | gcc | 768 |
| Leu | Gly | Arg | Ala | Glu | Ala | Ser | Val | Tyr | Leu | Phe | Arg | Phe | His | Gly | Ala |  |
|  |  |  |  | 245 |  |  |  |  | 250 |  |  |  |  | 255 |  |  |
| ccc | gga | gac | cca | gct | ttc | ttg | tac | aaa | gtg | gtt | gat | atc | gaa | ggt | cgt | 816 |
| Pro | Gly | Asp | Pro | Ala | Phe | Leu | Tyr | Lys | Val | Val | Asp | Ile | Glu | Gly | Arg |  |
|  |  |  | 260 |  |  |  |  | 265 |  |  |  |  | 270 |  |  |  |
| ggg | ggt | aag | cct | atc | cct | aac | cct | ctc | ctc | ggt | ctc | gat | tct | acg | cgt | 864 |
| Gly | Gly | Lys | Pro | Ile | Pro | Asn | Pro | Leu | Leu | Gly | Leu | Asp | Ser | Thr | Arg |  |
|  |  | 275 |  |  |  |  | 280 |  |  |  |  | 285 |  |  |  |  |
| acc | ggt | cat | cat | cac | cat | cac | cat | tga |  |  |  |  |  |  |  | 891 |
| Thr | Gly | His | His | His | His | His |  |  |  |  |  |  |  |  |  |  |
|  | 290 |  |  |  |  | 295 |  |  |  |  |  |  |  |  |  |  |

<210> SEQ ID NO 12
<211> LENGTH: 296
<212> TYPE: PRT
<213> ORGANISM: Artificial Sequence
<220> FEATURE:
<223> OTHER INFORMATION: Synthetic Construct

<400> SEQUENCE: 12

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255

Pro Gly Asp Pro Ala Phe Leu Tyr Lys Val Val Asp Ile Glu Gly Arg
            260                 265                 270

Gly Gly Lys Pro Ile Pro Asn Pro Leu Leu Gly Leu Asp Ser Thr Arg
        275                 280                 285

Thr Gly His His His His His His
    290                 295
```

<210> SEQ ID NO 13
<211> LENGTH: 1512
<212> TYPE: DNA
<213> ORGANISM: Artificial Sequence
<220> FEATURE:
<223> OTHER INFORMATION: Fc-fused mouse Siglec-15 cDNA
<220> FEATURE:
<221> NAME/KEY: CDS
<222> LOCATION: (1)..(1512)

<400> SEQUENCE: 13

```
atg gag ggg tcc ctc caa ctc ctg gcc tgc ttg gcc tgt gtg ctc cag    48
Met Glu Gly Ser Leu Gln Leu Leu Ala Cys Leu Ala Cys Val Leu Gln
1               5                   10                  15 atg gga tcc ctt gtg aaa act aga aga gac gct tcg ggg gat ctg ctc    96
Met Gly Ser Leu Val Lys Thr Arg Arg Asp Ala Ser Gly Asp Leu Leu
            20                  25                  30
```

-continued

| | | |
|---|---|---|
| aac aca gag gcg cac agt gcc ccg gcg cag cgc tgg tcc atg cag gtg<br>Asn Thr Glu Ala His Ser Ala Pro Ala Gln Arg Trp Ser Met Gln Val<br>              35                  40                45 | 144 |
| ccc gcg gag gtg aac gcg gag gct ggc gac gcg gcg gtg ctg ccc tgc<br>Pro Ala Glu Val Asn Ala Glu Ala Gly Asp Ala Ala Val Leu Pro Cys<br>50                      55                  60 | 192 |
| acc ttc acg cac ccg cac cgc cac tac gac ggg ccg ctg acg gcc atc<br>Thr Phe Thr His Pro His Arg His Tyr Asp Gly Pro Leu Thr Ala Ile<br>65                      70                  75              80 | 240 |
| tgg cgc tcg ggc gag ccg tac gcg ggc ccg cag gtg ttc cgc tgc acc<br>Trp Arg Ser Gly Glu Pro Tyr Ala Gly Pro Gln Val Phe Arg Cys Thr<br>              85                  90              95 | 288 |
| gcg gcg ccg ggc agc gag ctg tgc cag acg gcg ctg agc ctg cac ggc<br>Ala Ala Pro Gly Ser Glu Leu Cys Gln Thr Ala Leu Ser Leu His Gly<br>                  100                 105              110 | 336 |
| cgc ttc cgc ctg ctg ggc aac ccg cgc cgc aac gac ctg tcc ctg cgc<br>Arg Phe Arg Leu Leu Gly Asn Pro Arg Arg Asn Asp Leu Ser Leu Arg<br>              115                 120              125 | 384 |
| gtc gag cgc ctc gcc ctg gcg gac agc ggc cgc tac ttc tgc cgc gtg<br>Val Glu Arg Leu Ala Leu Ala Asp Ser Gly Arg Tyr Phe Cys Arg Val<br>130                     135                 140 | 432 |
| gag ttc acc ggc gac gcc cac gat cgc tat gag agt cgc cat ggg gtc<br>Glu Phe Thr Gly Asp Ala His Asp Arg Tyr Glu Ser Arg His Gly Val<br>145                     150                 155              160 | 480 |
| cgt ctg cgc gtg act gct gcg ccg cgg atc gtc aac atc tcg gtg ctg<br>Arg Leu Arg Val Thr Ala Ala Pro Arg Ile Val Asn Ile Ser Val Leu<br>                  165                 170              175 | 528 |
| ccg ggc ccc gcg cac gcc ttc cgc gcg ctc tgc acc gcc gag ggg gag<br>Pro Gly Pro Ala His Ala Phe Arg Ala Leu Cys Thr Ala Glu Gly Glu<br>                  180                 185              190 | 576 |
| ccc ccg ccc gcc ctc gcc tgg tcg ggt ccc gcc cca ggc aac agc tcc<br>Pro Pro Pro Ala Leu Ala Trp Ser Gly Pro Ala Pro Gly Asn Ser Ser<br>              195                 200              205 | 624 |
| gct gcc ctg cag ggc cag ggt cac ggc tac cag gtg acc gcc gag ttg<br>Ala Ala Leu Gln Gly Gln Gly His Gly Tyr Gln Val Thr Ala Glu Leu<br>210                     215                 220 | 672 |
| ccc gcg ctg acc cgc gac ggc cgc tac acg tgc acg gcg gcc aat agc<br>Pro Ala Leu Thr Arg Asp Gly Arg Tyr Thr Cys Thr Ala Ala Asn Ser<br>225                     230                 235              240 | 720 |
| ctg ggc cgc gcc gag gcc agc gtc tac ctg ttc cgc ttc cac ggc gcc<br>Leu Gly Arg Ala Glu Ala Ser Val Tyr Leu Phe Arg Phe His Gly Ala<br>                  245                 250              255 | 768 |
| ccc gga gac cca gct ttc ttg tac aaa gtg gtt gat atc cag gca gag<br>Pro Gly Asp Pro Ala Phe Leu Tyr Lys Val Val Asp Ile Gln Ala Glu<br>                  260                 265              270 | 816 |
| ccc aaa tct tgt gac aaa act cac aca tgc cca ccg tgc cca gca cct<br>Pro Lys Ser Cys Asp Lys Thr His Thr Cys Pro Pro Cys Pro Ala Pro<br>275                     280                 285 | 864 |
| gaa ctc ctg ggg gga ccg tca gtc ttc ctc ttc ccc cca aaa ccc aag<br>Glu Leu Leu Gly Gly Pro Ser Val Phe Leu Phe Pro Pro Lys Pro Lys<br>              290                 295              300 | 912 |
| gac acc ctc atg atc tcc cgg acc cct gag gtc aca tgc gtg gtg gtg<br>Asp Thr Leu Met Ile Ser Arg Thr Pro Glu Val Thr Cys Val Val Val<br>305                     310                 315              320 | 960 |
| gac gtg agc cac gaa gac cct gag gtc aag ttc aac tgg tac gtg gac<br>Asp Val Ser His Glu Asp Pro Glu Val Lys Phe Asn Trp Tyr Val Asp<br>                  325                 330              335 | 1008 |
| ggc gtg gag gtg cat aat gcc aag aca aag ccg cgg gag gag cag tac<br>Gly Val Glu Val His Asn Ala Lys Thr Lys Pro Arg Glu Glu Gln Tyr<br>340                     345                 350 | 1056 |

-continued

```
aac agc acg tac cgt gtg gtc agc gtc ctc acc gtg ctg cac cag gac      1104
Asn Ser Thr Tyr Arg Val Val Ser Val Leu Thr Val Leu His Gln Asp
            355                 360                 365 tgg ctg aat ggc aag gag tac aag tgc aag gtc tcc aac aaa gcc ctc      1152
Trp Leu Asn Gly Lys Glu Tyr Lys Cys Lys Val Ser Asn Lys Ala Leu
    370                 375                 380 cca gcc ccc atc gag aaa acc atc tcc aaa gcc aaa ggg cag ccc cga      1200
Pro Ala Pro Ile Glu Lys Thr Ile Ser Lys Ala Lys Gly Gln Pro Arg
385                 390                 395                 400 gaa cca cag gtg tac acc ctg cca cca tcc cgg gag gag atg acc aag      1248
Glu Pro Gln Val Tyr Thr Leu Pro Pro Ser Arg Glu Glu Met Thr Lys
                405                 410                 415 aac cag gtc agc ctg acc tgc ctg gtc aaa ggc ttc tat ccc agc gac      1296
Asn Gln Val Ser Leu Thr Cys Leu Val Lys Gly Phe Tyr Pro Ser Asp
            420                 425                 430 atc gcc gtg gag tgg gag agc aat ggg cag ccg gag aac aac tac aag      1344
Ile Ala Val Glu Trp Glu Ser Asn Gly Gln Pro Glu Asn Asn Tyr Lys
        435                 440                 445 acc acg cct ccc gtg ctg gac tcc gac ggc tcc ttc ttc ctc tat agc      1392
Thr Thr Pro Pro Val Leu Asp Ser Asp Gly Ser Phe Phe Leu Tyr Ser
    450                 455                 460 aag ctc acc gtg gac aag agc agg tgg cag cag ggg aac gtc ttc tca      1440
Lys Leu Thr Val Asp Lys Ser Arg Trp Gln Gln Gly Asn Val Phe Ser
465                 470                 475                 480 tgc tcc gtg atg cat gag gct ctg cac aac cac tac acg cag aag agc      1488
Cys Ser Val Met His Glu Ala Leu His Asn His Tyr Thr Gln Lys Ser
                485                 490                 495 ctc tcc ctg tct ccg ggt aaa taa                                      1512
Leu Ser Leu Ser Pro Gly Lys
            500
```

<210> SEQ ID NO 14
<211> LENGTH: 503
<212> TYPE: PRT
<213> ORGANISM: Artificial Sequence
<220> FEATURE:
<223> OTHER INFORMATION: Synthetic Construct

<400> SEQUENCE: 14

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
```

145                 150                 155                 160
Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
    210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255

Pro Gly Asp Pro Ala Phe Leu Tyr Lys Val Val Asp Ile Gln Ala Glu
            260                 265                 270

Pro Lys Ser Cys Asp Lys Thr His Thr Cys Pro Pro Cys Pro Ala Pro
        275                 280                 285

Glu Leu Leu Gly Gly Pro Ser Val Phe Leu Phe Pro Pro Lys Pro Lys
    290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
    370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
    450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
            500

<210> SEQ ID NO 15
<211> LENGTH: 780
<212> TYPE: DNA
<213> ORGANISM: Homo sapiens
<220> FEATURE:
<221> NAME/KEY: CDR
<222> LOCATION: (1)..(780)
<220> FEATURE:
<221> NAME/KEY: CDS
<222> LOCATION: (1)..(780)

<400> SEQUENCE: 15

```
atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctg cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc cgc aac gac ctc tcg ctg cgc     384
Arg Phe Arg Leu Leu Gly Asn Pro Arg Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
    130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccg ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
    210                 215                 220 gaa ctg ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240 aac agc ctg ggc cgc tcc gag gcc agc gtc tac ctg ttc cgc ttc cat     768
Asn Ser Leu Gly Arg Ser Glu Ala Ser Val Tyr Leu Phe Arg Phe His
                245                 250                 255 ggc gcc agc ggg                                                     780
Gly Ala Ser Gly
            260
```

<210> SEQ ID NO 16
<211> LENGTH: 260
<212> TYPE: PRT
<213> ORGANISM: Homo sapiens

<400> SEQUENCE: 16

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly
            260

<210> SEQ ID NO 17
<211> LENGTH: 56
<212> TYPE: DNA
<213> ORGANISM: Artificial Sequence
<220> FEATURE:
<223> OTHER INFORMATION: PCR primer of soluble human Siglec-15 cDNA

<400> SEQUENCE: 17
ggggacaagt ttgtacaaaa aagcaggctt caccatggaa agtccatct ggctgc         56

<210> SEQ ID NO 18
<211> LENGTH: 52
<212> TYPE: DNA
<213> ORGANISM: Artificial Sequence
<220> FEATURE:
<223> OTHER INFORMATION: PCR primer of soluble human Siglec-15 cDNA

<400> SEQUENCE: 18
ggggaccact ttgtacaaga aagctgggtc cccgctggcg ccatggaagc gg             52

<210> SEQ ID NO 19
<211> LENGTH: 897
<212> TYPE: DNA
```

<213> ORGANISM: Artificial Sequence
<220> FEATURE:
<223> OTHER INFORMATION: His-tagged human Siglec-15 cDNA
<220> FEATURE:
<221> NAME/KEY: CDS
<222> LOCATION: (1)..(897)

<400> SEQUENCE: 19

```
atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctg cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc aac gac ctc tcg ctg cgc         384
Arg Phe Arg Leu Leu Gly Asn Pro Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccg ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
    210                 215                 220 gaa ctg ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240 aac agc ctg ggc cgc tcc gag gcc agc gtc tac ctg ttc cgc ttc cat     768
Asn Ser Leu Gly Arg Ser Glu Ala Ser Val Tyr Leu Phe Arg Phe His
                245                 250                 255 ggc gcc agc ggg gac cca gct ttc ttg tac aaa gtg gtt gat atc gaa     816
Gly Ala Ser Gly Asp Pro Ala Phe Leu Tyr Lys Val Val Asp Ile Glu
            260                 265                 270 ggt cgt ggg ggt aag cct atc cct aac cct ctc ctc ggt ctc gat tct     864
Gly Arg Gly Gly Lys Pro Ile Pro Asn Pro Leu Leu Gly Leu Asp Ser
```

```
                275                 280                 285
acg cgt acc ggt cat cat cac cat cac cat tga                                897
Thr Arg Thr Gly His His His His His His
    290                 295
```

<210> SEQ ID NO 20
<211> LENGTH: 298
<212> TYPE: PRT
<213> ORGANISM: Artificial Sequence
<220> FEATURE:
<223> OTHER INFORMATION: Synthetic Construct

<400> SEQUENCE: 20

```
Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Asp Arg Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
        195                 200                 205

Ala Ala Val Arg Ser Pro Arg Glu Gly His Gly His Leu Val Thr Ala
    210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Asp Pro Ala Phe Leu Tyr Lys Val Val Asp Ile Glu
            260                 265                 270

Gly Arg Gly Gly Lys Pro Ile Pro Asn Pro Leu Leu Gly Leu Asp Ser
        275                 280                 285

Thr Arg Thr Gly His His His His His His
    290                 295
```

<210> SEQ ID NO 21
<211> LENGTH: 1518
<212> TYPE: DNA
<213> ORGANISM: Artificial Sequence
<220> FEATURE:

<223> OTHER INFORMATION: Fc-fused human Siglec-15 cDNA
<220> FEATURE:
<221> NAME/KEY: CDS
<222> LOCATION: (1)..(1518)

<400> SEQUENCE: 21

```
atg gaa aag tcc atc tgg ctg ctg gcc tgc ttg gcg tgg gtt ctc ccg      48
Met Glu Lys Ser Ile Trp Leu Leu Ala Cys Leu Ala Trp Val Leu Pro
1               5                   10                  15 aca ggc tca ttt gtg aga act aaa ata gat act acg gag aac ttg ctc      96
Thr Gly Ser Phe Val Arg Thr Lys Ile Asp Thr Thr Glu Asn Leu Leu
            20                  25                  30 aac aca gag gtg cac agc tcg cca gcg cag cgc tgg tcc atg cag gtg     144
Asn Thr Glu Val His Ser Ser Pro Ala Gln Arg Trp Ser Met Gln Val
        35                  40                  45 cca ccc gag gtg agc gcg gag gca ggc gac gcg gca gtg ctg ccc tgc     192
Pro Pro Glu Val Ser Ala Glu Ala Gly Asp Ala Ala Val Leu Pro Cys
    50                  55                  60 acc ttc acg cac ccg cac cgc cac tac gac ggg ccg ctg acg gcc atc     240
Thr Phe Thr His Pro His Arg His Tyr Asp Gly Pro Leu Thr Ala Ile
65                  70                  75                  80 tgg cgc gcg ggc gag ccc tat gcg ggc ccg cag gtg ttc cgc tgc gct     288
Trp Arg Ala Gly Glu Pro Tyr Ala Gly Pro Gln Val Phe Arg Cys Ala
                85                  90                  95 gcg gcg cgg ggc agc gag ctc tgc cag acg gcg ctg agc ctg cac ggc     336
Ala Ala Arg Gly Ser Glu Leu Cys Gln Thr Ala Leu Ser Leu His Gly
            100                 105                 110 cgc ttc cgg ctg ctg ggc aac ccg cgc cgc aac gac ctc tcg ctg cgc     384
Arg Phe Arg Leu Leu Gly Asn Pro Arg Arg Asn Asp Leu Ser Leu Arg
        115                 120                 125 gtc gag cgc ctc gcc ctg gct gac gac cgc cgc tac ttc tgc cgc gtc     432
Val Glu Arg Leu Ala Leu Ala Asp Asp Arg Arg Tyr Phe Cys Arg Val
    130                 135                 140 gag ttc gcc ggc gac gtc cat gac cgc tac gag agc cgc cac ggc gtc     480
Glu Phe Ala Gly Asp Val His Asp Arg Tyr Glu Ser Arg His Gly Val
145                 150                 155                 160 cgg ctg cac gtg aca gcc gcg ccg cgg atc gtc aac atc tcg gtg ctg     528
Arg Leu His Val Thr Ala Ala Pro Arg Ile Val Asn Ile Ser Val Leu
                165                 170                 175 ccc agt ccg gct cac gcc ttc cgc gcg ctc tgc act gcc gaa ggg gag     576
Pro Ser Pro Ala His Ala Phe Arg Ala Leu Cys Thr Ala Glu Gly Glu
            180                 185                 190 ccg ccc ccc gcc ctc gcc tgg tcc ggc ccg gcc ctg ggc aac agc ttg     624
Pro Pro Pro Ala Leu Ala Trp Ser Gly Pro Ala Leu Gly Asn Ser Leu
        195                 200                 205 gca gcc gtg cgg agc ccg cgt gag ggt cac ggc cac cta gtg acc gcc     672
Ala Ala Val Arg Ser Pro Arg Glu Gly His Gly His Leu Val Thr Ala
    210                 215                 220 gaa ctc ccc gca ctg acc cat gac ggc cgc tac acg tgt acg gcc gcc     720
Glu Leu Pro Ala Leu Thr His Asp Gly Arg Tyr Thr Cys Thr Ala Ala
225                 230                 235                 240 aac agc ctg ggc cgc tcc gag gcc agc gtc tac ctg ttc cgc ttc cat     768
Asn Ser Leu Gly Arg Ser Glu Ala Ser Val Tyr Leu Phe Arg Phe His
                245                 250                 255 ggc gcc agc ggg gac cca gct ttc ttg tac aaa gtg gtt gat atc cag     816
Gly Ala Ser Gly Asp Pro Ala Phe Leu Tyr Lys Val Val Asp Ile Gln
            260                 265                 270 gca gag ccc aaa tct tgt gac aaa act cac aca tgc cca ccg tgc cca     864
Ala Glu Pro Lys Ser Cys Asp Lys Thr His Thr Cys Pro Pro Cys Pro
        275                 280                 285
```

```
gca cct gaa ctc ctg ggg gga ccg tca gtc ttc ctc ttc ccc cca aaa      912
Ala Pro Glu Leu Leu Gly Gly Pro Ser Val Phe Leu Phe Pro Pro Lys
290             295                 300 ccc aag gac acc ctc atg atc tcc cgg acc cct gag gtc aca tgc gtg      960
Pro Lys Asp Thr Leu Met Ile Ser Arg Thr Pro Glu Val Thr Cys Val
305                 310                 315                 320 gtg gtg gac gtg agc cac gaa gac cct gag gtc aag ttc aac tgg tac     1008
Val Val Asp Val Ser His Glu Asp Pro Glu Val Lys Phe Asn Trp Tyr
                325                 330                 335 gtg gac ggc gtg gag gtg cat aat gcc aag aca aag ccg cgg gag gag     1056
Val Asp Gly Val Glu Val His Asn Ala Lys Thr Lys Pro Arg Glu Glu
        340                 345                 350 cag tac aac agc acg tac cgt gtg gtc agc gtc ctc acc gtc ctg cac     1104
Gln Tyr Asn Ser Thr Tyr Arg Val Val Ser Val Leu Thr Val Leu His
        355                 360                 365 cag gac tgg ctg aat ggc aag gag tac aag tgc aag gtc tcc aac aaa     1152
Gln Asp Trp Leu Asn Gly Lys Glu Tyr Lys Cys Lys Val Ser Asn Lys
370                 375                 380 gcc ctc cca gcc ccc atc gag aaa acc atc tcc aaa gcc aaa ggg cag     1200
Ala Leu Pro Ala Pro Ile Glu Lys Thr Ile Ser Lys Ala Lys Gly Gln
385                 390                 395                 400 ccc cga gaa cca cag gtg tac acc ctg ccc cca tcc cgg gag gag atg     1248
Pro Arg Glu Pro Gln Val Tyr Thr Leu Pro Pro Ser Arg Glu Glu Met
                405                 410                 415 acc aag aac cag gtc agc ctg acc tgc ctg gtc aaa ggc ttc tat ccc     1296
Thr Lys Asn Gln Val Ser Leu Thr Cys Leu Val Lys Gly Phe Tyr Pro
                420                 425                 430 agc gac atc gcc gtg gag tgg gag agc aat ggg cag ccg gag aac aac     1344
Ser Asp Ile Ala Val Glu Trp Glu Ser Asn Gly Gln Pro Glu Asn Asn
        435                 440                 445 tac aag acc acg cct ccc gtg ctg gac tcc gac ggc tcc ttc ttc ctc     1392
Tyr Lys Thr Thr Pro Pro Val Leu Asp Ser Asp Gly Ser Phe Phe Leu
        450                 455                 460 tat agc aag ctc acc gtg gac aag agc agg tgg cag cag ggg aac gtc     1440
Tyr Ser Lys Leu Thr Val Asp Lys Ser Arg Trp Gln Gln Gly Asn Val
465                 470                 475                 480 ttc tca tgc tcc gtg atg cat gag gct ctg cac aac cac tac acg cag     1488
Phe Ser Cys Ser Val Met His Glu Ala Leu His Asn His Tyr Thr Gln
                485                 490                 495 aag agc ctc tcc ctg tct ccg ggt aaa taa                             1518
Lys Ser Leu Ser Leu Ser Pro Gly Lys
                500                 505

<210> SEQ ID NO 22
<211> LENGTH: 505
<212> TYPE: PRT
<213> ORGANISM: Artificial Sequence
<220> FEATURE:
<223> OTHER INFORMATION: Synthetic Construct

<400> SEQUENCE: 22

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
                20                  25                  30

Asn Thr Glu Val His Ser Ser Pro Ala Gln Arg Trp Ser Met Gln Val
            35                  40                  45

Pro Pro Glu Val Ser Ala Glu Ala Gly Asp Ala Ala Val Leu Pro Cys
        50                  55                  60

Thr Phe Thr His Pro His Arg His Tyr Asp Gly Pro Leu Thr Ala Ile
```

```
                65                  70                  75                  80
Trp Arg Ala Gly Glu Pro Tyr Ala Gly Pro Gln Val Phe Arg Cys Ala
                    85                  90                  95
Ala Ala Arg Gly Ser Glu Leu Cys Gln Thr Ala Leu Ser Leu His Gly
                    100                 105                 110
Arg Phe Arg Leu Leu Gly Asn Pro Arg Arg Asn Asp Leu Ser Leu Arg
                    115                 120                 125
Val Glu Arg Leu Ala Leu Ala Asp Asp Arg Arg Tyr Phe Cys Arg Val
            130                 135                 140
Glu Phe Ala Gly Asp Val His Asp Arg Tyr Glu Ser Arg His Gly Val
145                 150                 155                 160
Arg Leu His Val Thr Ala Ala Pro Arg Ile Val Asn Ile Ser Val Leu
                        165                 170                 175
Pro Ser Pro Ala His Ala Phe Arg Ala Leu Cys Thr Ala Glu Gly Glu
                    180                 185                 190
Pro Pro Pro Ala Leu Ala Trp Ser Gly Pro Ala Leu Gly Asn Ser Leu
                    195                 200                 205
Ala Ala Val Arg Ser Pro Arg Glu Gly His Gly His Leu Val Thr Ala
            210                 215                 220
Glu Leu Pro Ala Leu Thr His Asp Gly Arg Tyr Thr Cys Thr Ala Ala
225                 230                 235                 240
Asn Ser Leu Gly Arg Ser Glu Ala Ser Val Tyr Leu Phe Arg Phe His
                        245                 250                 255
Gly Ala Ser Gly Asp Pro Ala Phe Leu Tyr Lys Val Val Asp Ile Gln
                    260                 265                 270
Ala Glu Pro Lys Ser Cys Asp Lys Thr His Thr Cys Pro Pro Cys Pro
            275                 280                 285
Ala Pro Glu Leu Leu Gly Gly Pro Ser Val Phe Leu Phe Pro Pro Lys
                    290                 295                 300
Pro Lys Asp Thr Leu Met Ile Ser Arg Thr Pro Glu Val Thr Cys Val
305                 310                 315                 320
Val Val Asp Val Ser His Glu Asp Pro Glu Val Lys Phe Asn Trp Tyr
                        325                 330                 335
Val Asp Gly Val Glu Val His Asn Ala Lys Thr Lys Pro Arg Glu Glu
                    340                 345                 350
Gln Tyr Asn Ser Thr Tyr Arg Val Val Ser Val Leu Thr Val Leu His
                    355                 360                 365
Gln Asp Trp Leu Asn Gly Lys Glu Tyr Lys Cys Lys Val Ser Asn Lys
            370                 375                 380
Ala Leu Pro Ala Pro Ile Glu Lys Thr Ile Ser Lys Ala Lys Gly Gln
385                 390                 395                 400
Pro Arg Glu Pro Gln Val Tyr Thr Leu Pro Pro Ser Arg Glu Glu Met
                        405                 410                 415
Thr Lys Asn Gln Val Ser Leu Thr Cys Leu Val Lys Gly Phe Tyr Pro
                    420                 425                 430
Ser Asp Ile Ala Val Glu Trp Glu Ser Asn Gly Gln Pro Glu Asn Asn
                    435                 440                 445
Tyr Lys Thr Thr Pro Pro Val Leu Asp Ser Asp Gly Ser Phe Phe Leu
            450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                        485                 490                 495
```

Lys Ser Leu Ser Leu Ser Pro Gly Lys
            500             505

<210> SEQ ID NO 23
<211> LENGTH: 33
<212> TYPE: DNA
<213> ORGANISM: Artificial Sequence
<220> FEATURE:
<223> OTHER INFORMATION: PCR primer of heavy chain cDNA of rat #32A1
      antibody

<400> SEQUENCE: 23
ggccgggtgg gctacgttgc aggtgacggt ctg                          33

<210> SEQ ID NO 24
<211> LENGTH: 35
<212> TYPE: DNA
<213> ORGANISM: Artificial Sequence
<220> FEATURE:
<223> OTHER INFORMATION: PCR primer of light chain cDNA of rat #32A1
      antibody

<400> SEQUENCE: 24
catgctgtac gtgctgtctt tgctgtcctg atcag                        35

<210> SEQ ID NO 25
<211> LENGTH: 29
<212> TYPE: DNA
<213> ORGANISM: Artificial Sequence
<220> FEATURE:
<223> OTHER INFORMATION: Sequencing primer of heavy chain cDNA of rat
      #32A1 antibody

<400> SEQUENCE: 25
ctccagagtt ccaggtcacg gtgactggc                               29

<210> SEQ ID NO 26
<211> LENGTH: 20
<212> TYPE: DNA
<213> ORGANISM: Artificial Sequence
<220> FEATURE:
<223> OTHER INFORMATION: Sequencing primer of light chain cDNA of rat
      #32A1 antibody

<400> SEQUENCE: 26
tccagttgct aactgttccg                                         20

<210> SEQ ID NO 27
<211> LENGTH: 501
<212> TYPE: DNA
<213> ORGANISM: Rattus norvegicus
<220> FEATURE:
<221> NAME/KEY: CDS
<222> LOCATION: (1)..(501)

<400> SEQUENCE: 27 atg aag ttg tgg ttg agc tgg ata ttc ctt gtt gtt ctt ttc aaa ggt    48
Met Lys Leu Trp Leu Ser Trp Ile Phe Leu Val Val Leu Phe Lys Gly
1               5                   10                  15 gtg agg tgt gag gtg caa att ttg gag act gga gga ggc ttg gtg aag    96
Val Arg Cys Glu Val Gln Ile Leu Glu Thr Gly Gly Gly Leu Val Lys
            20                  25                  30 ccc ggt ggt tcc ctg aga ctg tct tgt gca acg tct gga ttc aat ttc    144
Pro Gly Gly Ser Leu Arg Leu Ser Cys Ala Thr Ser Gly Phe Asn Phe
        35                  40                  45

```
aat gat tat ttc atg aac tgg gtc cgt cag gct cca gaa aag ggg cta         192
Asn Asp Tyr Phe Met Asn Trp Val Arg Gln Ala Pro Glu Lys Gly Leu
 50                  55                  60 gag tgg gtt gct caa ata agg aac aaa att tat act tat gcc aca ttt         240
Glu Trp Val Ala Gln Ile Arg Asn Lys Ile Tyr Thr Tyr Ala Thr Phe
 65                  70                  75                  80 tat gcg gag tct ttg gaa ggc aga gtc aca atc tca cga gac gat tcc         288
Tyr Ala Glu Ser Leu Glu Gly Arg Val Thr Ile Ser Arg Asp Asp Ser
                 85                  90                  95 gaa agc agt gtc tac ctg caa gtg agc agt tta aga gct gaa gac act         336
Glu Ser Ser Val Tyr Leu Gln Val Ser Ser Leu Arg Ala Glu Asp Thr
            100                 105                 110 gcc att tat tac tgt aca aga tcc cta act ggg gga gac tac ttt gat         384
Ala Ile Tyr Tyr Cys Thr Arg Ser Leu Thr Gly Gly Asp Tyr Phe Asp
        115                 120                 125 tac tgg ggc caa gga gtc atg gtc aca gtc tcc tta gct gaa aca aca         432
Tyr Trp Gly Gln Gly Val Met Val Thr Val Ser Leu Ala Glu Thr Thr
130                 135                 140 gcc cca tct gtc tat cca ctg gct cct gga act gct ctc aaa agt aac         480
Ala Pro Ser Val Tyr Pro Leu Ala Pro Gly Thr Ala Leu Lys Ser Asn
145                 150                 155                 160 tcc atg gtg acc ctg gga tgc                                             501
Ser Met Val Thr Leu Gly Cys
                165
```

<210> SEQ ID NO 28
<211> LENGTH: 167
<212> TYPE: PRT
<213> ORGANISM: Rattus norvegicus

<400> SEQUENCE: 28

```
Met Lys Leu Trp Leu Ser Trp Ile Phe Leu Val Val Leu Phe Lys Gly
 1               5                  10                  15

Val Arg Cys Glu Val Gln Ile Leu Glu Thr Gly Gly Gly Leu Val Lys
                 20                  25                  30

Pro Gly Gly Ser Leu Arg Leu Ser Cys Ala Thr Ser Gly Phe Asn Phe
             35                  40                  45

Asn Asp Tyr Phe Met Asn Trp Val Arg Gln Ala Pro Glu Lys Gly Leu
 50                  55                  60

Glu Trp Val Ala Gln Ile Arg Asn Lys Ile Tyr Thr Tyr Ala Thr Phe
 65                  70                  75                  80

Tyr Ala Glu Ser Leu Glu Gly Arg Val Thr Ile Ser Arg Asp Asp Ser
                 85                  90                  95

Glu Ser Ser Val Tyr Leu Gln Val Ser Ser Leu Arg Ala Glu Asp Thr
            100                 105                 110

Ala Ile Tyr Tyr Cys Thr Arg Ser Leu Thr Gly Gly Asp Tyr Phe Asp
        115                 120                 125

Tyr Trp Gly Gln Gly Val Met Val Thr Val Ser Leu Ala Glu Thr Thr
130                 135                 140

Ala Pro Ser Val Tyr Pro Leu Ala Pro Gly Thr Ala Leu Lys Ser Asn
145                 150                 155                 160

Ser Met Val Thr Leu Gly Cys
                165
```

<210> SEQ ID NO 29
<211> LENGTH: 417
<212> TYPE: DNA
<213> ORGANISM: Rattus norvegicus
<220> FEATURE:

<220> NAME/KEY: CDS
<222> LOCATION: (1)..(417)

<400> SEQUENCE: 29

```
atg gag aca gac aga ctc ctg cta tgg gca ctg ctc tcg gtt cca      48
Met Glu Thr Asp Arg Leu Leu Leu Trp Ala Leu Leu Leu Trp Val Pro
1               5                   10                  15 ggc tcc act ggt gac att gtc ttg acc cag tct cct gct ttg gct gtg  96
Gly Ser Thr Gly Asp Ile Val Leu Thr Gln Ser Pro Ala Leu Ala Val
                20                  25                  30 tct cta ggg cag agg gcc aca atc tcc tgt agg gcc agc caa agt gtc  144
Ser Leu Gly Gln Arg Ala Thr Ile Ser Cys Arg Ala Ser Gln Ser Val
            35                  40                  45 act att tct gga tat agt ttt ata cac tgg tac caa cag aaa cca gga  192
Thr Ile Ser Gly Tyr Ser Phe Ile His Trp Tyr Gln Gln Lys Pro Gly
        50                  55                  60 cag caa ccc aga ctc ctc atc tat cgt gca tcc aac cta gcc tct ggg  240
Gln Gln Pro Arg Leu Leu Ile Tyr Arg Ala Ser Asn Leu Ala Ser Gly
65                  70                  75                  80 atc ccg gcc agg ttc agt ggc agt ggg tct ggg aca gac ttc acc ctc  288
Ile Pro Ala Arg Phe Ser Gly Ser Gly Ser Gly Thr Asp Phe Thr Leu
                85                  90                  95 acc atc aat cct gtg cag gct gat gat att gca acc tat ttc tgt cag  336
Thr Ile Asn Pro Val Gln Ala Asp Asp Ile Ala Thr Tyr Phe Cys Gln
                100                 105                 110 cag agt agg aaa tct ccg tgg acg ttc gct gga ggc acc aag ctg gaa  384
Gln Ser Arg Lys Ser Pro Trp Thr Phe Ala Gly Gly Thr Lys Leu Glu
            115                 120                 125 ttg aga cgg gct gat gct gca cca act gta tct                      417
Leu Arg Arg Ala Asp Ala Ala Pro Thr Val Ser
        130                 135
```

<210> SEQ ID NO 30
<211> LENGTH: 139
<212> TYPE: PRT
<213> ORGANISM: Rattus norvegicus

<400> SEQUENCE: 30

```
Met Glu Thr Asp Arg Leu Leu Leu Trp Ala Leu Leu Leu Trp Val Pro
1               5                   10                  15

Gly Ser Thr Gly Asp Ile Val Leu Thr Gln Ser Pro Ala Leu Ala Val
                20                  25                  30

Ser Leu Gly Gln Arg Ala Thr Ile Ser Cys Arg Ala Ser Gln Ser Val
            35                  40                  45

Thr Ile Ser Gly Tyr Ser Phe Ile His Trp Tyr Gln Gln Lys Pro Gly
        50                  55                  60

Gln Gln Pro Arg Leu Leu Ile Tyr Arg Ala Ser Asn Leu Ala Ser Gly
65                  70                  75                  80

Ile Pro Ala Arg Phe Ser Gly Ser Gly Ser Gly Thr Asp Phe Thr Leu
                85                  90                  95

Thr Ile Asn Pro Val Gln Ala Asp Asp Ile Ala Thr Tyr Phe Cys Gln
                100                 105                 110

Gln Ser Arg Lys Ser Pro Trp Thr Phe Ala Gly Gly Thr Lys Leu Glu
            115                 120                 125

Leu Arg Arg Ala Asp Ala Ala Pro Thr Val Ser
        130                 135
```

<210> SEQ ID NO 31
<211> LENGTH: 28

```
<212> TYPE: DNA
<213> ORGANISM: Artificial Sequence
<220> FEATURE:
<223> OTHER INFORMATION: Primer EFF1

<400> SEQUENCE: 31
ccacgcgccc tgtagcggcg cattaagc                                          28

<210> SEQ ID NO 32
<211> LENGTH: 30
<212> TYPE: DNA
<213> ORGANISM: Artificial Sequence
<220> FEATURE:
<223> OTHER INFORMATION: Primer EFsmaR

<400> SEQUENCE: 32
aaacccggga gcttttttgca aaagcctagg                                       30

<210> SEQ ID NO 33
<211> LENGTH: 1704
<212> TYPE: DNA
<213> ORGANISM: Artificial Sequence
<220> FEATURE:
<223> OTHER INFORMATION: Fragment B

<400> SEQUENCE: 33
ggtaccaccc aagctggcta ggtaagcttg ctagcgccac catggtgctg cagacccagg       60
tgttcatctc cctgctgctg tggatctccg gcgcatatgg cgatatcgtg atgattaaac      120
gtacggtggc cgccccctcc gtgttcatct tccccccctc cgacgagcag ctgaagtccg      180
gcaccgcctc cgtggtgtgc ctgctgaata acttctaccc cagagaggcc aaggtgcagt      240
ggaaggtgga caacgccctg cagtccggga actcccagga gagcgtgacc gagcaggaca      300
gcaaggacag cacctacagc ctgagcagca ccctgaccct gagcaaagcc gactacgaga      360
agcacaaggt gtacgcctgc gaggtgaccc accagggcct gagctcccc  gtcaccaaga      420 gcttcaacag gggggagtgt tagggcccg tttaaacggg tggcatccct gtgacccctc       480
cccagtgcct ctcctggccc tggaagttgc cactccagtg cccaccagcc ttgtcctaat      540
aaaattaagt tgcatcattt tgtctgacta ggtgtccttc tataatatta tggggtggag      600
gggggtggta tggagcaagg ggcaagttgg gaagacaacc tgtagggcct gcggggtcta      660
ttgggaacca agctggagtg cagtggcaca atcttggctc actgcaatct ccgcctcctg      720
ggttcaagcg attctcctgc ctcagcctcc cgagttgttg ggattccagg catgcatgac      780
caggctcacc taatttttgt tttttggta gagacggggt ttcaccatat tggccaggct      840
ggtctccaac tcctaatctc aggtgatcta cccaccttgg cctcccaaat tgctgggatt      900
acaggcgtga accactgctc cacgcgcccc gtagcggcgc attaagcgcg gcgggtgtgg      960
tggttacgcg cagcgtgacc gctacacttg ccagcgccct agcgcccgct cctttcgctt     1020
tcttcccttc ctttctcgcc acgttcgccg gctttcccg tcaagctcta aatcgggggc      1080
tccctttagg gttccgattt agtgctttac ggcacctcga ccccaaaaaa cttgattagg     1140
gtgatggttc acgtagtggg ccatcgccct gatagacggt ttttcgccct ttgacgttgg     1200
agtccacgtt ctttaatagt ggactcttgt tccaaactgg aacaacactc aaccctatct     1260
cggtctattc ttttgattta agggatttt gccgatttc ggcctattgg ttaaaaaatg      1320
agctgattta acaaaaattt aacgcgaatt aattctgtgg aatgtgtgtc agttagggtg     1380
tggaaagtcc ccaggctccc cagcaggcag aagtatgcaa agcatgcatc tcaattagtc     1440
```

```
agcaaccagg tgtggaaagt ccccaggctc cccagcaggc agaagtatgc aaagcatgca    1500
tctcaattag tcagcaacca tagtcccgcc cctaactccg cccatcccgc ccctaactcc    1560
gcccagttcc gcccattctc cgccccatgg ctgactaatt tttttattt atgcagaggc    1620 cgaggccgcc tctgcctctg agctattcca gaagtagtga ggaggctttt ttggaggcct    1680
aggcttttgc aaaaagctcc cggg                                          1704
```

<210> SEQ ID NO 34
<211> LENGTH: 1120
<212> TYPE: DNA
<213> ORGANISM: Artificial Sequence
<220> FEATURE:
<223> OTHER INFORMATION: human IgG1 signal + human IgG1 constant

<400> SEQUENCE: 34

```
tgctagcgcc accatgaaac acctgtggtt cttcctcctg ctggtggcag ctcccagatg      60
ggtgctgagc caggtgcaat tgtgcaggcg gttagctcag cctccaccaa gggcccaagc     120
gtcttccccc tggcaccctc ctccaagagc acctctggcg cacagccgc cctgggctgc      180 ctggtcaagg actacttccc cgaacccgtg accgtgagct ggaactcagg cgccctgacc     240
agcggcgtgc acaccttccc cgctgtcctg cagtcctcag gactctactc cctcagcagc     300
gtggtgaccg tgccctccag cagcttgggc acccagacct acatctgcaa cgtgaatcac     360
aagcccagca caccaaggt ggacaagaga gttgagccca atcttgtga caaaactcac       420 acatgcccac cctgcccagc acctgaactc ctgggggac cctcagtctt cctcttcccc      480
ccaaaaccca aggacaccct catgatctcc cggacccctg aggtcacatg cgtggtggtg     540
gacgtgagcc acgaagaccc tgaggtcaag ttcaactggt acgtggacgg cgtggaggtg     600
cataatgcca agacaaagcc ccgggaggag cagtacaaca gcacgtaccg ggtggtcagc     660
gtcctcaccg tcctgcacca ggactggctg aatggcaagg agtacaagtg caaggtctcc     720
aacaaagccc tcccagcccc catcgagaaa accatctcca agccaaagg ccagccccgg      780 gaaccacagg tgtacaccct gcccccatcc cgggaggaga tgaccaagaa ccaggtcagc     840
ctgacctgcc tggtcaaagg cttctatccc agcgacatcg ccgtggagtg ggagagcaat     900
ggccagcccg agaacaacta caagaccacc cctcccgtgc tggactccga cggctccttc     960
ttcctctaca gcaagctcac cgtggacaag agcaggtggc agcagggcaa cgtcttctca    1020
tgctccgtga tgcatgaggc tctgcacaac cactacaccc agaagagcct ctccctgtct    1080
cccggcaaat gagatatcgg gcccgtttaa acgggtggca                          1120
```

<210> SEQ ID NO 35
<211> LENGTH: 40
<212> TYPE: DNA
<213> ORGANISM: Artificial Sequence
<220> FEATURE:
<223> OTHER INFORMATION: PCR primer of heavy chain variable region cDNA
    of #32A1 antibody

<400> SEQUENCE: 35

```
aaagctgagc gaggtgcaaa ttttggagac tggaggaggc                             40
```

<210> SEQ ID NO 36
<211> LENGTH: 39
<212> TYPE: DNA
<213> ORGANISM: Artificial Sequence
<220> FEATURE:
<223> OTHER INFORMATION: PCR primer of heavy chain variable region cDNA
    of #32A1 antibody

<400> SEQUENCE: 36
aaagctgagc tgactgtgac catgactcct tggccccag        39

<210> SEQ ID NO 37
<211> LENGTH: 20
<212> TYPE: DNA
<213> ORGANISM: Artificial Sequence
<220> FEATURE:
<223> OTHER INFORMATION: Sequencing primer of heavy chain variable
      region cDNA of #32A1 antibody

<400> SEQUENCE: 37
taatacgact cactataggg        20

<210> SEQ ID NO 38
<211> LENGTH: 42
<212> TYPE: DNA
<213> ORGANISM: Artificial Sequence
<220> FEATURE:
<223> OTHER INFORMATION: PCR primer of light chain variable region cDNA
      of #32A1 antibody

<400> SEQUENCE: 38
aaacatatgg cgacattgtc ttgacccagt ctcctgcttt gg        42

<210> SEQ ID NO 39
<211> LENGTH: 37
<212> TYPE: DNA
<213> ORGANISM: Artificial Sequence
<220> FEATURE:
<223> OTHER INFORMATION: PCR primer of light chain variable region cDNA
      of #32A1 antibody

<400> SEQUENCE: 39
aaacgtacgt ctcaattcca gcttggtgcc tccagcg        37

<210> SEQ ID NO 40
<211> LENGTH: 1413
<212> TYPE: DNA
<213> ORGANISM: Artificial Sequence
<220> FEATURE:
<223> OTHER INFORMATION: Chimeric heavy chain of #32A1
<220> FEATURE:
<221> NAME/KEY: CDS
<222> LOCATION: (1)..(1413)

<400> SEQUENCE: 40

| | | | | | | | | | | | | | | | |
|---|---|---|---|---|---|---|---|---|---|---|---|---|---|---|---|
| atg | aaa | cac | ctg | tgg | ttc | ttc | ctc | ctg | ctg | gtg | gca | gct | ccc | aga | tgg | 48 |
| Met | Lys | His | Leu | Trp | Phe | Phe | Leu | Leu | Leu | Val | Ala | Ala | Pro | Arg | Trp | |
| 1 | | | | 5 | | | | | 10 | | | | | 15 | | |

| gtg | ctg | agc | gag | gtg | caa | att | ttg | gag | act | gga | gga | ggc | ttg | gtg | aag | 96 |
|---|---|---|---|---|---|---|---|---|---|---|---|---|---|---|---|---|
| Val | Leu | Ser | Glu | Val | Gln | Ile | Leu | Glu | Thr | Gly | Gly | Gly | Leu | Val | Lys | |
| | | | 20 | | | | | 25 | | | | | 30 | | | |

| ccc | ggt | ggt | tcc | ctg | aga | ctg | tct | tgt | gca | acg | tct | gga | ttc | aat | ttc | 144 |
|---|---|---|---|---|---|---|---|---|---|---|---|---|---|---|---|---|
| Pro | Gly | Gly | Ser | Leu | Arg | Leu | Ser | Cys | Ala | Thr | Ser | Gly | Phe | Asn | Phe | |
| | | 35 | | | | | 40 | | | | | 45 | | | | |

| aat | gat | tat | ttc | atg | aac | tgg | gtc | cgt | cag | gct | cca | gaa | aag | ggg | cta | 192 |
|---|---|---|---|---|---|---|---|---|---|---|---|---|---|---|---|---|
| Asn | Asp | Tyr | Phe | Met | Asn | Trp | Val | Arg | Gln | Ala | Pro | Glu | Lys | Gly | Leu | |
| | 50 | | | | | 55 | | | | | 60 | | | | | |

| gag | tgg | gtt | gct | caa | ata | agg | aac | aaa | att | tat | act | tat | gcc | aca | ttt | 240 |
|---|---|---|---|---|---|---|---|---|---|---|---|---|---|---|---|---|
| Glu | Trp | Val | Ala | Gln | Ile | Arg | Asn | Lys | Ile | Tyr | Thr | Tyr | Ala | Thr | Phe | |
| 65 | | | | | 70 | | | | | 75 | | | | | 80 | |

| tat | gcg | gag | tct | ttg | gaa | ggc | aga | gtc | aca | atc | tca | cga | gac | gat | tcc | 288 |
|---|---|---|---|---|---|---|---|---|---|---|---|---|---|---|---|---|
| Tyr | Ala | Glu | Ser | Leu | Glu | Gly | Arg | Val | Thr | Ile | Ser | Arg | Asp | Asp | Ser | |

-continued

```
                   85                  90                  95
gaa agc agt gtc tac ctg caa gtg agc agt tta aga gct gaa gac act        336
Glu Ser Ser Val Tyr Leu Gln Val Ser Ser Leu Arg Ala Glu Asp Thr
            100                 105                 110 gcc att tat tac tgt aca aga tcc cta act ggg gga gac tac ttt gat        384
Ala Ile Tyr Tyr Cys Thr Arg Ser Leu Thr Gly Gly Asp Tyr Phe Asp
            115                 120                 125 tac tgg ggc caa gga gtc atg gtc aca gtc agc tca gcc tcc acc aag        432
Tyr Trp Gly Gln Gly Val Met Val Thr Val Ser Ser Ala Ser Thr Lys
130                 135                 140 ggc cca agc gtc ttc ccc ctg gca ccc tcc tcc aag agc acc tct ggc        480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc        528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc        576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg        624
Phe Pro Ala Val Leu Gln Ser Ser Gly Leu Tyr Ser Leu Ser Ser Val
            195                 200                 205 gtg acc gtg ccc tcc agc agc ttg ggc acc cag acc tac atc tgc aac        672
Val Thr Val Pro Ser Ser Ser Leu Gly Thr Gln Thr Tyr Ile Cys Asn
            210                 215                 220 gtg aat cac aag ccc agc aac acc aag gtg gac aag aga gtt gag ccc        720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa        768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac        816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac        864
Thr Leu Met Ile Ser Arg Thr Pro Glu Val Thr Cys Val Val Val Asp
            275                 280                 285 gtg agc cac gaa gac cct gag gtc aag ttc aac tgg tac gtg gac ggc        912
Val Ser His Glu Asp Pro Glu Val Lys Phe Asn Trp Tyr Val Asp Gly
            290                 295                 300 gtg gag gtg cat aat gcc aag aca aag ccc cgg gag gag cag tac aac        960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg       1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca       1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa       1104
Ala Pro Ile Glu Lys Thr Ile Ser Lys Ala Lys Gly Gln Pro Arg Glu
            355                 360                 365 cca cag gtg tac acc ctg ccc cca tcc cgg gag gag atg acc aag aac       1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc       1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc       1248
```

-continued

```
               Ala Val Glu Trp Glu Ser Asn Gly Gln Pro Glu Asn Asn Tyr Lys Thr
                               405                 410                 415 acc cct ccc gtg ctg gac tcc gac ggc tcc ttc ttc ctc tac agc aag            1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc            1344
Leu Thr Val Asp Lys Ser Arg Trp Gln Gln Gly Asn Val Phe Ser Cys
            435                 440                 445 tcc gtg atg cat gag gct ctg cac aac cac tac acc cag aag agc ctc            1392
Ser Val Met His Glu Ala Leu His Asn His Tyr Thr Gln Lys Ser Leu
        450                 455                 460 tcc ctg tct ccc ggc aaa tga                                                1413
Ser Leu Ser Pro Gly Lys
465                 470

<210> SEQ ID NO 41
<211> LENGTH: 470
<212> TYPE: PRT
<213> ORGANISM: Artificial Sequence
<220> FEATURE:
<223> OTHER INFORMATION: Synthetic Construct

<400> SEQUENCE: 41

Met Lys His Leu Trp Phe Phe Leu Leu Leu Val Ala Ala Pro Arg Trp
1               5                   10                  15

Val Leu Ser Glu Val Gln Ile Leu Glu Thr Gly Gly Gly Leu Val Lys
            20                  25                  30

Pro Gly Gly Ser Leu Arg Leu Ser Cys Ala Thr Ser Gly Phe Asn Phe
        35                  40                  45

Asn Asp Tyr Phe Met Asn Trp Val Arg Gln Ala Pro Glu Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Val Thr Ile Ser Arg Asp Asp Ser
                85                  90                  95

Glu Ser Ser Val Tyr Leu Gln Val Ser Ser Leu Arg Ala Glu Asp Thr
            100                 105                 110

Ala Ile Tyr Tyr Cys Thr Arg Ser Leu Thr Gly Gly Asp Tyr Phe Asp
        115                 120                 125

Tyr Trp Gly Gln Gly Val Met Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270
```

```
Thr Leu Met Ile Ser Arg Thr Pro Glu Val Thr Cys Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
        450                 455                 460

Ser Leu Ser Pro Gly Lys
465                 470

<210> SEQ ID NO 42
<211> LENGTH: 714
<212> TYPE: DNA
<213> ORGANISM: Artificial Sequence
<220> FEATURE:
<223> OTHER INFORMATION: Chimeric light chain of #32A1
<220> FEATURE:
<221> NAME/KEY: CDS
<222> LOCATION: (1)..(714)

<400> SEQUENCE: 42 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gca tat ggc gac att gtc ttg acc cag tct cct gct ttg gct gtg      96
Gly Ala Tyr Gly Asp Ile Val Leu Thr Gln Ser Pro Ala Leu Ala Val
            20                  25                  30 tct cta ggg cag agg gcc aca atc tcc tgt agg gcc agc caa agt gtc     144
Ser Leu Gly Gln Arg Ala Thr Ile Ser Cys Arg Ala Ser Gln Ser Val
        35                  40                  45 act att tct gga tat agt ttt ata cac tgg tac caa cag aaa cca gga     192
Thr Ile Ser Gly Tyr Ser Phe Ile His Trp Tyr Gln Gln Lys Pro Gly
    50                  55                  60 cag caa ccc aga ctc ctc atc tat cgt gca tcc aac cta gcc tct ggg     240
Gln Gln Pro Arg Leu Leu Ile Tyr Arg Ala Ser Asn Leu Ala Ser Gly
65                  70                  75                  80 atc ccg gcc agg ttc agt ggc agt ggg tct ggg aca gac ttc acc ctc     288
Ile Pro Ala Arg Phe Ser Gly Ser Gly Ser Gly Thr Asp Phe Thr Leu
                85                  90                  95 acc atc aat cct gtg cag gct gat gat att gca acc tat ttc tgt cag     336
Thr Ile Asn Pro Val Gln Ala Asp Asp Ile Ala Thr Tyr Phe Cys Gln
```

```
            100                 105                 110
cag agt agg aaa tct ccg tgg acg ttc gct gga ggc acc aag ctg gaa    384
Gln Ser Arg Lys Ser Pro Trp Thr Phe Ala Gly Gly Thr Lys Leu Glu
        115                 120                 125 ttg aga cgt acg gtg gcc gcc ccc tcc gtg ttc atc ttc ccc ccc tcc    432
Leu Arg Arg Thr Val Ala Ala Pro Ser Val Phe Ile Phe Pro Pro Ser
    130                 135                 140 gac gag cag ctg aag tcc ggc acc gcc tcc gtg gtg tgc ctg ctg aat    480
Asp Glu Gln Leu Lys Ser Gly Thr Ala Ser Val Val Cys Leu Leu Asn
145                 150                 155                 160 aac ttc tac ccc aga gag gcc aag gtg cag tgg aag gtg gac aac gcc    528
Asn Phe Tyr Pro Arg Glu Ala Lys Val Gln Trp Lys Val Asp Asn Ala
                165                 170                 175 ctg cag tcc ggg aac tcc cag gag agc gtg acc gag cag gac agc aag    576
Leu Gln Ser Gly Asn Ser Gln Glu Ser Val Thr Glu Gln Asp Ser Lys
            180                 185                 190 gac agc acc tac agc ctg agc agc acc ctg acc ctg agc aaa gcc gac    624
Asp Ser Thr Tyr Ser Leu Ser Ser Thr Leu Thr Leu Ser Lys Ala Asp
        195                 200                 205 tac gag aag cac aag gtg tac gcc tgc gag gtg acc cac cag ggc ctg    672
Tyr Glu Lys His Lys Val Tyr Ala Cys Glu Val Thr His Gln Gly Leu
    210                 215                 220 agc tcc ccc gtc acc aag agc ttc aac agg ggg gag tgt tag            714
Ser Ser Pro Val Thr Lys Ser Phe Asn Arg Gly Glu Cys
225                 230                 235
```

<210> SEQ ID NO 43
<211> LENGTH: 237
<212> TYPE: PRT
<213> ORGANISM: Artificial Sequence
<220> FEATURE:
<223> OTHER INFORMATION: Synthetic Construct

<400> SEQUENCE: 43

```
Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Thr Ile Ser Gly Tyr Ser Phe Ile His Trp Tyr Gln Gln Lys Pro Gly
    50                  55                  60

Gln Gln Pro Arg Leu Leu Ile Tyr Arg Ala Ser Asn Leu Ala Ser Gly
65                  70                  75                  80

Ile Pro Ala Arg Phe Ser Gly Ser Gly Ser Gly Thr Asp Phe Thr Leu
                85                  90                  95

Thr Ile Asn Pro Val Gln Ala Asp Asp Ile Ala Thr Tyr Phe Cys Gln
            100                 105                 110

Gln Ser Arg Lys Ser Pro Trp Thr Phe Ala Gly Gly Thr Lys Leu Glu
        115                 120                 125

Leu Arg Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190
```

-continued

```
Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 44
<211> LENGTH: 5
<212> TYPE: PRT
<213> ORGANISM: Rattus norvegicus

<400> SEQUENCE: 44

Asp Tyr Phe Met Asn
1               5

<210> SEQ ID NO 45
<211> LENGTH: 19
<212> TYPE: PRT
<213> ORGANISM: Rattus norvegicus

<400> SEQUENCE: 45

Gln Ile Arg Asn Lys Ile Tyr Thr Tyr Ala Thr Phe Tyr Ala Glu Ser
1               5                  10                  15

Leu Glu Gly

<210> SEQ ID NO 46
<211> LENGTH: 10
<212> TYPE: PRT
<213> ORGANISM: Rattus norvegicus

<400> SEQUENCE: 46

Ser Leu Thr Gly Gly Asp Tyr Phe Asp Tyr
1               5                  10

<210> SEQ ID NO 47
<211> LENGTH: 15
<212> TYPE: PRT
<213> ORGANISM: Rattus norvegicus

<400> SEQUENCE: 47

Arg Ala Ser Gln Ser Val Thr Ile Ser Gly Tyr Ser Phe Ile His
1               5                  10                  15

<210> SEQ ID NO 48
<211> LENGTH: 7
<212> TYPE: PRT
<213> ORGANISM: Rattus norvegicus

<400> SEQUENCE: 48

Arg Ala Ser Asn Leu Ala Ser
1               5

<210> SEQ ID NO 49
<211> LENGTH: 9
<212> TYPE: PRT
<213> ORGANISM: Rattus norvegicus

<400> SEQUENCE: 49

Gln Gln Ser Arg Lys Ser Pro Trp Thr
1               5
```

```
<210> SEQ ID NO 50
<211> LENGTH: 1410
<212> TYPE: DNA
<213> ORGANISM: Artificial Sequence
<220> FEATURE:
<223> OTHER INFORMATION: h#32A1-T1H
<220> FEATURE:
<221> NAME/KEY: CDS
<222> LOCATION: (1)..(1410)

<400> SEQUENCE: 50 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gag gtg caa ctg gtg gag agc ggc gga ctt gtg caa          96
Val Leu Ser Glu Val Gln Leu Val Glu Ser Gly Gly Gly Leu Val Gln
            20                  25                  30 cct ggc ggc tcc ctg aga ctt agc tgt gcc gcc tcc ggc ttc aac ttc     144
Pro Gly Gly Ser Leu Arg Leu Ser Cys Ala Ala Ser Gly Phe Asn Phe
        35                  40                  45 aac gac tac ttc atg aac tgg gtg aga caa gcc cct ggc aag ggc ctg     192
Asn Asp Tyr Phe Met Asn Trp Val Arg Gln Ala Pro Gly Lys Gly Leu
    50                  55                  60 gag tgg gtg gcc caa atc aga aac aag atc tac acc tac gcc acc ttc     240
Glu Trp Val Ala Gln Ile Arg Asn Lys Ile Tyr Thr Tyr Ala Thr Phe
65                  70                  75                  80 tac gcc gag agc ctt gag ggc aga ttc acc atc tcc aga gac aac gcc     288
Tyr Ala Glu Ser Leu Glu Gly Arg Phe Thr Ile Ser Arg Asp Asn Ala
                85                  90                  95 aag aac agc ctg tac ctt caa atg aac tcc ctg aga gcc gag gac acc     336
Lys Asn Ser Leu Tyr Leu Gln Met Asn Ser Leu Arg Ala Glu Asp Thr
            100                 105                 110 gcc gtg tac tac tgt gcc aga agc ctt acc ggc ggc gac tac ttc gac     384
Ala Val Tyr Tyr Cys Ala Arg Ser Leu Thr Gly Gly Asp Tyr Phe Asp
        115                 120                 125 tac tgg ggc caa ggc acc ctg gtg acc gtg agc tca gcc tcc acc aag     432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc     480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc     528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc     720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa     768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac     816
Leu Leu Gly Gly Pro Ser Val Phe Leu Phe Pro Pro Lys Pro Lys Asp
            260                 265                 270
```

```
acc ctc atg atc tcc cgg acc cct gag gtc aca tgc gtg gtg gtg gac       864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc       912
Val Ser His Glu Asp Pro Glu Val Lys Phe Asn Trp Tyr Val Asp Gly
290                 295                 300 gtg gag gtg cat aat gcc aag aca aag ccc cgg gag gag cag tac aac       960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg      1008
Ser Thr Tyr Arg Val Val Ser Val Leu Thr Val Leu His Gln Asp Trp
            325                 330                 335 ctg aat ggc aag gag tac aag tgc aag gtc tcc aac aaa gcc ctc cca      1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cgg gaa      1104
Ala Pro Ile Glu Lys Thr Ile Ser Lys Ala Lys Gly Gln Pro Arg Glu
            355                 360                 365 cca cag gtg tac acc ctg ccc cca tcc cgg gag gag atg acc aag aac      1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc      1248
Ala Val Glu Trp Glu Ser Asn Gly Gln Pro Glu Asn Asn Tyr Lys Thr
            405                 410                 415 acc cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc      1344
Leu Thr Val Asp Lys Ser Arg Trp Gln Gln Gly Asn Val Phe Ser Cys
            435                 440                 445 tcc gtg atg cat gag gct ctg cac aac cac tac acc cag aag agc ctc      1392
Ser Val Met His Glu Ala Leu His Asn His Tyr Thr Gln Lys Ser Leu
450                 455                 460 tcc ctg tct ccc ggc aaa                                              1410
Ser Leu Ser Pro Gly Lys
465                 470

<210> SEQ ID NO 51
<211> LENGTH: 470
<212> TYPE: PRT
<213> ORGANISM: Artificial Sequence
<220> FEATURE:
<223> OTHER INFORMATION: Synthetic Construct

<400> SEQUENCE: 51

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Phe
            35                  40                  45

Asn Asp Tyr Phe Met Asn Trp Val Arg Gln Ala Pro Gly Lys Gly Leu
        50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Phe Thr Ile Ser Arg Asp Asn Ala
```

```
            85                  90                  95
Lys Asn Ser Leu Tyr Leu Gln Met Asn Ser Leu Arg Ala Glu Asp Thr
            100                 105                 110

Ala Val Tyr Tyr Cys Ala Arg Ser Leu Thr Gly Gly Asp Tyr Phe Asp
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 52
<211> LENGTH: 1410
<212> TYPE: DNA
<213> ORGANISM: Artificial Sequence
```

```
<220> FEATURE:
<223> OTHER INFORMATION: h#32A1-T2H
<220> FEATURE:
<221> NAME/KEY: CDS
<222> LOCATION: (1)..(1410)

<400> SEQUENCE: 52 atg aaa cac ctg tgg ttc ttc ctc ctg ctg gtg gca gct ccc aga tgg    48
Met Lys His Leu Trp Phe Phe Leu Leu Leu Val Ala Ala Pro Arg Trp
1               5                   10                  15 gtg ctg agc gag gtg caa ctg gtg gag agc ggc gga gga ctg gtg caa    96
Val Leu Ser Glu Val Gln Leu Val Glu Ser Gly Gly Gly Leu Val Gln
            20                  25                  30 cct ggc ggc tcc ctg aga ctg agc tgt gcc gcc tcc ggc ttc aac ttc    144
Pro Gly Gly Ser Leu Arg Leu Ser Cys Ala Ala Ser Gly Phe Asn Phe
        35                  40                  45 aac gac tac ttc atg aac tgg gtg aga caa gcc cct gag aag ggc ctg    192
Asn Asp Tyr Phe Met Asn Trp Val Arg Gln Ala Pro Glu Lys Gly Leu
    50                  55                  60 gag tgg gtg gcc caa atc aga aac aag atc tac acc tac gcc acc ttc    240
Glu Trp Val Ala Gln Ile Arg Asn Lys Ile Tyr Thr Tyr Ala Thr Phe
65                  70                  75                  80 tac gcc gag agc ctg gag ggc aga gtg acc atc tcc aga gac aac gcc    288
Tyr Ala Glu Ser Leu Glu Gly Arg Val Thr Ile Ser Arg Asp Asn Ala
                85                  90                  95 aag aac agc ctg tac ctg caa atg tcc tcc ctg aga gcc gag gac acc    336
Lys Asn Ser Leu Tyr Leu Gln Met Ser Ser Leu Arg Ala Glu Asp Thr
            100                 105                 110 gcc gtg tac tac tgt gcc aga agc ctg acc ggc ggc gac tac ttc gac    384
Ala Val Tyr Tyr Cys Ala Arg Ser Leu Thr Gly Gly Asp Tyr Phe Asp
        115                 120                 125 tac tgg ggc caa ggc acc ctg gtg acc gtg agc tca gcc tcc acc aag    432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc    480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc    528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc    576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg    624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac    672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc    720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa    768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac    816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac    864
Thr Leu Met Ile Ser Arg Thr Pro Glu Val Thr Cys Val Val Val Asp
        275                 280                 285
```

```
gtg agc cac gaa gac cct gag gtc aag ttc aac tgg tac gtg gac ggc     912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac     960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg    1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca    1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa    1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac    1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc    1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc    1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag    1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc    1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc    1392
Ser Val Met His Glu Ala Leu His Asn His Tyr Thr Gln Lys Ser Leu
450                 455                 460 tcc ctg tct ccc ggc aaa                                            1410
Ser Leu Ser Pro Gly Lys
465                 470

<210> SEQ ID NO 53
<211> LENGTH: 470
<212> TYPE: PRT
<213> ORGANISM: Artificial Sequence
<220> FEATURE:
<223> OTHER INFORMATION: Synthetic Construct

<400> SEQUENCE: 53

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Glu Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Val Thr Ile Ser Arg Asp Asn Ala
                85                  90                  95

Lys Asn Ser Leu Tyr Leu Gln Met Ser Ser Leu Arg Ala Glu Asp Thr
            100                 105                 110
```

```
Ala Val Tyr Tyr Cys Ala Arg Ser Leu Thr Gly Gly Asp Tyr Phe Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 54
<211> LENGTH: 1410
<212> TYPE: DNA
<213> ORGANISM: Artificial Sequence
<220> FEATURE:
<223> OTHER INFORMATION: h#32A1-T3H
<220> FEATURE:
<221> NAME/KEY: CDS
```

```
<222> LOCATION: (1)..(1410)

<400> SEQUENCE: 54 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                  10                  15 gtg ctg agc gag gtg cag atc gtg gag agc ggc ggc gga ctt gtg cag      96
Val Leu Ser Glu Val Gln Ile Val Glu Ser Gly Gly Gly Leu Val Gln
            20                  25                  30 cct ggc ggc tcc ctg aga ctt agc tgt gcc acc tcc ggc ttc aac ttc     144
Pro Gly Gly Ser Leu Arg Leu Ser Cys Ala Thr Ser Gly Phe Asn Phe
        35                  40                  45 aac gac tac ttc atg aac tgg gtg aga cag gcc cct gag aag ggc ctg     192
Asn Asp Tyr Phe Met Asn Trp Val Arg Gln Ala Pro Glu Lys Gly Leu
    50                  55                  60 gag tgg gtg gcc cag atc aga aac aag atc tac acc tac gcc acc ttc     240
Glu Trp Val Ala Gln Ile Arg Asn Lys Ile Tyr Thr Tyr Ala Thr Phe
65                  70                  75                  80 tac gcc gag agc ctt gag ggc aga gtg acc atc tcc aga gac gac agc     288
Tyr Ala Glu Ser Leu Glu Gly Arg Val Thr Ile Ser Arg Asp Asp Ser
                85                  90                  95 gag tcc agc gtg tac ctt cag atg tcc agc ctg aga gcc gag gac acc     336
Glu Ser Ser Val Tyr Leu Gln Met Ser Ser Leu Arg Ala Glu Asp Thr
            100                 105                 110 gcc gtg tac tac tgt acc aga agc ctt acc ggc ggc gac tac ttc gac     384
Ala Val Tyr Tyr Cys Thr Arg Ser Leu Thr Gly Gly Asp Tyr Phe Asp
        115                 120                 125 tac tgg ggc cag ggc acc ctg gtg acc gtg agc tca gcc tcc acc aag     432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc     480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc     528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc     576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg     624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac     672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc     720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa     768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac     816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac     864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc     912
Val Ser His Glu Asp Pro Glu Val Lys Phe Asn Trp Tyr Val Asp Gly
    290                 295                 300
```

```
gtg gag gtg cat aat gcc aag aca aag ccc cgg gag gag cag tac aac        960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg       1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca       1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa       1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac       1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc       1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc       1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag       1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc       1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc       1392
Ser Val Met His Glu Ala Leu His Asn His Tyr Thr Gln Lys Ser Leu
    450                 455                 460 tcc ctg tct ccc ggc aaa                                               1410
Ser Leu Ser Pro Gly Lys
465                 470

<210> SEQ ID NO 55
<211> LENGTH: 470
<212> TYPE: PRT
<213> ORGANISM: Artificial Sequence
<220> FEATURE:
<223> OTHER INFORMATION: Synthetic Construct

<400> SEQUENCE: 55

Met Lys His Leu Trp Phe Phe Leu Leu Leu Val Ala Ala Pro Arg Trp
1               5                   10                  15

Val Leu Ser Glu Val Gln Ile Val Glu Ser Gly Gly Gly Leu Val Gln
            20                  25                  30

Pro Gly Gly Ser Leu Arg Leu Ser Cys Ala Thr Ser Gly Phe Asn Phe
        35                  40                  45

Asn Asp Tyr Phe Met Asn Trp Val Arg Gln Ala Pro Glu Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Val Thr Ile Ser Arg Asp Asp Ser
                85                  90                  95

Glu Ser Ser Val Tyr Leu Gln Met Ser Ser Leu Arg Ala Glu Asp Thr
            100                 105                 110

Ala Val Tyr Tyr Cys Thr Arg Ser Leu Thr Gly Gly Asp Tyr Phe Asp
        115                 120                 125
```

```
Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
450                 455                 460

Ser Leu Ser Pro Gly Lys
465                 470
```

<210> SEQ ID NO 56
<211> LENGTH: 1410
<212> TYPE: DNA
<213> ORGANISM: Artificial Sequence
<220> FEATURE:
<223> OTHER INFORMATION: h#32A1-T5H
<220> FEATURE:
<221> NAME/KEY: CDS
<222> LOCATION: (1)..(1410)

<400> SEQUENCE: 56

-continued

| | | |
|---|---|---|
| atg aaa cac ctg tgg ttc ttc ctc ctg ctg gtg gca gct ccc aga tgg<br>Met Lys His Leu Trp Phe Phe Leu Leu Leu Val Ala Ala Pro Arg Trp<br>1               5                   10                  15 | 48 | |
| gtg ctg agc gag gtg cag gtg gtg gag agc ggc ggc gga ctt gtg cag<br>Val Leu Ser Glu Val Gln Val Val Glu Ser Gly Gly Gly Leu Val Gln<br>        20                  25                  30 | 96 | |
| cct ggc ggc tcc ctg aga ctt agc tgt gcc acc tcc ggc ttc aac ttc<br>Pro Gly Gly Ser Leu Arg Leu Ser Cys Ala Thr Ser Gly Phe Asn Phe<br>                35                  40                  45 | 144 | |
| aac gac tac ttc atg aac tgg gtg aga cag gcc cct ggc aag ggc ctg<br>Asn Asp Tyr Phe Met Asn Trp Val Arg Gln Ala Pro Gly Lys Gly Leu<br>    50                  55                  60 | 192 | |
| gag tgg gtg gcc cag atc aga aac aag atc tac acc tac gcc acc ttc<br>Glu Trp Val Ala Gln Ile Arg Asn Lys Ile Tyr Thr Tyr Ala Thr Phe<br>65                  70                  75                  80 | 240 | |
| tac gcc gag agc ctt gag ggc aga ttc acc atc tcc aga gac aac agc<br>Tyr Ala Glu Ser Leu Glu Gly Arg Phe Thr Ile Ser Arg Asp Asn Ser<br>                85                  90                  95 | 288 | |
| aag tcc acc gtg tac ctt cag atg aac tcc ctg aga gcc gag gac acc<br>Lys Ser Thr Val Tyr Leu Gln Met Asn Ser Leu Arg Ala Glu Asp Thr<br>            100                 105                 110 | 336 | |
| gcc gtg tac tac tgt acc aga agc ctt acc ggc ggc gac tac ttc gac<br>Ala Val Tyr Tyr Cys Thr Arg Ser Leu Thr Gly Gly Asp Tyr Phe Asp<br>        115                 120                 125 | 384 | |
| tac tgg ggc cag ggc acc ctg gtg acc gtg agc tca gcc tcc acc aag<br>Tyr Trp Gly Gln Gly Thr Leu Val Thr Val Ser Ser Ala Ser Thr Lys<br>130                 135                 140 | 432 | |
| ggc cca agc gtc ttc ccc ctg gca ccc tcc tcc aag agc acc tct ggc<br>Gly Pro Ser Val Phe Pro Leu Ala Pro Ser Ser Lys Ser Thr Ser Gly<br>145                 150                 155                 160 | 480 | |
| ggc aca gcc gcc ctg ggc tgc ctg gtc aag gac tac ttc ccc gaa ccc<br>Gly Thr Ala Ala Leu Gly Cys Leu Val Lys Asp Tyr Phe Pro Glu Pro<br>                165                 170                 175 | 528 | |
| gtg acc gtg agc tgg aac tca ggc gcc ctg acc agc ggc gtg cac acc<br>Val Thr Val Ser Trp Asn Ser Gly Ala Leu Thr Ser Gly Val His Thr<br>            180                 185                 190 | 576 | |
| ttc ccc gct gtc ctg cag tcc tca gga ctc tac tcc ctc agc agc gtg<br>Phe Pro Ala Val Leu Gln Ser Ser Gly Leu Tyr Ser Leu Ser Ser Val<br>        195                 200                 205 | 624 | |
| gtg acc gtg ccc tcc agc agc ttg ggc acc cag acc tac atc tgc aac<br>Val Thr Val Pro Ser Ser Ser Leu Gly Thr Gln Thr Tyr Ile Cys Asn<br>    210                 215                 220 | 672 | |
| gtg aat cac aag ccc agc aac acc aag gtg gac aag aga gtt gag ccc<br>Val Asn His Lys Pro Ser Asn Thr Lys Val Asp Lys Arg Val Glu Pro<br>225                 230                 235                 240 | 720 | |
| aaa tct tgt gac aaa act cac aca tgc cca ccc tgc cca gca cct gaa<br>Lys Ser Cys Asp Lys Thr His Thr Cys Pro Pro Cys Pro Ala Pro Glu<br>                245                 250                 255 | 768 | |
| ctc ctg ggg gga ccc tca gtc ttc ctc ttc ccc cca aaa ccc aag gac<br>Leu Leu Gly Gly Pro Ser Val Phe Leu Phe Pro Pro Lys Pro Lys Asp<br>            260                 265                 270 | 816 | |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>        275                 280                 285 | 864 | |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>    290                 295                 300 | 912 | |
| gtg gag gtg cat aat gcc aag aca aag ccc cgg gag gag cag tac aac<br>Val Glu Val His Asn Ala Lys Thr Lys Pro Arg Glu Glu Gln Tyr Asn<br>305                 310                 315                 320 | 960 | |

```
agc acg tac cgg gtg gtc agc gtc ctc acc gtc ctg cac cag gac tgg    1008
Ser Thr Tyr Arg Val Val Ser Val Leu Thr Val Leu His Gln Asp Trp
            325                 330                 335 ctg aat ggc aag gag tac aag tgc aag gtc tcc aac aaa gcc ctc cca    1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa    1104
Ala Pro Ile Glu Lys Thr Ile Ser Lys Ala Lys Gly Gln Pro Arg Glu
            355                 360                 365 cca cag gtg tac acc ctg ccc cca tcc cgg gag gag atg acc aag aac    1152
Pro Gln Val Tyr Thr Leu Pro Pro Ser Arg Glu Glu Met Thr Lys Asn
370                 375                 380 cag gtc agc ctg acc tgc ctg gtc aaa ggc ttc tat ccc agc gac atc    1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc    1248
Ala Val Glu Trp Glu Ser Asn Gly Gln Pro Glu Asn Asn Tyr Lys Thr
            405                 410                 415 acc cct ccc gtg ctg gac tcc gac ggc tcc ttc ttc ctc tac agc aag    1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc    1344
Leu Thr Val Asp Lys Ser Arg Trp Gln Gln Gly Asn Val Phe Ser Cys
            435                 440                 445 tcc gtg atg cat gag gct ctg cac aac cac tac acc cag aag agc ctc    1392
Ser Val Met His Glu Ala Leu His Asn His Tyr Thr Gln Lys Ser Leu
450                 455                 460 tcc ctg tct ccc ggc aaa                                            1410
Ser Leu Ser Pro Gly Lys
465                 470

<210> SEQ ID NO 57
<211> LENGTH: 470
<212> TYPE: PRT
<213> ORGANISM: Artificial Sequence
<220> FEATURE:
<223> OTHER INFORMATION: Synthetic Construct

<400> SEQUENCE: 57

Met Lys His Leu Trp Phe Phe Leu Leu Leu Val Ala Ala Pro Arg Trp
1               5                   10                  15

Val Leu Ser Glu Val Gln Val Val Glu Ser Gly Gly Gly Leu Val Gln
            20                  25                  30

Pro Gly Gly Ser Leu Arg Leu Ser Cys Ala Thr Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Phe Thr Ile Ser Arg Asp Asn Ser
                85                  90                  95

Lys Ser Thr Val Tyr Leu Gln Met Asn Ser Leu Arg Ala Glu Asp Thr
            100                 105                 110

Ala Val Tyr Tyr Cys Thr Arg Ser Leu Thr Gly Gly Asp Tyr Phe Asp
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
```

```
                145                 150                 155                 160
        Gly Thr Ala Ala Leu Gly Cys Leu Val Lys Asp Tyr Phe Pro Glu Pro
                        165                 170                 175

Val Thr Val Ser Trp Asn Ser Gly Ala Leu Thr Ser Gly Val His Thr
                        180                 185                 190

Phe Pro Ala Val Leu Gln Ser Ser Gly Leu Tyr Ser Leu Ser Ser Val
                        195                 200                 205

Val Thr Val Pro Ser Ser Leu Gly Thr Gln Thr Tyr Ile Cys Asn
                        210                 215                 220

Val Asn His Lys Pro Ser Asn Thr Lys Val Asp Lys Arg Val Glu Pro
        225                 230                 235                 240

Lys Ser Cys Asp Lys Thr His Thr Cys Pro Pro Cys Pro Ala Pro Glu
                        245                 250                 255

Leu Leu Gly Gly Pro Ser Val Phe Leu Phe Pro Pro Lys Pro Lys Asp
                        260                 265                 270

Thr Leu Met Ile Ser Arg Thr Pro Glu Val Thr Cys Val Val Val Asp
                        275                 280                 285

Val Ser His Glu Asp Pro Glu Val Lys Phe Asn Trp Tyr Val Asp Gly
                        290                 295                 300

Val Glu Val His Asn Ala Lys Thr Lys Pro Arg Glu Glu Gln Tyr Asn
        305                 310                 315                 320

Ser Thr Tyr Arg Val Val Ser Val Leu Thr Val Leu His Gln Asp Trp
                        325                 330                 335

Leu Asn Gly Lys Glu Tyr Lys Cys Lys Val Ser Asn Lys Ala Leu Pro
                        340                 345                 350

Ala Pro Ile Glu Lys Thr Ile Ser Lys Ala Lys Gly Gln Pro Arg Glu
                        355                 360                 365

Pro Gln Val Tyr Thr Leu Pro Pro Ser Arg Glu Glu Met Thr Lys Asn
                        370                 375                 380

Gln Val Ser Leu Thr Cys Leu Val Lys Gly Phe Tyr Pro Ser Asp Ile
        385                 390                 395                 400

Ala Val Glu Trp Glu Ser Asn Gly Gln Pro Glu Asn Asn Tyr Lys Thr
                        405                 410                 415

Thr Pro Pro Val Leu Asp Ser Asp Gly Ser Phe Phe Leu Tyr Ser Lys
                        420                 425                 430

Leu Thr Val Asp Lys Ser Arg Trp Gln Gln Gly Asn Val Phe Ser Cys
                        435                 440                 445

Ser Val Met His Glu Ala Leu His Asn His Tyr Thr Gln Lys Ser Leu
        450                 455                 460

Ser Leu Ser Pro Gly Lys
        465                 470

<210> SEQ ID NO 58
<211> LENGTH: 1410
<212> TYPE: DNA
<213> ORGANISM: Artificial Sequence
<220> FEATURE:
<223> OTHER INFORMATION: h#32A1-T6H
<220> FEATURE:
<221> NAME/KEY: CDS
<222> LOCATION: (1)..(1410)

<400> SEQUENCE: 58 atg aaa cac ctg tgg ttc ttc ctc ctg ctg gtg gca gct ccc aga tgg       48
Met Lys His Leu Trp Phe Phe Leu Leu Leu Val Ala Ala Pro Arg Trp
1               5                   10                  15
```

| | | |
|---|---|---|
| gtg ctg agc gag gtg cag gtg gtg gag agc ggc gga ctt gtg cag<br>Val Leu Ser Glu Val Gln Val Val Glu Ser Gly Gly Leu Val Gln<br>20          25          30 | | 96 |
| cct ggc ggc tcc ctg aga ctt agc tgt gcc acc tcc ggc ttc aac ttc<br>Pro Gly Gly Ser Leu Arg Leu Ser Cys Ala Thr Ser Gly Phe Asn Phe<br>35          40          45 | | 144 |
| aac gac tac ttc atg aac tgg gtg aga cag gcc cct gag aag ggc ctg<br>Asn Asp Tyr Phe Met Asn Trp Val Arg Gln Ala Pro Glu Lys Gly Leu<br>50          55          60 | | 192 |
| gag tgg gtg gcc cag atc aga aac aag atc tac acc tac gcc acc ttc<br>Glu Trp Val Ala Gln Ile Arg Asn Lys Ile Tyr Thr Tyr Ala Thr Phe<br>65          70          75          80 | | 240 |
| tac gcc gag agc ctt gag ggc aga gtg acc atc tcc aga gac aac agc<br>Tyr Ala Glu Ser Leu Glu Gly Arg Val Thr Ile Ser Arg Asp Asn Ser<br>85          90          95 | | 288 |
| aag tcc acc gtg tac ctt cag atg tcc agc ctt aga gcc gag gac acc<br>Lys Ser Thr Val Tyr Leu Gln Met Ser Ser Leu Arg Ala Glu Asp Thr<br>100          105          110 | | 336 |
| gcc gtg tac tac tgt acc aga agc ctt acc ggc ggc gac tac ttc gac<br>Ala Val Tyr Tyr Cys Thr Arg Ser Leu Thr Gly Gly Asp Tyr Phe Asp<br>115          120          125 | | 384 |
| tac tgg ggc cag ggc acc ctt gtg aca gtg agc tca gcc tcc acc aag<br>Tyr Trp Gly Gln Gly Thr Leu Val Thr Val Ser Ser Ala Ser Thr Lys<br>130          135          140 | | 432 |
| ggc cca agc gtc ttc ccc ctg gca ccc tcc tcc aag agc acc tct ggc<br>Gly Pro Ser Val Phe Pro Leu Ala Pro Ser Ser Lys Ser Thr Ser Gly<br>145          150          155          160 | | 480 |
| ggc aca gcc gcc ctg ggc tgc ctg gtc aag gac tac ttc ccc gaa ccc<br>Gly Thr Ala Ala Leu Gly Cys Leu Val Lys Asp Tyr Phe Pro Glu Pro<br>165          170          175 | | 528 |
| gtg acc gtg agc tgg aac tca ggc gcc ctg acc agc ggc gtg cac acc<br>Val Thr Val Ser Trp Asn Ser Gly Ala Leu Thr Ser Gly Val His Thr<br>180          185          190 | | 576 |
| ttc ccc gct gtc ctg cag tcc tca gga ctc tac tcc ctc agc agc gtg<br>Phe Pro Ala Val Leu Gln Ser Ser Gly Leu Tyr Ser Leu Ser Ser Val<br>195          200          205 | | 624 |
| gtg acc gtg ccc tcc agc agc ttg ggc acc cag acc tac atc tgc aac<br>Val Thr Val Pro Ser Ser Ser Leu Gly Thr Gln Thr Tyr Ile Cys Asn<br>210          215          220 | | 672 |
| gtg aat cac aag ccc agc aac acc aag gtg gac aag aga gtt gag ccc<br>Val Asn His Lys Pro Ser Asn Thr Lys Val Asp Lys Arg Val Glu Pro<br>225          230          235          240 | | 720 |
| aaa tct tgt gac aaa act cac aca tgc cca ccc tgc cca gca cct gaa<br>Lys Ser Cys Asp Lys Thr His Thr Cys Pro Pro Cys Pro Ala Pro Glu<br>245          250          255 | | 768 |
| ctc ctg ggg gga ccc tca gtc ttc ctc ttc ccc cca aaa ccc aag gac<br>Leu Leu Gly Gly Pro Ser Val Phe Leu Phe Pro Pro Lys Pro Lys Asp<br>260          265          270 | | 816 |
| acc ctc atg atc tcc cgg acc cct gag gtc aca tgc gtg gtg gtg gac<br>Thr Leu Met Ile Ser Arg Thr Pro Glu Val Thr Cys Val Val Val Asp<br>275          280          285 | | 864 |
| gtg agc cac gaa gac cct gag gtc aag ttc aac tgg tac gtg gac ggc<br>Val Ser His Glu Asp Pro Glu Val Lys Phe Asn Trp Tyr Val Asp Gly<br>290          295          300 | | 912 |
| gtg gag gtg cat aat gcc aag aca aag ccc cgg gag gag cag tac aac<br>Val Glu Val His Asn Ala Lys Thr Lys Pro Arg Glu Glu Gln Tyr Asn<br>305          310          315          320 | | 960 |
| agc acg tac cgg gtg gtc agc gtc ctc acc gtc ctg cac cag gac tgg<br>Ser Thr Tyr Arg Val Val Ser Val Leu Thr Val Leu His Gln Asp Trp<br>325          330          335 | | 1008 |

```
ctg aat ggc aag gag tac aag tgc aag gtc tcc aac aaa gcc ctc cca      1056
Leu Asn Gly Lys Glu Tyr Lys Cys Lys Val Ser Asn Lys Ala Leu Pro
        340                 345                 350 gcc ccc atc gag aaa acc atc tcc aaa gcc aaa ggc cag ccc cgg gaa      1104
Ala Pro Ile Glu Lys Thr Ile Ser Lys Ala Lys Gly Gln Pro Arg Glu
355                 360                 365 cca cag gtg tac acc ctg ccc cca tcc cgg gag gag atg acc aag aac      1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc      1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc      1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc      1392
Ser Val Met His Glu Ala Leu His Asn His Tyr Thr Gln Lys Ser Leu
450                 455                 460 tcc ctg tct ccc ggc aaa                                               1410
Ser Leu Ser Pro Gly Lys
465                 470

<210> SEQ ID NO 59
<211> LENGTH: 470
<212> TYPE: PRT
<213> ORGANISM: Artificial Sequence
<220> FEATURE:
<223> OTHER INFORMATION: Synthetic Construct

<400> SEQUENCE: 59

Met Lys His Leu Trp Phe Phe Leu Leu Leu Val Ala Ala Pro Arg Trp
1               5                   10                  15

Val Leu Ser Glu Val Gln Val Val Glu Ser Gly Gly Gly Leu Val Gln
            20                  25                  30

Pro Gly Gly Ser Leu Arg Leu Ser Cys Ala Thr Ser Gly Phe Asn Phe
        35                  40                  45

Asn Asp Tyr Phe Met Asn Trp Val Arg Gln Ala Pro Glu Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Val Thr Ile Ser Arg Asp Asn Ser
                85                  90                  95

Lys Ser Thr Val Tyr Leu Gln Met Ser Ser Leu Arg Ala Glu Asp Thr
            100                 105                 110

Ala Val Tyr Tyr Cys Thr Arg Ser Leu Thr Gly Gly Asp Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175
```

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Leu Gly Thr Gln Thr Tyr Ile Cys Asn
            210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 60
<211> LENGTH: 714
<212> TYPE: DNA
<213> ORGANISM: Artificial Sequence
<220> FEATURE:
<223> OTHER INFORMATION: h#32A1-T1L
<220> FEATURE:
<221> NAME/KEY: CDS
<222> LOCATION: (1)..(714)

<400> SEQUENCE: 60 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gca tat ggc gac atc gtg atg acc cag agc cct gac tcc ctt gcc    96
Gly Ala Tyr Gly Asp Ile Val Met Thr Gln Ser Pro Asp Ser Leu Ala
            20                  25                  30

```
gtg tcc ctg ggc gag aga gcc acc atc aac tgt aga gcc tcc cag agc      144
Val Ser Leu Gly Glu Arg Ala Thr Ile Asn Cys Arg Ala Ser Gln Ser
        35                  40                  45 gtg acc atc tcc ggc tac agc ttc atc cac tgg tac cag cag aag cct      192
Val Thr Ile Ser Gly Tyr Ser Phe Ile His Trp Tyr Gln Gln Lys Pro
50                  55                  60 ggc cag cct cct aag ctt ctg atc tac aga gcc tcc aac ctt gcc agc      240
Gly Gln Pro Pro Lys Leu Leu Ile Tyr Arg Ala Ser Asn Leu Ala Ser
65                  70                  75                  80 ggc gtg cct gcc aga ttc tcc ggc agc ggc tcc ggc acc gac ttc acc      288
Gly Val Pro Ala Arg Phe Ser Gly Ser Gly Ser Gly Thr Asp Phe Thr
                85                  90                  95 ctg acc atc agc tcc ctt cag gcc gag gac gtg gcc gtg tac tac tgt      336
Leu Thr Ile Ser Ser Leu Gln Ala Glu Asp Val Ala Val Tyr Tyr Cys
            100                 105                 110 cag cag agc aga aag tcc cct tgg acc ttc ggc ggc ggc acc aag gtg      384
Gln Gln Ser Arg Lys Ser Pro Trp Thr Phe Gly Gly Gly Thr Lys Val
        115                 120                 125 gag atc aag cgt acg gtg gcc gcc ccc tcc gtg ttc atc ttc ccc ccc      432
Glu Ile Lys Arg Thr Val Ala Ala Pro Ser Val Phe Ile Phe Pro Pro
    130                 135                 140 tcc gac gag cag ctg aag tcc ggc acc gcc tcc gtg gtg tgc ctg ctg      480
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac      528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc      576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc      624
Lys Asp Ser Thr Tyr Ser Leu Ser Ser Thr Leu Thr Leu Ser Lys Ala
        195                 200                 205 gac tac gag aag cac aag gtg tac gcc tgc gag gtg acc cac cag ggc      672
Asp Tyr Glu Lys His Lys Val Tyr Ala Cys Glu Val Thr His Gln Gly
    210                 215                 220 ctg agc tcc ccc gtc acc aag agc ttc aac agg ggg gag tgt              714
Leu Ser Ser Pro Val Thr Lys Ser Phe Asn Arg Gly Glu Cys
225                 230                 235
```

<210> SEQ ID NO 61
<211> LENGTH: 238
<212> TYPE: PRT
<213> ORGANISM: Artificial Sequence
<220> FEATURE:
<223> OTHER INFORMATION: Synthetic Construct

<400> SEQUENCE: 61

```
Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Arg Ala Ser Gln Ser
            35                  40                  45

Val Thr Ile Ser Gly Tyr Ser Phe Ile His Trp Tyr Gln Gln Lys Pro
        50                  55                  60

Gly Gln Pro Pro Lys Leu Leu Ile Tyr Arg Ala Ser Asn Leu Ala Ser
65                  70                  75                  80

Gly Val Pro Ala Arg Phe Ser Gly Ser Gly Ser Gly Thr Asp Phe Thr
                85                  90                  95
```

```
Leu Thr Ile Ser Ser Leu Gln Ala Glu Asp Val Ala Val Tyr Tyr Cys
            100                 105                 110

Gln Gln Ser Arg Lys Ser Pro Trp Thr Phe Gly Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 62
<211> LENGTH: 714
<212> TYPE: DNA
<213> ORGANISM: Artificial Sequence
<220> FEATURE:
<223> OTHER INFORMATION: h#32A1-T2L
<220> FEATURE:
<221> NAME/KEY: CDS
<222> LOCATION: (1)..(714)

<400> SEQUENCE: 62
```

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gca tat ggc gac atc gtg atg acc cag agc cct gac tcc ctt gcc      96
Gly Ala Tyr Gly Asp Ile Val Met Thr Gln Ser Pro Asp Ser Leu Ala
            20                  25                  30 gtg tcc ctg ggc gag aga gcc acc atc agc tgt aga gcc tcc cag agc     144
Val Ser Leu Gly Glu Arg Ala Thr Ile Ser Cys Arg Ala Ser Gln Ser
        35                  40                  45 gtg acc atc tcc ggc tac agc ttc atc cac tgg tac cag cag aag cct     192
Val Thr Ile Ser Gly Tyr Ser Phe Ile His Trp Tyr Gln Gln Lys Pro
    50                  55                  60 ggc cag cct cct aga ctt ctg atc tac aga gcc tcc aac ctt gcc agc     240
Gly Gln Pro Pro Arg Leu Leu Ile Tyr Arg Ala Ser Asn Leu Ala Ser
65                  70                  75                  80 ggc gtg cct gcc aga ttc tcc ggc agc ggc tcc ggc acc gac ttc acc     288
Gly Val Pro Ala Arg Phe Ser Gly Ser Gly Ser Gly Thr Asp Phe Thr
                85                  90                  95 ctg acc atc agc tcc ctt cag gcc gag gac gtg gcc gtg tac ttc tgt     336
Leu Thr Ile Ser Ser Leu Gln Ala Glu Asp Val Ala Val Tyr Phe Cys
            100                 105                 110 cag cag agc aga aag tcc cct tgg acc ttc gcc ggc ggc acc aag gtg     384
Gln Gln Ser Arg Lys Ser Pro Trp Thr Phe Ala Gly Gly Thr Lys Val
        115                 120                 125 gag atc aag cgt acg gtg gcc gcc ccc tcc gtg ttc atc ttc ccc ccc     432
Glu Ile Lys Arg Thr Val Ala Ala Pro Ser Val Phe Ile Phe Pro Pro
    130                 135                 140 tcc gac gag cag ctg aag tcc ggc acc gcc tcc gtg gtg tgc ctg ctg     480
Ser Asp Glu Gln Leu Lys Ser Gly Thr Ala Ser Val Val Cys Leu Leu
```

| | | | | | | | | | | | | | | | |
|---|---|---|---|---|---|---|---|---|---|---|---|---|---|---|---|
| | | | 145 | | | | 150 | | | | 155 | | | | 160 |

```
aat aac ttc tac ccc aga gag gcc aag gtg cag tgg aag gtg gac aac    528
Asn Asn Phe Tyr Pro Arg Glu Ala Lys Val Gln Trp Lys Val Asp Asn
            165                 170                 175 gcc ctg cag tcc ggg aac tcc cag gag agc gtg acc gag cag gac agc    576
Ala Leu Gln Ser Gly Asn Ser Gln Glu Ser Val Thr Glu Gln Asp Ser
        180                 185                 190 aag gac agc acc tac agc ctg agc agc acc ctg acc ctg agc aaa gcc    624
Lys Asp Ser Thr Tyr Ser Leu Ser Ser Thr Leu Thr Leu Ser Lys Ala
    195                 200                 205 gac tac gag aag cac aag gtg tac gcc tgc gag gtg acc cac cag ggc    672
Asp Tyr Glu Lys His Lys Val Tyr Ala Cys Glu Val Thr His Gln Gly
210                 215                 220 ctg agc tcc ccc gtc acc aag agc ttc aac agg ggg gag tgt            714
Leu Ser Ser Pro Val Thr Lys Ser Phe Asn Arg Gly Glu Cys
225                 230                 235

<210> SEQ ID NO 63
<211> LENGTH: 238
<212> TYPE: PRT
<213> ORGANISM: Artificial Sequence
<220> FEATURE:
<223> OTHER INFORMATION: Synthetic Construct

<400> SEQUENCE: 63

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Ser Cys Arg Ala Ser Gln Ser
        35                  40                  45

Val Thr Ile Ser Gly Tyr Ser Phe Ile His Trp Tyr Gln Gln Lys Pro
    50                  55                  60

Gly Gln Pro Pro Arg Leu Leu Ile Tyr Arg Ala Ser Asn Leu Ala Ser
65                  70                  75                  80

Gly Val Pro Ala Arg Phe Ser Gly Ser Gly Ser Gly Thr Asp Phe Thr
                85                  90                  95

Leu Thr Ile Ser Ser Leu Gln Ala Glu Asp Val Ala Val Tyr Phe Cys
            100                 105                 110

Gln Gln Ser Arg Lys Ser Pro Trp Thr Phe Ala Gly Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 64
```

<211> LENGTH: 714
<212> TYPE: DNA
<213> ORGANISM: Artificial Sequence
<220> FEATURE:
<223> OTHER INFORMATION: h#32A1-T3L
<220> FEATURE:
<221> NAME/KEY: CDS
<222> LOCATION: (1)..(714)

<400> SEQUENCE: 64

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gca tat ggc gac atc gtg ctt acc cag agc cct gac tcc ctt gcc      96
Gly Ala Tyr Gly Asp Ile Val Leu Thr Gln Ser Pro Asp Ser Leu Ala
                20                  25                  30 gtg tcc ctg ggc gag aga gcc acc atc agc tgt aga gcc tcc cag agc     144
Val Ser Leu Gly Glu Arg Ala Thr Ile Ser Cys Arg Ala Ser Gln Ser
            35                  40                  45 gtg acc atc tcc ggc tac agc ttc atc cac tgg tac cag cag aag cct     192
Val Thr Ile Ser Gly Tyr Ser Phe Ile His Trp Tyr Gln Gln Lys Pro
        50                  55                  60 ggc cag cag cct aga ctt ctg atc tac aga gcc tcc aac ctt gcc agc     240
Gly Gln Gln Pro Arg Leu Leu Ile Tyr Arg Ala Ser Asn Leu Ala Ser
65                  70                  75                  80 ggc atc cct gcc aga ttc tcc ggc agc ggc tcc ggc acc gac ttc acc     288
Gly Ile Pro Ala Arg Phe Ser Gly Ser Gly Ser Gly Thr Asp Phe Thr
                85                  90                  95 ctg acc atc agc tcc ctt cag gcc gag gac gtg gcc acc tac ttc tgt     336
Leu Thr Ile Ser Ser Leu Gln Ala Glu Asp Val Ala Thr Tyr Phe Cys
                100                 105                 110 cag cag agc aga aag tcc cct tgg acc ttc gcc ggc ggc acc aag gtg     384
Gln Gln Ser Arg Lys Ser Pro Trp Thr Phe Ala Gly Gly Thr Lys Val
            115                 120                 125 gag atc aag cgt acg gtg gcc gcc ccc tcc gtg ttc atc ttc ccc ccc     432
Glu Ile Lys Arg Thr Val Ala Ala Pro Ser Val Phe Ile Phe Pro Pro
        130                 135                 140 tcc gac gag cag ctg aag tcc ggc acc gcc tcc gtg gtg tgc ctg ctg     480
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac     528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc     576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc     624
Lys Asp Ser Thr Tyr Ser Leu Ser Ser Thr Leu Thr Leu Ser Lys Ala
        195                 200                 205 gac tac gag aag cac aag gtg tac gcc tgc gag gtg acc cac cag ggc     672
Asp Tyr Glu Lys His Lys Val Tyr Ala Cys Glu Val Thr His Gln Gly
    210                 215                 220 ctg agc tcc ccc gtc acc aag agc ttc aac agg ggg gag tgt              714
Leu Ser Ser Pro Val Thr Lys Ser Phe Asn Arg Gly Glu Cys
225                 230                 235
```

<210> SEQ ID NO 65
<211> LENGTH: 238
<212> TYPE: PRT
<213> ORGANISM: Artificial Sequence
<220> FEATURE:
<223> OTHER INFORMATION: Synthetic Construct -continued

```
<400> SEQUENCE: 65

Met Val Leu Gln Thr Gln Val Phe Ile Ser Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Ser Cys Arg Ala Ser Gln Ser
        35                  40                  45

Val Thr Ile Ser Gly Tyr Ser Phe Ile His Trp Tyr Gln Gln Lys Pro
    50                  55                  60

Gly Gln Gln Pro Arg Leu Leu Ile Tyr Arg Ala Ser Asn Leu Ala Ser
65                  70                  75                  80

Gly Ile Pro Ala Arg Phe Ser Gly Ser Gly Ser Thr Asp Phe Thr
                85                  90                  95

Leu Thr Ile Ser Ser Leu Gln Ala Glu Asp Val Ala Thr Tyr Phe Cys
                100                 105                 110

Gln Gln Ser Arg Lys Ser Pro Trp Thr Phe Ala Gly Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 66
<211> LENGTH: 711
<212> TYPE: DNA
<213> ORGANISM: Artificial Sequence
<220> FEATURE:
<223> OTHER INFORMATION: h#32A1-T4L
<220> FEATURE:
<221> NAME/KEY: CDS
<222> LOCATION: (1)..(711)

<400> SEQUENCE: 66 atg gtg ctg cag acc cag gtg ttc atc tcc ctg ctg tgg atc tcc       48
Met Val Leu Gln Thr Gln Val Phe Ile Ser Leu Leu Trp Ile Ser
1               5                   10                  15 ggc gca tat ggc gac atc gtg ctt acc cag agc cct gcc ctt gcc gtg   96
Gly Ala Tyr Gly Asp Ile Val Leu Thr Gln Ser Pro Ala Leu Ala Val
            20                  25                  30 tcc ctg ggc gag aga gcc acc atc agc tgt aga gcc tcc cag agc gtg   144
Ser Leu Gly Glu Arg Ala Thr Ile Ser Cys Arg Ala Ser Gln Ser Val
        35                  40                  45 acc atc tcc ggc tac agc ttc atc cac tgg tac cag cag aag cct ggc   192
Thr Ile Ser Gly Tyr Ser Phe Ile His Trp Tyr Gln Gln Lys Pro Gly
    50                  55                  60 cag cag cct aga ctt ctg atc tac aga gcc tcc aac ctt gcc agc ggc   240
Gln Gln Pro Arg Leu Leu Ile Tyr Arg Ala Ser Asn Leu Ala Ser Gly
65                  70                  75                  80
```

```
atc cct gcc aga ttc tcc ggc agc ggc tcc ggc acc gac ttc acc ctg    288
Ile Pro Ala Arg Phe Ser Gly Ser Gly Ser Gly Thr Asp Phe Thr Leu
                85                  90                  95 acc atc agc tcc ctt cag gcc gag gac gtg gcc acc tac ttc tgt cag    336
Thr Ile Ser Ser Leu Gln Ala Glu Asp Val Ala Thr Tyr Phe Cys Gln
            100                 105                 110 cag agc aga aag tcc cct tgg acc ttc gcc ggc ggc acc aag ctg gag    384
Gln Ser Arg Lys Ser Pro Trp Thr Phe Ala Gly Gly Thr Lys Leu Glu
        115                 120                 125 atc aag cgt acg gtg gcc gcc ccc tcc gtg ttc atc ttc ccc ccc tcc    432
Ile Lys Arg Thr Val Ala Ala Pro Ser Val Phe Ile Phe Pro Pro Ser
    130                 135                 140 gac gag cag ctg aag tcc ggc acc gcc tcc gtg gtg tgc ctg ctg aat    480
Asp Glu Gln Leu Lys Ser Gly Thr Ala Ser Val Val Cys Leu Leu Asn
145                 150                 155                 160 aac ttc tac ccc aga gag gcc aag gtg cag tgg aag gtg gac aac gcc    528
Asn Phe Tyr Pro Arg Glu Ala Lys Val Gln Trp Lys Val Asp Asn Ala
                165                 170                 175 ctg cag tcc ggg aac tcc cag gag agc gtg acc gag cag gac agc aag    576
Leu Gln Ser Gly Asn Ser Gln Glu Ser Val Thr Glu Gln Asp Ser Lys
            180                 185                 190 gac agc acc tac agc ctg agc agc acc ctg acc ctg agc aaa gcc gac    624
Asp Ser Thr Tyr Ser Leu Ser Ser Thr Leu Thr Leu Ser Lys Ala Asp
        195                 200                 205 tac gag aag cac aag gtg tac gcc tgc gag gtg acc cac cag ggc ctg    672
Tyr Glu Lys His Lys Val Tyr Ala Cys Glu Val Thr His Gln Gly Leu
    210                 215                 220 agc tcc ccc gtc acc aag agc ttc aac agg ggg gag tgt                711
Ser Ser Pro Val Thr Lys Ser Phe Asn Arg Gly Glu Cys
225                 230                 235
```

<210> SEQ ID NO 67
<211> LENGTH: 237
<212> TYPE: PRT
<213> ORGANISM: Artificial Sequence
<220> FEATURE:
<223> OTHER INFORMATION: Synthetic Construct

<400> SEQUENCE: 67

```
Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Ala Leu Ala Val
            20                  25                  30

Ser Leu Gly Glu Arg Ala Thr Ile Ser Cys Arg Ala Ser Gln Ser Val
        35                  40                  45

Thr Ile Ser Gly Tyr Ser Phe Ile His Trp Tyr Gln Gln Lys Pro Gly
    50                  55                  60

Gln Gln Pro Arg Leu Leu Ile Tyr Arg Ala Ser Asn Leu Ala Ser Gly
65                  70                  75                  80

Ile Pro Ala Arg Phe Ser Gly Ser Gly Ser Gly Thr Asp Phe Thr Leu
                85                  90                  95

Thr Ile Ser Ser Leu Gln Ala Glu Asp Val Ala Thr Tyr Phe Cys Gln
            100                 105                 110

Gln Ser Arg Lys Ser Pro Trp Thr Phe Ala Gly Gly Thr Lys Leu Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
```

| | | | | | | | | | | | | | | | | |
|---|---|---|---|---|---|---|---|---|---|---|---|---|---|---|---|---|
| | | | 145 | | | 150 | | | | 155 | | | | 160 | | |

Asn Phe Tyr Pro Arg Glu Ala Lys Val Gln Trp Lys Val Asp Asn Ala
                  165                    170                  175

Leu Gln Ser Gly Asn Ser Gln Glu Ser Val Thr Glu Gln Asp Ser Lys
           180                   185                   190

Asp Ser Thr Tyr Ser Leu Ser Ser Thr Leu Thr Leu Ser Lys Ala Asp
            195                 200                205

Tyr Glu Lys His Lys Val Tyr Ala Cys Glu Val Thr His Gln Gly Leu
        210                   215                220

Ser Ser Pro Val Thr Lys Ser Phe Asn Arg Gly Glu Cys
225             230                 235

<210> SEQ ID NO 68
<211> LENGTH: 714
<212> TYPE: DNA
<213> ORGANISM: Artificial Sequence
<220> FEATURE:
<223> OTHER INFORMATION: h#32A1-T5L
<220> FEATURE:
<221> NAME/KEY: CDS
<222> LOCATION: (1)..(714)

<400> SEQUENCE: 68

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gca tat ggc gac atc gtg ctt acc cag agc cct gac tcc ctt gcc      96
Gly Ala Tyr Gly Asp Ile Val Leu Thr Gln Ser Pro Asp Ser Leu Ala
            20                  25                  30 gtg tcc ctg ggc gag aga gcc acc atc aac tgt aga gcc tcc cag agc     144
Val Ser Leu Gly Glu Arg Ala Thr Ile Asn Cys Arg Ala Ser Gln Ser
        35                  40                  45 gtg acc atc tcc ggc tac agc ttc atc cac tgg tac cag cag aag cct     192
Val Thr Ile Ser Gly Tyr Ser Phe Ile His Trp Tyr Gln Gln Lys Pro
    50                  55                  60 ggc cag cct cct aag ctt ctg atc tac aga gcc tcc aac ctt gcc agc     240
Gly Gln Pro Pro Lys Leu Leu Ile Tyr Arg Ala Ser Asn Leu Ala Ser
65                  70                  75                  80 ggc atc cct gcc aga ttc tcc ggc agc ggc tcc ggc acc gac ttc acc     288
Gly Ile Pro Ala Arg Phe Ser Gly Ser Gly Ser Gly Thr Asp Phe Thr
                85                  90                  95 ctg acc atc agc tcc ctt cag gcc gag gac gtg gcc acc tac tac tgt     336
Leu Thr Ile Ser Ser Leu Gln Ala Glu Asp Val Ala Thr Tyr Tyr Cys
            100                 105                 110 cag cag agc aga aag tcc cct tgg acc ttc ggc cag ggc acc aag gtg     384
Gln Gln Ser Arg Lys Ser Pro Trp Thr Phe Gly Gln Gly Thr Lys Val
        115                 120                 125 gag atc aag cgt acg gtg gcc gcc ccc tcc gtg ttc atc ttc ccc ccc     432
Glu Ile Lys Arg Thr Val Ala Ala Pro Ser Val Phe Ile Phe Pro Pro
    130                 135                 140 tcc gac gag cag ctg aag tcc ggc acc gcc tcc gtg gtg tgc ctg ctg     480
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac     528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc     576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc     624
Lys Asp Ser Thr Tyr Ser Leu Ser Ser Thr Leu Thr Leu Ser Lys Ala
```

```
Lys Asp Ser Thr Tyr Ser Leu Ser Ser Thr Leu Thr Leu Ser Lys Ala
            195                 200                 205 gac tac gag aag cac aag gtg tac gcc tgc gag gtg acc cac cag ggc     672
Asp Tyr Glu Lys His Lys Val Tyr Ala Cys Glu Val Thr His Gln Gly
        210                 215                 220 ctg agc tcc ccc gtc acc aag agc ttc aac agg ggg gag tgt             714
Leu Ser Ser Pro Val Thr Lys Ser Phe Asn Arg Gly Glu Cys
225                 230                 235

<210> SEQ ID NO 69
<211> LENGTH: 238
<212> TYPE: PRT
<213> ORGANISM: Artificial Sequence
<220> FEATURE:
<223> OTHER INFORMATION: Synthetic Construct

<400> SEQUENCE: 69

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Asn Cys Arg Ala Ser Gln Ser
        35                  40                  45

Val Thr Ile Ser Gly Tyr Ser Phe Ile His Trp Tyr Gln Gln Lys Pro
    50                  55                  60

Gly Gln Pro Pro Lys Leu Leu Ile Tyr Arg Ala Ser Asn Leu Ala Ser
65                  70                  75                  80

Gly Ile Pro Ala Arg Phe Ser Gly Ser Gly Ser Gly Thr Asp Phe Thr
                85                  90                  95

Leu Thr Ile Ser Ser Leu Gln Ala Glu Asp Val Ala Thr Tyr Tyr Cys
            100                 105                 110

Gln Gln Ser Arg Lys Ser Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 70
<211> LENGTH: 714
<212> TYPE: DNA
<213> ORGANISM: Artificial Sequence
<220> FEATURE:
<223> OTHER INFORMATION: h#32A1-T6L
<220> FEATURE:
<221> NAME/KEY: CDS
<222> LOCATION: (1)..(714)

<400> SEQUENCE: 70
```

| | | |
|---|---|---|
| atg gtg ctg cag acc cag gtg ttc atc tcc ctg ctg ctg tgg atc tcc<br>Met Val Leu Gln Thr Gln Val Phe Ile Ser Leu Leu Leu Trp Ile Ser<br>1               5                   10                  15 | | 48 |
| ggc gca tat ggc gac atc gtg ctt acc cag agc cct gac tcc ctt gcc<br>Gly Ala Tyr Gly Asp Ile Val Leu Thr Gln Ser Pro Asp Ser Leu Ala<br>            20                  25                  30 | | 96 |
| gtg tcc ctg ggc gag aga gcc acc atc agc tgt aga gcc tcc cag agc<br>Val Ser Leu Gly Glu Arg Ala Thr Ile Ser Cys Arg Ala Ser Gln Ser<br>        35                  40                  45 | | 144 |
| gtg acc atc tcc ggc tac agc ttc atc cac tgg tac cag cag aag cct<br>Val Thr Ile Ser Gly Tyr Ser Phe Ile His Trp Tyr Gln Gln Lys Pro<br>    50                  55                  60 | | 192 |
| ggc cag cct cct aga ctg ctg atc tac aga gcc tcc aac ctt gcc agc<br>Gly Gln Pro Pro Arg Leu Leu Ile Tyr Arg Ala Ser Asn Leu Ala Ser<br>65                  70                  75                  80 | | 240 |
| ggc atc cct gcc aga ttc tcc ggc agc ggc tcc ggc acc gac ttc acc<br>Gly Ile Pro Ala Arg Phe Ser Gly Ser Gly Ser Gly Thr Asp Phe Thr<br>                85                  90                  95 | | 288 |
| ctg acc atc agc tcc ctt cag gcc gag gac gtg gcc acc tac ttc tgt<br>Leu Thr Ile Ser Ser Leu Gln Ala Glu Asp Val Ala Thr Tyr Phe Cys<br>            100                 105                 110 | | 336 |
| cag cag agc aga aag tcc cct tgg acc ttc gcc ggc ggc acc aag gtg<br>Gln Gln Ser Arg Lys Ser Pro Trp Thr Phe Ala Gly Gly Thr Lys Val<br>        115                 120                 125 | | 384 |
| gag atc aag cgt acg gtg gcc gcc ccc tcc gtg ttc atc ttc ccc ccc<br>Glu Ile Lys Arg Thr Val Ala Ala Pro Ser Val Phe Ile Phe Pro Pro<br>    130                 135                 140 | | 432 |
| tcc gac gag cag ctg aag tcc ggc acc gcc tcc gtg gtg tgc ctg ctg<br>Ser Asp Glu Gln Leu Lys Ser Gly Thr Ala Ser Val Val Cys Leu Leu<br>145                 150                 155                 160 | | 480 |
| aat aac ttc tac ccc aga gag gcc aag gtg cag tgg aag gtg gac aac<br>Asn Asn Phe Tyr Pro Arg Glu Ala Lys Val Gln Trp Lys Val Asp Asn<br>                165                 170                 175 | | 528 |
| gcc ctg cag tcc ggg aac tcc cag gag agc gtg acc gag cag gac agc<br>Ala Leu Gln Ser Gly Asn Ser Gln Glu Ser Val Thr Glu Gln Asp Ser<br>            180                 185                 190 | | 576 |
| aag gac agc acc tac agc ctg agc agc acc ctg acc ctg agc aaa gcc<br>Lys Asp Ser Thr Tyr Ser Leu Ser Ser Thr Leu Thr Leu Ser Lys Ala<br>        195                 200                 205 | | 624 |
| gac tac gag aag cac aag gtg tac gcc tgc gag gtg acc cac cag ggc<br>Asp Tyr Glu Lys His Lys Val Tyr Ala Cys Glu Val Thr His Gln Gly<br>    210                 215                 220 | | 672 |
| ctg agc tcc ccc gtc acc aag agc ttc aac agg ggg gag tgt<br>Leu Ser Ser Pro Val Thr Lys Ser Phe Asn Arg Gly Glu Cys<br>225                 230                 235 | | 714 |

<210> SEQ ID NO 71
<211> LENGTH: 238
<212> TYPE: PRT
<213> ORGANISM: Artificial Sequence
<220> FEATURE:
<223> OTHER INFORMATION: Synthetic Construct

<400> SEQUENCE: 71

Met Val Leu Gln Thr Gln Val Phe Ile Ser Leu Leu Leu Trp Ile Ser
1               5                   10                  15

Gly Ala Tyr Gly Asp Ile Val Leu Thr Gln Ser Pro Asp Ser Leu Ala
            20                  25                  30

Val Ser Leu Gly Glu Arg Ala Thr Ile Ser Cys Arg Ala Ser Gln Ser
        35                  40                  45

```
Val Thr Ile Ser Gly Tyr Ser Phe Ile His Trp Tyr Gln Gln Lys Pro
 50                  55                  60

Gly Gln Pro Pro Arg Leu Leu Ile Tyr Arg Ala Ser Asn Leu Ala Ser
 65                  70                  75                  80

Gly Ile Pro Ala Arg Phe Ser Gly Ser Gly Ser Gly Thr Asp Phe Thr
                 85                  90                  95

Leu Thr Ile Ser Ser Leu Gln Ala Glu Asp Val Ala Thr Tyr Phe Cys
            100                 105                 110

Gln Gln Ser Arg Lys Ser Pro Trp Thr Phe Ala Gly Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 72
<211> LENGTH: 451
<212> TYPE: PRT
<213> ORGANISM: Artificial Sequence
<220> FEATURE:
<223> OTHER INFORMATION: h#32A1-T7H

<400> SEQUENCE: 72

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Phe Asn Asp Tyr
                20                  25                  30

Phe Met Asn Trp Val Arg Gln Ala Pro Glu Lys Gly Leu Glu Trp Val
            35                  40                  45

Ala Gln Ile Arg Asn Lys Ile Tyr Thr Tyr Ala Thr Phe Tyr Ala Glu
 50                  55                  60

Ser Leu Glu Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                 90                  95

Tyr Cys Ala Arg Ser Leu Thr Gly Gly Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 73
<211> LENGTH: 451
<212> TYPE: PRT
<213> ORGANISM: Artificial Sequence
<220> FEATURE:
<223> OTHER INFORMATION: h#32A1-T8H

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
            35                  40                  45

Ala Gln Ile Arg Asn Lys Ile Tyr Thr Tyr Ala Thr Phe Tyr Ala Glu
            50                  55                  60

Ser Leu Glu Gly Arg Val Thr Ile Ser Arg Asp Asn Ala Lys Asn Ser
65                  70                  75                  80

```
Leu Tyr Leu Gln Met Asn Ser Leu Arg Ala Glu Asp Thr Ala Val Tyr
                85                  90                  95

Tyr Cys Ala Arg Ser Leu Thr Gly Gly Asp Tyr Phe Asp Tyr Trp Gly
           100                 105                 110

Gln Gly Thr Leu Val Thr Val Ser Ser Ala Ser Thr Lys Gly Pro Ser
       115                 120                 125

Val Phe Pro Leu Ala Pro Ser Ser Lys Ser Thr Ser Gly Gly Thr Ala
   130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
               165                 170                 175

Val Leu Gln Ser Ser Gly Leu Tyr Ser Leu Ser Ser Val Val Thr Val
           180                 185                 190

Pro Ser Ser Ser Leu Gly Thr Gln Thr Tyr Ile Cys Asn Val Asn His
       195                 200                 205

Lys Pro Ser Asn Thr Lys Val Asp Lys Arg Val Glu Pro Lys Ser Cys
   210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
               245                 250                 255

Ile Ser Arg Thr Pro Glu Val Thr Cys Val Val Val Asp Val Ser His
           260                 265                 270

Glu Asp Pro Glu Val Lys Phe Asn Trp Tyr Val Asp Gly Val Glu Val
       275                 280                 285

His Asn Ala Lys Thr Lys Pro Arg Glu Glu Gln Tyr Asn Ser Thr Tyr
   290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
               325                 330                 335

Glu Lys Thr Ile Ser Lys Ala Lys Gly Gln Pro Arg Glu Pro Gln Val
           340                 345                 350

Tyr Thr Leu Pro Pro Ser Arg Glu Glu Met Thr Lys Asn Gln Val Ser
       355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
               405                 410                 415

Asp Lys Ser Arg Trp Gln Gln Gly Asn Val Phe Ser Cys Ser Val Met
           420                 425                 430

His Glu Ala Leu His Asn His Tyr Thr Gln Lys Ser Leu Ser Leu Ser
       435                 440                 445

Pro Gly Lys
    450

<210> SEQ ID NO 74
<211> LENGTH: 451
<212> TYPE: PRT
<213> ORGANISM: Artificial Sequence
<220> FEATURE:
<223> OTHER INFORMATION: h#32A1-T9H
```

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Gly Lys Gly Leu Glu Trp Val
        35                  40                  45

Ala Gln Ile Arg Asn Lys Ile Tyr Thr Tyr Ala Thr Phe Tyr Ala Glu
    50                  55                  60

Ser Leu Glu Gly Arg Phe Thr Ile Ser Arg Asp Asn Ala Lys Asn Ser
65                  70                  75                  80

Leu Tyr Leu Gln Met Ser Ser Leu Arg Ala Glu Asp Thr Ala Val Tyr
                85                  90                  95

Tyr Cys Ala Arg Ser Leu Thr Gly Gly Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val

```
                      405                 410                 415
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 75
<211> LENGTH: 451
<212> TYPE: PRT
<213> ORGANISM: Artificial Sequence
<220> FEATURE:
<223> OTHER INFORMATION: h#32A1-T10H

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
            20                  25                  30

Phe Met Asn Trp Val Arg Gln Ala Pro Glu Lys Gly Leu Glu Trp Val
        35                  40                  45

Ala Gln Ile Arg Asn Lys Ile Tyr Thr Tyr Ala Thr Phe Tyr Ala Glu
    50                  55                  60

Ser Leu Glu Gly Arg Val Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Ser Leu Thr Gly Gly Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
305                 310                 315                 320
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 76
<211> LENGTH: 451
<212> TYPE: PRT
<213> ORGANISM: Artificial Sequence
<220> FEATURE:
<223> OTHER INFORMATION: h#32A1-T11H

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
                20                  25                  30

Phe Met Asn Trp Val Arg Gln Ala Pro Glu Lys Gly Leu Glu Trp Val
            35                  40                  45

Ala Gln Ile Arg Asn Lys Ile Tyr Thr Tyr Ala Thr Phe Tyr Ala Glu
50                  55                  60

Ser Leu Glu Gly Arg Phe Thr Ile Ser Arg Asp Asn Ala Lys Asn Ser
65                  70                  75                  80

Leu Tyr Leu Gln Met Ser Ser Leu Arg Ala Glu Asp Thr Ala Val Tyr
                85                  90                  95

Tyr Cys Ala Arg Ser Leu Thr Gly Gly Asp Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
```

```
                  210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 77
<211> LENGTH: 451
<212> TYPE: PRT
<213> ORGANISM: Artificial Sequence
<220> FEATURE:
<223> OTHER INFORMATION: h#32A1-T12H

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Phe Asn Asp Tyr
                20                  25                  30

Phe Met Asn Trp Val Arg Gln Ala Pro Gly Lys Gly Leu Glu Trp Val
            35                  40                  45

Ala Gln Ile Arg Asn Lys Ile Tyr Thr Tyr Ala Thr Phe Tyr Ala Glu
        50                  55                  60

Ser Leu Glu Gly Arg Val Thr Ile Ser Arg Asp Asn Ala Lys Asn Ser
65                  70                  75                  80

Leu Tyr Leu Gln Met Ser Ser Leu Arg Ala Glu Asp Thr Ala Val Tyr
                85                  90                  95

Tyr Cys Ala Arg Ser Leu Thr Gly Gly Asp Tyr Phe Asp Tyr Trp Gly
            100                 105                 110

Gln Gly Thr Leu Val Thr Val Ser Ser Ala Ser Thr Lys Gly Pro Ser
```

|   | 115 |   |   |   | 120 |   |   |   | 125 |   |   |
|---|---|---|---|---|---|---|---|---|---|---|---|

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 78
<211> LENGTH: 218
<212> TYPE: PRT
<213> ORGANISM: Artificial Sequence
<220> FEATURE:
<223> OTHER INFORMATION: h#32A1-T7L

<400> SEQUENCE: 78

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Thr Ile Ser

```
            20                  25                  30
Gly Tyr Ser Phe Ile His Trp Tyr Gln Gln Lys Pro Gly Gln Pro Pro
            35                  40                  45

Lys Leu Leu Ile Tyr Arg Ala Ser Asn Leu Ala Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Ser Pro Trp Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 79
<211> LENGTH: 218
<212> TYPE: PRT
<213> ORGANISM: Artificial Sequence
<220> FEATURE:
<223> OTHER INFORMATION: h#32A1-T8L

<400> SEQUENCE: 79

Asp Ile Val Met Thr Gln Ser Pro Asp Ser Leu Ala Val Ser Leu Gly
 1               5                  10                  15

Glu Arg Ala Thr Ile Asn Cys Arg Ala Ser Gln Ser Val Thr Ile Ser
            20                  25                  30

Gly Tyr Ser Phe Ile His Trp Tyr Gln Gln Lys Pro Gly Gln Pro Pro
            35                  40                  45

Arg Leu Leu Ile Tyr Arg Ala Ser Asn Leu Ala Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Ser Pro Trp Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

-continued 165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
        210                 215

<210> SEQ ID NO 80
<211> LENGTH: 218
<212> TYPE: PRT
<213> ORGANISM: Artificial Sequence
<220> FEATURE:
<223> OTHER INFORMATION: h#32A1-T9L

<400> SEQUENCE: 80

Asp Ile Val Met Thr Gln Ser Pro Asp Ser Leu Ala Val Ser Leu Gly
1               5                   10                  15
Glu Arg Ala Thr Ile Asn Cys Arg Ala Ser Gln Ser Val Thr Ile Ser
            20                  25                  30
Gly Tyr Ser Phe Ile His Trp Tyr Gln Gln Lys Pro Gly Gln Pro Pro
        35                  40                  45
Lys Leu Leu Ile Tyr Arg Ala Ser Asn Leu Ala Ser Gly Val Pro Ala
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Phe Cys Gln Gln Ser Arg
                85                  90                  95
Lys Ser Pro Trp Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
        210                 215

<210> SEQ ID NO 81
<211> LENGTH: 218
<212> TYPE: PRT
<213> ORGANISM: Artificial Sequence
<220> FEATURE:
<223> OTHER INFORMATION: h#32A1-T10L

<400> SEQUENCE: 81

Asp Ile Val Met Thr Gln Ser Pro Asp Ser Leu Ala Val Ser Leu Gly
1               5                   10                  15
Glu Arg Ala Thr Ile Asn Cys Arg Ala Ser Gln Ser Val Thr Ile Ser
            20                  25                  30

-continued

```
Gly Tyr Ser Phe Ile His Trp Tyr Gln Gln Lys Pro Gly Gln Pro Pro
         35                  40                  45

Lys Leu Leu Ile Tyr Arg Ala Ser Asn Leu Ala Ser Gly Val Pro Ala
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Ser Pro Trp Thr Phe Ala Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215
```

<210> SEQ ID NO 82
<211> LENGTH: 218
<212> TYPE: PRT
<213> ORGANISM: Artificial Sequence
<220> FEATURE:
<223> OTHER INFORMATION: h#32A1-T11L

<400> SEQUENCE: 82

```
Asp Ile Val Met Thr Gln Ser Pro Asp Ser Leu Ala Val Ser Leu Gly
 1               5                  10                  15

Glu Arg Ala Thr Ile Ser Cys Arg Ala Ser Gln Ser Val Thr Ile Ser
             20                  25                  30

Gly Tyr Ser Phe Ile His Trp Tyr Gln Gln Lys Pro Gly Gln Pro Pro
         35                  40                  45

Arg Leu Leu Ile Tyr Arg Ala Ser Asn Leu Ala Ser Gly Val Pro Ala
 50                      55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Ser Pro Trp Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 83
<211> LENGTH: 218
<212> TYPE: PRT
<213> ORGANISM: Artificial Sequence
<220> FEATURE:
<223> OTHER INFORMATION: h#32A1-T12L

<400> SEQUENCE: 83

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45

Lys Leu Leu Ile Tyr Arg Ala Ser Asn Leu Ala Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Phe Cys Gln Gln Ser Arg
                85                  90                  95

Lys Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 84
<211> LENGTH: 218
<212> TYPE: PRT
<213> ORGANISM: Artificial Sequence
<220> FEATURE:
<223> OTHER INFORMATION: h#32A1-T13L

<400> SEQUENCE: 84

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45
```

Lys Leu Leu Ile Tyr Arg Ala Ser Asn Leu Ala Ser Gly Val Pro Ala
             50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Arg
                 85                  90                  95

Lys Ser Pro Trp Thr Phe Ala Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
            210                 215

<210> SEQ ID NO 85
<211> LENGTH: 218
<212> TYPE: PRT
<213> ORGANISM: Artificial Sequence
<220> FEATURE:
<223> OTHER INFORMATION: h#32A1-T14L

<400> SEQUENCE: 85

Asp Ile Val Met Thr Gln Ser Pro Asp Ser Leu Ala Val Ser Leu Gly
 1               5                  10                  15

Glu Arg Ala Thr Ile Asn Cys Arg Ala Ser Gln Ser Val Thr Ile Ser
                 20                  25                  30

Gly Tyr Ser Phe Ile His Trp Tyr Gln Gln Lys Pro Gly Gln Pro Pro
             35                  40                  45

Arg Leu Leu Ile Tyr Arg Ala Ser Asn Leu Ala Ser Gly Val Pro Ala
             50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Phe Cys Gln Gln Ser Arg
                 85                  90                  95

Lys Ser Pro Trp Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

-continued

```
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 86
<211> LENGTH: 218
<212> TYPE: PRT
<213> ORGANISM: Artificial Sequence
<220> FEATURE:
<223> OTHER INFORMATION: h#32A1-T15L

<400> SEQUENCE: 86

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45

Arg Leu Leu Ile Tyr Arg Ala Ser Asn Leu Ala Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 87
<211> LENGTH: 218
<212> TYPE: PRT
<213> ORGANISM: Artificial Sequence
<220> FEATURE:
<223> OTHER INFORMATION: h#32A1-T16L

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45

Lys Leu Leu Ile Tyr Arg Ala Ser Asn Leu Ala Ser Gly Val Pro Ala
```

```
                  50                  55                  60
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Phe Cys Gln Gln Ser Arg
                 85                  90                  95

Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 88
<211> LENGTH: 218
<212> TYPE: PRT
<213> ORGANISM: Artificial Sequence
<220> FEATURE:
<223> OTHER INFORMATION: h#32A1-T17L

<400> SEQUENCE: 88

Asp Ile Val Met Thr Gln Ser Pro Asp Ser Leu Ala Val Ser Leu Gly
 1               5                  10                  15

Glu Arg Ala Thr Ile Ser Cys Arg Ala Ser Gln Ser Val Thr Ile Ser
             20                  25                  30

Gly Tyr Ser Phe Ile His Trp Tyr Gln Gln Lys Pro Gly Gln Pro Pro
         35                  40                  45

Arg Leu Leu Ile Tyr Arg Ala Ser Asn Leu Ala Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Phe Cys Gln Gln Ser Arg
                 85                  90                  95

Lys Ser Pro Trp Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
```

```
                    195                 200                 205

Val Thr Lys Ser Phe Asn Arg Gly Glu Cys
    210                 215

<210> SEQ ID NO 89
<211> LENGTH: 218
<212> TYPE: PRT
<213> ORGANISM: Artificial Sequence
<220> FEATURE:
<223> OTHER INFORMATION: h#32A1-T18L

<400> SEQUENCE: 89

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45

Arg Leu Leu Ile Tyr Arg Ala Ser Asn Leu Ala Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Arg
                85                  90                  95

Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 90
<211> LENGTH: 218
<212> TYPE: PRT
<213> ORGANISM: Artificial Sequence
<220> FEATURE:
<223> OTHER INFORMATION: h#32A1-T19L

<400> SEQUENCE: 90

Asp Ile Val Met Thr Gln Ser Pro Asp Ser Leu Ala Val Ser Leu Gly
1               5                   10                  15

Glu Arg Ala Thr Ile Ser Cys Arg Ala Ser Gln Ser Val Thr Ile Ser
            20                  25                  30

Gly Tyr Ser Phe Ile His Trp Tyr Gln Gln Lys Pro Gly Gln Pro Pro
        35                  40                  45

Lys Leu Leu Ile Tyr Arg Ala Ser Asn Leu Ala Ser Gly Val Pro Ala
    50                  55                  60
```

```
Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Phe Cys Gln Gln Ser Arg
                 85                  90                  95

Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 91
<211> LENGTH: 218
<212> TYPE: PRT
<213> ORGANISM: Artificial Sequence
<220> FEATURE:
<223> OTHER INFORMATION: h#32A1-T20L

<400> SEQUENCE: 91

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Gln Ser Val Thr Ile Ser
                 20                  25                  30

Gly Tyr Ser Phe Ile His Trp Tyr Gln Gln Lys Pro Gly Gln Pro Pro
             35                  40                  45

Arg Leu Leu Ile Tyr Arg Ala Ser Asn Leu Ala Ser Gly Val Pro Ala
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Phe Cys Gln Gln Ser Arg
                 85                  90                  95

Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

<210> SEQ ID NO 92
<211> LENGTH: 218
<212> TYPE: PRT
<213> ORGANISM: Artificial Sequence
<220> FEATURE:
<223> OTHER INFORMATION: h#32A1-T21L

<400> SEQUENCE: 92

```
Glu Ile Leu Met Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ile Ser
            20                  25                  30

Gly Tyr Ser Phe Ile His Trp Tyr Gln Gln Lys Pro Gly Gln Ala Pro
        35                  40                  45

Arg Leu Leu Ile Tyr Arg Ala Ser Asn Leu Ala Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Leu Tyr Tyr Cys Gln Gln Ser Arg
                85                  90                  95

Lys Ser Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 93
<211> LENGTH: 218
<212> TYPE: PRT
<213> ORGANISM: Artificial Sequence
<220> FEATURE:
<223> OTHER INFORMATION: h#32A1-T22L

<400> SEQUENCE: 93

```
Glu Ile Leu Met Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ile Ser
            20                  25                  30

Gly Tyr Ser Phe Ile His Trp Tyr Gln Gln Lys Pro Gly Gln Ala Pro
        35                  40                  45

Arg Leu Leu Ile Tyr Arg Ala Ser Asn Leu Ala Ser Gly Ile Pro Ala
    50                  55                  60

Arg Phe Ser Gly Ser Gly Ser Gly Thr Asp Phe Thr Leu Thr Ile Ser
65                  70                  75                  80
```

```
Ser Leu Glu Pro Glu Asp Phe Ala Leu Tyr Phe Cys Gln Gln Ser Arg
                85                  90                  95

Lys Ser Pro Trp Thr Phe Ala Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 94
<211> LENGTH: 218
<212> TYPE: PRT
<213> ORGANISM: Artificial Sequence
<220> FEATURE:
<223> OTHER INFORMATION: h#32A1-T23L

<400> SEQUENCE: 94

Glu Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ile Ser
            20                  25                  30

Gly Tyr Ser Phe Ile His Trp Tyr Gln Gln Lys Pro Gly Gln Ala Pro
        35                  40                  45

Arg Leu Leu Ile Tyr Arg Ala Ser Asn Leu Ala Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Leu Tyr Tyr Cys Gln Gln Ser Arg
                85                  90                  95

Lys Ser Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 95
<211> LENGTH: 218
<212> TYPE: PRT
<213> ORGANISM: Artificial Sequence
<220> FEATURE:
<223> OTHER INFORMATION: h#32A1-T24L

<400> SEQUENCE: 95

Glu Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ile Ser
            20                  25                  30

Gly Tyr Ser Phe Ile His Trp Tyr Gln Gln Lys Pro Gly Gln Ala Pro
        35                  40                  45

Arg Leu Leu Ile Tyr Arg Ala Ser Asn Leu Ala Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Leu Tyr Tyr Cys Gln Gln Ser Arg
                85                  90                  95

Lys Ser Pro Trp Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 96
<211> LENGTH: 218
<212> TYPE: PRT
<213> ORGANISM: Artificial Sequence
<220> FEATURE:
<223> OTHER INFORMATION: h#32A1-T25L

<400> SEQUENCE: 96

Asp Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Thr Ile Ser
            20                  25                  30

Gly Tyr Ser Phe Ile His Trp Tyr Gln Gln Lys Pro Gly Gln Gln Pro
        35                  40                  45

Arg Leu Leu Ile Tyr Arg Ala Ser Asn Leu Ala Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Thr Tyr Phe Cys Gln Gln Ser Arg

```
                 85                 90                  95
Lys Ser Pro Trp Thr Phe Ala Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 97
<211> LENGTH: 14
<212> TYPE: PRT
<213> ORGANISM: Rattus norvegicus

<400> SEQUENCE: 97

```
Gln Ile Arg Asn Lys Ile Tyr Thr Tyr Ala Thr Phe Tyr Ala
1               5                   10
```

<210> SEQ ID NO 98
<211> LENGTH: 1398
<212> TYPE: DNA
<213> ORGANISM: Artificial Sequence
<220> FEATURE:
<223> OTHER INFORMATION: h#32A1-H1-1
<220> FEATURE:
<221> NAME/KEY: CDS
<222> LOCATION: (1)..(1398)

<400> SEQUENCE: 98

```
atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtc cag ctt gtg gaa agc gga ggg gga ctc gtt cag      96
Val Leu Ser Glu Val Gln Leu Val Glu Ser Gly Gly Gly Leu Val Gln
            20                  25                  30 cca gga ggc tct ctg cgc ctg tca tgc gct gcc agc gga ttt aat ttc     144
Pro Gly Gly Ser Leu Arg Leu Ser Cys Ala Ala Ser Gly Phe Asn Phe
        35                  40                  45 aat gat tat ttt atg aac tgg gtc agg cag gct ccg gga aaa ggg ctg     192
Asn Asp Tyr Phe Met Asn Trp Val Arg Gln Ala Pro Gly Lys Gly Leu
    50                  55                  60 gaa tgg gtc gcc cag atc aga aac aag atc tat act tac gct aca ttc     240
Glu Trp Val Ala Gln Ile Arg Asn Lys Ile Tyr Thr Tyr Ala Thr Phe
65                  70                  75                  80 tac gcc gca tct gta aag ggg agg ttt aca att agt cgc gac aat gca     288
Tyr Ala Ala Ser Val Lys Gly Arg Phe Thr Ile Ser Arg Asp Asn Ala
                85                  90                  95 aaa aat agt ctg tat ctc caa atg aac tcc ctc cgc gca gag gat act     336
Lys Asn Ser Leu Tyr Leu Gln Met Asn Ser Leu Arg Ala Glu Asp Thr
            100                 105                 110 gct gtc tac tac tgc gcc agg tcc ttg act ggc ggc gac tat ttt gat     384
Ala Val Tyr Tyr Cys Ala Arg Ser Leu Thr Gly Gly Asp Tyr Phe Asp
```

```
                Ala Val Tyr Tyr Cys Ala Arg Ser Leu Thr Gly Gly Asp Tyr Phe Asp
                            115                 120                 125 tac tgg gga cag ggc acc ctg gtg acg gtg agc tca gcc agc acc aag              432
Tyr Trp Gly Gln Gly Thr Leu Val Thr Val Ser Ser Ala Ser Thr Lys
130                 135                 140 ggc cct tcc gtg ttc cct ctg gcc cct tgt agc cgt tcc acc agc gag              480
Gly Pro Ser Val Phe Pro Leu Ala Pro Cys Ser Arg Ser Thr Ser Glu
145                 150                 155                 160 tcc acc gcc gcc ctt ggc tgt ctg gtg aag gac tac ttc cct gag cct              528
Ser Thr Ala Ala Leu Gly Cys Leu Val Lys Asp Tyr Phe Pro Glu Pro
                165                 170                 175 gtg acc gtg agc tgg aac tcc gga gcc ctt acc agc ggc gtg cac acc              576
Val Thr Val Ser Trp Asn Ser Gly Ala Leu Thr Ser Gly Val His Thr
            180                 185                 190 ttc cct gcc gtg ctg cag tcc agc ggc ctt tac tcc ctg agc tcc gtg              624
Phe Pro Ala Val Leu Gln Ser Ser Gly Leu Tyr Ser Leu Ser Ser Val
        195                 200                 205 gtg acc gtg cct agc tcc aac ttc ggc acc caa acc tac acc tgt aac              672
Val Thr Val Pro Ser Ser Asn Phe Gly Thr Gln Thr Tyr Thr Cys Asn
210                 215                 220 gtg gac cac aag cct agc aac acc aag gtg gac aag acc gtg gag cgt              720
Val Asp His Lys Pro Ser Asn Thr Lys Val Asp Lys Thr Val Glu Arg
225                 230                 235                 240 aag tgt tgt gtg gag tgt cct cct tgt cct gcc cct cct gtg gcc gga              768
Lys Cys Cys Val Glu Cys Pro Pro Cys Pro Ala Pro Pro Val Ala Gly
                245                 250                 255 cct tcc gtg ttc ctt ttc cct cct aag cct aag gac acc ctg atg atc              816
Pro Ser Val Phe Leu Phe Pro Pro Lys Pro Lys Asp Thr Leu Met Ile
            260                 265                 270 agc cgt acc cct gag gtg acc tgt gtg gtg gtg gac gtg tcc cac gag              864
Ser Arg Thr Pro Glu Val Thr Cys Val Val Val Asp Val Ser His Glu
        275                 280                 285 gac cct gag gtg cag ttc aac tgg tac gtg gac ggc gtg gag gtg cac              912
Asp Pro Glu Val Gln Phe Asn Trp Tyr Val Asp Gly Val Glu Val His
290                 295                 300 aac gcc aag acc aag cct cgt gag gag caa ttc aac agc acc ttc cgt              960
Asn Ala Lys Thr Lys Pro Arg Glu Glu Gln Phe Asn Ser Thr Phe Arg
305                 310                 315                 320 gtg gtg tcc gtg ctt acc gtg gtg cac caa gac tgg ctg aac ggc aag             1008
Val Val Ser Val Leu Thr Val Val His Gln Asp Trp Leu Asn Gly Lys
                325                 330                 335 gag tac aag tgt aag gtg agc aac aag gga ctt cct gcc cct atc gag             1056
Glu Tyr Lys Cys Lys Val Ser Asn Lys Gly Leu Pro Ala Pro Ile Glu
            340                 345                 350 aag acc atc tcc aag acc aag ggc caa cct cgt gag cct caa gtg tac             1104
Lys Thr Ile Ser Lys Thr Lys Gly Gln Pro Arg Glu Pro Gln Val Tyr
        355                 360                 365 acc ctt cct cct agc cgt gag gag atg acc aag aac caa gtg tcc ctt             1152
Thr Leu Pro Pro Ser Arg Glu Glu Met Thr Lys Asn Gln Val Ser Leu
370                 375                 380 acc tgt ctg gtg aag ggc ttc tac cct agc gac atc gcc gtg gag tgg             1200
Thr Cys Leu Val Lys Gly Phe Tyr Pro Ser Asp Ile Ala Val Glu Trp
385                 390                 395                 400 gag tcc aac gga caa cct gag aac aac tac aag acc acc cct cct atg             1248
Glu Ser Asn Gly Gln Pro Glu Asn Asn Tyr Lys Thr Thr Pro Pro Met
                405                 410                 415 ctt gac agc gac ggc tcc ttc ttc ctg tac agc aag ctg acc gtg gac             1296
Leu Asp Ser Asp Gly Ser Phe Phe Leu Tyr Ser Lys Leu Thr Val Asp
            420                 425                 430
```

-continued

```
aag tcc cgt tgg caa caa ggc aac gtg ttc agc tgt tcc gtg atg cac     1344
Lys Ser Arg Trp Gln Gln Gly Asn Val Phe Ser Cys Ser Val Met His
    435                 440                 445 gag gcc ctg cac aac cac tac acc caa aag agc ctt tcc ctg agc cct     1392
Glu Ala Leu His Asn His Tyr Thr Gln Lys Ser Leu Ser Leu Ser Pro
450                 455                 460 gga aag                                                              1398
Gly Lys
465

<210> SEQ ID NO 99
<211> LENGTH: 466
<212> TYPE: PRT
<213> ORGANISM: Artificial Sequence
<220> FEATURE:
<223> OTHER INFORMATION: Synthetic Construct

<400> SEQUENCE: 99

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys Ile Tyr Thr Tyr Ala Thr Phe
65                  70                  75                  80

Tyr Ala Ala Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Ser Leu Thr Gly Gly Asp Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300
```

```
Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
            325                 330                 335

Glu Tyr Lys Cys Lys Val Ser Asn Lys Gly Leu Pro Ala Pro Ile Glu
        340                 345                 350

Lys Thr Ile Ser Lys Thr Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
450                 455                 460

Gly Lys
465

<210> SEQ ID NO 100
<211> LENGTH: 1398
<212> TYPE: DNA
<213> ORGANISM: Artificial Sequence
<220> FEATURE:
<223> OTHER INFORMATION: h#32A1-H5
<220> FEATURE:
<221> NAME/KEY: CDS
<222> LOCATION: (1)..(1398)

<400> SEQUENCE: 100 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gag gtg cag gtg gtg gag agc ggc ggc gga ctt gtg cag      96
Val Leu Ser Glu Val Gln Val Val Glu Ser Gly Gly Gly Leu Val Gln
            20                  25                  30 cct ggc ggc tcc ctg aga ctt agc tgt gcc acc tcc ggc ttc aac ttc     144
Pro Gly Gly Ser Leu Arg Leu Ser Cys Ala Thr Ser Gly Phe Asn Phe
        35                  40                  45 aac gac tac ttc atg aac tgg gtg aga cag gcc cct ggc aag ggc ctg     192
Asn Asp Tyr Phe Met Asn Trp Val Arg Gln Ala Pro Gly Lys Gly Leu
    50                  55                  60 gag tgg gtg gcc cag atc aga aac aag atc tac acc tac gcc acc ttc     240
Glu Trp Val Ala Gln Ile Arg Asn Lys Ile Tyr Thr Tyr Ala Thr Phe
65                  70                  75                  80 tac gcc gag agc ctt gag ggc aga ttc acc atc tcc aga gac aac agc     288
Tyr Ala Glu Ser Leu Glu Gly Arg Phe Thr Ile Ser Arg Asp Asn Ser
                85                  90                  95 aag tcc acc gtg tac ctt cag atg aac tcc ctg aga gcc gag gac acc     336
Lys Ser Thr Val Tyr Leu Gln Met Asn Ser Leu Arg Ala Glu Asp Thr
            100                 105                 110 gcc gtg tac tac tgt acc aga agc ctt acc ggc ggc gac tac ttc gac     384
Ala Val Tyr Tyr Cys Thr Arg Ser Leu Thr Gly Gly Asp Tyr Phe Asp
        115                 120                 125 tac tgg ggc cag ggc acc ctg gtg acc gtg agc tca gcc agc acc aag     432
```

```
                 Tyr Trp Gly Gln Gly Thr Leu Val Thr Val Ser Ser Ala Ser Thr Lys
                     130                 135                 140 ggc cct tcc gtg ttc cct ctg gcc cct tgt agc cgt tcc acc agc gag              480
Gly Pro Ser Val Phe Pro Leu Ala Pro Cys Ser Arg Ser Thr Ser Glu
145                 150                 155                 160 tcc acc gcc gcc ctt ggc tgt ctg gtg aag gac tac ttc cct gag cct              528
Ser Thr Ala Ala Leu Gly Cys Leu Val Lys Asp Tyr Phe Pro Glu Pro
                165                 170                 175 gtg acc gtg agc tgg aac tcc gga gcc ctt acc agc ggc gtg cac acc              576
Val Thr Val Ser Trp Asn Ser Gly Ala Leu Thr Ser Gly Val His Thr
            180                 185                 190 ttc cct gcc gtg ctg cag tcc agc ggc ctt tac tcc ctg agc tcc gtg              624
Phe Pro Ala Val Leu Gln Ser Ser Gly Leu Tyr Ser Leu Ser Ser Val
        195                 200                 205 gtg acc gtg cct agc tcc aac ttc ggc acc caa acc tac acc tgt aac              672
Val Thr Val Pro Ser Ser Asn Phe Gly Thr Gln Thr Tyr Thr Cys Asn
    210                 215                 220 gtg gac cac aag cct agc aac acc aag gtg gac aag acc gtg gag cgt              720
Val Asp His Lys Pro Ser Asn Thr Lys Val Asp Lys Thr Val Glu Arg
225                 230                 235                 240 aag tgt tgt gtg gag tgt cct cct tgt cct gcc cct cct gtg gcc gga              768
Lys Cys Cys Val Glu Cys Pro Pro Cys Pro Ala Pro Pro Val Ala Gly
                245                 250                 255 cct tcc gtg ttc ctt ttc cct cct aag cct aag gac acc ctg atg atc              816
Pro Ser Val Phe Leu Phe Pro Pro Lys Pro Lys Asp Thr Leu Met Ile
                260                 265                 270 agc cgt acc cct gag gtg acc tgt gtg gtg gtg gac gtg tcc cac gag              864
Ser Arg Thr Pro Glu Val Thr Cys Val Val Val Asp Val Ser His Glu
            275                 280                 285 gac cct gag gtg cag ttc aac tgg tac gtg gac ggc gtg gag gtg cac              912
Asp Pro Glu Val Gln Phe Asn Trp Tyr Val Asp Gly Val Glu Val His
        290                 295                 300 aac gcc aag acc aag cct cgt gag gag caa ttc aac agc acc ttc cgt              960
Asn Ala Lys Thr Lys Pro Arg Glu Glu Gln Phe Asn Ser Thr Phe Arg
305                 310                 315                 320 gtg gtg tcc gtg ctt acc gtg gtg cac caa gac tgg ctg aac ggc aag             1008
Val Val Ser Val Leu Thr Val Val His Gln Asp Trp Leu Asn Gly Lys
                325                 330                 335 gag tac aag tgt aag gtg agc aac aag gga ctt cct gcc cct atc gag             1056
Glu Tyr Lys Cys Lys Val Ser Asn Lys Gly Leu Pro Ala Pro Ile Glu
                340                 345                 350 aag acc atc tcc aag acc aag ggc caa cct cgt gag cct caa gtg tac             1104
Lys Thr Ile Ser Lys Thr Lys Gly Gln Pro Arg Glu Pro Gln Val Tyr
            355                 360                 365 acc ctt cct cct agc cgt gag gag atg acc aag aac caa gtg tcc ctt             1152
Thr Leu Pro Pro Ser Arg Glu Glu Met Thr Lys Asn Gln Val Ser Leu
        370                 375                 380 acc tgt ctg gtg aag ggc ttc tac cct agc gac atc gcc gtg gag tgg             1200
Thr Cys Leu Val Lys Gly Phe Tyr Pro Ser Asp Ile Ala Val Glu Trp
385                 390                 395                 400 gag tcc aac gga caa cct gag aac aac tac aag acc acc cct cct atg             1248
Glu Ser Asn Gly Gln Pro Glu Asn Asn Tyr Lys Thr Thr Pro Pro Met
                405                 410                 415 ctt gac agc gac ggc tcc ttc ttc ctg tac agc aag ctg acc gtg gac             1296
Leu Asp Ser Asp Gly Ser Phe Phe Leu Tyr Ser Lys Leu Thr Val Asp
                420                 425                 430 aag tcc cgt tgg caa caa ggc aac gtg ttc agc tgt tcc gtg atg cac             1344
Lys Ser Arg Trp Gln Gln Gly Asn Val Phe Ser Cys Ser Val Met His
            435                 440                 445
```

-continued

```
gag gcc ctg cac aac cac tac acc caa aag agc ctt tcc ctg agc cct    1392
Glu Ala Leu His Asn His Tyr Thr Gln Lys Ser Leu Ser Leu Ser Pro
    450                 455                 460 gga aag                                                              1398
Gly Lys
465
```

<210> SEQ ID NO 101
<211> LENGTH: 466
<212> TYPE: PRT
<213> ORGANISM: Artificial Sequence
<220> FEATURE:
<223> OTHER INFORMATION: Synthetic Construct

<400> SEQUENCE: 101

```
Met Lys His Leu Trp Phe Phe Leu Leu Leu Val Ala Ala Pro Arg Trp
1               5                   10                  15

Val Leu Ser Glu Val Gln Val Glu Ser Gly Gly Gly Leu Val Gln
            20                  25                  30

Pro Gly Gly Ser Leu Arg Leu Ser Cys Ala Thr Ser Gly Phe Asn Phe
            35                  40                  45

Asn Asp Tyr Phe Met Asn Trp Val Arg Gln Ala Pro Gly Lys Gly Leu
    50                  55                  60

Glu Trp Val Ala Gln Ile Arg Asn Lys Ile Tyr Thr Tyr Ala Thr Phe
65                  70                  75                  80

Tyr Ala Glu Ser Leu Glu Gly Arg Phe Thr Ile Ser Arg Asp Asn Ser
                85                  90                  95

Lys Ser Thr Val Tyr Leu Gln Met Asn Ser Leu Arg Ala Glu Asp Thr
            100                 105                 110

Ala Val Tyr Tyr Cys Thr Arg Ser Leu Thr Gly Gly Asp Tyr Phe Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
```

```
                         325                 330                 335
Glu Tyr Lys Cys Lys Val Ser Asn Lys Gly Leu Pro Ala Pro Ile Glu
                340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
450                 455                 460

Gly Lys
465

<210> SEQ ID NO 102
<211> LENGTH: 714
<212> TYPE: DNA
<213> ORGANISM: Artificial Sequence
<220> FEATURE:
<223> OTHER INFORMATION: h#32A1-L2-15
<220> FEATURE:
<221> NAME/KEY: CDS
<222> LOCATION: (1)..(714)

<400> SEQUENCE: 102 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gca tat ggc gaa att ctg atg acg cag agt cct gca act ctt agt      96
Gly Ala Tyr Gly Glu Ile Leu Met Thr Gln Ser Pro Ala Thr Leu Ser
            20                  25                  30 ctg tca cct ggc gag aga gcc aca ctc agc tgc cga gcg tcc cag tcc     144
Leu Ser Pro Gly Glu Arg Ala Thr Leu Ser Cys Arg Ala Ser Gln Ser
        35                  40                  45 gtg acc att agc ggc tat tct ttt att cat tgg tat cag caa aag cct     192
Val Thr Ile Ser Gly Tyr Ser Phe Ile His Trp Tyr Gln Gln Lys Pro
    50                  55                  60 gga cag gcg cca agg ctg ctc att tac aga gca agc aac ctt gcc tct     240
Gly Gln Ala Pro Arg Leu Leu Ile Tyr Arg Ala Ser Asn Leu Ala Ser
65                  70                  75                  80 ggc att cca gca aga ttc agc ggg agc gga tca ggg aca gat ttc acc     288
Gly Ile Pro Ala Arg Phe Ser Gly Ser Gly Ser Gly Thr Asp Phe Thr
                85                  90                  95 ttg acc atc tcc tcc ctg gag ccg gag gat ttc gcg ttg tat tat tgt     336
Leu Thr Ile Ser Ser Leu Glu Pro Glu Asp Phe Ala Leu Tyr Tyr Cys
            100                 105                 110 cag caa tct agg aag agt cca tgg aca ttt ggc cag ggc acc aaa gtg     384
Gln Gln Ser Arg Lys Ser Pro Trp Thr Phe Gly Gln Gly Thr Lys Val
        115                 120                 125 gag atc aag cgt acg gtg gcc gcc ccc tcc gtg ttc atc ttc ccc ccc     432
Glu Ile Lys Arg Thr Val Ala Ala Pro Ser Val Phe Ile Phe Pro Pro
    130                 135                 140 tcc gac gag cag ctg aag tcc ggc acc gcc tcc gtg gtg tgc ctg ctg     480
Ser Asp Glu Gln Leu Lys Ser Gly Thr Ala Ser Val Val Cys Leu Leu
```

```
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac    528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc    576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc    624
Lys Asp Ser Thr Tyr Ser Leu Ser Ser Thr Leu Thr Leu Ser Lys Ala
        195                 200                 205 gac tac gag aag cac aag gtg tac gcc tgc gag gtg acc cac cag ggc    672
Asp Tyr Glu Lys His Lys Val Tyr Ala Cys Glu Val Thr His Gln Gly
    210                 215                 220 ctg agc tcc ccc gtc acc aag agc ttc aac agg ggg gag tgt            714
Leu Ser Ser Pro Val Thr Lys Ser Phe Asn Arg Gly Glu Cys
225                 230                 235
```

<210> SEQ ID NO 103
<211> LENGTH: 238
<212> TYPE: PRT
<213> ORGANISM: Artificial Sequence
<220> FEATURE:
<223> OTHER INFORMATION: Synthetic Construct

<400> SEQUENCE: 103

```
Met Val Leu Gln Thr Gln Val Phe Ile Ser Leu Leu Leu Trp Ile Ser
1               5                   10                  15

Gly Ala Tyr Gly Glu Ile Leu Met Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Thr Ile Ser Gly Tyr Ser Phe Ile His Trp Tyr Gln Gln Lys Pro
    50                  55                  60

Gly Gln Ala Pro Arg Leu Leu Ile Tyr Arg Ala Ser Asn Leu Ala Ser
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Leu Tyr Tyr Cys
            100                 105                 110

Gln Gln Ser Arg Lys Ser Pro Trp Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 104
<211> LENGTH: 714
<212> TYPE: DNA
<213> ORGANISM: Artificial Sequence
<220> FEATURE:
<223> OTHER INFORMATION: h#32A1-L2-16
<220> FEATURE:
<221> NAME/KEY: CDS
<222> LOCATION: (1)..(714)

<400> SEQUENCE: 104

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                  10                  15 ggc gca tat ggc gaa atc ctg atg aca cag agt cct gcg acc ctc tcc      96
Gly Ala Tyr Gly Glu Ile Leu Met Thr Gln Ser Pro Ala Thr Leu Ser
            20                  25                  30 ctc tca cca ggc gag agg gcc acc ctg tct tgt aga gcc agc cag tca     144
Leu Ser Pro Gly Glu Arg Ala Thr Leu Ser Cys Arg Ala Ser Gln Ser
        35                  40                  45 gtc act att agt gga tac tca ttt atc cat tgg tat caa cag aaa cca     192
Val Thr Ile Ser Gly Tyr Ser Phe Ile His Trp Tyr Gln Gln Lys Pro
    50                  55                  60 gga cag gcg cct cgg ctt ctg atc tac cgc gcc tca aac ctt gcc tct     240
Gly Gln Ala Pro Arg Leu Leu Ile Tyr Arg Ala Ser Asn Leu Ala Ser
65                  70                  75                  80 ggc atc ccc gcg agg ttc tct ggc tct ggc agc ggt acc gat ttt aca     288
Gly Ile Pro Ala Arg Phe Ser Gly Ser Gly Ser Gly Thr Asp Phe Thr
                85                  90                  95 ctg act atc tca agc ctc gaa cct gaa gac ttc gca ctg tac ttt tgc     336
Leu Thr Ile Ser Ser Leu Glu Pro Glu Asp Phe Ala Leu Tyr Phe Cys
            100                 105                 110 cag cag agc agg aag tcc ccc tgg act ttt gca cag gga acc aaa gtc     384
Gln Gln Ser Arg Lys Ser Pro Trp Thr Phe Ala Gln Gly Thr Lys Val
        115                 120                 125 gaa atc aag cgt acg gtg gcc gcc ccc tcc gtg ttc atc ttc ccc ccc     432
Glu Ile Lys Arg Thr Val Ala Ala Pro Ser Val Phe Ile Phe Pro Pro
    130                 135                 140 tcc gac gag cag ctg aag tcc ggc acc gcc tcc gtg gtg tgc ctg ctg     480
Ser Asp Glu Gln Leu Lys Ser Gly Thr Ala Ser Val Val Cys Leu Leu
145                 150                 155                 160 aat aac ttc tac ccc aga gag gcc aag gtg cag tgg aag gtg gac aac     528
Asn Asn Phe Tyr Pro Arg Glu Ala Lys Val Gln Trp Lys Val Asp Asn
                165                 170                 175 gcc ctg cag tcc ggg aac tcc cag gag agc gtg acc gag cag gac agc     576
Ala Leu Gln Ser Gly Asn Ser Gln Glu Ser Val Thr Glu Gln Asp Ser
            180                 185                 190 aag gac agc acc tac agc ctg agc agc acc ctg acc ctg agc aaa gcc     624
Lys Asp Ser Thr Tyr Ser Leu Ser Ser Thr Leu Thr Leu Ser Lys Ala
        195                 200                 205 gac tac gag aag cac aag gtg tac gcc tgc gag gtg acc cac cag ggc     672
Asp Tyr Glu Lys His Lys Val Tyr Ala Cys Glu Val Thr His Gln Gly
    210                 215                 220 ctg agc tcc ccc gtc acc aag agc ttc aac agg ggg gag tgt             714
Leu Ser Ser Pro Val Thr Lys Ser Phe Asn Arg Gly Glu Cys
225                 230                 235
```

<210> SEQ ID NO 105
<211> LENGTH: 238
<212> TYPE: PRT
<213> ORGANISM: Artificial Sequence
<220> FEATURE:
<223> OTHER INFORMATION: Synthetic Construct

<400> SEQUENCE: 105

Met Val Leu Gln Thr Gln Val Phe Ile Ser Leu Leu Trp Ile Ser
1               5                   10                  15

Gly Ala Tyr Gly Glu Ile Leu Met Thr Gln Ser Pro Ala Thr Leu Ser
            20                  25                  30

Leu Ser Pro Gly Glu Arg Ala Thr Leu Ser Cys Arg Ala Ser Gln Ser
            35                  40                  45

Val Thr Ile Ser Gly Tyr Ser Phe Ile His Trp Tyr Gln Gln Lys Pro
50                  55                  60

Gly Gln Ala Pro Arg Leu Leu Ile Tyr Arg Ala Ser Asn Leu Ala Ser
65                  70                  75                  80

Gly Ile Pro Ala Arg Phe Ser Gly Ser Gly Ser Gly Thr Asp Phe Thr
                85                  90                  95

Leu Thr Ile Ser Ser Leu Glu Pro Glu Asp Phe Ala Leu Tyr Phe Cys
                100                 105                 110

Gln Gln Ser Arg Lys Ser Pro Trp Thr Phe Ala Gln Gly Thr Lys Val
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
210                 215                 220

Leu Ser Ser Pro Val Thr Lys Ser Phe Asn Arg Gly Glu Cys
225                 230                 235

<210> SEQ ID NO 106
<211> LENGTH: 1111
<212> TYPE: DNA
<213> ORGANISM: Artificial Sequence
<220> FEATURE:
<223> OTHER INFORMATION: Nuleic acid sequence coding signal peptide and
      constant region of human IgG2 heavy chain

<400> SEQUENCE: 106
aagcttgcta gcgccaccat gaaacacctg tggttcttcc tcctgctggt ggcagctccc      60
agatgggtgc tgagccaggt gcaattgtgc aggcggttag ctcagccagc accagggggcc    120 cttccgtgtt ccctctggcc ccttgtagcc gttccaccag cgagtccacc gccgcccttg    180
gctgtctggt gaaggactac ttccctgagc ctgtgaccgt gagctggaac tccggagccc    240
ttaccagcgg cgtgcacacc ttccctgccg tgctgcagtc cagcggcctt tactccctga    300
gctccgtggt gaccgtgcct agctccaact tcggcaccca aacctacacc tgtaacgtgg    360
accacaagcc tagcaacacc aaggtggaca agaccgtgga gcgtaagtgt tgtgtggagt    420
gtcctccttg tcctgcccct cctgtggccg accttccgt gttccttttc cctcctaagc     480
ctaaggacac cctgatgatc agccgtaccc tgaggtgac ctgtgtggtg gtggacgtgt      540
cccacgagga ccctgaggtg cagttcaact ggtacgtgga cggcgtggag gtgcacaacg    600

-continued

```
ccaagaccaa gcctcgtgag gagcaattca acagcacctt ccgtgtggtg tccgtgctta      660
ccgtggtgca ccaagactgg ctgaacggca aggagtacaa gtgtaaggtg agcaacaagg      720
gacttcctgc ccctatcgag aagaccatct ccaagaccaa gggccaacct cgtgagcctc      780
aagtgtacac ccttcctcct agccgtgagg agatgaccaa gaaccaagtg tcccttacct      840
gtctggtgaa gggcttctac cctagcgaca tcgccgtgga gtgggagtcc aacggacaac      900
ctgagaacaa ctacaagacc accctccta tgcttgacag cgacggctcc ttcttcctgt       960
acagcaagct gaccgtggac aagtcccgtt ggcaacaagg caacgtgttc agctgttccg     1020
tgatgcacga ggccctgcac aaccactaca cccaaaagag cctttccctg agccctggaa     1080
agtgatatcg ggcccgttta aacgggtggc a                                    1111
```

ANTI-SIGLEC-15 ANTIBODY

CROSS-REFERENCE TO RELATED APPLICATIONS

This application is a Divisional of U.S. application Ser. No. 14/041,479, filed Sep. 30, 2013, now U.S. Pat. No. 9,079,959, which is a Continuation of U.S. application Ser. No. 13/143,253, filed Jul. 5, 2011, now U.S. Pat. No. 8,575,316, which is the U.S. National Stage application of PCT/JP2010/056294, filed Apr. 7, 2010, which claims priority from Japanese application JP 2009-094613, filed Apr. 9, 2009, the entire contents of which are incorporated herein by reference.

SEQUENCE LISTING

The instant application contains a Sequence Listing which has been submitted in ASCII format via EFS-WEB and is hereby incorporated by reference in its entirety. Said ASCII copy, created on Jun. 26, 2015, is named sequence.txt and is 278 KB.

TECHNICAL FIELD

The present invention relates to a substance useful as a therapeutic and/or preventive agent for abnormal bone metabolism, and a method of treating and/or preventing abnormal bone metabolism.

BACKGROUND ART

Bone is known to be a dynamic organ which is continuously remodeled by repeated formation and resorption so as to change its own morphology and maintain blood calcium levels. Healthy bone maintains an equilibrium between bone formation by osteoblasts and bone resorption by osteoclasts, and bone mass is maintained constant. In contrast, when the equilibrium between bone formation and bone resorption is lost, abnormal bone metabolism such as osteoporosis occurs (WO 07/093042 and Endocrinological Review, (1992) 13, pp. 66-80).

As factors which regulate bone metabolism, many systemic hormones and local cytokines have been reported, and these factors collaborate with one another to form and maintain bone (WO 07/093042 and Endocrinological Review, (1996) 17, pp. 308-332). As a change in bone tissue due to aging, the occurrence of osteoporosis is widely known, but the mechanism of its occurrence encompasses various factors such as a decrease in secretion of sex hormones and an abnormality in the receptors for the hormones; variation in cytokine expression locally in bone; expression of aging genes; and osteoclast or osteoblast differentiation failure or dysfunction, and thus it is difficult to consider it as a simple age-related physiological phenomenon. Primary osteoporosis is largely divided into postmenopausal osteoporosis due to a decrease in secretion of estrogen and senile osteoporosis due to aging, but advancement of basic research on the mechanisms of regulation of bone formation and bone resorption is essential to elucidate the mechanism of its occurrence and to develop a therapeutic agent therefor.

Osteoclasts are multinucleated cells derived from hematopoietic stem cells, and by releasing chloride ions and hydrogen ions on a bone surface to which osteoclasts adhere, osteoclasts acidify a gap between the bone surface and the osteoclasts and also secrete cathepsin K which is an acid protease or the like (American Journal of Physiology, (1991) 260, C1315-C1324). This causes degradation of calcium phosphate, activation of acid proteases and degradation of bone matrix proteins, resulting in bone resorption.

Osteoclast precursor cells have been found to be differentiated into osteoclasts by stimulation with RANKL (receptor activator of NF-κB ligand) expressed on the cell membrane of osteoblasts/stromal cells present on the surface of bone (Proceedings of the National Academy of Science of the United States of America, (1998) 95, pp. 3597-3602, and Cell, (1998) 93, pp. 165-176). It has been revealed that RANKL is a membrane protein produced by osteoblasts/stromal cells, its expression is regulated by a bone resorption factor, RANKL induces differentiation of osteoclast precursor cells into mature multinucleated osteoclasts, and the like (Proceedings of the National Academy of Science of the United States of America, (1998) 95, pp. 3597-3602, and Journal of Bone and Mineral Research, (1998) 23, S222). Further, knockout mice devoid of RANKL have been found to develop an osteopetrosis-like disease, and therefore, RANKL has been proved to be a physiological osteoclast differentiation-inducing factor (Nature, (1999) 397, pp. 315-323).

As pharmaceutical preparations for treating bone metabolism diseases or shortening the duration of treatment, bisphosphonates, active vitamin $D_3$, calcitonin and derivatives thereof, hormones such as estradiol, SERMs (selective estrogen receptor modulators), ipriflavone, vitamin $K_2$ (menatetrenone), PTH, calcium preparations, and the like are used. However, these medicinal agents are not always satisfactory in terms of therapeutic outcome and the development of a medicinal agent with a more potent therapeutic effect has been demanded.

The cell membranes of immune cells are covered with a dense coating of various glycans such as sialylated glycans which are recognized by various glycan-binding proteins. Sialic-acid-binding immunoglobulin-like lectins (hereinafter referred to as "siglecs") are a family of type I membrane proteins which recognize sialylated glycans and bind thereto. Many siglecs are expressed on the cell membranes of immune cells and recognize sialic acid similarly present on the cell membranes of immune cells and regulate cell interaction or cell function and are considered to be involved in immune responses (Nature Reviews Immunology, (2007) 7, pp. 255-266). However, there are also a lot of siglec molecules whose physiological functions have not been elucidated yet. Siglec-15 (Sialic-acid binding immunoglobulin-like lectin 15) is a molecule which has been newly reported to belong to the Siglecs (see, for example, Non-patent document 10) and is identical to a molecule called CD33L3 (CD33 molecule-like 3). This molecule is highly evolutionarily conserved from fish to humans and has been found to be strongly expressed in dendritic cells and/or macrophages of human spleen and lymph nodes. Further, as a result of a binding test using a sialic acid probe, it has also been found that human Siglec-15 binds to Neu5Acα2-6GalNAc and that mouse Siglec-15 binds further to Neu5Acα2-3Galβ1-4Glc, and the like (see, for example, Glycobiology, (2007) 17, pp. 838-846). Until recently, the physiological role of Siglec-15 had not been revealed, however, it has been reported that the expression of Siglec-15 increases with the differentiation and maturation of osteoclasts, and the differentiation of osteoclasts is inhibited by decreasing the expression of Siglec-15 by RNA interference (see, for example, WO 07/093042). Further, the effect of an anti-Siglec-15 antibody on osteoclast differentiation has been revealed for the first time in WO 09/48072 (published on Apr. 16, 2009), however, an antibody sequence which can be administered to humans has not been elucidated yet.

SUMMARY OF THE INVENTION

Problems that the Invention is to Solve

An object of the invention is to provide a gene which is specifically expressed in various forms of abnormal bone metabolism which are seen in osteoporosis, rheumatoid arthritis, cancer metastasis to bone or the like, a substance which inhibits the differentiation and maturation of osteoclasts and the activity thereof, and a therapeutic and/or preventive agent for abnormal bone metabolism.

Means for Solving the Problems

The present inventors studied to elucidate the mechanism of osteoclast differentiation, maturation and activation in order to find a substance having a therapeutic and/or preventive effect on abnormal bone metabolism. As a result, the present inventors found that the expression of Siglec-15 gene increases with the differentiation and maturation of osteoclasts, and also found that the differentiation of osteoclasts is inhibited by an antibody which specifically binds to Siglec-15. Further, the present inventors humanized an obtained rat anti-mouse Siglec-15 antibody, and thus completed the invention.

That is, the invention includes the following inventions.

An antibody which binds to a polypeptide comprising amino acid residues 39 to 165 of an amino acid sequence represented by SEQ ID NO: 2 and inhibits osteoclast formation and/or osteoclastic bone resorption, or a functional fragment of the antibody.

(2) The antibody or a functional fragment of the antibody according to (1), characterized in that:
a heavy chain sequence contains a variable region having CDRH1, CDRH2, and CDRH3, and the CDRH1 comprises an amino acid sequence represented by SEQ ID NO: 44, the CDRH2 comprises any one of amino acid sequences represented by SEQ ID NO: 45 and SEQ ID NO: 97, and the CDRH3 comprises an amino acid sequence represented by SEQ ID NO: 46; and
a light chain sequence contains a variable region having CDRL1, CDRL2, and CDRL3, and the CDRL1 comprises an amino acid sequence represented by SEQ ID NO: 47, the CDRL2 comprises an amino acid sequence represented by SEQ ID NO: 48, and the CDRL3 comprises an amino acid sequence represented by SEQ ID NO: 49.

(3) The antibody or a functional fragment of the antibody according to (2), characterized by containing a heavy chain variable region sequence comprising amino acid residues 20 to 140 of an amino acid sequence represented by SEQ ID NO: 41 and a light chain variable region sequence comprising amino acid residues 21 to 132 of an amino acid sequence represented by SEQ ID NO: 43.

(4) The functional fragment of the antibody according to any one of (1) to (3) which is selected from the group consisting of Fab, F(ab')2, Fab' and Fv.

(5) The antibody according to any one of (1) to (3), characterized by being an scFv.

(6) The antibody or a functional fragment of the antibody according to any one of (1) to (4), characterized in that the antibody is a chimeric antibody.

(7) The antibody or a functional fragment of the antibody according to (6), characterized by comprising a heavy chain sequence comprising amino acid residues 20 to 470 of an amino acid sequence represented by SEQ ID NO: 41 and a light chain sequence comprising amino acid residues 21 to 237 of an amino acid sequence represented by SEQ ID NO: 43.

(8) The antibody or a functional fragment of the antibody according to any one of (1) to (4), and (6), characterized in that the antibody is humanized.

(9) The antibody according to (7) or (8), wherein the heavy chain has a constant region of a human immunoglobulin G2 heavy chain and the light chain has a constant region of a human immunoglobulin κ light chain.

(10) An antibody which inhibits osteoclast formation and/or osteoclastic bone resorption or a functional fragment of the antibody, wherein the antibody contains:
a heavy chain variable region selected from the group consisting of the following amino acid sequences:
a1) an amino acid sequence comprising amino acid residues 20 to 140 of an amino acid sequence represented by SEQ ID NO: 51;
a2) an amino acid sequence comprising amino acid residues 20 to 140 of an amino acid sequence represented by SEQ ID NO: 53;
a3) an amino acid sequence comprising amino acid residues 20 to 140 of an amino acid sequence represented by SEQ ID NO: 55;
a4) an amino acid sequence comprising amino acid residues 20 to 140 of an amino acid sequence represented by SEQ ID NO: 57;
a5) an amino acid sequence comprising amino acid residues 20 to 140 of an amino acid sequence represented by SEQ ID NO: 59;
a6) an amino acid sequence comprising amino acid residues 20 to 140 of an amino acid sequence represented by SEQ ID NO: 99;
a7) an amino acid sequence comprising amino acid residues 20 to 140 of an amino acid sequence represented by SEQ ID NO: 101;
a8) an amino acid sequence having a homology of at least 95% with any one of the amino acid sequences selected from a1) to a7);
a9) an amino acid sequence having a homology of at least 99% with any one of the amino acid sequences selected from a1) to a7); and
a10) an amino acid sequence including a substitution, deletion, or addition of one to several amino acid residues in any one of the amino acid sequences selected from a1) to a7); and
(b) a light chain variable region selected from the group consisting of the following amino acid sequences:
b1) an amino acid sequence comprising amino acid residues 21 to 133 of an amino acid sequence represented by SEQ ID NO: 61;
b2) an amino acid sequence comprising amino acid residues 21 to 133 of an amino acid sequence represented by SEQ ID NO: 63;
b3) an amino acid sequence comprising amino acid residues 21 to 133 of an amino acid sequence represented by SEQ ID NO: 65;
b4) an amino acid sequence comprising amino acid residues 21 to 132 of an amino acid sequence represented by SEQ ID NO: 67;
b5) an amino acid sequence comprising amino acid residues 21 to 133 of an amino acid sequence represented by SEQ ID NO: 69;

b6) an amino acid sequence comprising amino acid residues 21 to 133 of an amino acid sequence represented by SEQ ID NO: 71;

b7) an amino acid sequence comprising amino acid residues 21 to 133 of an amino acid sequence represented by SEQ ID NO: 103;

b8) an amino acid sequence comprising amino acid residues 21 to 133 of an amino acid sequence represented by SEQ ID NO: 105;

b9) an amino acid sequence having a homology of at least 95% with any one of the amino acid sequences selected from b1) to b8);

b10) an amino acid sequence having a homology of at least 99% with any one of the amino acid sequences selected from b1) to b8); and b11) an amino acid sequence including a substitution, deletion, or addition of one to several amino acid residues in any one of the amino acid sequences selected from b1) to b8).

(11) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 51 and a light chain sequence containing a light chain variable region comprising an amino acid sequence comprising amino acid residues 21 to 133 of an amino acid sequence represented by SEQ ID NO: 61.

(12) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 53 and a light chain sequence containing a light chain variable region comprising an amino acid sequence comprising amino acid residues 21 to 133 of an amino acid sequence represented by SEQ ID NO: 63.

(13) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 55 and a light chain sequence containing a light chain variable region comprising an amino acid sequence comprising amino acid residues 21 to 133 of an amino acid sequence represented by SEQ ID NO: 65.

(14) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 55 and a light chain sequence containing a light chain variable region comprising an amino acid sequence comprising amino acid residues 21 to 132 of an amino acid sequence represented by SEQ ID NO: 67.

(15) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 57 and a light chain sequence containing a light chain variable region comprising an amino acid sequence comprising amino acid residues 21 to 133 of an amino acid sequence represented by SEQ ID NO: 69.

(16) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 59 and a light chain sequence containing a light chain variable region comprising an amino acid sequence comprising amino acid residues 21 to 133 of an amino acid sequence represented by SEQ ID NO: 71.

(17) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 99 and a light chain sequence containing a light chain variable region comprising an amino acid sequence comprising amino acid residues 21 to 133 of an amino acid sequence represented by SEQ ID NO: 69.

(18) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 101 and a light chain sequence containing a light chain variable region comprising an amino acid sequence comprising amino acid residues 21 to 133 of an amino acid sequence represented by SEQ ID NO: 69.

(19) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 99 and a light chain sequence containing a light chain variable region comprising an amino acid sequence comprising amino acid residues 21 to 133 of an amino acid sequence represented by SEQ ID NO: 103.

(20) The antibody or a functional fragment of the antibody according to (10), characterized by containing a heavy chain sequence containing a heavy chain variable region comprising an amino acid sequence comprising amino acid residues 20 to 140 of an amino acid sequence represented by SEQ ID NO: 99 and a light chain sequence containing a light chain variable region comprising an amino acid sequence comprising amino acid residues 21 to 133 of an amino acid sequence represented by SEQ ID NO: 105.

(21) The antibody or a functional fragment of the antibody according to (10), characterized by containing a heavy chain sequence comprising amino acid residues 20 to 470 of an amino acid sequence represented by SEQ ID NO: 51 and a light chain sequence comprising amino acid residues 21 to 238 of an amino acid sequence represented by SEQ ID NO: 61.

(22) The antibody or a functional fragment of the antibody according to (10), characterized by containing a heavy chain sequence comprising amino acid residues 20 to 470 of an amino acid sequence represented by SEQ ID NO: 53 and a light chain sequence comprising amino acid residues 21 to 238 of an amino acid sequence represented by SEQ ID NO: 63.

(23) The antibody or a functional fragment of the antibody according to (10), characterized by containing a heavy chain sequence comprising amino acid residues 20 to 470 of an amino acid sequence represented by SEQ ID NO: 55 and a light chain sequence comprising amino acid residues 21 to 238 of an amino acid sequence represented by SEQ ID NO: 65.

(24) The antibody or a functional fragment of the antibody according to (10), characterized by containing a heavy chain sequence comprising amino acid residues 20 to 470 of an amino acid sequence represented by SEQ ID NO: 55 and a light chain sequence comprising amino acid residues 21 to 237 of an amino acid sequence represented by SEQ ID NO: 67.

(25) The antibody or a functional fragment of the antibody according to (10), characterized by containing a heavy chain sequence comprising amino acid residues 20 to 470 of an amino acid sequence represented by SEQ ID NO: 57 and a light chain sequence comprising amino acid residues 21 to 238 of an amino acid sequence represented by SEQ ID NO: 69.

(26) The antibody or a functional fragment of the antibody according to (10), characterized by containing a heavy chain sequence comprising amino acid residues 20 to 470 of an amino acid sequence represented by SEQ ID NO: 59 and a light chain sequence comprising amino acid residues 21 to 238 of an amino acid sequence represented by SEQ ID NO: 71.

(27) The antibody or a functional fragment of the antibody according to (10), characterized by containing a heavy chain sequence comprising amino acid residues 20 to 466 of an amino acid sequence represented by SEQ ID NO: 99 and a light chain sequence comprising amino acid residues 21 to 238 of an amino acid sequence represented by SEQ ID NO: 69.

(28) The antibody or a functional fragment of the antibody according to (10), characterized by containing a heavy chain sequence comprising amino acid residues 20 to 466 of an amino acid sequence represented by SEQ ID NO: 101 and a light chain sequence comprising amino acid residues 21 to 238 of an amino acid sequence represented by SEQ ID NO: 69.

(29) The antibody or a functional fragment of the antibody according to (10), characterized by containing a heavy chain sequence comprising amino acid residues 20 to 466 of an amino acid sequence represented by SEQ ID NO: 99 and a light chain sequence comprising amino acid residues 21 to 238 of an amino acid sequence represented by SEQ ID NO: 103.

(30) The antibody or a functional fragment of the antibody according to (10), characterized by containing a heavy chain sequence comprising amino acid residues 20 to 466 of an amino acid sequence represented by SEQ ID NO: 99 and a light chain sequence comprising amino acid residues 21 to 238 of an amino acid sequence represented by SEQ ID NO: 105.

(31) A pharmaceutical composition, characterized by comprising at least one of the antibodies or functional fragments of the antibodies according to (1) to (30).

(32) The pharmaceutical composition according to (31), characterized by being a therapeutic and/or preventive agent for abnormal bone metabolism.

(33) A pharmaceutical composition for treating and/or preventing abnormal bone metabolism, characterized by comprising at least one of the antibodies or functional fragments of the antibodies according to (1) to (30) and at least one member selected from the group consisting of bisphosphonates, active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies, and OCIF (osteoclastogenesis inhibitory factor).

(34) The pharmaceutical composition according to (32) or (33), wherein the abnormal bone metabolism is selected from the group consisting of osteoporosis, bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, Paget's disease of bone, renal osteodystrophy, and osteogenesis imperfecta.

(35) The pharmaceutical composition according to (34), characterized in that the abnormal bone metabolism is osteoporosis, bone destruction accompanying rheumatoid arthritis, or bone destruction accompanying cancer metastasis to bone.

(36) The pharmaceutical composition according to (35), characterized in that the abnormal bone metabolism is osteoporosis.

(37) The pharmaceutical composition according to (36), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(38) A method of treating and/or preventing abnormal bone metabolism, characterized by administering at least one of the antibodies or functional fragments of the antibodies according to (1) to (30).

(39) A method of treating and/or preventing abnormal bone metabolism, characterized by simultaneously or successively administering at least one of the antibodies or functional fragments of the antibodies according to (1) to (30) and at least one member selected from the group consisting of bisphosphonates, active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents, soluble TNF receptors, anti-TNF-α antibodies or functional fragments of the antibodies, anti-PTHrP (parathyroid hormone-related protein) antibodies or functional fragments of the antibodies, IL-1 receptor antagonists, anti-IL-6 receptor antibodies or functional fragments of the antibodies, anti-RANKL antibodies or functional fragments of the antibodies, and OCIF (osteoclastogenesis inhibitory factor).

(40) The treatment and/or prevention method according to (38) or (39), characterized in that the abnormal bone metabolism is osteoporosis, bone destruction accompanying rheumatoid arthritis, or bone destruction accompanying cancer metastasis to bone.

(41) The treatment and/or prevention method according to (40), characterized in that the abnormal bone metabolism is osteoporosis.

(42) The treatment and/or prevention method according to (41), characterized in that the osteoporosis is postmenopausal osteoporosis, senile osteoporosis, secondary osteoporosis due to the use of a therapeutic agent such as a steroid or an immunosuppressant, or osteoporosis accompanying rheumatoid arthritis.

(43) A polynucleotide encoding the antibody according to any one of (3), (7), and (10) to (30).

(44) The polynucleotide according to (43), characterized by containing a nucleotide sequence comprising nucleotides 58 to 420 of a nucleotide sequence represented by SEQ ID NO: 40 and a nucleotide sequence comprising nucleotides 61 to 396 of a nucleotide sequence represented by SEQ ID NO: 42.

(45) The polynucleotide according to (44), characterized by containing a nucleotide sequence comprising nucleotides 58 to 1410 of a nucleotide sequence represented by SEQ ID NO: 40 and a nucleotide sequence comprising nucleotides 61 to 711 of a nucleotide sequence represented by SEQ ID NO: 42.

(46) The polynucleotide according to (43), characterized by containing:

a polynucleotide selected from the group consisting of the following nucleotide sequences:

a1) a nucleotide sequence comprising nucleotides 58 to 420 of a nucleotide sequence represented by SEQ ID NO: 50;

a2) a nucleotide sequence comprising nucleotides 58 to 420 of a nucleotide sequence represented by SEQ ID NO: 52;

a3) a nucleotide sequence comprising nucleotides 58 to 420 of a nucleotide sequence represented by SEQ ID NO: 54;

a4) a nucleotide sequence comprising nucleotides 58 to 420 of a nucleotide sequence represented by SEQ ID NO: 56;

a5) a nucleotide sequence comprising nucleotides 58 to 420 of a nucleotide sequence represented by SEQ ID NO: 58;

a6) a nucleotide sequence comprising nucleotides 58 to 420 of a nucleotide sequence represented by SEQ ID NO: 98;

a7) a nucleotide sequence comprising nucleotides 58 to 420 of a nucleotide sequence represented by SEQ ID NO: 100;

a8) a nucleotide sequence of a polynucleotide which hybridizes to a polynucleotide comprising a nucleotide sequence complementary to any one of the nucleotide sequences selected from a1) to a7) under stringent conditions; and a9) a nucleotide sequence including a substitution, deletion, or addition of one to several nucleotides in any one of the nucleotide sequences selected from a1) to a7); and (b) a polynucleotide selected from the group consisting of the following nucleotide sequences:

b1) a nucleotide sequence comprising nucleotides 61 to 399 of a nucleotide sequence represented by SEQ ID NO: 60;

b2) a nucleotide sequence comprising nucleotides 61 to 399 of a nucleotide sequence represented by SEQ ID NO: 62;

b3) a nucleotide sequence comprising nucleotides 61 to 399 of a nucleotide sequence represented by SEQ ID NO: 64;

b4) a nucleotide sequence comprising nucleotides 61 to 396 of a nucleotide sequence represented by SEQ ID NO: 66;

b5) a nucleotide sequence comprising nucleotides 61 to 399 of a nucleotide sequence represented by SEQ ID NO: 68;

b6) a nucleotide sequence comprising nucleotides 61 to 399 of a nucleotide sequence represented by SEQ ID NO: 70;

b7) a nucleotide sequence comprising nucleotides 61 to 399 of a nucleotide sequence represented by SEQ ID NO: 102;

b8) a nucleotide sequence comprising nucleotides 61 to 399 of a nucleotide sequence represented by SEQ ID NO: 104;

b9) a nucleotide sequence of a polynucleotide which hybridizes to a polynucleotide comprising a nucleotide sequence complementary to any one of the nucleotide sequences selected from b1) to b8) under stringent conditions; and b10) a nucleotide sequence including a substitution, deletion, or addition of one to several nucleotides in any one of the nucleotide sequences selected from b1) to b8).

(47) The polynucleotide according to (46), characterized by containing a polynucleotide comprising a nucleotide sequence comprising nucleotides 58 to 420 of a nucleotide sequence represented by SEQ ID NO: 50, and a polynucleotide comprising a nucleotide sequence comprising nucleotides 61 to 399 of a nucleotide sequence represented by SEQ ID NO: 60.

(48) The polynucleotide according to (46), characterized by containing a polynucleotide comprising a nucleotide sequence comprising nucleotides 58 to 420 of a nucleotide sequence represented by SEQ ID NO: 52, and a polynucleotide comprising a nucleotide sequence comprising nucleotides 61 to 399 of a nucleotide sequence represented by SEQ ID NO: 62.

(49) The polynucleotide according to (46), characterized by containing a polynucleotide comprising a nucleotide sequence comprising nucleotides 58 to 420 of a nucleotide sequence represented by SEQ ID NO: 54, and a polynucleotide comprising a nucleotide sequence comprising nucleotides 61 to 399 of a nucleotide sequence represented by SEQ ID NO: 64.

(50) The polynucleotide according to (46), characterized by containing a polynucleotide comprising a nucleotide sequence comprising nucleotides 58 to 420 of a nucleotide sequence represented by SEQ ID NO: 54, and a polynucleotide comprising a nucleotide sequence comprising nucleotides 61 to 396 of a nucleotide sequence represented by SEQ ID NO: 66.

(51) The polynucleotide according to (46), characterized by containing a polynucleotide comprising a nucleotide sequence comprising nucleotides 58 to 420 of a nucleotide sequence represented by SEQ ID NO: 56, and a polynucleotide comprising a nucleotide sequence comprising nucleotides 61 to 399 of a nucleotide sequence represented by SEQ ID NO: 68.

(52) The polynucleotide according to (46), characterized by containing a polynucleotide comprising a nucleotide sequence comprising nucleotides 58 to 420 of a nucleotide sequence represented by SEQ ID NO: 58, and a polynucleotide comprising a nucleotide sequence comprising nucleotides 61 to 399 of a nucleotide sequence represented by SEQ ID NO: 70.

(53) The polynucleotide according to (46), characterized by containing a polynucleotide comprising a nucleotide sequence comprising nucleotides 58 to 420 of a nucleotide sequence represented by SEQ ID NO: 98, and a polynucleotide comprising a nucleotide sequence comprising nucleotides 61 to 399 of a nucleotide sequence represented by SEQ ID NO: 68.

(54) The polynucleotide according to (46), characterized by containing a polynucleotide comprising a nucleotide sequence comprising nucleotides 58 to 420 of a nucleotide sequence represented by SEQ ID NO: 100, and a polynucleotide comprising a nucleotide sequence comprising nucleotides 61 to 399 of a nucleotide sequence represented by SEQ ID NO: 68.

(55) The polynucleotide according to (46), characterized by containing a polynucleotide comprising a nucleotide sequence comprising nucleotides 58 to 420 of a nucleotide sequence represented by SEQ ID NO: 98, and a polynucleotide comprising a nucleotide sequence comprising nucleotides 61 to 399 of a nucleotide sequence represented by SEQ ID NO: 102.

(56) The polynucleotide according to (46), characterized by containing a polynucleotide comprising a nucleotide sequence comprising nucleotides 58 to 420 of a nucleotide sequence represented by SEQ ID NO: 98, and a polynucleotide comprising a nucleotide sequence comprising nucleotides 61 to 399 of a nucleotide sequence represented by SEQ ID NO: 104.

(57) The polynucleotide according to (46), characterized by containing a polynucleotide comprising a nucleotide sequence comprising nucleotides 58 to 1410 of a nucleotide sequence represented by SEQ ID NO: 50, and a polynucleotide comprising a nucleotide sequence comprising nucleotides 61 to 714 of a nucleotide sequence represented by SEQ ID NO: 60.

(58) The polynucleotide according to (46), characterized by containing a polynucleotide comprising a nucleotide sequence comprising nucleotides 58 to 1410 of a nucleotide sequence represented by SEQ ID NO: 52, and a polynucleotide comprising a nucleotide sequence comprising nucleotides 61 to 714 of a nucleotide sequence represented by SEQ ID NO: 62.

(59) The polynucleotide according to (46), characterized by containing a polynucleotide comprising a nucleotide sequence comprising nucleotides 58 to 1410 of a nucleotide sequence represented by SEQ ID NO: 54, and a polynucleotide comprising a nucleotide sequence comprising nucleotides 61 to 714 of a nucleotide sequence represented by SEQ ID NO: 64.

(60) The polynucleotide according to (46), characterized by containing a polynucleotide comprising a nucleotide sequence comprising nucleotides 58 to 1410 of a nucleotide sequence represented by SEQ ID NO: 54, and a polynucleotide comprising a nucleotide sequence comprising nucleotides 61 to 711 of a nucleotide sequence represented by SEQ ID NO: 66.

(61) The polynucleotide according to (46), characterized by containing a polynucleotide comprising a nucleotide sequence comprising nucleotides 58 to 1410 of a nucleotide sequence represented by SEQ ID NO: 56, and a polynucleotide comprising a nucleotide sequence comprising nucleotides 61 to 714 of a nucleotide sequence represented by SEQ ID NO: 68.

(62) The polynucleotide according to (46), characterized by containing a polynucleotide comprising a nucleotide sequence comprising nucleotides 58 to 1410 of a nucleotide sequence represented by SEQ ID NO: 58, and a polynucleotide comprising a nucleotide sequence comprising nucleotides 61 to 714 of a nucleotide sequence represented by SEQ ID NO: 70.

(63) The polynucleotide according to (46), characterized by containing a polynucleotide comprising a nucleotide sequence comprising nucleotides 58 to 1398 of a nucleotide sequence represented by SEQ ID NO: 98, and a polynucleotide comprising a nucleotide sequence comprising nucleotides 61 to 714 of a nucleotide sequence represented by SEQ ID NO: 68.

(64) The polynucleotide according to (46), characterized by containing a polynucleotide comprising a nucleotide sequence comprising nucleotides 58 to 1398 of a nucleotide sequence represented by SEQ ID NO: 100, and a polynucleotide comprising a nucleotide sequence comprising nucleotides 61 to 714 of a nucleotide sequence represented by SEQ ID NO: 68.

(65) The polynucleotide according to (46), characterized by containing a polynucleotide comprising a nucleotide sequence comprising nucleotides 58 to 1398 of a nucleotide sequence represented by SEQ ID NO: 98, and a polynucleotide comprising a nucleotide sequence comprising nucleotides 61 to 714 of a nucleotide sequence represented by SEQ ID NO: 102.

(66) The polynucleotide according to (46), characterized by containing a polynucleotide comprising a nucleotide sequence comprising nucleotides 58 to 1398 of a nucleotide sequence represented by SEQ ID NO: 98, and a polynucleotide comprising a nucleotide sequence comprising nucleotides 61 to 714 of a nucleotide sequence represented by SEQ ID NO: 104.

(67) A vector, comprising any one of the polynucleotides according to (43) to (66).

(68) A transformed host cell, comprising any one of the polynucleotides according to (43) to (66).

(69) A transformed host cell, comprising the vector according to (67).

(70) A method of producing the antibody according to any one of (3), (7), and (10) to (30), comprising culturing the host cell according to (68) or (69), and purifying an antibody from the resulting culture product.

Advantage of the Invention

According to the invention, a therapeutic and/or preventive agent for abnormal bone metabolism whose mechanism of action is to inhibit the differentiation and maturation of osteoclasts and the bone resorption activity thereof can be obtained.

BRIEF DESCRIPTION OF THE DRAWINGS

FIG. 23 shows a cloned nucleotide sequence of a rat #32A1 heavy chain and an amino acid sequence thereof.

FIG. 24 shows a cloned nucleotide sequence of a rat #32A1 light chain and an amino acid sequence thereof.

FIG. 25 shows a nucleotide sequence of a #32A1 human chimeric antibody heavy chain and an amino acid sequence thereof.

FIG. 26 shows a nucleotide sequence of a #32A1 human chimeric antibody light chain and an amino acid sequence thereof.

FIG. 27 shows a nucleotide sequence of h#32A1-T1H and an amino acid sequence thereof.

FIG. 28 shows a nucleotide sequence of h#32A1-T2H and an amino acid sequence thereof.

FIG. 29 shows a nucleotide sequence of h#32A1-T3H and an amino acid sequence thereof.

FIG. 30 shows a nucleotide sequence of h#32A1-T5H and an amino acid sequence thereof.

FIG. 31 shows a nucleotide sequence of h#32A1-T6H and an amino acid sequence thereof.

FIG. 32 shows a nucleotide sequence of h#32A1-T1L and an amino acid sequence thereof.

FIG. 33 shows a nucleotide sequence of h#32A1-T2L and an amino acid sequence thereof.

FIG. 34 shows a nucleotide sequence of h#32A1-T3L and an amino acid sequence thereof.

FIG. 35 shows a nucleotide sequence of h#32A1-T4L and an amino acid sequence thereof.

FIG. 36 shows a nucleotide sequence of h#32A1-T5L and an amino acid sequence thereof.

FIG. 37 shows a nucleotide sequence of h#32A1-T6L and an amino acid sequence thereof.

FIG. 38 shows amino acid sequences of h#32A1-T7H, h#32A1-T8H, and h#32A1-T9H.

FIG. 39 shows amino acid sequences of h#32A1-T10H, h#32A1-T11H, and h#32A1-T12H.

FIG. 40 shows amino acid sequences of h#32A1-T7L, h#32A1-T8L, h#32A1-T9L, h#32A1-T10L, and h#32A1-T11L.

FIG. 41 shows amino acid sequences of h#32A1-T12L, h#32A1-T13L, h#32A1-T14L, h#32A1-T15L, and h#32A1-T16L.

FIG. 42 shows amino acid sequences of h#32A1-T17L, h#32A1-T18L, h#32A1-T19L, h#32A1-T20L, and h#32A1-T21L.

FIG. 43 shows amino acid sequences of h#32A1-T22L, h#32A1-T23L, h#32A1-T24L, and h#32A1-T25L.

FIG. 46 shows graphs depicting, by the enzymatic activity of TRAP, the inhibition of mouse osteoclast formation by the addition of a humanized rat anti-mouse Siglec-15 antibody (h#32A1-H1-1/L5 or h#32A1-H5/L5). Incidentally, the rat #32A1 antibody and #32A1 human chimeric antibody in the drawing are positive controls common to FIGS. 46 and 47.

FIG. 54 shows a nucleotide sequence of h#32A1-H1-1 and the amino acid sequence thereof.

FIG. 55 shows a nucleotide sequence of h#32A1-H5 and the amino acid sequence thereof.

FIG. 56 shows a nucleotide sequence of h#32A1-L2-15 and the amino acid sequence thereof.

FIG. 57 shows a nucleotide sequence of h#32A1-L2-16 and the amino acid sequence thereof.

MODE FOR CARRYING OUT THE INVENTION

Figure 1:
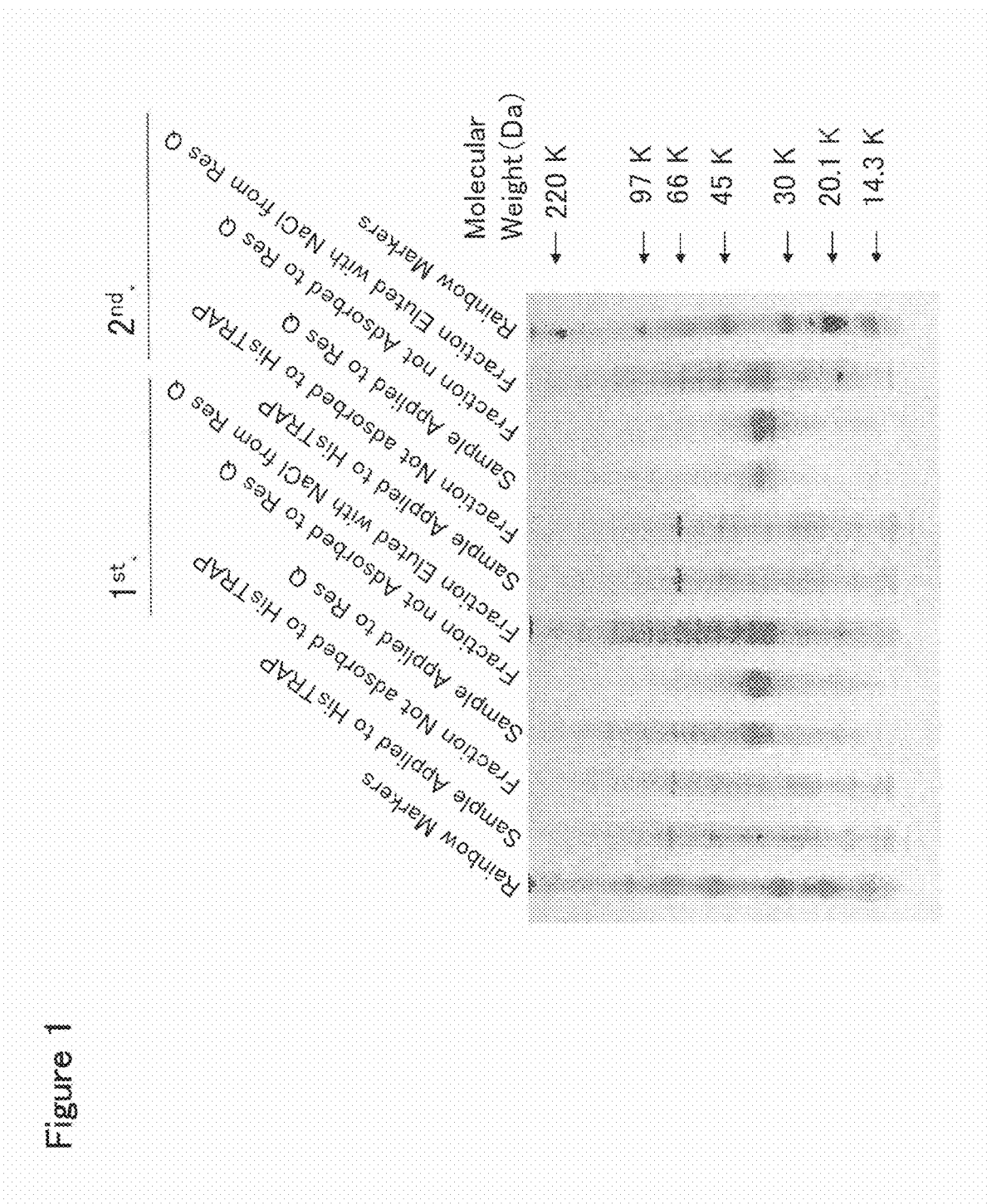
FIG. 1 shows the results of evaluating the purity of mouse Siglec-15-His purified by HisTrap HP column chromatography and Resource Q column chromatography through SDS-polyacrylamide electrophoresis and silver staining.

The term "gene" as used herein includes not only DNA, but also mRNA, cDNA, and cRNA.

The term "polynucleotide" as used herein is used with the same meaning as a "nucleic acid" and also includes DNA, RNA, probes, oligonucleotides, and primers.

The terms "polypeptide" and "protein" as used herein are used without distinction.

The term "RNA fraction" as used herein refers to a fraction containing RNA.

The term "cell" as used herein also includes cells in an animal individual and cultured cells.

The term "Siglec-15" as used herein is used with the same meaning as "Siglec-15 protein".

The term "osteoclast formation" as used herein is used with the same meaning as "osteoclast differentiation" or "osteoclast maturation".

The term "functional fragment of an antibody" as used herein refers to a partial fragment of an antibody having an antigen-binding activity and includes Fab, F(ab')2, Fv, scFv, diabodies, linear antibodies, polyspecific antibodies formed from antibody fragments, and the like. The term also encompasses Fab' which is a monovalent fragment in a variable region of an antibody obtained by treating F(ab')2 under reducing conditions. However, the term is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The term "epitope" as used herein refers to a partial peptide or a partial tertiary structure of Siglec-15 to which a specific anti-Siglec-15 antibody binds. The above-mentioned epitope which is a partial peptide of Siglec-15 can be determined by a method well known to those skilled in the art such as an immunoassay. However, the following method can be employed, for example. Various partial structures of Siglec-15 are produced. In the production of the partial structures, a known oligopeptide synthesis technique can be used. For example, a series of polypeptides having appropriately reduced lengths obtained by sequentially shortening Siglec-15 from the C terminus or N terminus are produced using a genetic recombination technique known to those skilled in the art. Thereafter, the reactivity of an antibody against these polypeptides is examined and a recognition site is roughly determined. Then, peptides having shorter lengths are synthesized and the reactivity with these peptides is examined, whereby the epitope can be determined. Further, the epitope which is a partial tertiary structure of Siglec-15 which binds to a specific Siglec-15 antibody can be determined by specifying the amino acid residues of Siglec-15 adjacent to the antibody by an X-ray structural analysis. If a second anti-Siglec-15 antibody binds to a partial peptide or a partial tertiary structure to which a first anti-Siglec-15 antibody binds, it can be determined that the first antibody and the second antibody share the same epitope. Further, by confirming that the second anti-Siglec-15 antibody competes with the first anti-Siglec-15 antibody for the binding to Siglec-15 (that is, the second antibody inhibits the binding between Siglec-15 and the first antibody), it can be determined that the first antibody and the second antibody share the same epitope even if the sequence or structure of a specific epitope has not been determined. Further, when the first antibody and the second antibody bind to the same epitope and also the first antibody has a special effect such as an antigen-neutralizing activity, the second antibody can be expected to have the same activity.

It is known that each heavy and light chain of an antibody molecule has three complementarity determining regions (CDRs). The complementarity determining region is also called the hypervariable domain, and is present in a variable region of each heavy and light chain of an antibody. It is a site which has unusually high variability in its primary structure, and there are three separate CDRs in the primary structure of each heavy and light polypeptide chain. In this description, as for the complementarity determining regions of an antibody, the complementarity determining regions of the heavy chain are represented by CDRH1, CDRH2, and CDRH3 from the amino-terminal side of the amino acid sequence of the heavy chain, and the complementarity determining regions of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to hybridization that is performed under conditions under which identification can be achieved by performing hybridization at 68° C. in a commercially available hybridization solution, ExpressHyb Hybridization Solution (manufactured by Clontech, Inc.) or performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

Siglec-15

The present inventors have found that the Siglec-15 gene is specifically expressed in giant cell tumors and have also found that the expression level of the Siglec-15 gene increases when a monocyte-derived cell line differentiates into osteoclasts.

As for the Siglec-15 to be used in the invention, Siglec-15 is directly purified from monocytes or bone marrow cells of a human, non-human mammal (such as guinea pig, rat, mouse, rabbit, pig, sheep, cattle, or monkey) or chicken and is used, or a cell membrane fraction of the above-mentioned cells is prepared and can be used. Further, Siglec-15 can be obtained by in vitro synthesis thereof or production thereof in a host cell through genetic engineering. In the genetic engineering production, specifically, Siglec-15 cDNA is integrated into a vector capable of expressing Siglec-15 cDNA, and Siglec-15 is synthesized in a solution containing an enzyme, a substrate, and an energy substance required for transcription and translation, or another prokaryotic or eucaryotic host cell is transformed to express Siglec-15, whereby the protein can be obtained.

The nucleotide sequence of human Siglec-15 cDNA has been registered in GenBank with an accession number of NM_213602 and is represented by SEQ ID NO: 1 in the Sequence Listing, and its amino acid sequence is represented by SEQ ID NO: 2 in the Sequence Listing. The nucleotide sequence of mouse Siglec-15 cDNA has been registered in GenBank with an accession number of XM_884636 and is represented by SEQ ID NO: 3 in the Sequence Listing, and its amino acid sequence is represented by SEQ ID NO: 4 in the Sequence Listing. Mature human Siglec-15 from which the signal sequence has been removed corresponds to an amino acid sequence comprising amino acid residues 21 to 328 of the amino acid sequence represented by SEQ ID NO: 2. Further, mouse Siglec-15 from which the signal sequence has been removed corresponds to an amino acid sequence comprising amino acid residues 21 to 341 of the amino acid sequence represented by SEQ ID NO: 4. Incidentally, Siglec-15 is sometimes called CD33 antigen-like 3, CD33 molecule-like 3, CD33-like 3, or CD33L3, and all of these represent the same molecule.

Siglec-15 cDNA can be obtained by, for example, a so-called PCR method in which a polymerase chain reaction (hereinafter referred to as "PCR") is performed using a cDNA library expressing Siglec-15 cDNA as a template and primers which specifically amplify Siglec-15 cDNA (Saiki, R. K., et al., Science, (1988) 239, 487-49).

Further, a polynucleotide which hybridizes to a polynucleotide comprising a nucleotide sequence complementary to at least one nucleotide sequence selected from the nucleotide sequences represented by SEQ ID NOS: 1 and 3 in the Sequence Listing under stringent conditions and encodes a protein having a biological activity comparable to that of Siglec-15 is also regarded as Siglec-15 cDNA. Further, a polynucleotide which is a splicing variant transcribed from the human or mouse Siglec-15 locus or a polynucleotide which hybridizes to a sequence complementary thereto under stringent conditions and encodes a protein having a biological activity comparable to that of Siglec-15 is also regarded as Siglec-15 cDNA.

Further, a protein which comprises an amino acid sequence including substitution, deletion or addition of one or several amino acids in at least one amino acid sequence selected from the amino acid sequences represented by SEQ ID NOS: 2 and 4 in the Sequence Listing or an amino acid sequence obtained by removing the signal sequence from any of these sequences and has a biological activity comparable to that of Siglec-15 is also regarded as Siglec-15. Further, a protein which comprises an amino acid sequence encoded by a splicing variant transcribed from the human or mouse Siglec-15 locus or an amino acid sequence including a substitution, deletion or addition of one or several amino acids therein and has a biological activity comparable to that of Siglec-15 is also regarded as Siglec-15.

2. Detection of Abnormal Bone Metabolism

An analysis of the expression level of the Siglec-15 gene in a group of test samples from various human bone tissues showed that the expression level of the gene significantly increases in giant cell tumor (GCT) which is a bone tumor with a large number of osteoclast-like multinucleated giant cells arising and is characterized by clinical findings of osteolytic bone destruction (Bullough et al., Atlas of Orthopedic Pathology 2nd edition, pp. 17.6-17.8, Lippincott Williams & Wilkins Publishers (1992)).

It was also found that the expression level of the Siglec-15 gene increases when a monocyte-derived cell line is differentiated into osteoclasts.

Accordingly, Siglec-15 is considered to be associated with human pathologies such as GCT in which bone resorption is increased. In other words, measurement of the expression level of the Siglec-15 gene and/or Siglec-15 in each cell and/or each tissue enables determination of the state of abnormal bone metabolism accompanied by overexpression of Siglec-15. The abnormal bone metabolism as used herein refers to a disorder characterized by net bone loss, and specific examples thereof include, but are not limited to, osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, Paget's disease of bone, renal osteodystrophy, and osteogenesis imperfecta.

In the invention, the "test sample" to be used for examining the expression level of the Siglec-15 gene and/or Siglec-15 refers to a sample from a tissue of bone marrow, bone, prostate, testis, penis, bladder, kidney, oral cavity, pharynx, lip, tongue, gingiva, nasopharynx, esophagus, stomach, small intestine, large intestine, colon, liver, gallbladder, pancreas, nose, lung, soft tissue, skin, breast, uterus, ovary, brain, thyroid, lymph node, muscle, fat tissue or the like, or blood, a body fluid, an excretion, or the like obtained from a test subject, a clinical specimen, etc., however, in the invention, blood or bone marrow is more preferred.

As for RANKL which is known to be associated with osteoclast differentiation, a knockout mouse has been produced, and the phenotype when the function of RANKL has been lost has been analyzed (Young-Yun Kong, et. al., Nature (1999) 397, pp. 315-323). By producing a knockout mouse devoid of Siglec-15 in the same manner as above, the phenotype when the function of Siglec-15 has been lost can be analyzed.

3. Production of Anti-Siglec-15 Antibody

The antibody of the invention, which is against Siglec-15, can be obtained by immunizing an animal with Siglec-15 or an arbitrary polypeptide selected from the amino acid sequence of Siglec-15, and collecting and purifying the antibody produced in vivo according to a common procedure. The biological species of Siglec-15 to be used as an antigen is not limited to being human, and an animal can be immunized with Siglec-15 derived from an animal other than humans such as a mouse or a rat. In this case, by examining the cross-reactivity between an antibody binding to the obtained heterologous Siglec-15 and human Siglec-15, an antibody applicable to a human disease can be selected.

Further, a monoclonal antibody can be obtained by fusing antibody-producing cells which produce an antibody against Siglec-15 with myeloma cells to establish a hybridoma according to a known method (for example, Kohler and Milstein, Nature, (1975) 256, pp. 495-497; Kennet, R. ed., Monoclonal Antibodies, pp. 365-367, Plenum Press, N.Y. (1980)).

Incidentally, Siglec-15 to be used as an antigen can be obtained by genetic engineering to cause a host cell to produce the Siglec-15 gene.

Specifically, a vector capable of expressing Siglec-15 gene is produced, and the resulting vector is transfected into a host cell to express the gene, and then the expressed Siglec-15 is purified. Hereinafter, a method of obtaining an antibody against Siglec-15 will be specifically described.

Preparation of Antigen

Examples of the antigen to be used for producing the anti-Siglec-15 antibody include Siglec-15, a polypeptide comprising a partial amino acid sequence containing at least 6 consecutive amino acids of Siglec-15, and a derivative obtained by adding a given amino acid sequence or carrier thereto.

Siglec-15 can be purified directly from human tumor tissues or tumor cells and used. Further, Siglec-15 can be obtained by synthesizing it in vitro or by causing a host cell to produce it by genetic engineering.

With respect to the genetic engineering, specifically, Siglec-15 cDNA is integrated into a vector capable of expressing Siglec-15 cDNA and Siglec-15 is synthesized in a solution containing an enzyme, a substrate, and an energy substance required for transcription and translation, or another prokaryotic or eucaryotic host cell is transformed to express Siglec-15, whereby the antigen can be obtained.

Further, the antigen can also be obtained as a secretory protein by expressing a fusion protein obtained by ligating the extracellular domain of Siglec-15, which is a membrane protein, to the constant region of an antibody in an appropriate host-vector system.

Siglec-15 cDNA can be obtained by, for example, a so-called PCR method in which a polymerase chain reaction (hereinafter referred to as "PCR") is performed using a cDNA library expressing Siglec-15 cDNA as a template and primers which specifically amplify Siglec-15 cDNA (see Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host include *Escherichia coli* and *Bacillus subtilis*. In order to transform the host cell with a target gene, the host cell is transformed using a plasmid vector containing a replicon, i.e., a replication origin derived from a species compatible with the host, and a regulatory sequence. Further, the vector preferably has a sequence capable of imposing phenotypic selectivity on the transformed cell.

Examples of the eucaryotic host cell include vertebrate cells, insect cells, and yeast cells. As the vertebrate cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61); and the like are often used, however, they are not limited thereto.

The thus obtained transformant can be cultured according to a common procedure, and by the culturing of the transformant, a target polypeptide is produced intracellularly or extracellularly.

A suitable medium to be used for the culturing can be selected from various commonly used culture media depending on the employed host cell. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching a IgG Fc region to a recombinant protein to be expressed, the protein can be efficiently purified with a protein A column.

By combining the above-mentioned methods, a large amount of a target polypeptide can be easily produced in high yield and high purity.

Production of Anti-Siglec-15 Monoclonal Antibody

Examples of the antibody specifically binding to Siglec-15 include a monoclonal antibody specifically binding to Siglec-15, and a method of obtaining the antibody are as described below.

The production of a monoclonal antibody generally requires the following operational steps of:

purifying a biopolymer to be used as an antigen;

preparing antibody-producing cells by immunizing an animal by injection of the antigen, collecting the blood, assaying its antibody titer to determine when the spleen is to be excised;

preparing myeloma cells (hereinafter referred to as "myeloma");

fusing the antibody-producing cells with the myeloma;

screening a group of hybridomas producing a target antibody;

dividing the hybridomas into single cell clones (cloning);

optionally, culturing the hybridoma or rearing an animal implanted with the hybridoma for producing a large amount of a monoclonal antibody;

examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells and myeloma can be used other than spleen cells.

Purification of Antigen

As the antigen, Siglec-15 prepared by the method as described above or a partial peptide thereof can be used.

Further, a membrane fraction prepared from recombinant cells expressing Siglec-15 or the recombinant cells expressing Siglec-15 themselves, and also a partial peptide of the protein of the invention chemically synthesized by a method known to those skilled in the art can also be used as the antigen.

(b) Preparation of Antibody-Producing Cells

The antigen obtained in step (a) is mixed with an adjuvant such as Freund's complete or incomplete adjuvant, or aluminum potassium sulfate and the resulting mixture is used as an immunogen to immunize an experimental animal. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of mouse or rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 can be used, and in the case of a rat, for example, Wistar, Low, Lewis, Sprague, Dawley, ACI, BN, Fischer, and the like can be used.

These mice and rats are commercially available from breeders/distributors of experimental animals, for example, CLEA Japan, Inc. and Charles River Laboratories Japan, Inc.

Among these, in consideration of compatibility of fusing with myeloma cells as described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove autoantibodies, that is, a mouse with an autoimmune disease.

The age of the mouse or rat at the time of immunization is preferably 5 to 12 weeks of age, more preferably 6 to 8 weeks of age.

In order to immunize an animal with Siglec-15 or a recombinant thereof, for example, a known method described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Ill. (1964), or the like can be used.

Among these immunization methods, a preferred specific method in the invention is, for example, as follows.

That is, first, a membrane protein fraction serving as the antigen or cells caused to express the antigen is/are intradermally or intraperitoneally administered to an animal.

However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual differences, or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal to be immunized, individual differences, or the like, however, the dose is generally set to 0.05 to 5 mg, preferably about 0.1 to 0.5 mg.

A booster immunization is performed 1 to 6 weeks, preferably 2 to 4 weeks, more preferably 2 to 3 weeks after the administration of the antigen as described above.

The dose of the antigen at the time of performing the booster immunization varies depending on the type or size of animal or the like, however, in the case of a mouse, the dose is generally set to 0.05 to 5 mg, preferably 0.1 to 0.5 mg, more preferably about 0.1 to 0.2 mg.

Spleen cells or lymphocytes including antibody-producing cells are aseptically removed from the immunized animal 1 to 10 days, preferably 2 to 5 days, more preferably 2 to 3 days after the booster immunization.

At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto.

For example, if an ELISA method is employed, the measurement of the antibody titer in the invention can be carried out according to the procedures as described below.

First, a purified or partially purified antigen is adsorbed onto the surface of a solid phase such as a 96-well plate for ELISA, and the surface of the solid phase having no antigen adsorbed thereto is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495).

For example, in the case of spleen cells, a general method in which the antibody-producing cells are separated by homogenizing the spleen to obtain cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500•GTG-A12 (GM1500), UC729-6, LICR-LOW-HMy2(HMy2) and 8226AR/NIP4-1(NP41) derived from humans.

These HGPRT-deficient strains are available from, for example, the American Type Culture Collection (ATCC) or the like.

These cell strains are subcultured in an appropriate medium such as an 8-azaguanine medium [a medium obtained by adding 8-azaguanine to an RPMI-1640 medium supplemented with glutamine, 2-mercaptoethanol, gentamicin, and fetal calf serum (hereinafter referred to as "FCS")]; Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FCS] to obtain not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, a chemical method in which the antibody-producing cells and the myeloma cells are mixed in a solution containing a polymer such as polyethylene glycol at a high concentration, a physical method using electric stimulation, or the like can be used.

Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-mentioned cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin.

That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a limiting dilution method is preferred.

In this method, a fibroblast cell strain derived from a rat fetus or feeder cells such as normal mouse spleen cells, thymus gland cells, or ascites cells are seeded on a microplate.

Meanwhile, hybridomas are diluted in a medium to give a cell density of 0.2 to 0.5 cells per 0.2 ml. A 0.1 ml aliquot of the diluted hybridoma suspension is added to each well and culturing is continued for about 2 weeks while replacing about ⅓ of the culture solution with fresh medium at predetermined time intervals (for example, every 3 days), whereby hybridoma clones can be proliferated.

The hybridomas in wells for which the antibody titer has been confirmed are subjected to, for example, cloning by the limiting dilution method repeatedly 2 to 4 times. A hybridoma which has been confirmed to have a stable antibody titer is selected as an anti-Siglec-15 monoclonal antibody-producing hybridoma strain.

Examples of the hybridoma strain thus cloned include hybridoma #32A1 described in WO 09/48072. The hybridoma #32A1 was deposited at the International Patent Organism Depositary of the National Institute of Advanced Industrial Science and Technology (located at Central 6, 1-1-1 Higashi, Tsukuba-shi, Ibaraki-ken, 305-8566, Japan) on Aug. 28, 2008, and has been given an accession number of FERM BP-10999 under the name of anti-Siglec-15 Hybridoma #32A1. Incidentally, in this description, the antibody produced by the hybridoma #32A1 is referred to as "#32A1 antibody" or simply "#32A1". Further, antibodies obtained in the Examples of this description other than the #32A1 antibody are also represented by the antibody names in the same manner. A partial fragment containing the heavy chain variable region of the #32A1 antibody has an amino acid sequence comprising amino acid residues 20 to 167 of SEQ ID NO: 28 in the Sequence Listing. Further, a partial fragment containing the light chain variable region sequence of the #32A1 antibody has an amino acid sequence comprising amino acid residues 21 to 139 of SEQ ID NO: 30 in the Sequence Listing.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed. The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture.

From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-mentioned BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristane) is administered 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is injected into the abdominal cavity of the mouse. In general, when the abdomen is expanded and filled with the ascites, the ascites is collected from the mouse.

By this method, the monoclonal antibody can be obtained at a concentration which is about 100 times or more higher than that in the culture solution.

The monoclonal antibody obtained by the above-mentioned method can be purified by a method described in, for example, Weir, D. M.: Handbook of Experimental Immunology Vol. I, II, III, Blackwell Scientific Publications, Oxford (1978).

That is, examples of the method include an ammonium sulfate precipitation method, gel filtration, ion exchange chromatography, and affinity chromatography.

As a simple purification method, a commercially available monoclonal antibody purification kit (for example, MAbTrap GII Kit manufactured by Pharmacia, Inc.) or the like can also be used.

The thus obtained monoclonal antibody has high antigen specificity for Siglec-15.

(h) Assay of Monoclonal Antibody

The isotype and subclass of the thus obtained monoclonal antibody can be determined as follows.

First, examples of the identification method include an Ouchterlony method, an ELISA method and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/ml].

Other Antibodies

The antibody of the invention includes not only the above-mentioned monoclonal antibody against Siglec-15 but also a recombinant antibody obtained by artificial modification for the purpose of decreasing heterologous antigenicity to human such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived constant region can be exemplified (see Proc. Natl. Acad. Sci. USA, 81, 6851-6855, (1984)). As one example of the chimeric antibody derived from a rat anti-mouse antibody #32A1, an antibody comprising a heavy chain having an amino acid sequence comprising amino acid residues 20 to 470 of SEQ ID NO: 41 in the Sequence Listing and a light chain having an amino acid sequence comprising amino acid residues 21 to 237 of SEQ ID NO: 43 in the Sequence Listing can be exemplified.

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861) can be exemplified. As an example of the humanized antibody of a rat antibody #32A1, an arbitrary combination of a heavy chain containing a heavy chain variable region comprising an amino acid sequence comprising amino acid residues 20 to 140 of SEQ ID NO: 51 in the Sequence Listing, amino acid residues 20 to 140 of SEQ ID NO: 53, amino acid residues 20 to 140 of SEQ ID NO: 55, amino acid residues 20 to 140 of SEQ ID NO: 57, amino acid residues 20 to 140 of SEQ ID NO: 59, amino acid residues 20 to 140 of SEQ ID NO: 99, amino acid residues 20 to 140 of SEQ ID NO: 101, or amino acid residues 1 to 121 of any one of amino acid sequences represented by SEQ ID NOS: 72 to 77 and a light chain containing a light chain variable region comprising an amino acid sequence comprising amino acid residues 21 to 133 of SEQ ID NO: 61, amino acid residues 21 to 133 of SEQ ID NO: 63, amino acid residues 21 to 133 of SEQ ID NO: 65, amino acid residues 21 to 132 of SEQ ID NO: 67, amino acid residues 21 to 133 of SEQ ID NO: 69, amino acid residues 21 to 133 of SEQ ID NO: 71, amino acid residues 21 to 133 of SEQ ID NO: 103, amino acid residues 21 to 133 of SEQ ID NO: 105, or amino acid residues 1 to 113 of any one of amino acid sequences represented by SEQ ID NOS: 78 to 96 can be exemplified.

As a preferred combination, an antibody comprising a heavy chain containing a heavy chain variable region comprising an amino acid sequence comprising amino acid residues 20 to 140 of SEQ ID NO: 51 and a light chain containing a light chain variable region comprising an amino acid sequence comprising amino acid residues 21 to 133 of SEQ ID NO: 61, an antibody comprising a heavy chain containing a heavy chain variable region comprising an amino acid sequence comprising amino acid residues 20 to 140 of SEQ ID NO: 53 and a light chain containing a light chain variable region comprising an amino acid sequence comprising amino acid residues 21 to 133 of SEQ ID NO:

63, an antibody comprising a heavy chain containing a heavy chain variable region comprising an amino acid sequence comprising amino acid residues 20 to 140 of SEQ ID NO: 55 and a light chain containing a light chain variable region comprising an amino acid sequence comprising amino acid residues 21 to 133 of SEQ ID NO: 65, an antibody comprising a heavy chain containing a heavy chain variable region comprising an amino acid sequence comprising amino acid residues 20 to 140 of SEQ ID NO: 55 and a light chain containing a light chain variable region comprising an amino acid sequence comprising amino acid residues 21 to 132 of SEQ ID NO: 67, an antibody comprising a heavy chain containing a heavy chain variable region comprising an amino acid sequence comprising amino acid residues 20 to 140 of SEQ ID NO: 57 and a light chain containing a light chain variable region comprising an amino acid sequence comprising amino acid residues 21 to 133 of SEQ ID NO: 69, an antibody comprising a heavy chain containing a heavy chain variable region comprising an amino acid sequence comprising amino acid residues 20 to 140 of SEQ ID NO: 59 and a light chain containing a light chain variable region comprising an amino acid sequence comprising amino acid residues 21 to 133 of SEQ ID NO: 71, an antibody comprising a heavy chain containing a heavy chain variable region comprising an amino acid sequence comprising amino acid residues 20 to 140 of SEQ ID NO: 99 and a light chain containing a light chain variable region comprising an amino acid sequence comprising amino acid residues 21 to 133 of SEQ ID NO: 69, an antibody comprising a heavy chain containing a heavy chain variable region comprising an amino acid sequence comprising amino acid residues 20 to 140 of SEQ ID NO: 101 and a light chain containing a light chain variable region comprising an amino acid sequence comprising amino acid residues 21 to 133 of SEQ ID NO: 69, an antibody comprising a heavy chain containing a heavy chain variable region comprising an amino acid sequence comprising amino acid residues 20 to 140 of SEQ ID NO: 99 and a light chain containing a light chain variable region comprising an amino acid sequence comprising amino acid residues 21 to 133 of SEQ ID NO: 103, or an antibody comprising a heavy chain containing a heavy chain variable region comprising an amino acid sequence comprising amino acid residues 20 to 140 of SEQ ID NO: 99 and a light chain containing a light chain variable region comprising an amino acid sequence comprising amino acid residues 21 to 133 of SEQ ID NO: 105 can be exemplified.

As a more preferred combination, an antibody comprising a heavy chain having an amino acid sequence comprising amino acid residues 20 to 470 of SEQ ID NO: 51 and a light chain having an amino acid sequence comprising amino acid residues 21 to 238 of SEQ ID NO: 61, an antibody comprising a heavy chain having an amino acid sequence comprising amino acid residues 20 to 470 of SEQ ID NO: 53 and a light chain having an amino acid sequence comprising amino acid residues 21 to 238 of SEQ ID NO: 63, an antibody comprising a heavy chain having an amino acid sequence comprising amino acid residues 20 to 470 of SEQ ID NO: 55 and a light chain having an amino acid sequence comprising amino acid residues 21 to 238 of SEQ ID NO: 65, an antibody comprising a heavy chain having an amino acid sequence comprising amino acid residues 20 to 470 of SEQ ID NO: 55 and a light chain having an amino acid sequence comprising amino acid residues 21 to 237 of SEQ ID NO: 67, an antibody comprising a heavy chain having an amino acid sequence comprising amino acid residues 20 to 470 of SEQ ID NO: 57 and a light chain having an amino acid sequence comprising amino acid residues 21 to 238 of SEQ ID NO: 69, an antibody comprising a heavy chain having an amino acid sequence comprising amino acid residues 20 to 470 of SEQ ID NO: 59 and a light chain having an amino acid sequence comprising amino acid residues 21 to 238 of SEQ ID NO: 71, an antibody comprising a heavy chain having an amino acid sequence comprising amino acid residues 20 to 466 of SEQ ID NO: 99 and a light chain having an amino acid sequence comprising amino acid residues 21 to 238 of SEQ ID NO: 69, an antibody comprising a heavy chain having an amino acid sequence comprising amino acid residues 20 to 466 of SEQ ID NO: 101 and a light chain having an amino acid sequence comprising amino acid residues 21 to 238 of SEQ ID NO: 69, an antibody comprising a heavy chain having an amino acid sequence comprising amino acid residues 20 to 466 of SEQ ID NO: 99 and a light chain having an amino acid sequence comprising amino acid residues 21 to 238 of SEQ ID NO: 103, or an antibody comprising a heavy chain having an amino acid sequence comprising amino acid residues 20 to 466 of SEQ ID NO: 99 and a light chain having an amino acid sequence comprising amino acid residues 21 to 238 of SEQ ID NO: 105 can be exemplified.

However, the humanized antibody derived from the #32A1 antibody is not limited to the above-mentioned humanized antibodies as long as the humanized antibody has all 6 types of CDR sequences of #32A1 and has an activity of inhibiting osteoclast formation. Incidentally, the heavy chain variable region of the #32A1 antibody has CDRH1 (DYFMN) comprising an amino acid sequence represented by SEQ ID NO: 44, either one of CDRH2 (QIRNKIYTYAT-FYAESLEG) comprising an amino acid sequence represented by SEQ ID NO: 45 and CDRH2 (QIRNKIYTYAT-FYA) represented by SEQ ID NO: 97, and CDRH3 (SLTGGDYFDY) comprising an amino acid sequence represented by SEQ ID NO: 46. The CDRH2 represented by SEQ ID NO: 45 is in accordance with the Kabat definition (SEQUENCES OF PROTEINS OF IMMUNOLOGICAL INTEREST VOL. I, FIFTH EDITION (1991)). The CDRH2 represented by SEQ ID NO: 97 is made shorter by five residues at the C terminus than the Kabat definition. In the heavy chain sequence containing this CDRH2, the CDR sequence derived from a rat is made shorter and more of a human framework sequence is incorporated, and therefore, when it is administered to humans, it is much less likely to be recognized as a heterologous antigen. Further, the light chain variable region of the #32A1 antibody has CDRL1 (RASQSVTISGYSFIH) comprising an amino acid sequence represented by SEQ ID NO: 47, CDRL2 (RASNLAS) comprising an amino acid sequence represented by SEQ ID NO: 48, and CDRL3 (QQSRKSPWT) comprising an amino acid sequence represented by SEQ ID NO: 49.

Further, the antibody of the invention includes a human antibody. A human anti-Siglec-15 antibody refers to a human antibody having only a gene sequence of an antibody derived from a human chromosome. The human anti-Siglec-15 antibody can be obtained by a method using a human antibody-producing mouse having a human chromosome fragment containing heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a genetic engineering technique, by using cDNAs encoding such a heavy chain and a light chain of a human antibody, respectively, and preferably a vector containing the cDNAs, eukaryotic cells are transformed, and a transformant which produces a recombinant human monoclonal antibody is cultured, whereby the antibody can also be obtained from the culture supernatant.

Here, as the host, for example, eukaryotic cells, preferably mammalian cells such as CHO cells, lymphocytes or myeloma cells can be used.

Further, a method of obtaining a phage display-derived human antibody screened from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Opthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector having the sequence and introducing the vector into an appropriate host to express it (WO 92/01047, WO 92/20791, WO 93/06213, WO 93/11236, WO 93/19172, WO 95/01438, WO 95/15388, Annu Rev. Immunol (1994) 12, pp. 433-455, Nature Biotechnology (2005) 23 (9), pp. 1105-1116).

The antibodies obtained by the above method are evaluated for the property of binding to an antigen by the method described in Example 25 or the like, and a preferred antibody can be selected. As one example of another index when the properties of antibodies are compared, the stability of antibodies can be exemplified. The differential scanning calorimetry (DSC) shown in Example 33 is an instrument capable of rapidly and accurately measuring a thermal denaturation midpoint temperature (Tm) which is a favorable index of relative structural stability of proteins. By measuring Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include as follows: the yield in an appropriate host cell is high and the aggregability in an aqueous solution is low. For example, an antibody which shows the highest yield does not always show high thermal stability, and therefore, it is necessary to select an antibody most suitable for administering to humans by making comprehensive evaluation based on the above-mentioned indices.

Further, a method in which the full-length heavy and light chain sequences of an antibody are ligated using an appropriate linker, whereby a single-chain immunoglobulin is obtained is also known (Lee, H-S, et. al., Molecular Immunology (1999) 36, pp. 61-71; Shirrmann, T. et. al., mAbs (2010), 2, (1) pp. 1-4). By dimerizing such a single-chain immunoglobulin, the resulting dimer can have a structure and an activity similar to those of an antibody which is a tetramer itself. Further, the antibody of the invention may be an antibody which has a single heavy chain variable region and does not have a light chain sequence. Such an antibody is called a single domain antibody (sdAb) or a nanobody, and in fact, it is observed in camels and llamas and has been reported to have an antigen-binding affinity (Muyldemans S. et. al., Protein Eng. (1994) 7(9), 1129-35, Hamers-Casterman C. et. al., Nature (1993) 363 (6428) 446-8). It can be understood that the above-mentioned antibodies are types of functional fragments of the antibody according to the invention.

Further, by controlling glycosylation in which a glycan is bound to the antibody of the invention, it is possible to enhance antibody-dependent cellular cytotoxic activity. As regards techniques for controlling the glycosylation of antibodies, WO 99/54342, WO 00/61739, WO 02/31140, etc. are known. However, the techniques are not limited thereto.

In cases where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this description and a gene encoding a light chain sequence thereof. When a host cell is transformed, it is possible to insert the heavy chain sequence gene and the light chain sequence gene into the same expression vector, and also into different expression vectors separately. In cases where eukaryotic cells are used as the host, animal cells, plant cells, and eukaryotic microorganisms can be used. As the animal cells, (1) mammalian cells, for example, dihydrofolate reductase-deficient strains (Urlaub, G. and Chasin, L. A., Proc. Natl. Acad. Sci. USA (1980) 77, pp. 4126-4220) of simian COS cells (Gluzman, Y., Cell, (1981) 23, pp. 175-182, ATCC CRL-1650), murine fibroblasts NIH3T3 (ATCC No. CRL-1658), and Chinese hamster ovarian cells (CHO cells; ATCC: CCL-61); can be exemplified. Further, in cases where prokaryotic cells are used, for example, *Escherichia coli* and *Bacillus subtilis* can be exemplified. By introducing a target antibody gene into these cells through transformation, and culturing the thus transformed cells in vitro, the antibody can be obtained. In the above-mentioned culture method, the yield may sometimes vary depending on the sequence of the antibody, and therefore, it is possible to select one which is easily produced as a pharmaceutical by using the yield as an index among the antibodies having a comparable binding activity.

There is no limitation on isotype of the antibody of the invention, and examples thereof include IgG (IgG1, IgG2, IgG3, IgG4), IgM, IgA (IgA1, IgA2), IgD, and IgE, and preferred examples thereof include IgG and IgM, and further, more preferred examples thereof include IgG1 and IgG2.

Further, the antibody of the invention may be a functional fragment of the antibody having an antigen-binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or part of the functions of the full-length molecule of the antibody can be called a functional fragment of the antibody. As the functions of the antibody, generally an antigen-binding activity, an activity of neutralizing the activity of an antigen, an activity of increasing the activity of an antigen, an antibody-dependent cytotoxic activity, a complement-dependent cytotoxic activity, and a complement-dependent cellular cytotoxic activity can be exemplified. The function of the functional fragment of the antibody according to the invention is a binding activity to Siglec-15, preferably an activity of inhibiting the formation of osteoclasts, more preferably an activity of inhibiting the process of cell fusion of osteoclasts.

Examples of the fragment of the antibody include Fab, F(ab')2, Fv, single-chain Fv (scFv) in which Fv molecules of the heavy chain and the light chain are ligated via an appropriate linker, a diabody (diabodies), a linear antibody, and a polyspecific antibody composed of the antibody fragment. Further, Fab' which is a monovalent fragment in a variable region of an antibody obtained by treating F(ab')2 under reducing conditions is also regarded as a fragment of the antibody.

Further, the antibody of the invention may be a polyspecific antibody with specificity for at least two different antigens. In general, such a molecule binds to two antigens (that is, a bispecific antibody), however, the "polyspecific antibody" as used herein includes an antibody having specificity for two or more (for example, three) antigens.

The polyspecific antibody of the invention may be a full-length antibody or a fragment of such an antibody (for example, a F(ab')2 bispecific antibody). The bispecific antibody can be produced by ligating the heavy and light chains (HL pairs) of two types of antibodies, or can also be produced by fusing hybridomas which produce different monoclonal antibodies to prepare bispecific antibody-producing fused cells (Millstein et al., Nature (1983) 305, pp. 537-539).

The antibody of the invention may be a single-chain antibody (also referred to as scFv). The single-chain antibody can be obtained by ligating the heavy chain variable region and the light chain variable region of an antibody via a polypeptide linker (Pluckthun, The Pharmacology of Monoclonal Antibodies, 113 (edited by Rosenburg and Moore, Springer Verlag, New York, pp. 269-315 (1994), Nature Biotechnology (2005), 23, pp. 1126-1136). Further, a BiscFv fragment produced by ligating two scFv molecules via a polypeptide linker can also be used as the bispecific antibody.

The method of producing a single-chain antibody is known in this technical field (see, for example, U.S. Pat. Nos. 4,946,778, 5,260,203, 5,091,513, 5,455,030, etc.). In this scFv, the heavy chain variable region and the light chain variable region are ligated via a linker which does not form a conjugate, preferably via a polypeptide linker (Huston, J. S. et al., Proc. Natl. Acad. Sci. USA (1988), 85, pp. 5879-5883). In the scFv, the heavy chain variable region and the light chain variable region may be derived from the same antibody or different antibodies.

As the polypeptide linker to be used for ligating the variable regions, for example, a given single-chain peptide composed of 12 to 19 residues is used.

DNA encoding scFv can be obtained by performing amplification using a DNA encoding the entire amino acid sequence, or a desired partial amino acid sequence, selected from the heavy chain or the heavy chain variable region of the above-mentioned antibody and the light chain or the light chain variable region thereof as a template by a PCR method using a primer pair that defines both ends thereof, and further performing amplification by combining a DNA encoding a polypeptide linker portion and a primer pair that defines both ends thereof so as to ligate both of the ends to the heavy chain and the light chain, respectively.

Further, once DNA encoding scFv is produced, an expression vector containing the same and a host transformed by the expression vector can be obtained according to common procedures. Further, by using the resulting host, scFv can be obtained according to common procedures. An antibody fragment thereof can be produced in a host by obtaining a gene and expressing the gene in the same manner as described above.

The antibody of the invention may be multimerized to increase its affinity for an antigen. The antibody to be multimerized may be one type of antibody or a plurality of antibodies which recognize a plurality of epitopes of the same antigen. As a method of multimerization of the antibody, binding of the IgG CH3 domain to two scFv molecules, binding to streptavidin, introduction of a helix-turn-helix motif and the like can be exemplified.

The antibody of the invention may be a polyclonal antibody which is a mixture of plural types of anti-Siglec-15 antibodies having different amino acid sequences. As one example of the polyclonal antibody, a mixture of plural types of antibodies having different CDR can be exemplified. As such a polyclonal antibody, a mixture of cells which produce different antibodies is cultured, and an antibody purified from the resulting culture can be used (see WO 2004/061104).

As a modified antibody, an antibody bound to any of various types of molecules such as polyethylene glycol (PEG) can also be used.

Further, the antibody of the invention may be in the form of a conjugate formed between any of these antibodies and another medicinal agent (immunoconjugate). Examples of such an antibody include one in which the antibody is conjugated to a radioactive material or a compound having a pharmacological action (Nature Biotechnology (2005) 23, pp. 1137-1146).

The obtained antibody can be purified to homogeneity. The separation and purification of the antibody can be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified.

For example, as a column using a Protein A column, Hyper D, POROS, Sepharose FF (Pharmacia) and the like can be exemplified.

Further, by using a carrier having an antigen immobilized thereon, the antibody can also be purified utilizing the binding property of the antibody to the antigen.

4. Pharmaceutical Containing Anti-Siglec-15 Antibody

From the anti-Siglec-15 antibodies obtained by the method described in the above item "3. Production of anti-Siglec-15 antibody", an antibody which neutralizes the biological activity of Siglec-15 can be obtained. Such an antibody which neutralizes the biological activity of Siglec-15 inhibits the biological activity of Siglec-15 in vivo, i.e., the differentiation and/or maturation of osteoclasts, and therefore can be used as a therapeutic and/or preventive agent for abnormal bone metabolism caused by abnormal differentiation and/or maturation of osteoclasts as a pharmaceutical. The abnormal bone metabolism may be any disorder characterized by net bone loss (osteopenia or osteolysis). In general, the treatment and/or prevention by the anti-Siglec-15 antibody are/is applied to a case where inhibition of bone resorption is required. Examples of the abnormal bone metabolism which can be treated and/or prevented by the anti-Siglec-15 antibody include osteoporosis (postmenopausal osteoporosis, senile osteoporosis, secondary osteoporosis due to the use of a therapeutic agent such as a steroid or an immunosuppressant, or osteoporosis accompanying rheumatoid arthritis), bone destruction accompanying rheumatoid arthritis, cancerous hypercalcemia, bone destruction accompanying multiple myeloma or cancer metastasis to bone, giant cell tumor, osteopenia, tooth loss due to periodontitis, osteolysis around a prosthetic joint, bone destruction in chronic osteomyelitis, Paget's disease of bone, renal osteodystrophy, and osteogenesis imperfecta, however, the abnormal bone metabolism is not limited thereto as long as it is a disease accompanied by net bone loss caused by osteoclasts. Examples of the anti-Siglec-15 antibody to be used as the above-mentioned pharmaceutical include a chimeric antibody and a humanized antibody produced from the #32A1 antibody by the method described in item 3. "(3) Other antibodies". Further, a chimeric antibody, a humanized antibody, and a human antibody sharing the same epitope as the #32A1 antibody can also be used as a pharmaceutical. Whether a certain anti-Siglec-15 antibody shares the same epitope as the #32A1 antibody can be confirmed by observing whether or not these antibodies bind to the same specific partial peptide of Siglec-15. Further, it can also be determined that if a certain anti-Siglec-15 antibody competes with the #32A1 antibody for binding to Siglec-15, these antibodies share the same epitope.

The in vitro activity of the anti-Siglec-15 antibody of neutralizing the biological activity of Siglec-15 can be determined by, for example, the activity of inhibiting the differentiation of the cells which overexpress Siglec-15 into osteoclasts. For example, the anti-Siglec-15 antibody is added to RAW 264.7 cells or RAW 264 cells which are a mouse monocyte-derived cell line at various concentrations, and the activity of inhibiting the differentiation into osteoclasts by stimulation with RANKL or TNF-α can be determined. Further, the anti-Siglec-15 antibody is added to bone marrow-derived primary cultured cells at various concentrations, and the activity of inhibiting the differentiation into osteoclasts by stimulation with RANKL, TNF-α, or active vitamin $D_3$ can be determined. Further, the anti-Siglec-15 antibody is added to normal human osteoclast precursor cells (Normal Human Natural Osteoclast Precursor Cells, available from Sanko Junyaku Co., Ltd., Cat. No. 2T-110) at various concentrations, and the activity of inhibiting the differentiation into osteoclasts by stimulation with RANKL or M-CSF can be determined. Such an inhibitory effect on osteoclast differentiation can be determined by using the inhibition of tartrate-resistant acid phosphatase (TRAP) activity of osteoclasts as an index. Further, the inhibitory effect on osteoclast differentiation can also be determined by using the inhibition of formation of TRAP-positive multinucleated osteoclasts, i.e., the inhibition of cell fusion of osteoclasts as an index. Further, in an experiment utilising a pit assay (Takada et al., Bone and Mineral, (1992) 17, 347-359) using femur- and/or tibia-derived cells, the in vitro activity of inhibiting the bone resorption by osteoclasts can be determined by adding the anti-Siglec-15 antibody to femur- and/or tibia-derived cells at various concentrations, and observing pit formation on a dentine slice. As a system for determining the in vitro activity of inhibiting the bone resorption by osteoclasts, it is also possible to use a plate coated with human collagen conjugated to europium. The in vivo therapeutic or preventive effect of the anti-Siglec-15 antibody on abnormal bone metabolism using an experimental animal can be confirmed by administering the anti-Siglec-15 antibody to an animal model of osteoporosis or a transgenic animal which overexpresses Siglec-15 and measuring any change in osteoclasts.

The thus obtained antibody which neutralizes the biological activity of Siglec-15 is useful as a pharmaceutical, particularly as a pharmaceutical composition for treating or preventing abnormal bone metabolism such as osteoporosis, bone destruction accompanying rheumatoid arthritis, or bone destruction accompanying cancer metastasis to bone, or as an antibody for immunological diagnosis of such a disease.

In the treatment of rheumatoid arthritis (RA), a major problem is bone loss accompanying the occurrence of the disease. It has been reported that in this bone loss accompanying RA, osteoclasts play a primary role. The cytokines considered to be most important for osteoclast induction (differentiation and maturation) and activation and as the cause of bone destruction in RA are RANKL and TNF-α (Romas E. et al., Bone 30, pp. 340-346, 2002). OCIF/OPG which is a decoy receptor for RANKL can inhibit osteoclast formation induced by RANKL but does not inhibit osteoclast formation induced by TNF-α. On the other hand, the anti-Siglec-15 antibody according to the invention effectively inhibited osteoclast formation induced by both RANKL and TNF-α. Therefore, it is expected that the anti-Siglec-15 antibody of the invention can inhibit bone loss and bone destruction induced by TNF-α in RA or the like more strongly than an RANKL blocker (OCIF/OPG, an anti-RANKL antibody, or the like).

As one example, for the treatment or prevention of abnormal bone metabolism, the anti-Siglec-15 antibody can be administered alone or in combination with at least one other therapeutic agent for a bone-related disease. As another example, the anti-Siglec-15 antibody can be administered in combination with a therapeutically effective amount of a therapeutic agent for abnormal bone metabolism. Examples of the therapeutic agent which can be administered in combination with the anti-Siglec-15 antibody include, but are not limited to: bisphosphonates (for example, alendronate, etidronate, ibandronate, incadronate, pamidronate, risedronate, and zoledronate), active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents (for example, celecoxib and rofecoxib), soluble TNF receptors (for example, etanercept), anti-TNF-α antibodies or functional fragments of the antibodies (for example, infliximab), anti-PTHrP (parathyroid hormone-related protein) antibodies or functional fragments of the antibodies, IL-1 receptor antagonists (for example, anakinra), anti-IL-6 receptor antibodies or functional fragments of the antibodies (for example, tocilizumab), anti-RANKL antibodies or functional fragments of the antibodies (for example, denosumab), and OCIF (osteoclastogenesis inhibitory factor). Depending on the state of abnormal bone metabolism or the intended degree of the treatment and/or prevention, two or three, or more types of medicinal agents can be administered, and these medicinal agents can be supplied all together by encapsulating them in the same preparation. These medicinal agents and the anti-Siglec-15 antibody can be supplied all together by encapsulating them in the same preparation. Further, these medicinal agents can be supplied all together by encapsulating them as a kit to be used for treatment and/or prevention. Further, these medicinal agents and the anti-Siglec-15 antibody can be supplied separately. In the case of administration in gene therapy, a gene of a proteinous therapeutic agent for a bone disease and a gene of the anti-Siglec-15 antibody can be inserted downstream of the same promoter region or different promoter regions, and can be introduced into the same vector or different vectors.

By conjugating a therapeutic agent for a bone disease to the anti-Siglec-15 antibody or a fragment thereof, a targeted drug conjugate as described in M. C. Garnet "Targeted drug conjugates: principles and progress", Advanced Drug Delivery Reviews, (2001) 53, 171-216 can be produced. For achieving this purpose, other than the antibody molecule, any antibody fragment can be applied as long as it does not completely lose the ability to recognize osteoclasts, and examples thereof include fragments such as Fab, F(ab')2, and Fv. In the invention, the antibody and the fragment can be used in the same manner. The conjugate formed by the anti-Siglec-15 antibody or a fragment thereof and a therapeutic agent for a bone disease can be any of various forms described in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123 and the like. That is, a conjugate in which the anti-Siglec-15 antibody and a therapeutic agent for a bone disease are conjugated to each other chemically and directly or via a spacer such as an oligopeptide and a conjugate formed via an appropriate drug carrier can be exemplified. Examples of the drug carrier include a liposome and a water-soluble polymer. More specific examples of the conjugate formed via such a drug carrier include a conjugate in which the antibody and a therapeutic agent for a bone disease are incorporated in a liposome and the liposome and the antibody are conjugated to each other, and a conjugate in which a therapeutic agent for a bone disease is conjugated to a water-soluble polymer (a compound having a molecular weight of from about 1000 to 100000) chemically and directly or via a spacer such as an oligopeptide and the antibody is conjugated to the water-soluble polymer. The conjugation of the antibody (or a fragment thereof) to a therapeutic agent for a bone disease or a drug carrier such as a liposome or a water-soluble polymer can be effected by a method known to those skilled in the art such as the method described in G. T. Hermanson "Bioconjugate Techniques" Academic Press, California (1996), Putnam and J. Kopecek "Polymer Conjugates with Anticancer Activity" Advances in Polymer Science (1995) 122, 55-123. The incorporation of a therapeutic agent for a bone disease in a liposome can be effected by a method known to those skilled in the art such as the method described in D. D. Lasic "Liposomes: From Physics to Applications" Elsevier Science Publishers B. V., Amsterdam (1993) or the like. The conjugation of a therapeutic agent for a bone disease to a water-soluble polymer can be effected by a method known to those skilled in the art such as the method described in D. Putnam and J. Kopecek "Polymer Conjugates with Anticancer Activity" Advances in Polymer Science (1995) 122, 55-123. A conjugate of the antibody (or a fragment thereof) and a proteinous therapeutic agent for a bone disease (or a fragment thereof) can be produced by methods known to those skilled in the art through genetic engineering other than the above-mentioned method.

The invention also provides a pharmaceutical composition containing a therapeutically and/or preventively effective amount of the anti-Siglec-15 antibody and a pharmaceutically acceptable diluent, carrier, solubilizing agent, emulsifying agent, preservative, and/or adjuvant.

The invention also provides a pharmaceutical composition containing a therapeutically and/or preventively effective amount of the anti-Siglec-15 antibody, a therapeutically and/or preventively effective amount of at least one therapeutic agent for a bone disease, and a pharmaceutically acceptable diluent, carrier, solubilizing agent, emulsifying agent, preservative, and/or adjuvant. Examples of the therapeutic agent for a bone disease include, but are not limited to, bisphosphonates (for example, alendronate, etidronate, ibandronate, incadronate, pamidronate, risedronate, and zoledronate), active vitamin $D_3$, calcitonin and derivatives thereof, hormones such as estradiol, SERMs (selective estrogen receptor modulators), ipriflavone, vitamin $K_2$ (menatetrenone), calcium preparations, PTH (parathyroid hormone), nonsteroidal anti-inflammatory agents (for example, celecoxib and rofecoxib), soluble TNF receptors (for example, etanercept), anti-TNF-α antibodies or functional fragments of the antibodies (for example, infliximab), anti-PTHrP (parathyroid hormone-related protein) antibodies or functional fragments of the antibodies, IL-1 receptor antagonists (for example, anakinra), anti-IL-6 receptor antibodies or functional fragments of the antibodies (for example, tocilizumab), anti-RANKL antibodies or functional fragments of the antibodies (for example, denosumab) and OCIF (osteoclastogenesis inhibitory factor).

A substance to be used in a preparation acceptable in the pharmaceutical composition according to the invention is preferably non-toxic to a person to whom the pharmaceutical composition is to be administered in terms of the dose and concentration.

The pharmaceutical composition of the invention can contain a substance for pharmaceutical use which is capable of changing or maintaining the pH, osmotic pressure, viscosity, transparency, color, isotonicity, aseptic condition, stability, solubility, release rate, absorption rate, and permeability thereof. Examples of such a substance for pharmaceutical use include, but are not limited to, amino acids such as glycine, alanine, glutamine, asparagine, arginine, and lysine; antimicrobial agents; antioxidants such as ascorbic acid, sodium sulfate, and sodium hydrogen sulfite; buffers such as phosphate, citrate, borate buffers, sodium hydrogen carbonate, and Tris-HCl solutions; fillers such as mannitol and glycine; chelating agents such as ethylenediamine tetraacetate (EDTA); complexing agents such as caffeine, polyvinylpyrrolidine, β-cyclodextrin, and hydroxypropyl-β- cyclodextrin; expanders such as glucose, mannose, and dextrin; other carbohydrates such as monosaccharides and disaccharides; coloring agents; flavors; diluents; emulsifying agents; hydrophilic polymers such as polyvinylpyrrolidine; preservatives such as low molecular weight polypeptides, salt forming counter ions, benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates including polysorbate 20 and polysorbate 80, Triton, tromethamine, lecithin, and cholesterol; stability enhancing agents such as sucrose and sorbitol; elasticity enhancing agents such as sodium chloride, potassium chloride, and mannitol and sorbitol; transport agents; excipients; and/or pharmaceutical adjuvants. The amount of these substances added for pharmaceutical use is preferably from 0.01 to 100 times, particularly preferably from 0.1 to 10 times the weight of the anti-Siglec-15 antibody. Those skilled in the art can appropriately determine a preferred formulation of the pharmaceutical composition in a preparation depending on the disease to which the composition is applied, the route of administration to be applied, or the like.

The excipient or carrier in the pharmaceutical composition may be in the form of a liquid or a solid. An appropriate excipient or carrier may be injectable water, physiological saline, an artificial cerebral spinal fluid, or other substance commonly used for parenteral administration. Further, neutral physiological saline or physiological saline containing serum albumin can also be used as a carrier. The pharmaceutical composition may contain a Tris buffer of pH 7.0 to 8.5, an acetate buffer of pH 4.0 to 5.5, or a citrate buffer of pH 3.0 to 6.2. Further, such a buffer may be supplemented with sorbitol or another compound. Examples of the pharmaceutical composition of the invention include a pharmaceutical composition containing the anti-Siglec-15 antibody and a pharmaceutical composition containing the anti-Siglec-15 antibody and at least one therapeutic agent for a bone disease. The pharmaceutical composition of the invention is prepared in the form of a lyophilized product or a liquid as a medicinal agent having a selected composition and a required purity. The pharmaceutical composition containing the anti-Siglec-15 antibody and the pharmaceutical composition containing the anti-Siglec-15 antibody and at least one therapeutic agent for abnormal bone metabolism can also be formed into a lyophilized product using an appropriate excipient such as sucrose.

The pharmaceutical composition of the invention can be prepared for parenteral administration or for gastrointestinal absorption through oral administration. The composition and concentration of a preparation can be determined depending on the administration method. The higher the affinity of the anti-Siglec-15 antibody contained in the pharmaceutical composition of the invention is for Siglec-15, that is, the lower the dissociation constant (Kd value) thereof is for Siglec-15, the more the anti-Siglec-15 antibody can exhibit its drug efficacy even when decreasing the dose for humans. Hence, the dose of the pharmaceutical composition of the invention for humans can also be determined based on this consideration. As for the dose, in the case where a human anti-Siglec-15 antibody is administered to humans, the antibody may be administered at a dose of from about 0.1 to 100 mg/kg once per one to 180 days.

Examples of the dosage form of the pharmaceutical composition of the invention include injections including infusions, suppositories, transnasal agents, sublingual agents, and percutaneous absorbents.

EXAMPLES

Hereinafter, the invention will be more specifically described with reference to the Examples, however, the invention is not limited thereto. Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, they are used according to the protocols attached thereto unless otherwise stated.

Example 1

Production of Soluble Mouse Siglec-15 Protein Expression Construct

A partial nucleotide sequence encoding the extracellular domain of mouse Siglec-15 protein is represented by SEQ ID NO: 5 in the Sequence Listing and an amino acid sequence thereof is represented by SEQ ID NO: 6 in the Sequence Listing. By utilizing such a partial sequence, soluble mouse Siglec-15 protein can be produced in a culture supernatant of an animal cell or the like.

Amplification of Soluble Mouse Siglec-15 Gene by PCR

As primers for amplifying the mouse Siglec-15 extracellular domain cDNA by PCR, an oligonucleotide having a sequence of 5'-ggggacaagt ttgtacaaaa aagcaggctt caccATG-GAG GGGTCCCTCC AACTC-3' (mSiglec-15-ECD-F: SEQ ID NO: 7 in the Sequence Listing); and an oligonucleotide having a sequence of 5 '-ggggaccact ttgtacaaga aagctgggtc TCCGGGGGCG CCGTGGAAGC GGAAC-3' (mSiglec-15-ECD-R: SEQ ID NO: 8 in the Sequence Listing) were synthesized according to a common procedure. Incidentally, these primers were designed as amplification primers for producing a gateway entry clone, such that an attB1 sequence is added to mSiglec-15-ECD-F and an attB2 sequence is added to mSiglec-15-ECD-R. The PCR was performed using this combination of primers and a polynucleotide containing an open reading frame sequence of the mouse Siglec-15 as a template according to a common procedure. The conditions for a thermal cycler were set as follows: after heating at 94° C. for 5 minutes, a temperature cycle of "94° C. for 0.5 minutes, 55° C. for 0.5 minutes, and 68° C. for 1.5 minutes" was repeated 15 times, followed by heating at 68° C. for 5 minutes and incubating at 4° C.

b) Production of Entry Clone by Gateway BP Reaction

An entry clone into which the mouse Siglec-15 extracellular domain cDNA was integrated by the Gateway technology (Invitrogen, Inc.) employing a lambda phage site-specific recombination system was produced by the following method. First, a BP reaction using BP Clonase was performed between the PCR product having an attB sequence at both ends produced in a) and pDNOR221 (manufactured by Invitrogen, Inc.) which is a donor vector having an attP sequence. By using this reaction solution, *Escherichia coli* DH10B was transformed, colony PCR was performed for drug-resistant clones, and the size of inserts was confirmed. Then, for a clone confirmed to have an insert with the correct size, a sequence analysis of the total DNA sequence of the insert was performed. As a result, an entry clone which is completely identical to the target nucleotide sequence (SEQ ID NO: 5 in the Sequence Listing) encoding the extracellular domain of the mouse Siglec-15 protein was obtained.

c) Production of Expression Clone by Gateway LR Reaction

An expression clone into which the mouse Siglec-15 extracellular domain cDNA was integrated by the Gateway technology (Invitrogen, Inc.) employing a lambda phage site-specific recombination system was produced by the following method. The entry clone produced in b) contains an insert having an attL sequence at both ends. An LR reaction using LR Clonase was performed between this entry clone and two types of destination vectors having an attR sequence. Incidentally, as the destination vectors, two types of destination vectors: pDONM designed such that a V5 epitope tag and a 6×His tag are added to the C terminus of the insert; and phIgFc designed such that a human Fc tag is added to the C terminus of the insert were used. By using the reaction solution obtained by the LR reaction, *Escherichia coli* DH10B was transformed, and colony PCR was performed for the obtained drug-resistant clones, and the size of inserts was confirmed. Then, for a clone confirmed to have an insert with the correct size, a sequence analysis of both ends from the insert side to the vector side was performed.

Primer Sequences for Sequence Analysis:

5'-tgcgtgaagg tgcagggcag-3' (mSiglec-15-ECD-seq-upstm: SEQ ID NO: 9 in the Sequence Listing) and 5'-cctcgcctgg tcgggtc-3' (mSiglec-15-ECD-seq-dnstm: SEQ ID NO: 10 in the Sequence Listing)

As a result of the sequence analysis, expression clones (soluble mouse Siglec-15/pDONM and soluble mouse Siglec-15/phIgFc) in which correct recombination occurred for both pDONM and phIgFc, respectively, were obtained. By transfecting the soluble mouse Siglec-15/pDONM into an animal cell or the like, mRNA having a base sequence represented by SEQ ID NO: 11 in the Sequence Listing is transcribed and translated into a protein (mouse Siglec-15-His) having an amino acid sequence represented by SEQ ID NO: 12 in the Sequence Listing. Further, by transfecting the soluble mouse Siglec-15/phIgFc into an animal cell or the like, mRNA having a base sequence represented by SEQ ID NO: 13 in the Sequence Listing is transcribed and translated into a protein (mouse Siglec-15-Fc) having an amino acid sequence represented by SEQ ID NO: 14 in the Sequence Listing.

Example 2

Large-Scale Preparation of Culture Solution Containing Soluble Mouse Siglec-15 Protein Using 293-F Cells The two types of expression vectors (soluble mouse Siglec-15/pDONM and soluble mouse Siglec-15/phIgFc) obtained in Example 1 were prepared in an amount of about 5 mg, respectively. Incidentally, in the purification of plasmids from *Escherichia coli* cultured on a large scale, Invitrogen PureLink HiPure Plasmid Gigaprep Kit (manufactured by Invitrogen, Inc.) was used. The thus prepared plasmid was mixed with Opti-MEM (manufactured by Invitrogen, Inc.), the resulting mixture was sterilized by filtration, 10 ml of a transfection reagent 293fectin (manufactured by Invitrogen, Inc.) was added thereto, and the resulting mixture was incubated at room temperature for 20 minutes. This mixture was added to FreeStyle 293-F cells (manufactured by Invitrogen, Inc.) cultured in Erlenmeyer flasks such that the cell density reached $1.1 \times 10^6$ cells/ml×5 L (1 L/flask×5 flasks) in FreeStyle 293 Expression Medium (manufactured by Invitrogen, Inc.). After the cells had been subjected to culture with agitation (125 rotations/min) at a $CO_2$ concentration of 8.0% for 96 hours (4 days) at 37° C., the culture solution was collected and centrifuged to prepare a culture supernatant. It is considered that in the thus prepared culture supernatant, a protein in which a V5 epitope tag and a 6×His tag have been added to the C-terminal side of the mouse Siglec-15 extracellular domain (mouse Siglec-15-His) and a protein in which a human Fc tag has been added to the C-terminal side of the mouse Siglec-15 extracellular domain (mouse Siglec-15-Fc) are expressed, respectively.

Example 3

Purification of Mouse Siglec-15-his
HisTrap HP Column Chromatography

To 2 L of the culture solution of mouse Siglec-15-His-expressing 293F cells prepared in Example 2, 225 mL of 10× buffer (500 mM Tris, 1.5 M NaCl, 200 mM imidazole, pH 8.0) was added, and the resulting mixture was stirred well and filtered through a Sterivex-GV filter (manufactured by Millipore Co., Ltd.). This culture solution was applied at a flow rate of 2 ml/min to a column which comprised three HisTrap HP 5 ml columns (manufactured by Amersham Biosciences, Inc.) connected in series and was previously treated with a pyrogen removing agent PyroCLEAN (manufactured by ALerCHEK, Inc.) and washed with distilled water for injection. After the column was washed with 60 ml of 50 mM Tris-HCl buffer (pH 8.0) containing 300 mM NaCl at a flow rate of 1 ml/min, a protein adsorbed to the column was eluted with 50 ml of 50 mM Tris-HCl buffer (pH 8.0) containing 300 mM NaCl and 500 mM imidazole at a flow rate of 1 ml/min. The eluate was fractionated at 1 ml per fraction into mini-sorp tubes (manufactured by Nunc, Inc.) to which 10 μl of 10% Tween 20 had previously been added. After about 20 ml of a solution obtained by combining the fractions (fractions 14 to 20) and containing the eluted protein was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which had previously been equilibrated with phosphate-buffered saline containing 0.01% Tween 20 (T-PBS), followed by elution with T-PBS, whereby 3.5 ml of a sample whose solvent was replaced with T-PBS was obtained.

b) Resource Q Column Chromatography

To 3.5 ml of the sample which was purified by HisTrap HP column chromatography and whose solvent was replaced with T-PBS, 22.5 ml of 50 mM Tris-HCl buffer (pH 7.5) containing 0.1% CHAPS was added and the resulting mixture was stirred. Then, the mixture was centrifuged at 4° C. for 30 minutes at 3,000 rpm and the precipitate was removed. After the resulting supernatant was filtered through a Millex-GV filter (manufactured by Millipore Co., Ltd.), the filtrate was applied at a flow rate of 1 ml/min to a Resource Q 6 ml column (manufactured by Amersham Biosciences, Inc.) which had previously been equilibrated with 50 mM Tris-HCl buffer (pH 7.5) containing 0.1% CHAPS. Thereafter, the column was washed with this buffer at a flow rate of 1 ml/min and a protein fraction which was not adsorbed to the column was collected. A protein adsorbed to the column was eluted with 50 mM Tris-HCl buffer (pH 7.5) containing 0.1% CHAPS and 1 M NaCl at a flow rate of 1 ml/min. After 26.5 ml of the fraction which was not adsorbed to the column was concentrated to 2.0 ml with a centrifugal membrane concentrator Amicon Ultra-15 (manufactured by Millipore Co., Ltd.), the concentrate was centrifuged at 4° C. for 10 minutes at 3,000 rpm and the precipitate was removed. The supernatant after centrifugation was cryopreserved at −80° C. until use. The above-mentioned purification procedure (HisTrap HP column chromatography and Resource Q column chromatography) was performed by repeating it twice.

c) Detection and Purity Assay of Purified Mouse Siglec-15-His

By using a sample prepared by the above-mentioned purification procedure (HisTrap HP column chromatography and Resource Q column chromatography), SDS-polyacrylamide electrophoresis under reducing conditions and silver staining were performed. That is, to 5 µl of each of the samples purified by the respective purification steps, an equivalent amount of an SDS-treatment solution was added, and the resulting mixture was thermally treated at 95° C. for 10 minutes. 0.3 µl of each of the thermally treated samples was used for SDS-polyacrylamide electrophoresis. As a gel for electrophoresis, an 8-25% polyacrylamide gradient gel (manufactured by Amersham Biosciences, Inc.) was used, and the electrophoresis was performed using PhastSystem (manufactured by Amersham Biosciences, Inc.). Further, as molecular weight markers, Rainbow Molecular Weight Markers (manufactured by Amersham Biosciences, Inc.) were used. After completion of the electrophoresis, silver staining was performed using PhastGel Silver Kit (manufactured by Amersham Biosciences, Inc.) and PhastSystem. The results are shown in FIG. 1. It was shown that a protein having a molecular weight of about 35 kDa (mouse Siglec-15-His) was efficiently purified and concentrated in the protein fraction which was not adsorbed to the Resource Q column.

Figure 2:
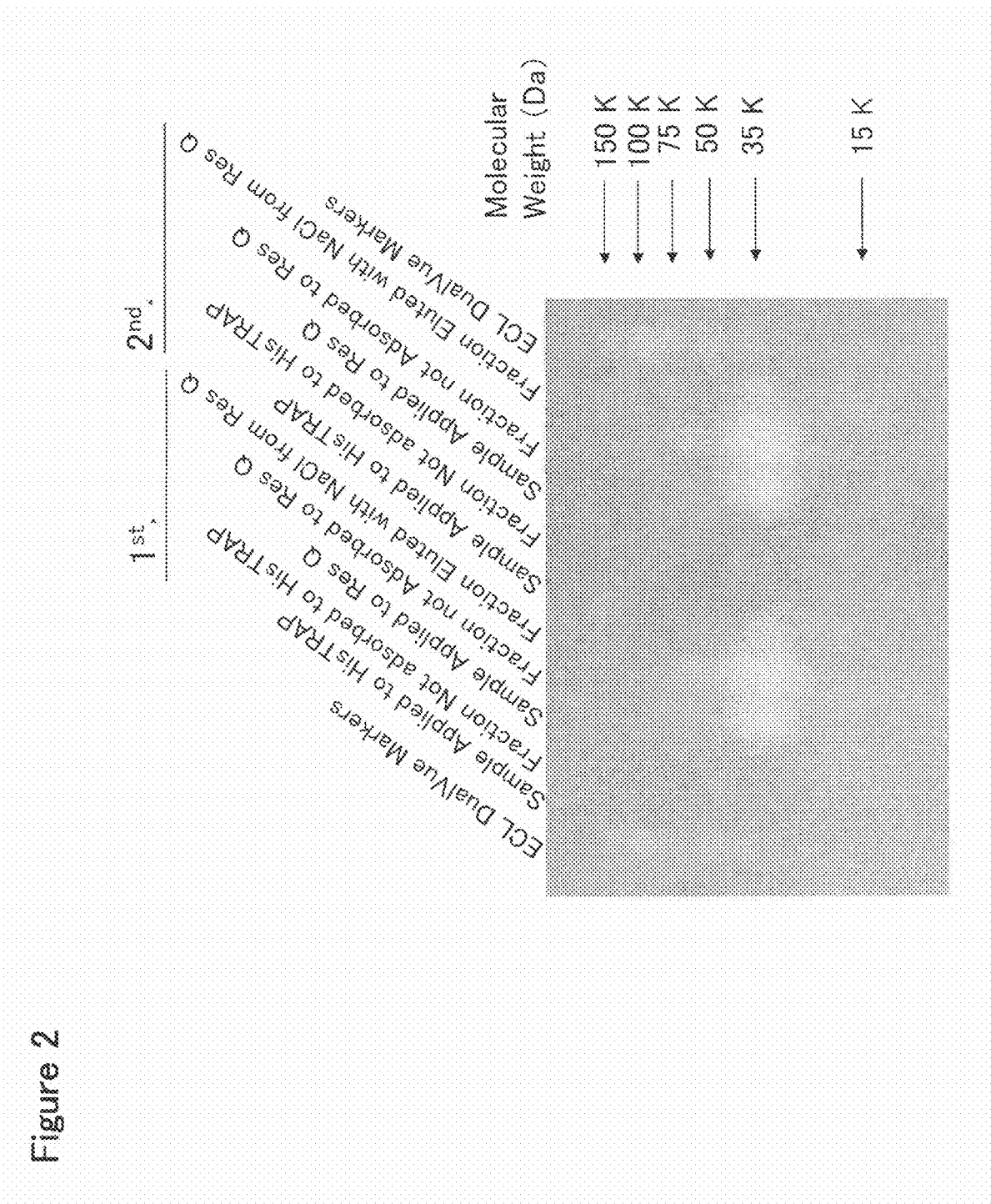
FIG. 2 shows the results of detecting the characteristics of mouse Siglec-15-His purified by HisTrap HP column chromatography and Resource Q column chromatography through SDS-polyacrylamide electrophoresis and Western blotting using an anti-V5-HRP antibody.

Electrophoresis was performed under the same conditions except that ECL DualVue Western Blotting Markers (manufactured by Amersham Biosciences, Inc.) were used as the molecular weight markers, and the protein in the gel was transferred (blotted) to a PVDF membrane (Hybond-P, manufactured by Amersham Biosciences, Inc.) using a PhastTransfer Semi-dry Transfer Kit (manufactured by Amersham Biosciences, Inc.) and PhastSystem. This PVDF membrane was gently shaken in 10 ml of a blocking agent (BlockAce, manufactured by Snow Brand Milk Products, Co., Ltd.) containing 0.1% Tween 20 at room temperature for 1 hour. To this blocking solution, 10 µl of S-protein HRP (manufactured by Amersham Biosciences, Inc.) and 10 µl of an anti-V5-HRP antibody (Monoclonal Antibody to Pk-TAG-HRP, manufactured by Acris Antibodies) were added and the membrane in the solution was gently shaken at room temperature for an additional 1 hour. The PVDF membrane was washed 4 times by gently shaking it in 50 mL of phosphate-buffered saline (PBS) containing 0.01% Tween 20 for 5 minutes. After washing, the PVDF membrane was treated according to the protocol accompanying an ECL detection kit (manufactured by Amersham Biosciences, Inc.) to develop the color of the band of the protein, and the developed color was detected using an ECL Mini-Camera (manufactured by Amersham Biosciences, Inc.) and Polaroid film (Polapan 3200B, manufactured by Polaroid, Inc.). The results are shown in FIG. 2. Also from these results, it could be confirmed that a protein which has a molecular weight of about 35 kDa (mouse Siglec-15-His) and reacts with an anti-V5-HRP antibody was efficiently purified and concentrated in the protein fraction which was not adsorbed to the Resource Q column.

d) Measurement of Protein Concentration of Purified Mouse Siglec-15-His

For the purified mouse Siglec-15-His (the protein fraction which was not adsorbed to the Resource Q column), the protein concentration was measured with a DC protein assay kit (manufactured by Bio-Rad Laboratories, Inc.) using bovine serum albumin as a standard sample. As shown in Table 1, a total of 1.66 mg of purified mouse Siglec-15-His protein was obtained by performing the purification procedure twice.

TABLE 1

| | Protein Conc. (mg/ml) | Sample Vol. (ml) | Total protein (mg) |
|---|---|---|---|
| 1st | 0.475 | 2.0 | 0.95 |
| 2nd | 0.354 | 2.0 | 0.71 |
| Total | | | 1.66 |

Example 4

Purification of Mouse Siglec-15-Fc

HiTrap Protein a Column Chromatography 1.8 L of the culture solution of mouse Siglec-15-Fc-expressing 293F cells prepared in Example 2 was filtered through a Sterivex-GV filter (manufactured by Millipore Co., Ltd.), and then the filtrate was applied to a HiTrap Protein A 5 ml column (manufactured by Amersham Biosciences, Inc.) which had previously been equilibrated with Dulbecco's PBS (D-PBS, manufactured by Invitrogen, Inc.) at a flow rate of 5 ml/min. After the column was washed with D-PBS at a flow rate of 5 ml/min, a protein adsorbed to the column was eluted with 50 ml of 0.1 M sodium citrate buffer (pH 3.0) at a flow rate of 5 ml/min. The eluate was fractionated at 5 ml per fraction into mini-sorp tubes (manufactured by Nunc, Inc.), and immediately thereafter, 1.3 ml of 1 M Tris was added thereto to neutralize the eluate. After a solution obtained by combining the fractions (fractions 1 and 2) in which the eluted protein was detected was concentrated to 2.5 ml with a centrifugal membrane concentrator Amicon Ultra-15 (manufactured by Millipore Co., Ltd.), the concentrate was applied to a PD-10 desalting column (manufactured by Amersham Biosciences, Inc.) which had previously been equilibrated with Otsuka Physiological Saline for Injection (TO-SS, manufactured by Otsuka Pharmaceutical Co., Ltd.) containing 0.01% Tween 20, followed by elution with TO-SS, whereby 3.5 ml of a sample whose solvent was replaced with TO-SS was obtained. This sample was cryopreserved at −80° C. until use. By using 2.9 L of a culture solution of 293F cells, the same purification procedure was performed by repeating it once more.

b) Detection and Purity Assay of Purified Mouse Siglec-15-Fc

Figure 3:
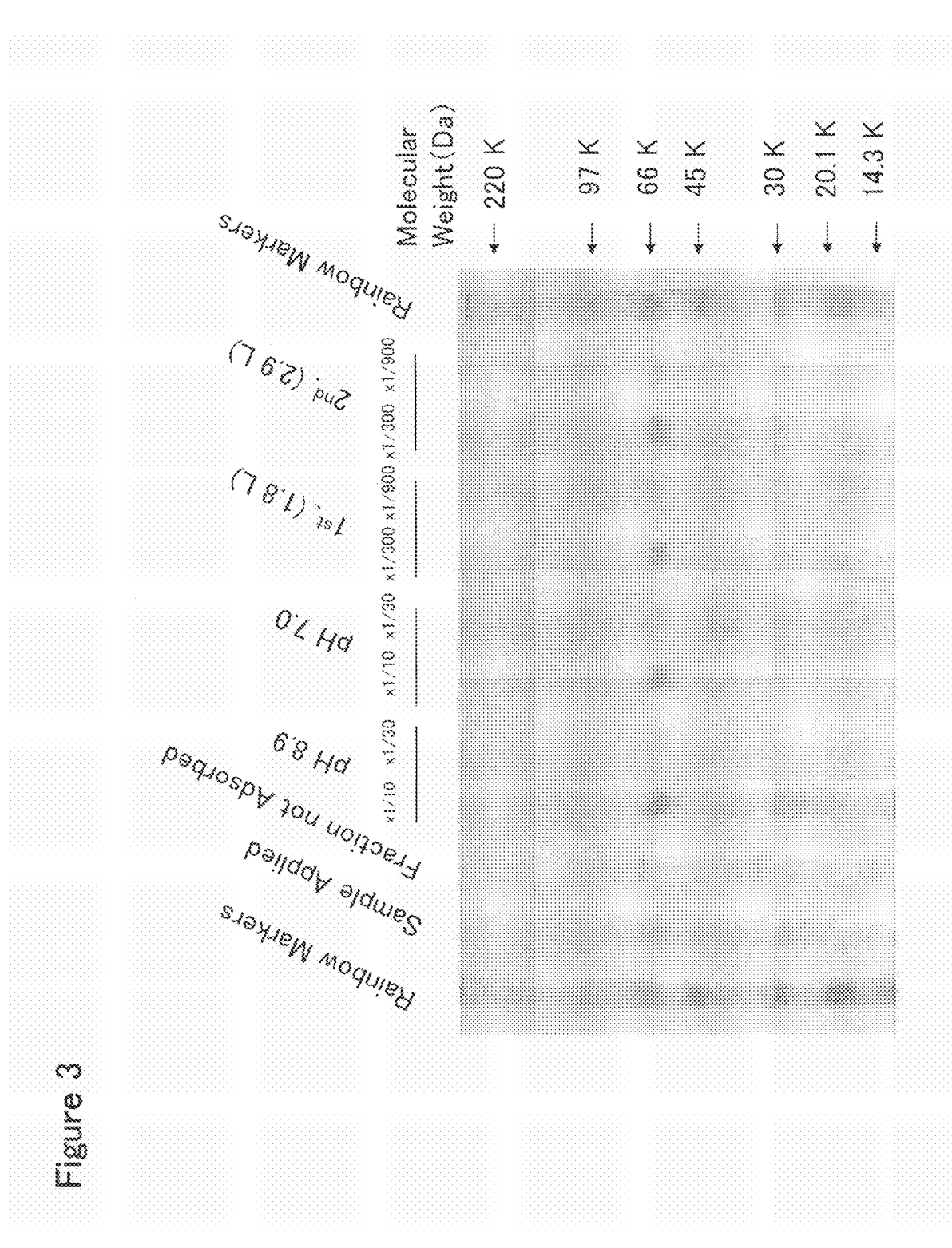
FIG. 3 shows the results of evaluating the purity of mouse Siglec-15-Fc purified by HiTrap Protein A column chromatography through SDS-polyacrylamide electrophoresis and silver staining.

By using a sample prepared by the above-mentioned purification procedure, SDS-polyacrylamide electrophoresis under reducing conditions and silver staining were performed. That is, to 5 µl of each of the samples purified by the respective purification steps, an equivalent amount of an SDS-treatment solution was added, and the resulting mixture was heated at 95° C. for 10 minutes. 0.3 µl of a sample obtained by diluting each of the thermally treated samples to 1/300 or 1/900 with a half concentration of the SDS-treatment solution was used for SDS-polyacrylamide electrophoresis. The electrophoresis and silver staining were performed in the same manner as the purity assay of mouse Siglec-15-His described in c) of Example 3. The results are shown in FIG. 3 along with the results of examining preliminary purification conditions on a small scale (the pH of the applied culture solution was 8.9 or 7.0). It was shown that a protein having a molecular weight of about 55 kDa (mouse Siglec-15-Fc) was efficiently purified and concentrated in the protein fraction which was eluted from the HiTrap Protein A column.

c) Measurement of Protein Concentration of Purified Mouse Siglec-15-Fc

For the purified mouse Siglec-15-Fc (the protein fraction eluted from the PD-10 desalting column), the protein concentration was measured with a DC protein assay kit (manufactured by Bio-Rad Laboratories, Inc.) using bovine serum albumin as a standard sample. As shown in Table 2, a total of 92 mg of purified mouse Siglec-15-Fc protein was obtained by performing the purification procedure twice.

TABLE 2

|  | Protein Conc. (mg/ml) | Sample Vol. (ml) | Total protein (mg) |
|---|---|---|---|
| 1st | 8.0 | 3.5 | 28 |
| 2nd | 18.5 | 3.5 | 64 |
| Total |  |  | 92 |

Example 5

Establishment of Rat Anti-Mouse Siglec-15 Monoclonal Antibody-Producing Hybridoma Preparation of Antigen The mouse Siglec-15-His protein produced in Example 3 was prepared at 100 μg/0.5 ml, and an equivalent amount of an adjuvant was added thereto and an emulsion was produced using a glass syringe. As the adjuvant, Freund's complete adjuvant (FCA, Manufactured by Difco Laboratories, Inc.) was used only for the first immunization, and Freund's incomplete adjuvant (FICA, Manufactured by Difco Laboratories, Inc.) was used for the second immunization and thereafter.

b) Immunization of Rat

Four rats (Wistar, female, 6 weeks of age, purchased from CLEA Japan, Inc.) were used as immunized animals. The emulsion obtained in a) was injected subcutaneously and intradermally using a 27 G injection needle such that the amount of the antigen was 50 μg per rat. Immunization was performed a total of 4 times every 7 days after the first immunization. A small amount (200 μl) of the blood was collected from the tail vein after 7 days from the date of the 4th immunization, and an antiserum was prepared. In order to confirm the antibody titer of the antiserum, ELISA using the mouse Siglec-15-His protein that had been used as the antigen, the mouse Siglec-15-Fc protein produced in Example 4, or bovine serum albumin (BSA), each of which was immobilized, was performed. As a result, the reactivity with the mouse Siglec-15-His protein and the mouse Siglec-15-Fc protein was observed in all four rats (rat Nos. 1 to 4). On the other hand, the reactivity with BSA was not observed. From these results, it was confirmed that the antibody titer in the serum of each of the immunized rats increased, and therefore, the No. 2 rat which showed the highest antibody titer was subjected to a cell fusion procedure.

c) Cell Fusion

Cell fusion was performed according to a common method of fusing mouse (rat) spleen cells with myeloma cells. The whole blood was collected from the heart of the rat under ether anesthesia and the rat was euthanized, and then the spleen was excised. The collected spleen cells and P3X63Ag8.653 cells (ATCC CRL 1580) which are mouse myeloma cells were subjected to cell fusion using polyethylene glycol (PEG). The resulting cells were seeded in a 96-well plate, and a medium containing hypoxanthine (H), aminopterin (A) and thymidine (T) (HAT selection medium) was added thereto, and then, the cells were cultured for 7 to 10 days. The culture supernatant was collected from 61 wells in which the survival of hybridomas obtained by cell fusion was confirmed. Then, the antibody titer was evaluated by ELISA using the mouse Siglec-15-His protein that had been used as the antigen, the mouse Siglec-15-Fc protein produced in Example 4, or BSA, each of which was immobilized, and anti-mouse Siglec-15 monoclonal antibody-producing hybridomas were screened. From the results of the screening, 12 wells showing a high antibody titer were selected and the hybridomas contained in the wells were subjected to a cloning procedure.

d) Cloning of Hybridoma

For the thus selected hybridomas, a first cloning step was performed by a limiting dilution method. After the limiting dilution, the hybridomas were cultured for 2 weeks, and the antibody titer in the culture supernatant was confirmed by ELISA using the mouse Siglec-15-Fc protein produced in Example 4 or BSA, each of which was immobilized. For 11 clones which were confirmed to be positive clones, a second cloning step was performed (in the same manner as the first cloning step), whereby 10 clones of the anti-mouse Siglec-15 monoclonal antibody-producing hybridomas (#1A1, #3A1, #8A1, #24A1, #32A1, #34A1, #39A1, #40A1, #41B1, #61A1) were established in the end. Incidentally, the hybridoma #32A1 was deposited at the International Patent Organism Depositary of the National Institute of Advanced Industrial Science and Technology (located at Central 6, 1-1-1 Higashi, Tsukuba-shi, Ibaraki-ken, 305-8566, Japan) on Aug. 28, 2008, and has been given an accession number of FERM BP-10999 under the name of anti-Siglec-15 Hybridoma #32A1.

Example 6

Preparation of Rat Anti-Mouse Siglec-15 Monoclonal Antibody

Preparation of Nude Mouse Ascites

The hybridomas established in Example 5 were cultured using TIL Media I (manufactured by Immuno-biological Laboratories Co., Ltd.) medium containing 10% FCS. Subculturing of the cells was carried out by performing a procedure in which the culture solution was diluted to about one-fourth every two to three days by using the time point when the cells were grown to about $5 \times 10^5$ cells/ml as an index. Each of the thus cultured hybridomas was intraperitoneally implanted in a nude mouse to which pristane had been intraperitoneally administered (0.2 ml/mouse) previously at $1 \times 10^7$ cells per mouse. In the implantation, three nude mice were used for each of the 10 clones of hybridomas. After the implantation, the ascites was collected when sufficient accumulation of ascites was observed, which was combined with those collected from the other two mice implanted with the same hybridoma, the amount of the ascites thus combined was measured, and the ascites was cryopreserved until purification of the antibody. The amounts of the collected ascites for the respective hybridomas were summarized in Table 3.

TABLE 3

| Hybridoma | Amount of collected ascites (ml) |
|---|---|
| #1A1 | 12.5 |
| #3A1 | 8.0 |
| #8A1 | 6.0 |
| #24A1 | 7.8 |
| #32A1 | 5.5 |
| #34A1 | 8.2 |
| #39A1 | 14.5 |
| #40A1 | 20.3 |
| #41B1 | 10.5 |
| #61A1 | 12.3 | b) Purification of Antibody

The total amount of the collected ascites was subjected to IgG purification using a 20 ml Protein G column (manufactured by GE Healthcare, Co., Ltd.). The purified IgG was assayed for purity by gel filtration analysis (Superdex 200 column chromatography), and some of the antibodies were subjected to centrifugal membrane concentration. That is, among the purified anti-mouse Siglec-15 monoclonal antibodies, 9 types of antibodies except for the #24A1 antibody were concentrated to about one-sixth to one-eighth of the original volume by centrifuging the antibodies at 3,000 rpm for 30 to 60 minutes at 4° C. using a centrifugal membrane concentrator Amicon Ultra-15 (manufactured by Millipore Co., Ltd.). Subsequently, for the #24A1 antibody and the other concentrated 9 types of antibodies, the protein concentration was measured with a DC protein assay kit (manufactured by Bio-Rad Laboratories, Inc.) using bovine serum albumin (BSA) as a standard sample. By the above-mentioned procedure, the anti-mouse Siglec-15 monoclonal antibody was prepared.

Example 7

Figure 4:
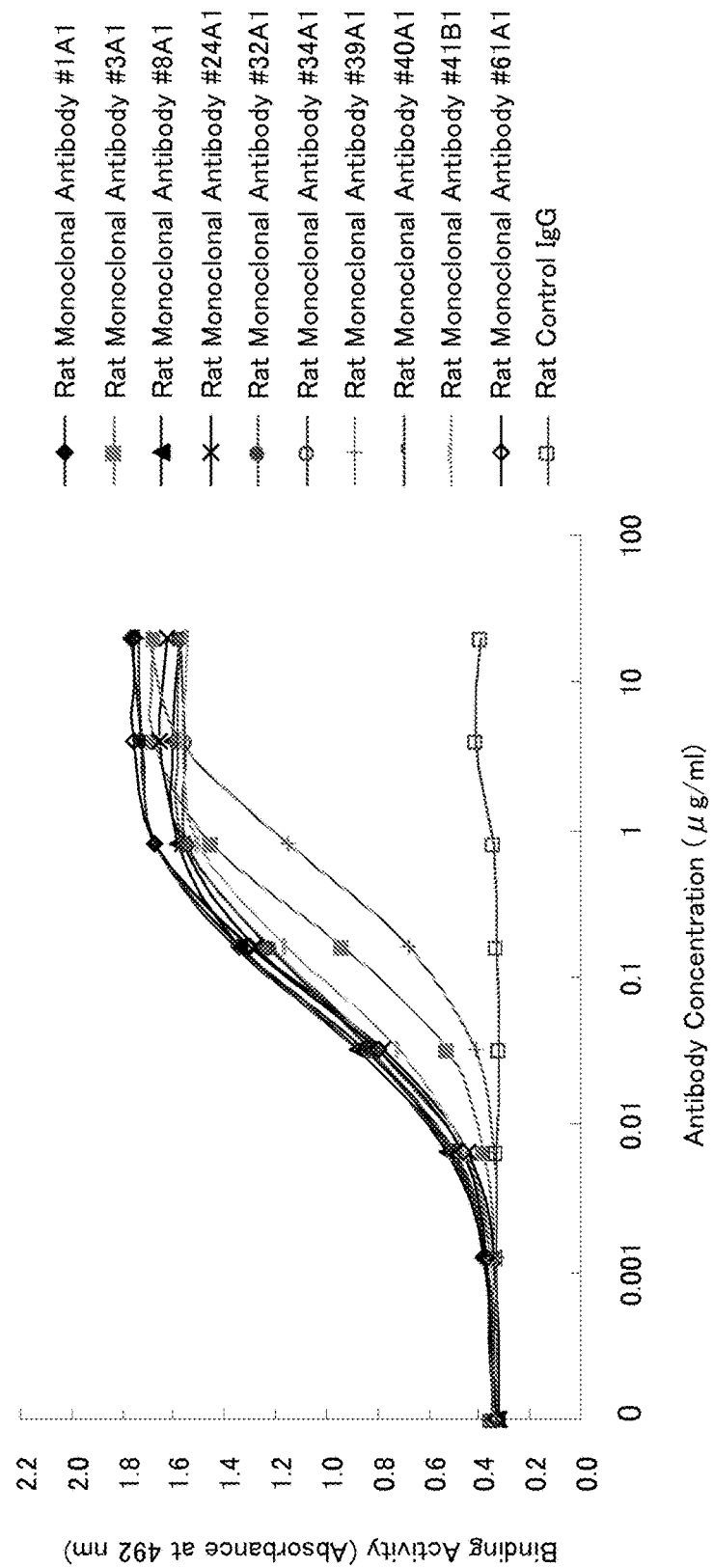
FIG. 4 shows the results of testing the binding of a rat anti-mouse Siglec-15 monoclonal antibody to a plate having mouse Siglec-15-Fc immobilized thereon by an ELISA method. The symbol (♦) denotes #1A1 antibody, the symbol (■) denotes #3A1 antibody, the symbol (▲) denotes #8A1 antibody, the symbol (x) denotes #24A1 antibody, the symbol (●) denotes #32A1 antibody, the symbol (○) denotes #34A1 antibody, the symbol (+) denotes #39A1 antibody, the symbol (–) denotes #40A1 antibody, the symbol (—) denotes #41B1 antibody, the symbol (◇) denotes #61A1 antibody, and the symbol (□) denotes control IgG.

Evaluation of Property of Rat Anti-Mouse Siglec-15 Monoclonal Antibody Binding to Mouse Siglec-15 Protein The property of the rat anti-mouse Siglec-15 monoclonal antibody binding to mouse Siglec-15 protein was evaluated by an ELISA method. The mouse Siglec-15-Fc protein produced in Example 4 was diluted to 5 µg/ml with 0.1 M sodium carbonate buffer (pH 9.5), and the resulting solution was added to a 96-well plate (manufactured by Nalge Nunc International, Inc., Cat. No. 430341) at 100 µl/well. After the plate was left at room temperature for 1 hour, the solution was removed and a washing buffer (phosphate-buffered saline containing 0.05% Tween 20) was added at 300 µl/well and then removed. After this washing procedure was performed one more time, phosphate-buffered saline containing 25% BlockAce (manufactured by Dainippon Sumitomo Pharma Co., Ltd.) was added at 200 µl/well, and the plate was left at room temperature for 1 hour, whereby blocking was performed. The liquid was removed, and the plate was washed twice with 300 µl/well of the washing buffer. Then, each of the rat anti-mouse Siglec-15 monoclonal antibodies prepared in Example 6 or rat control IgG (manufactured by R&D Systems, Inc.) was diluted to a final concentration of from 1.28 to 20,000 ng/ml (5-fold dilution series) with an ELISA buffer (phosphate-buffered saline containing 12.5% BlockAce and 0.05% Tween 20), and the resulting diluted antibody solution was added to the plate at 100 µl/well. After the plate was left at room temperature for 1 hour, the liquid was removed, and the plate was washed 3 times with 300 µl/well of the washing buffer. Subsequently, an HRP (horseradish peroxidase)-labeled goat anti-rat IgG antibody (manufactured by Beckman Coulter, Inc.) diluted to 1,000-fold with an ELISA buffer was added at 100 µl/well, and the plate was left at room temperature for 1 hour. The liquid was removed and the plate was washed 3 times with 300 µl/well of the washing buffer, and then, by using a color developing kit for peroxidase (manufactured by Sumitomo Bakelite Co., Ltd.), the color was developed according to the protocol accompanying the kit. After developing the color, an absorbance at 492 nm was measured using a microplate reader (manufactured by Nihon Molecular Devices Corporation). As a result, it was confirmed that all of the examined 10 test samples of the rat anti-mouse Siglec-15 monoclonal antibodies bind to the mouse Siglec-15 protein in an antibody concentration-dependent manner (FIG. 4). On the other hand, in the case of the rat control IgG, binding to the mouse Siglec-15 protein was not observed.

Example 8

Preparation of Mouse Bone Marrow Nonadherent Cells

The femur and tibia were excised from a male ddY mouse at the age of 5 to 8 weeks and soft tissues were removed. Both ends of the femur or tibia were cut off, and D-PBS was injected using a syringe with a 25-gauge injection needle to push out bone marrow cells, which were collected in a centrifugal tube. Centrifugation was performed at room temperature for 5 minutes at 100 g, and the supernatant was removed. To the resulting cell pellet, 1 ml of a hemolytic buffer (Red Blood Cell Lysing Buffer, manufactured by Sigma Co., Ltd.) was added to suspend it, and the resulting suspension was left at room temperature for 5 minutes. 20 ml of D-PBS was added thereto, and the suspension was centrifuged at room temperature for 5 minutes at 100 g, and the supernatant was removed. To the resulting cell pellet, 10 ml of MEM-α medium (manufactured by Invitrogen, Inc.) containing 5 ng/ml of M-CSF (manufactured by R&D Systems, Inc.) and 10% fetal bovine serum (FBS) was added to suspend it. Then, the resulting suspension was passed through a cell strainer (40 µm Nylon, manufactured by BD Falcon) to remove aggregates. The resulting cells were transferred to a 75 cm$^2$ T-flask (for the attachment of adherent cells) and cultured overnight in a $CO_2$ incubator. After the overnight culture, the cells which did not adhere to the T-flask were recovered and used as mouse bone marrow nonadherent cells.

Example 9

Figure 5:
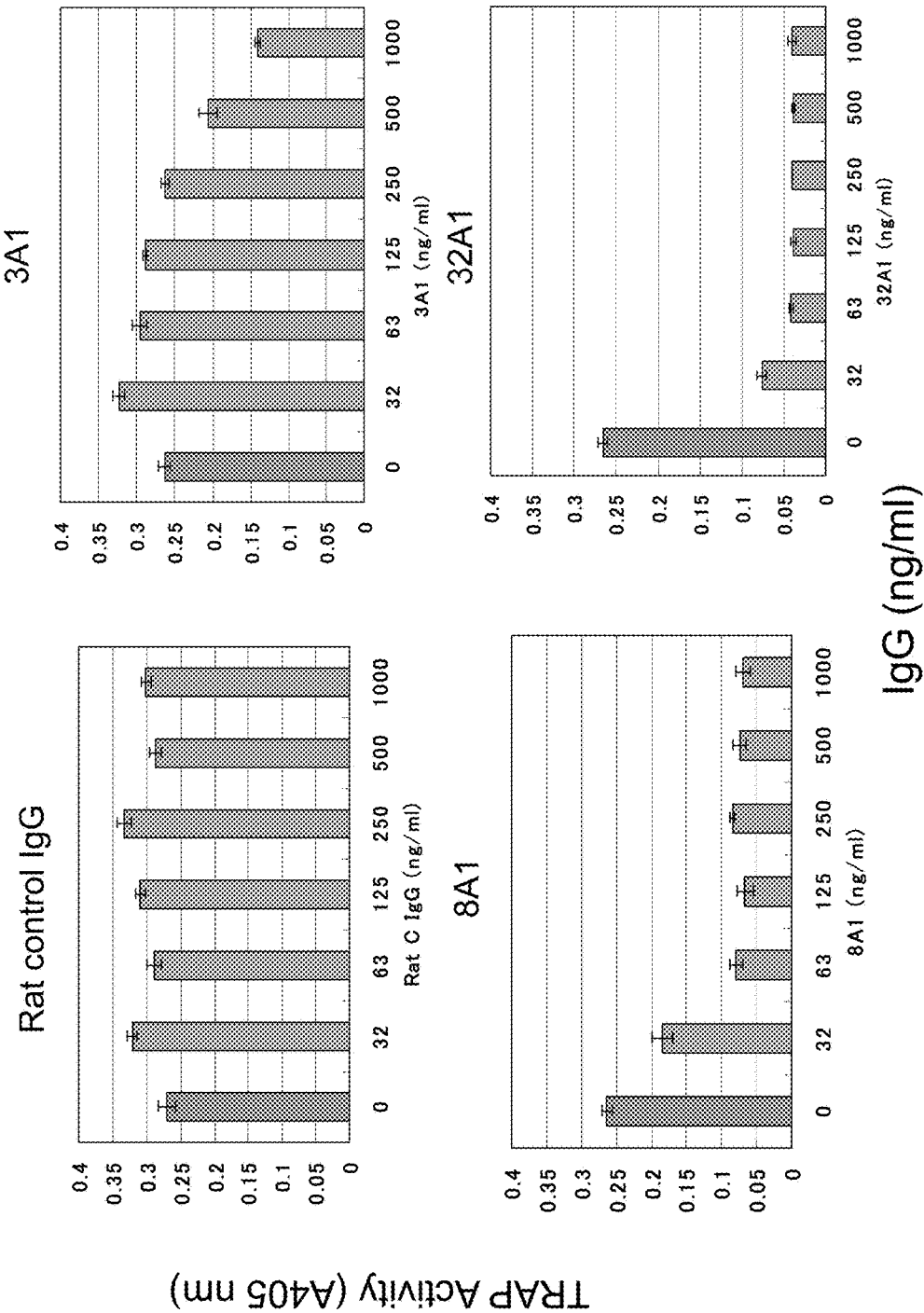
FIG. 5 shows the results of testing the effect of the addition of a rat anti-mouse Siglec-15 monoclonal antibody (#3A1, #8A1, or #32A1) on osteoclast differentiation (stimulation with RANKL) of mouse bone marrow nonadherent cells. Incidentally, the rat control IgG in the drawing is a negative control common to FIGS. 5 and 6.
Figure 6:
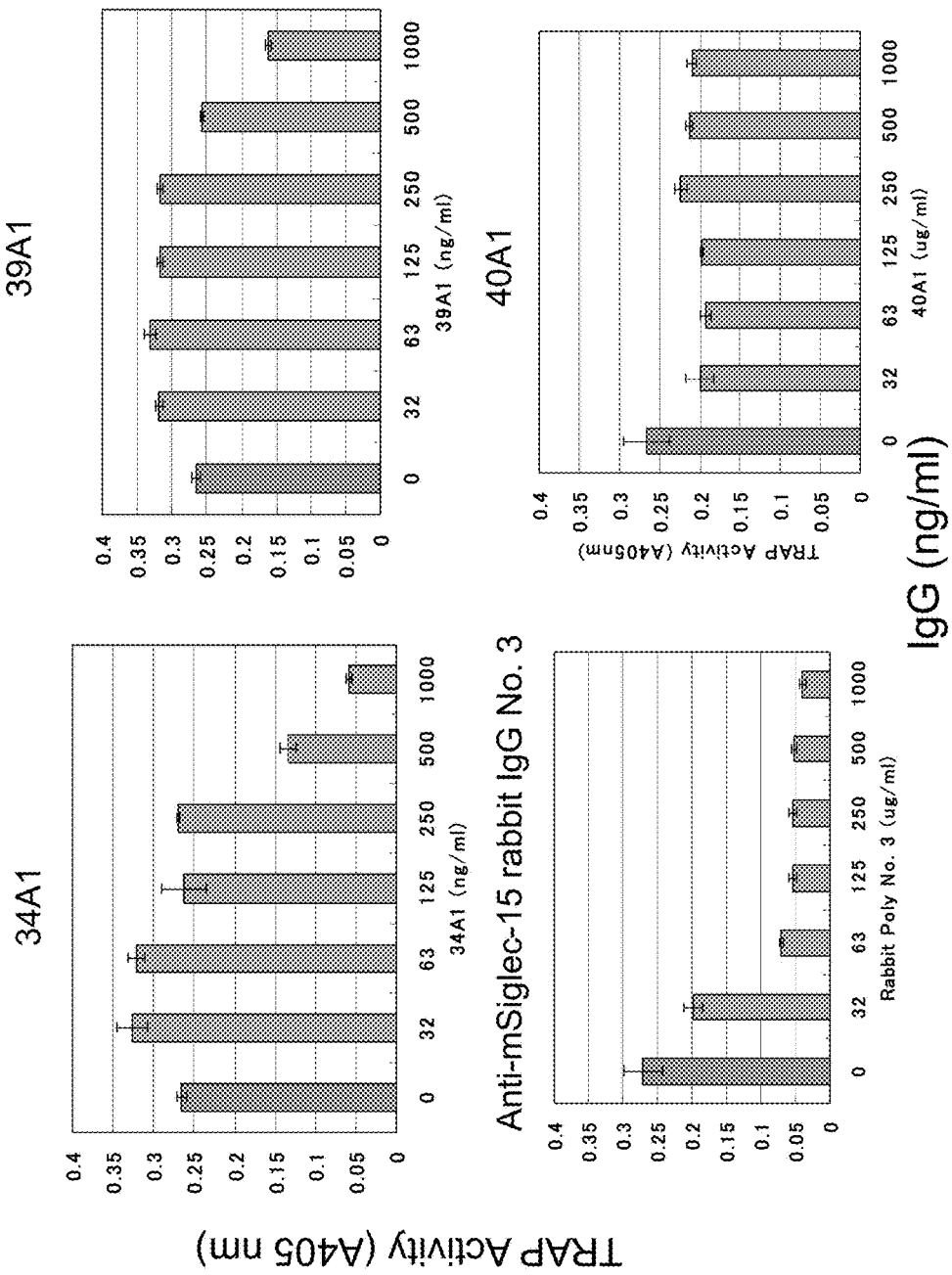
FIG. 6 shows the results of testing the effect of the addition of a rat anti-mouse Siglec-15 monoclonal antibody (#34A1, #39A1, or #40A1) on osteoclast differentiation (stimulation with RANKL) of mouse bone marrow nonadherent cells. Incidentally, the rabbit anti-mouse Siglec-15 polyclonal antibody No. 3 in the drawing is a positive control common to FIGS. 5 and 6.

Evaluation of Biological Activity of Rat Anti-Mouse Siglec-15 Monoclonal Antibody Based on Test for Mouse Osteoclast Formation By using all of the 10 test samples of the anti-mouse Siglec-15 monoclonal antibodies produced in Example 6, an effect on osteoclast differentiation of mouse bone marrow nonadherent cells was examined. The mouse bone marrow nonadherent cells prepared by the method of Example 8 were prepared at $1.5 \times 10^5$ cells/ml in α-MEM medium containing 10% FBS and 10 ng/ml of M-CSF (manufactured by R&D Systems, Inc.), and the resulting cell preparation was seeded in each well of a 96-well plate in an amount of 200 µl and the cells were cultured for 2 days in a $CO_2$ incubator. The old culture solution in the 96-well plate was removed, and 100 µl of MEM-α medium was added to each well, the 100 µl of MEM-α medium containing 10% FBS to which human RANKL (RANKL, manufactured by Peprotech, Inc.) and M-CSF had been added to give final concentrations of 20 ng/ml and 10 ng/ml, respectively. To the cell culture solution, each of the rat anti-mouse Siglec-15 monoclonal antibodies produced in Example 6, a sample obtained by removing sodium azide from commercially available rat control IgG (purified rat IgG, manufactured by R&D Systems, Inc.), or a separately produced rabbit anti-mouse Siglec-15 polyclonal antibody (No. 3) was added at a concentration of from 32 to 1,000 ng/ml, and the cells were cultured for an additional 3 days in a $CO_2$ incubator. Incidentally, the polyclonal antibody (No. 3) is an antibody which has already been confirmed to inhibit osteoclast formation in the experimental system described in this Example. After completion of the culturing, the activity of tartrate-resistant acid phosphatase (TRAP) of the formed osteoclasts was measured by a procedure described below. The culture solution in each well of the 96-well plate was removed by suction, and 50 µl of 50 mM sodium citrate buffer (pH 6.1) containing 1% Triton X-100 was added to each well. Then, the plate was shaken for 5 minutes on a plate shaker to lyse the cells. To each well, 50 µl of a substrate solution (50 mM sodium citrate buffer (pH 6.1) containing 5 mg/ml p-nitrophenyl phosphate and 0.46% sodium tartrate) was added, and the plate was incubated at room temperature for 5 minutes. After the incubation, 50 µl of a 1 N sodium hydroxide solution was added to each well of the 96-well plate to stop the enzymatic reaction. After stopping the enzymatic reaction, an absorbance of each well at 405 nm was measured, and the obtained measurement was used as an index of TRAP activity. The results are shown in FIGS. 5 and 6. A significant inhibition of TRAP activity was not observed in the case of the commercially available rat control IgG. On the other hand, a significant inhibition of TRAP activity was observed in the cases of the #32A1 antibody added in the range of from 32 ng/ml to 1000 ng/ml, and the #8A1 antibody and the affinity-purified rabbit polyclonal No. 3 antibody added in the range of from 63 ng/ml to 1000 ng/ml. Also in the cases of the #3A1 antibody, #34A1 antibody, and #39A1 antibody, a dose-dependent inhibition of TRAP activity was observed at a relatively high concentration of 500 ng/ml or higher. The inhibition of mouse osteoclast formation by the other antibodies was not observed. From the above results, antibodies which strongly inhibit mouse osteoclast formation (osteoclast differentiation and maturation) were found among the prepared rat anti-mouse Siglec-15 monoclonal antibodies. Further, as a property common to the #3A1 antibody, #8A1 antibody, #32A1 antibody, #34A1 antibody, and #39A1 antibody, the activity of inhibiting osteoclast formation at a concentration of 1000 ng/ml, i.e., 1 µg/ml or less can be exemplified.

Example 10

Production of Soluble Human Siglec-15 Protein Expression Construct

A partial nucleotide sequence encoding the extracellular domain of human Siglec-15 protein is represented by SEQ ID NO: 15 in the Sequence Listing and the amino acid sequence thereof is represented by SEQ ID NO: 16 in the Sequence Listing. By utilizing such a partial sequence, soluble human Siglec-15 protein can be produced in a culture supernatant of an animal cell or the like.

Amplification of Soluble Human Siglec-15 Gene by PCR

As primers for amplifying the human Siglec-15 extracellular domain cDNA by PCR, an oligonucleotide having a sequence of 5'-ggggacaagt ttgtacaaaa aagcaggctt caccATG-GAA AAGTCCATCT GGCTGC-3' (hSiglec-15-ECD-F: SEQ ID NO: 17 in the Sequence Listing); and an oligonucleotide having a sequence of 5'-ggggaccact ttgtacaaga aagctgggtc CCCGCTGGCG CCATGGAAGC GG-3' (hSi-glec-15-ECD-R: SEQ ID NO: 18 in the Sequence Listing) were synthesized according to a common procedure. Incidentally, these primers were designed, as amplification primers for producing a gateway entry clone, such that an attB1 sequence is added to hSiglec-15-ECD-F and an attB2 sequence is added to hSiglec-15-ECD-R. The PCR was performed using this combination of primers and a polynucleotide containing an open reading sequence of the human Siglec-15 as a template according to a common procedure. The resulting PCR reaction solution was purified using PureLink PCR Purification Kit (manufactured by Invitrogen, Inc.).

b) Production of Entry Clone by Gateway BP Reaction

An entry clone into which the human Siglec-15 extracellular domain cDNA was integrated by the Gateway technology (Invitrogen, Inc.) employing a lambda phage site-specific recombination system was produced by the following method. First, a BP reaction using BP Clonase was performed between the PCR product having an attB sequence at both ends produced in a) and pDNOR221 (manufactured by Invitrogen, Inc.) which is a donor vector having an attP sequence. By using this reaction solution, *Escherichia coli* TOP10 was transformed, colony PCR was performed for drug-resistant clones, and the size of inserts was confirmed. Then, for a clone confirmed to have an insert with the correct size, a sequence analysis of the total DNA sequence of the insert was performed. As a result, an entry clone which is completely identical to the target nucleotide sequence (SEQ ID NO: 15 in the Sequence Listing) encoding the extracellular domain of the human Siglec-15 protein was obtained.

c) Production of Expression Clone by Gateway LR Reaction

An expression clone into which the human Siglec-15 extracellular domain cDNA was integrated by the Gateway technology (Invitrogen, Inc.) employing a lambda phage site-specific recombination system was produced by the following method. The entry clone produced in b) contains an insert having an attL sequence at both ends. An LR reaction using LR Clonase was performed between this entry clone and two types of destination vectors having an attR sequence. Incidentally, as the destination vectors, two types of destination vectors: pDONM designed such that a V5 epitope tag and a 6×His tag are added to the C terminus of the insert; and phIgFc designed such that a human Fc tag is added to the C terminus of the insert, were used. By using the reaction solution obtained by the LR reaction, *Escherichia coli* TOP10 was transformed, and a sequence analysis was performed for the resulting drug-resistant clones to confirm whether correct recombination occurred.

As a result of the sequence analysis, expression clones (soluble human Siglec-15/pDONM and soluble human Siglec-15/phIgFc) in which correct recombination occurred for both pDONM and phIgFc, respectively, were obtained. By transfecting the soluble human Siglec-15/pDONM into an animal cell or the like, mRNA having a base sequence represented by SEQ ID NO: 19 in the Sequence Listing is transcribed and translated into a protein (human Siglec-15-His) having an amino acid sequence represented by SEQ ID NO: 20 in the Sequence Listing. Further, by transfecting the soluble human Siglec-15/phIgFc into an animal cell or the like, mRNA having a base sequence represented by SEQ ID NO: 21 in the Sequence Listing is transcribed and translated into a protein (human Siglec-15-Fc) having an amino acid sequence represented by SEQ ID NO: 22 in the Sequence Listing.

Example 11

Large-Scale Preparation of Culture Solution Containing Soluble Human Siglec-15 Protein Using 293-F Cells Preparation of Culture Solution Containing Human Siglec-15-His The soluble human Siglec-15/pDONM obtained in Example 10 was prepared in an amount of about 25 mg. Incidentally, in the purification of plasmids from *Escherichia coli* cultured on a large scale, Invitrogen PureLink HiPure Plasmid Gigaprep Kit (manufactured by Invitrogen, Inc.) was used. The thus prepared plasmid was mixed with Opti-MEM (manufactured by Invitrogen, Inc.), 50 ml of transfection reagent 293fectin (manufactured by Invitrogen, Inc.) was added thereto, and the resulting mixture was incubated at room temperature for 20 minutes. This mixture was added to FreeStyle 293-F cells (manufactured by Invitrogen, Inc.) cultured in FreeStyle 293 Expression Medium (manufactured by Invitrogen, Inc.) containing 1% penicillin-streptomycin such that the cell density reached 1.0 to $3.4 \times 10^6$ cells/ml using a 25 L bioprocess culture apparatus (WAVE Bioreactor). After the cells had been subjected to culture with agitation (30 rotations/min) at a $CO_2$ concentration of from 6 to 12% for 96 hours (4 days) at 37° C., the culture solution was collected and centrifuged to prepare a culture supernatant. It is observed that in the thus prepared culture supernatant, a protein in which a V5 epitope tag and a 6×His tag have been added to the C-terminal side of the human Siglec-15 extracellular domain (human Siglec-15-His) is expressed.

b) Preparation of Culture Solution Containing Human Siglec-15-Fc

The soluble human Siglec-15/phIgFc obtained in Example 10 was prepared in an amount of about 5 mg. Incidentally, in the purification of plasmids from *Escherichia coli* cultured on a large scale, Invitrogen PureLink HiPure Plasmid Gigaprep Kit (manufactured by Invitrogen, Inc.) was used. The thus prepared plasmid was mixed with Opti-MEM (manufactured by Invitrogen, Inc.), followed by filter sterilization. Then, 10 ml of a transfection reagent 293fectin (manufactured by Invitrogen, Inc.) was added thereto, and the resulting mixture was incubated at room temperature for 20 minutes. This mixture was added to FreeStyle 293-F cells (manufactured by Invitrogen, Inc.) cultured in Erlenmeyer flasks such that the cell density reached 1.0 to $3.0 \times 10^6$ cells/ml×5 L (1 L/flask×5 flasks) in FreeStyle 293 Expression Medium (manufactured by Invitrogen, Inc.). After the cells had been subjected to culture with agitation (125 rotations/min) at a $CO_2$ concentration of 8.0% for 96 hours (4 days) at 37° C., the culture solution was collected and centrifuged to prepare a culture supernatant. It is observed that in the thus prepared culture supernatant, a protein in which a human Fc tag has been added to the C-terminal side of the human Siglec-15 extracellular domain (human Siglec-15-Fc) is expressed.

Example 12

Purification of Soluble Human Siglec-15 Protein
Purification of Soluble Human Siglec-15-his
a-i) HisTrap HP Column Chromatography To 12 L of the culture solution of 293F cells expressing human Siglec-15-His prepared in a) of Example 11, 1350 mL of 10× buffer (500 mM Tris, 1.5 M NaCl, 200 mM imidazole, pH 8.0) was added, and the resulting mixture was stirred well and filtered through a MilliPak-60 filter (manufactured by Millipore Co., Ltd.). This culture solution was applied at a flow rate of 10 ml/min to a Ni-Sepharose HP (manufactured by Amersham Biosciences, Inc.) 100 ml column which had previously been washed with pure water (Milli-Q water). After the column had been washed with 400 ml of 50 mM Tris-HCl buffer (pH 8.0) containing 300 mM NaCl at a flow rate of 8 mL/min, a protein adsorbed to the column was eluted with 200 ml of 50 mM Tris-HCl buffer (pH 8.0) containing 300 mM NaCl and 500 mM imidazole at a flow rate of 2.5 ml/min, and the eluate was fractionated into mini-sorp tubes (manufactured by Nunc, Inc.). In order to prevent precipitation of the protein, 8 ml of a 5 M NaCl solution was added to about 40 ml of a fraction containing the eluted protein, followed by stirring, and then the resulting mixture was concentrated to about 20 ml with a centrifugal membrane concentrator Amicon Ultra-15 (manufactured by Millipore Co., Ltd.). Insoluble matter generated during the concentration was removed by centrifugation at 3000 rpm for 30 minutes at 4° C., and 2.5 ml of the resulting supernatant was applied to a PD-10 desalting column (manufactured by Amersham Biosciences, Inc.) which had previously been equilibrated with phosphate-buffered saline containing 1 M NaCl (N—PBS), followed by elution with N—PBS, whereby 3.5 ml of a sample whose solvent was replaced with N—PBS was obtained. This procedure was performed by repeating it 7 more times, and about 28 ml of a solution of partially purified human Siglec-15-His was obtained.

a-ii) Resource Q Column Chromatography 12 ml of the sample which had been purified by Ni-Sepharose HP column chromatography and whose solvent had been replaced with N—PBS was dialyzed overnight at 4° C. against 50 mM Tris-HCl buffer (pH 7.5) containing 0.1% CHAPS (1 L, 3 times) and the resulting dialysate was centrifuged at 3,000 rpm for 30 minutes at 4° C., and the precipitate was removed. After the resulting supernatant had been filtered through a Millex-GV filter (manufactured by Millipore Co., Ltd.), the filtrate was applied at a flow rate of 1 ml/min to a Resource Q 6 ml column (manufactured by Amersham Biosciences, Inc.) which had previously been equilibrated with 50 mM Tris-HCl buffer (pH 7.5) containing 0.1% CHAPS. Thereafter, the column was washed with this buffer at a flow rate of 1 ml/min and a protein fraction which was not adsorbed to the column was collected. A protein adsorbed to the column was eluted with 50 mM Tris-HCl buffer (pH 7.5) containing 0.1% CHAPS and 1 M NaCl at a flow rate of 1 ml/min. After 26.5 ml of the fraction which had not been adsorbed to the column was concentrated to 3.0 ml with a centrifugal membrane concentrator Amicon Ultra-15 (manufactured by Millipore Co., Ltd.), the concentrate was centrifuged at 3,000 rpm for 10 minutes at 4° C. and the precipitate was removed. 2.5 ml of the resulting supernatant was applied to a PD-10 desalting column (manufactured by Amersham Biosciences, Inc.) which had previously been equilibrated with phosphate-buffered saline containing 50 mM arginine hydrochloride (pH 7.0, A-PBS), followed by elution with A-PBS, whereby 3.5 ml of a sample whose solvent was replaced with A-PBS was obtained. The arginine hydrochloride in the solvent of the prepared sample was added in order to prevent soluble human Siglec-15-His from precipitating. The supernatant after centrifugation was cryopreserved at −80° C. until use. The above-mentioned purification procedure (Resource Q column chromatography) was performed by repeating it twice.

a-iii) Detection and Purity Assay of Purified Human Siglec-15-His

Figure 7:
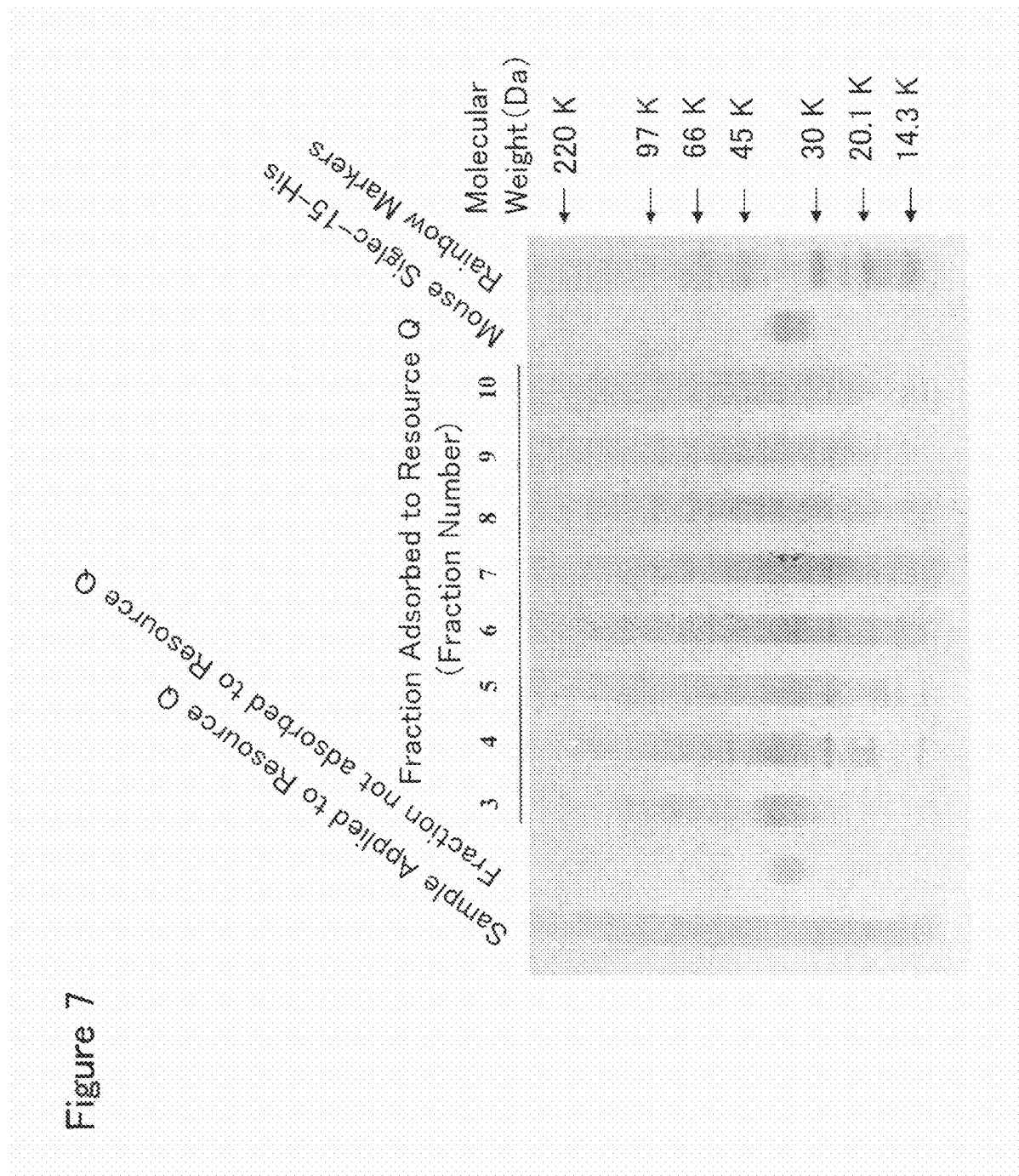
FIG. 7 shows the results of evaluating the purity of human Siglec-15-His purified by HisTrap HP column chromatography and Resource Q column chromatography through SDS-polyacrylamide electrophoresis and silver staining.

By using a sample prepared by the above-mentioned purification procedure (Ni-Sepharose HP column chromatography and Resource Q column chromatography), SDS-polyacrylamide electrophoresis under reducing conditions and silver staining were performed. That is, to 5 µl of each of the samples purified by the respective purification steps, an equivalent amount of an SDS-treatment solution was added, and the resulting mixture was thermally treated at 95° C. for 10 minutes. 0.3 µl of each of the thermally treated samples was used for SDS-polyacrylamide electrophoresis. The electrophoresis procedure was performed in the same manner as in Example 3 except that Rainbow Molecular Weight Markers (manufactured by Amersham Biosciences, Inc.) were used as the molecular weight markers. After completion of the electrophoresis, silver staining was performed using a PhastGel Silver Kit (manufactured by Amersham Biosciences, Inc.) and PhastSystem. The results are shown in FIG. 7. It was shown that a protein having a molecular weight of about 35 kDa (human Siglec-15-His) was efficiently purified and concentrated in the protein fraction which was not adsorbed to the Resource Q column.

a-iv) Measurement of Protein Concentration of Purified Human Siglec-15-His

For the purified human Siglec-15-His (the protein fraction which was not adsorbed to the Resource Q column), the protein concentration was measured with a DC protein assay kit (manufactured by Bio-Rad Laboratories, Inc.) using bovine serum albumin as a standard sample. By performing the purification procedure twice, a total of 1.66 mg of purified human Siglec-15-His was obtained.

b) Purification of Soluble Human Siglec-15-Fc b-i) HiTrap Protein a Column Chromatography 1.5 L of the culture solution of 293F cells expressing human Siglec-15-Fc prepared in b) of Example 11 was filtered through a Sterivex-GV filter (manufactured by Millipore Co., Ltd.), and then the filtrate was applied at a flow rate of 5 ml/min to a HiTrap Protein A 5 ml column (manufactured by Amersham Biosciences, Inc.) which had previously been equilibrated with Dulbecco's PBS (D-PBS, manufactured by Invitrogen, Inc.). After the column had been washed with 70 ml of D-PBS at a flow rate of 5 ml/min, a protein adsorbed to the column was eluted with 24 ml of 0.1 M sodium citrate buffer (pH 3.0) at a flow rate of 1.2 ml/min. The eluate was fractionated at 1.2 ml per fraction into mini-sorp tubes (manufactured by Nunc, Inc.), and immediately thereafter, 0.31 ml of 1 M Tris was added thereto to neutralize the eluate. A 2.5 ml aliquot of a solution (about 7.5 ml) obtained by combining the eluted protein fractions (fractions 5 to 9) was applied to a PD-10 desalting column (manufactured by Amersham Biosciences, Inc.) which had previously been equilibrated with phosphate-buffered saline containing 50 mM arginine hydrochloride (pH 7.0, A-PBS), followed by elution with A-PBS, whereby 3.5 ml of a sample whose solvent was replaced with A-PBS was obtained. This procedure was performed by repeating it twice. The arginine hydrochloride in the solvent was added in order to prevent soluble human Siglec-15-Fc from precipitating. 2.5 ml of the remaining solution of the eluted protein fractions (fractions 5 to 9) was applied to a PD-10 desalting column (manufactured by Amersham Biosciences, Inc.) which had previously been equilibrated with phosphate-buffered saline containing 1 M NaCl (pH 6.7, N—PBS), followed by elution with N—PBS, whereby 3.5 ml of a sample whose solvent was replaced with N—PBS was obtained. NaCl in the solvent in the prepared sample was added in order to prevent soluble human Siglec-15-Fc from precipitating without adding an amino group-containing compound such as arginine. The samples prepared by the above-mentioned procedure were cryopreserved at −80° C. until use.

b-ii) Detection and Purity Assay of Purified Human Siglec-15-Fc

Figure 8:
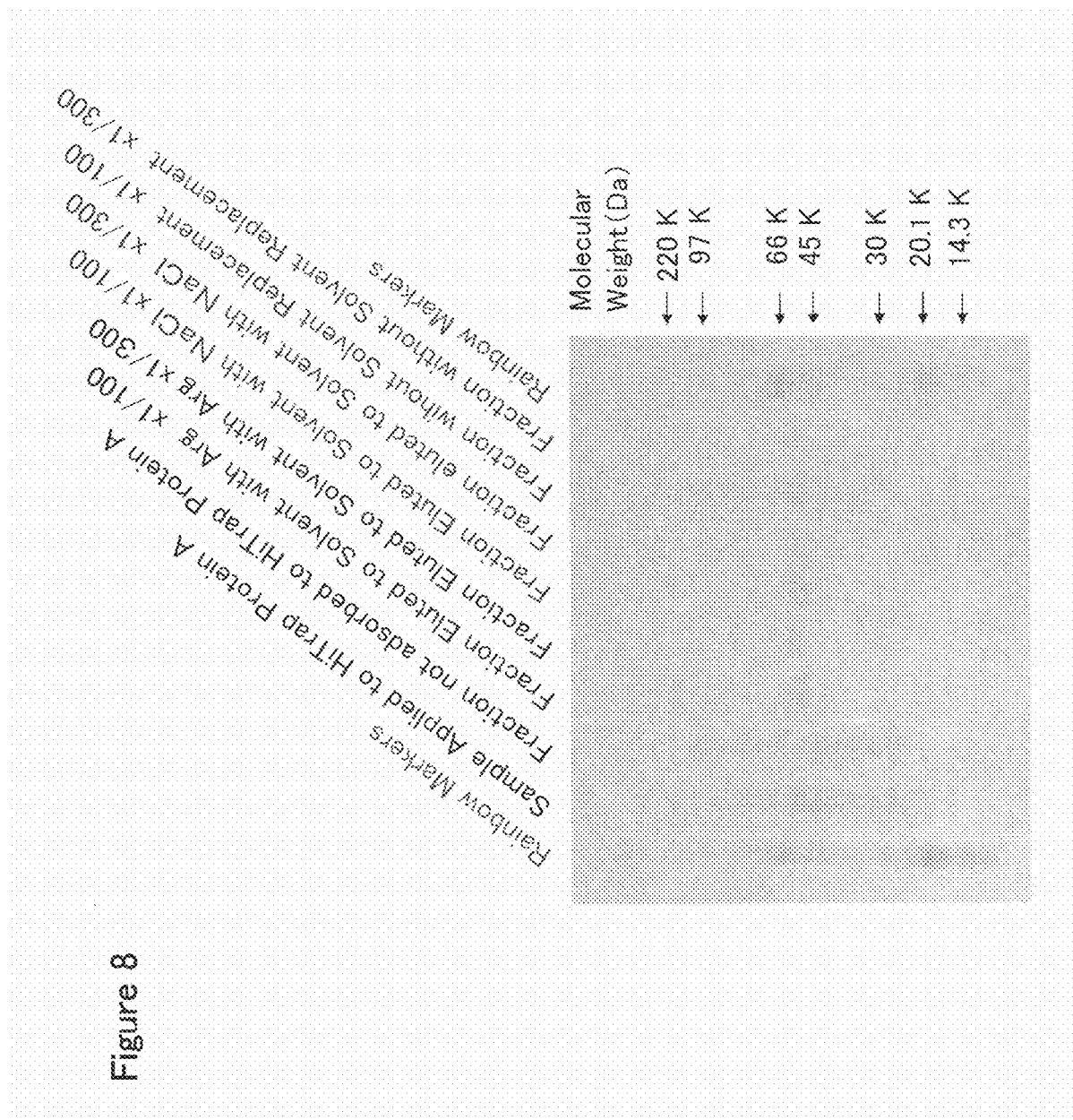
FIG. 8 shows the results of evaluating the purity of human Siglec-15-Fc purified by Protein A column chromatography through SDS-polyacrylamide electrophoresis.

By using the samples prepared by the above-mentioned purification procedure, SDS-polyacrylamide electrophoresis under reducing conditions and silver staining were performed. That is, to 5 µl of each of the samples purified by the respective purification steps, an equivalent amount of an SDS-treatment solution was added, and the resulting mixture was heated at 95° C. for 10 minutes. 0.3 µl of a sample obtained by diluting each of the thermally treated samples to 1/100 or 1/300 with a half concentration of the SDS-treatment solution was used for SDS-polyacrylamide electrophoresis. The electrophoresis and silver staining were performed in the same manner as the purity assay of human Siglec-15-His described in a-iii). The results are shown in FIG. 8. It was shown that a protein having a molecular weight of about 55 kDa (human Siglec-15-Fc) was efficiently purified and concentrated in the protein fraction which was eluted from the HiTrap Protein A column.

b-iii) Measurement of Protein Concentration of Purified Human Siglec-15-Fc

For the purified human Siglec-15-Fc (the protein fraction eluted from the PD-10 desalting column), the protein concentration was measured with a DC protein assay kit (manufactured by Bio-Rad Laboratories, Inc.) using bovine serum albumin as a standard sample. As shown in Table 4, a total of 25.2 mg of purified human Siglec-15-Fc was obtained by performing the purification procedure twice.

TABLE 4

|  | Protein Conc. (mg/ml) | Sample Vol. (ml) | Total protein (mg) |
| --- | --- | --- | --- |
| Arg-containing solvent | 2.3 | 7.0 | 16.1 |
| NaCl-containing solvent | 2.6 | 3.5 | 9.1 |
| Total |  |  | 25.2 |

Example 13

Figure 9:
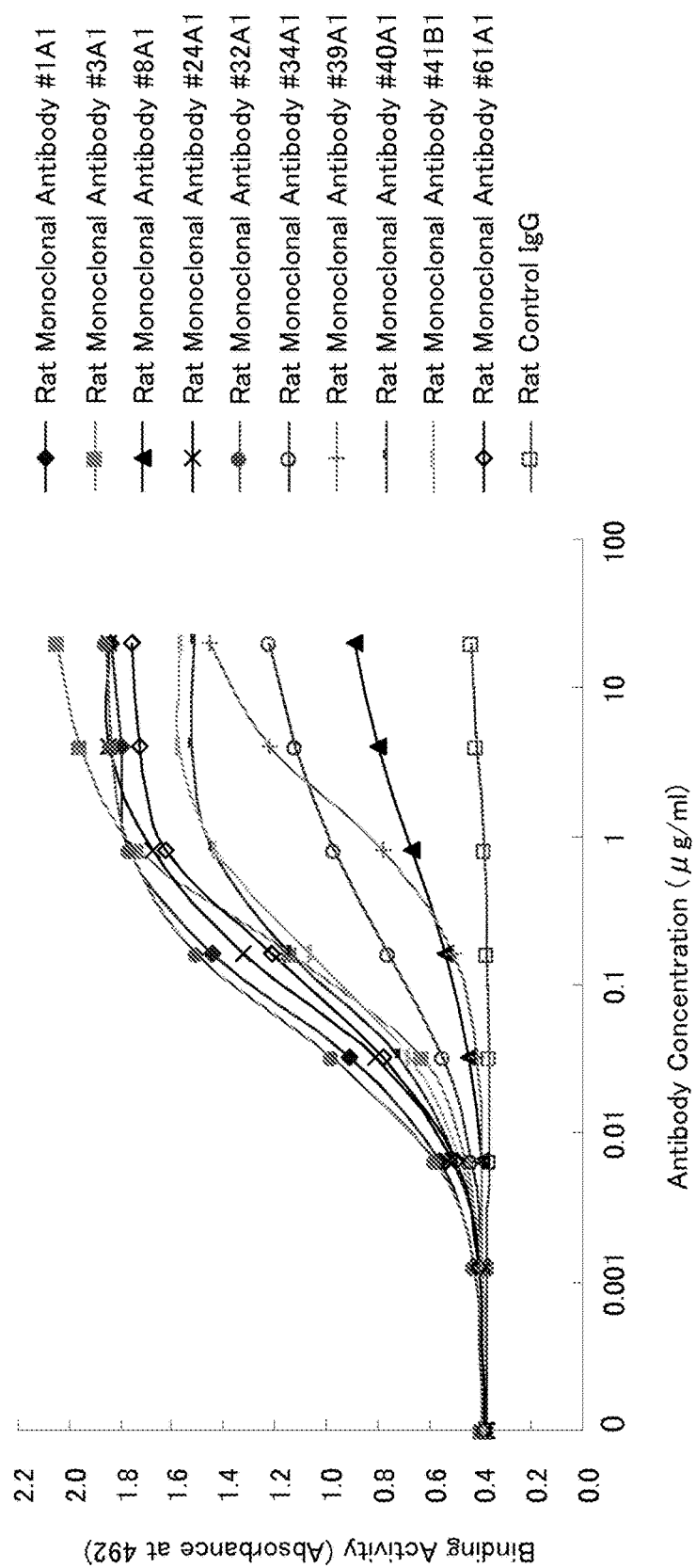
FIG. 9 shows the results of testing the binding of a rat anti-mouse Siglec-15 monoclonal antibody to a plate having human Siglec-15-Fc immobilized thereon by an ELISA method. The symbol (♦) denotes #1A1 antibody, the symbol (■) denotes #3A1 antibody, the symbol (▲) denotes #8A1 antibody, the symbol (x) denotes #24A1 antibody, the symbol (●) denotes #32A1 antibody, the symbol (α) denotes #34A1 antibody, the symbol (+) denotes #39A1 antibody, the symbol (−) denotes #40A1 antibody, the symbol (—) denotes #41B1 antibody, the symbol (◇) denotes #61A1 antibody, and the symbol (□) denotes control IgG.

Evaluation of Property of Rat Anti-Mouse Siglec-15 Monoclonal Antibody Binding to Human Siglec-15 Protein The property of the rat anti-mouse Siglec-15 monoclonal antibody binding to human Siglec-15 protein was evaluated by an ELISA method. The human Siglec-15-Fc protein (subjected to replacement with A-PBS) produced in b) of Example 12 was diluted to 5 µg/ml with 0.1 M sodium carbonate buffer (pH 9.5), and the resulting solution was added to a 96-well plate (manufactured by Nalge Nunc International, Inc., Cat. No. 430341) at 100 µl/well. After the plate had been left at room temperature for 1 hour, the solution was removed and a washing buffer (phosphate-buffered saline containing 0.05% Tween 20) was added at 300 µl/well and then removed. After this washing procedure had been performed one more time, phosphate-buffered saline containing 25% BlockAce (manufactured by Dainippon Sumitomo Pharma Co., Ltd.) was added at 200 µl/well, and the plate was left at room temperature for 1 hour, whereby blocking was performed. The liquid was removed, and the plate was washed twice with 300 µl/well of the washing buffer. Then, each of the rat anti-mouse Siglec-15 monoclonal antibodies prepared in Example 6 or rat control IgG (manufactured by R&D Systems, Inc.) was diluted to a final concentration of from 1.28 to 20,000 ng/ml (5-fold dilution series) with an ELISA buffer (phosphate-buffered saline containing 12.5% BlockAce and 0.05% Tween 20), and the resulting diluted antibody solution was added to the plate at 100 μl/well. After the plate was left at room temperature for 1 hour, the liquid was removed, and the plate was washed 3 times with 300 μl/well of the washing buffer. Subsequently, an HRP (horseradish peroxidase)-labeled goat anti-rat IgG antibody (manufactured by Beckman Coulter, Inc.) diluted to 1,000-fold with an ELISA buffer was added at 100 μl/well, and the plate was left at room temperature for 1 hour. The liquid was removed and the plate was washed 3 times with 300 μl/well of the washing buffer, and then, by using a color developing kit for peroxidase (manufactured by Sumitomo Bakelite Co., Ltd.), the color was developed according to the protocol accompanying the kit. After developing the color, an absorbance at 492 nm was measured using a microplate reader (manufactured by Nihon Molecular Devices Corporation). As a result, it was confirmed that all of the examined 10 test samples of the rat anti-mouse Siglec-15 monoclonal antibodies bind to the human Siglec-15 protein in an antibody concentration-dependent manner (FIG. 9). In particular, the binding activity of 5 test samples, namely #1A1, #3A1, #24A1, #32A1, and #61A1, was high, and the binding activity of 3 test samples, namely #8A1, #34A1, and #39A1, was relatively low. On the other hand, in the case of the rat control IgG, binding to the human Siglec-15 protein was not observed. From the above results, it was shown that the rat anti-mouse Siglec-15 monoclonal antibodies prepared in Example 6 bind not only to mouse Siglec-15, but also to human Siglec-15, and moreover, it was found that some antibodies strongly bind to human Siglec-15.

Example 14

Effect of Addition of Rat Anti-Mouse Siglec-15 Monoclonal Antibody on Cell Fusion and Bone Resorption Activity of Normal Human Osteoclast Precursor Cells (Evaluation of In Vitro Biological Activity)

Since it was confirmed that the rat anti-mouse Siglec-15 monoclonal antibodies bind also to human Siglec-15 in Example 13, the effects of these antibodies on human osteoclast formation and bone resorption activity were examined.

Effect of addition of rat anti-mouse Siglec-15 monoclonal antibody on cell fusion of osteoclasts from normal human osteoclast precursor cells (TRAP Staining)

Figure 10:
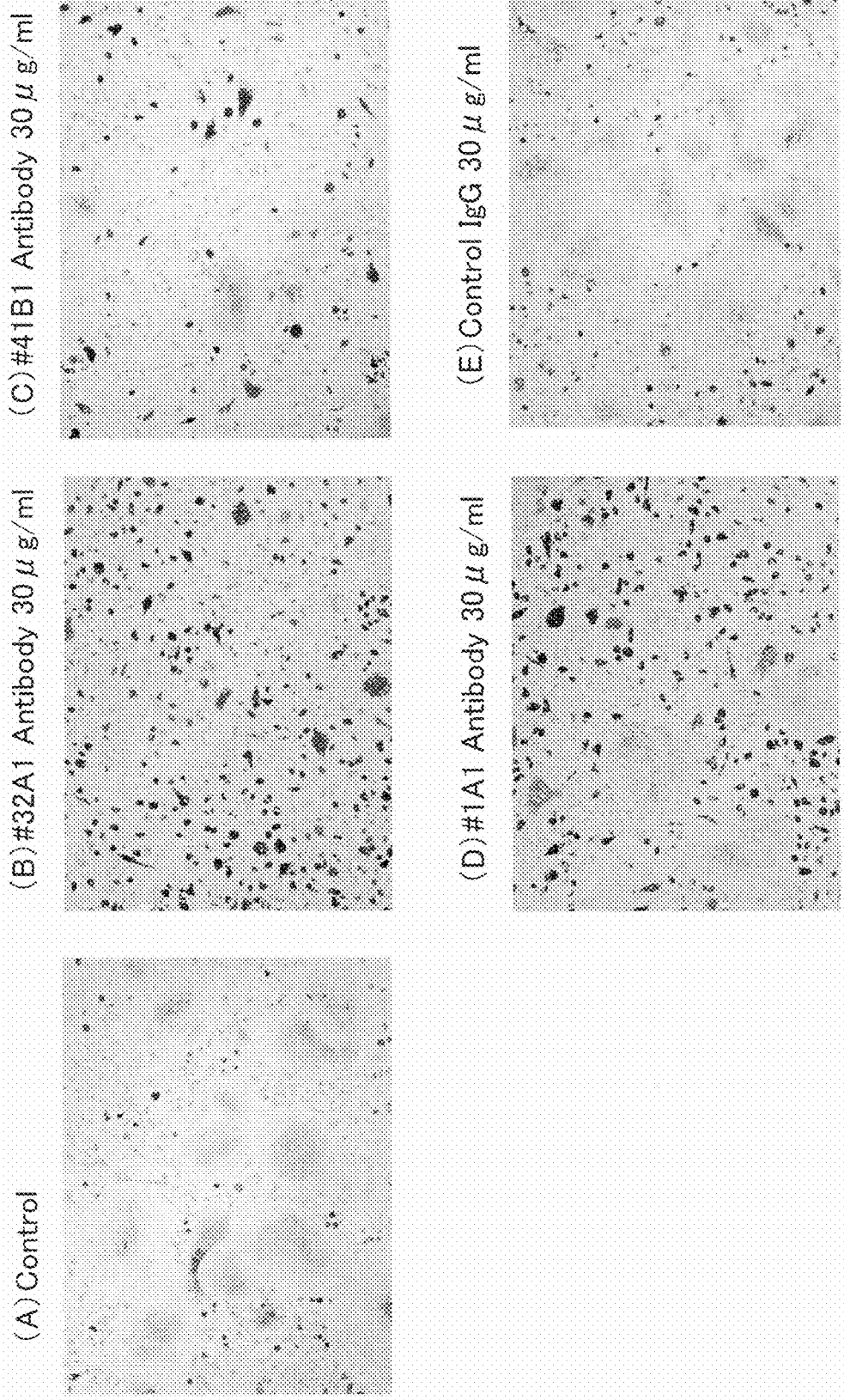
FIG. 10 shows photomicrographs depicting, by TRAP staining, the inhibition of giant osteoclast formation from normal human osteoclast precursor cells by the addition of a rat anti-mouse Siglec-15 monoclonal antibody.

Normal human osteoclast precursor cells (Normal Human Natural Osteoclast Precursor Cells, purchased from Sanko Junyaku Co., Ltd., Cat. No. 2T-110) were seeded in a 96-well plate at 1×10$^4$ cells/well according to the protocol accompanying the cells. As the medium, a minimal essential medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 66 ng/ml), human M-CSF (final concentration: 33 ng/ml), and the like was used. To the resulting culture supernatant, each of the rat anti-mouse Siglec-15 monoclonal antibodies prepared in Example 6 or rat control IgG (manufactured by R&D Systems, Inc.) was added to give a final concentration of 30 μg/ml, and the cells were cultured for 4 days in a $CO_2$ incubator. After the culturing, the supernatant was removed, and 10% neutral formalin was added to fix the cells. After fixing the cells, the cells were washed twice with distilled water, a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 μl/well, and a reaction was allowed to proceed at room temperature for 5 minutes. After the reaction, the cells were washed twice with distilled water, and then observed by microscopy (FIG. 10). As a result, the formation of giant osteoclasts resulting from a high degree of cell fusion was almost completely inhibited by the addition of the #32A1 antibody. Further, in the case of the #41B1 antibody, the formation of giant osteoclasts resulting from a high degree of cell fusion was also significantly inhibited. On the other hand, in the case of the other rat anti-mouse Siglec-15 monoclonal antibodies (the #1A1 antibody and others) and the rat control IgG, such a significant inhibition of osteoclast cell fusion was not observed. In this manner, it was revealed that multinucleation and cell fusion of TRAP-positive osteoclasts from normal human osteoclast precursor cells are inhibited by monoclonal antibodies specifically binding to the Siglec-15 protein.

b) Effect of Addition of Rat Anti-Mouse Siglec-15 Monoclonal Antibody (#32A1) on Cell Fusion of Osteoclasts from Normal Human Osteoclast Precursor Cells (TRAP Staining)

Figure 11:
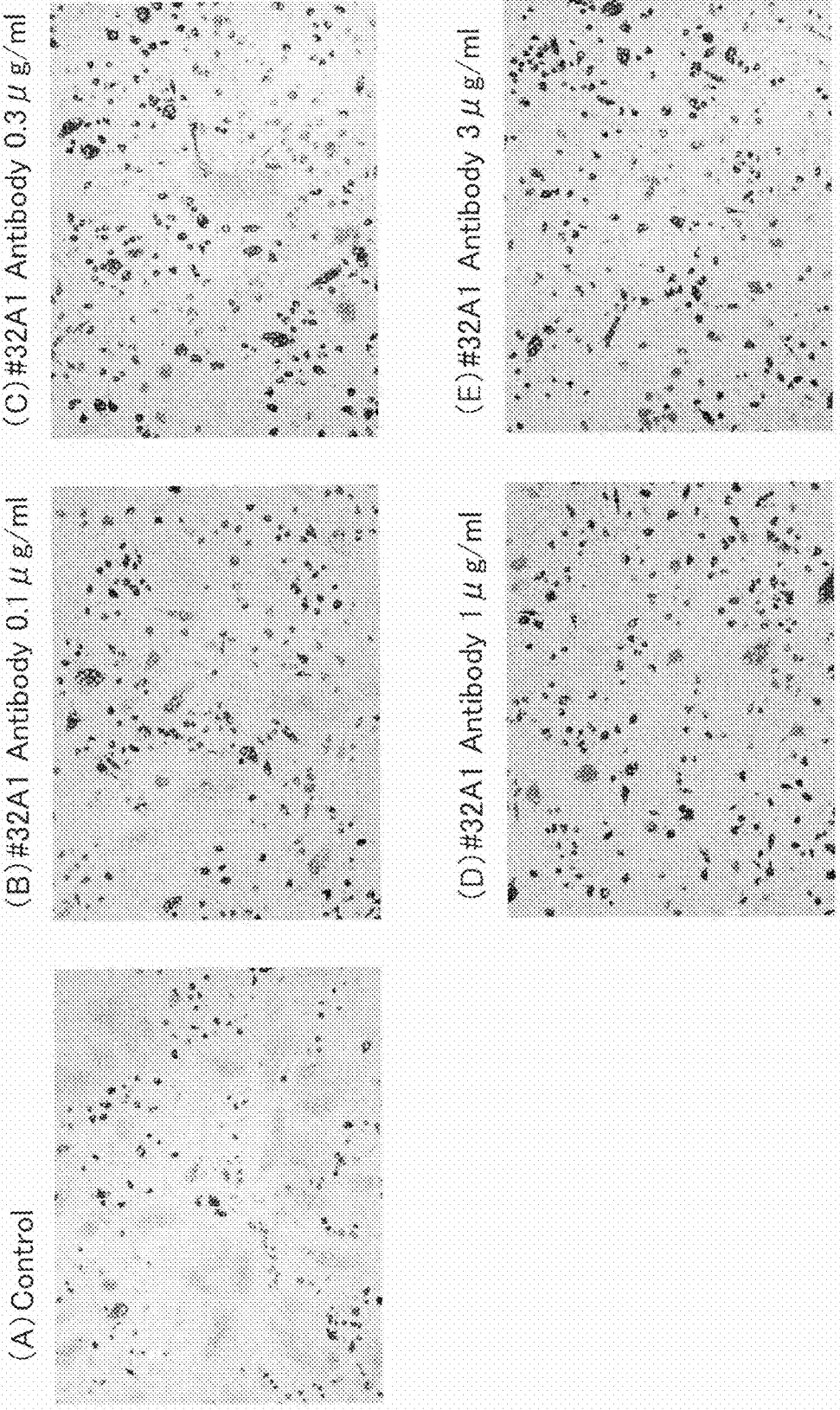
FIG. 11 shows photomicrographs depicting, by TRAP staining, the inhibition of giant osteoclast formation from normal human osteoclast precursor cells by the addition of a rat anti-mouse Siglec-15 monoclonal antibody (#32A1 antibody).

Normal human osteoclast precursor cells (Normal Human Natural Osteoclast Precursor Cells, purchased from Sanko Junyaku Co., Ltd., Cat. No. 2T-110) were seeded in a 96-well plate at 1×10$^4$ cells/well according to the protocol accompanying the cells. As the medium, a minimal essential medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 68.4 ng/ml), human M-CSF (final concentration: 33 ng/ml), and the like was used. To the resulting culture supernatant, the rat anti-mouse Siglec-15 monoclonal antibody (#32A1 antibody) prepared in Example 6 was added to give a final concentration of 0.1, 0.3, 1, or 3 μg/ml, and the cells were cultured for 3 days in a $CO_2$ incubator. After the culturing, the supernatant was removed, and 10% neutral formalin was added to fix the cells. After fixing the cells, the cells were washed twice with distilled water, and a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 μl/well, and a reaction was allowed to proceed at room temperature for 5 minutes. After the reaction, the cells were washed twice with distilled water, and then, observed by microscopy (FIG. 11). As a result, the formation of TRAP-positive multinucleated osteoclasts was inhibited in a #32A1 antibody concentration-dependent manner within the range of from 0.3 μg/ml to 3 μg/ml.

c) Effect of Addition of Rat Anti-Mouse Siglec-15 Monoclonal Antibody (#32A1) on Bone Resorption Activity of Normal Human Osteoclast Precursor Cells (Evaluation Using Collagen-Coated Plate)

Figure 12:
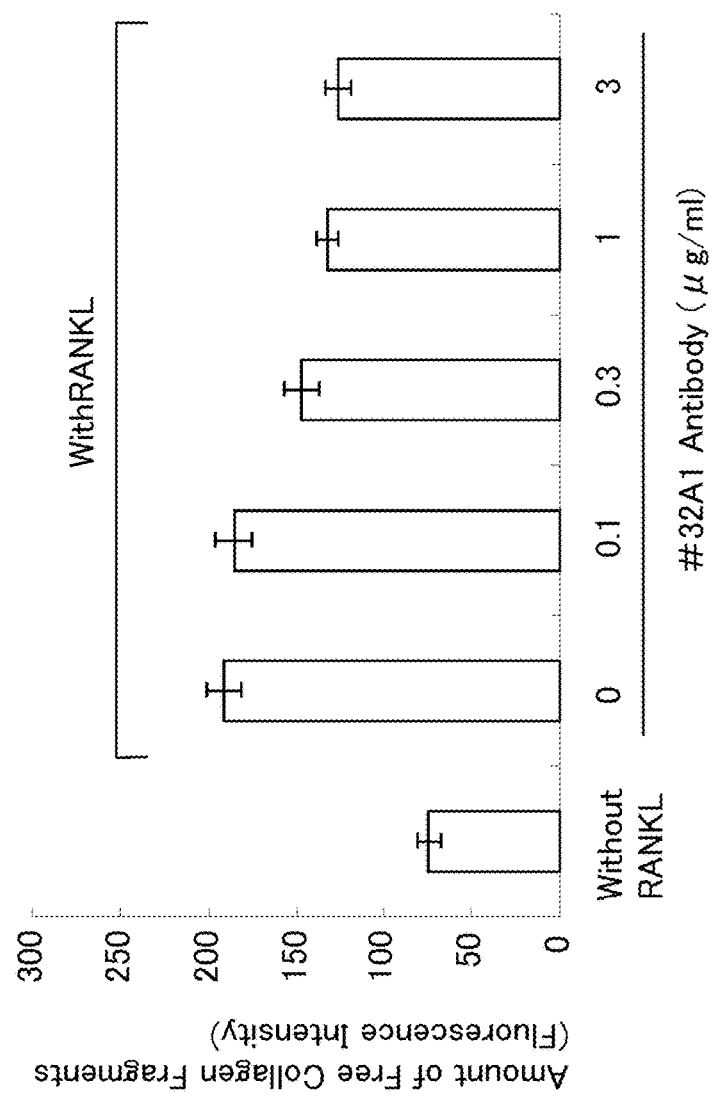
FIG. 12 is a graph showing the inhibition of the bone resorption activity of normal human osteoclasts by the addition of a rat anti-mouse Siglec-15 monoclonal antibody (#32A1 antibody) (N=6).

It is known that osteoclasts release a protease such as cathepsin K and degrade type I collagen which is a constitutional component of bone tissue. The OsteoLyse Assay Kit (manufactured by Lonza, Inc., Cat. No. PA-1500) provides a 96-well plate coated with europium-conjugated human collagen (96-well OsteoLyse cell culture plate), and it is possible to evaluate the bone resorption activity of osteoclasts in vitro by measuring the amount of fluorescent collagen fragments released into the supernatant when osteoclasts are cultured on the plate. Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate at $1 \times 10^4$ cells/well according to the protocol accompanying the cells. As the medium, a minimal essential medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 68.4 ng/ml), human M-CSF (final concentration: 33 ng/ml), and the like was used. To the resulting culture supernatant, the rat anti-mouse Siglec-15 monoclonal antibody (#32A1 antibody) prepared in Example 6 was added to give a final concentration of 0.1, 0.3, 1, or 3 µg/ml, and the cells were cultured for 3 days in a $CO_2$ incubator. A 10 µl aliquot of the culture supernatant was collected, and 200 µl of Fluorophore Releasing Reagent included in the OsteoLyse Assay Kit was added thereto, and a fluorescence intensity was measured (Excitation: 340 nm, Emission: 615 nm) using a fluorescence plate reader (ARVO MX, manufactured by Perkin Elmer Inc.), whereby the amount of free fluorescent collagen fragments released in the culture supernatant was determined (FIG. 12). As a result, the amount of fluorescent collagen fragments increased by the addition of RANKL was reduced by the #32A1 antibody in a concentration-dependent manner within the range of from 0.3 µg/ml to 3 µg/ml. From this result, it was revealed that the bone resorption activity of human osteoclasts is inhibited by the studied monoclonal antibody specifically binding to the Siglec-15 protein.

Example 15

Evaluation of Biological Activity of Rat Anti-Mouse Siglec-15 Monoclonal Antibody Using Ovariectomized Rats
Protocol of Animal Experiment The ovaries on both sides were removed from female F344 rats (obtained from Charles River Laboratories Japan, Inc.) at the age of 12 weeks, and the rats were divided into three groups: a vehicle administration group; a rat anti-mouse Siglec-15 monoclonal antibody #8A1 administration group; and a rat anti-mouse Siglec-15 monoclonal antibody #32A1 administration group. Further, one group was prepared as a sham operation group. In the antibody administration groups, the rat anti-mouse Siglec-15 monoclonal antibody #8A1 or the rat anti-mouse Siglec-15 monoclonal antibody #32A1 prepared in Example 6 was intraperitoneally administered at a dose of 1 mg/kg three times a week repeatedly for 4 weeks from the next day of the operation. In the vehicle administration group and the sham operation group, PBS containing 0.01% Tween 20 was intraperitoneally administered as the vehicle. At 4 weeks after the initiation of administration, urine was collected for 24 hours under fasting conditions, and the urine samples were stored at −80° C. until measurement. After completion of the urine collection, the rats were euthanized, and the lumbar spine was excised from each rat.

b) Measurement of Lumbar Spine Bone Mineral Density

Figure 13A:
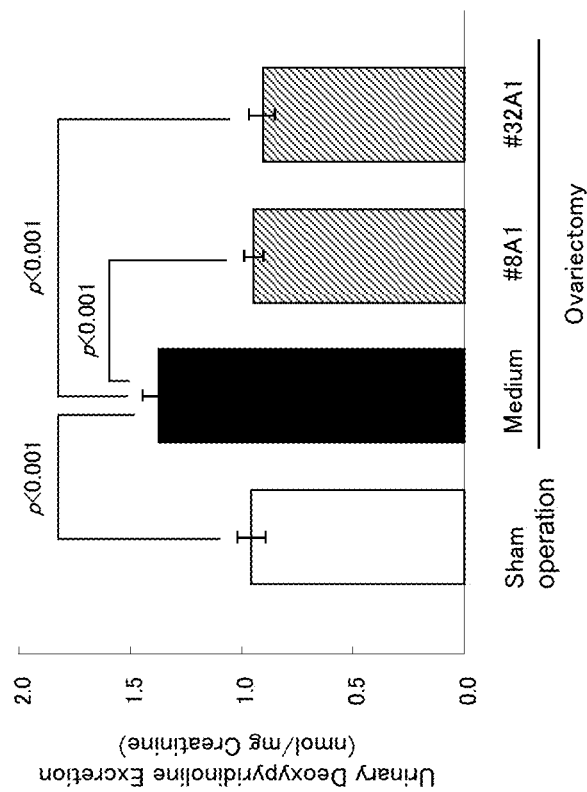
FIG. 13A is a graph showing the effect of increasing lumbar spine bone mineral density when a rat anti-mouse Siglec-15 monoclonal antibody was administered to ovariectomized rats for 4 weeks.

Soft tissues adhered to the excised lumbar spine were removed, and the 4th to 6th lumbar vertebrae were extracted. The extracted lumbar vertebrae were degreased and dehydrated by being shaken in ethanol and then air-dried, and the bone mineral density was measured using a bone densitometer (DCS-600EX, manufactured by Aloka Co., Ltd.). The results are shown in FIG. 13(A). A significant decrease in lumbar spine bone mineral density was observed in the ovariectomized group as compared with the sham operation group, however, in the #8A1 and #32A1 antibody administration groups, a decrease in bone mineral density due to ovariectomy was significantly inhibited.

c) Measurement of Urinary Deoxypyridinoline Excretion

A variety of type I collagen crosslinked metabolites sharply reflect bone metabolic turnover, particularly bone resorption. Above all, deoxypyridinoline is localized mainly in bone collagen, and therefore, is considered to be highly reliable as an index of bone resorption.

Figure 13B:
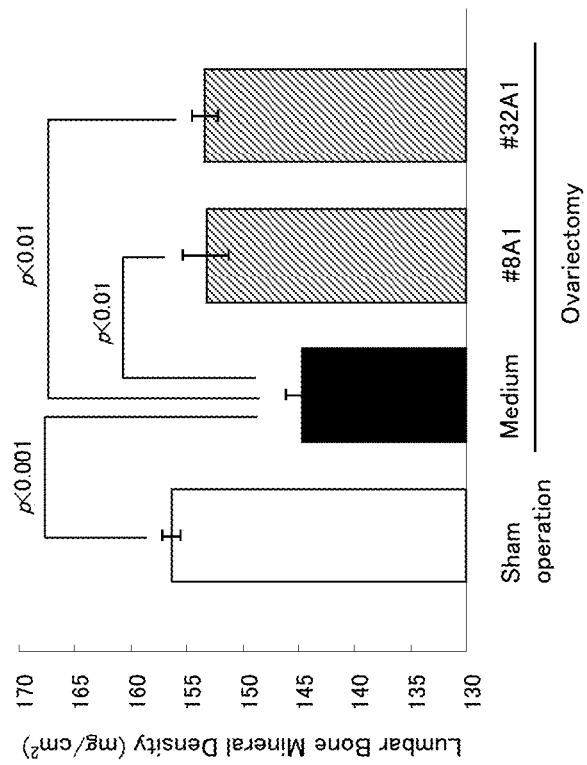
FIG. 13B is a graph showing the effect of decreasing urinary deoxypyridinoline excretion when a rat anti-mouse Siglec-15 monoclonal antibody was administered to ovariectomized rats for 4 weeks.

The cryopreserved urine sample was thawed, and insoluble matter was precipitated by a centrifugal operation, whereby a supernatant was obtained. The amount of deoxypyridinoline contained in this supernatant was measured using Osteolinks "DPD" (manufactured by DS Pharma Biomedical Co., Ltd.). Further, by using Creatinine Test Wako (manufactured by Wako Pure Chemical Industries, Ltd.), the content of creatinine in the supernatant was also measured, and the amount of deoxypyridinoline corrected for creatinine was calculated. The results are shown in FIG. 13(B). The urinary deoxypyridinoline excretion was significantly increased in the ovariectomized group as compared with the sham group, and therefore, it was indicated that in the ovariectomized rats, osteoclastic bone resorption is increased. On the other hand, in the #8A1 and #32A1 antibody administration groups, an increase in deoxypyridinoline excretion due to ovariectomy was inhibited such that the level of deoxypyridinoline excretion was comparable to that of the sham operation group. From this result, it was also confirmed in the animal models that the studied monoclonal antibodies specifically binding to Siglec-15 inhibit osteoclastic bone resorption, and it was strongly indicated that due to the inhibitory effect on bone resorption, a decrease in lumbar spine bone mineral density in the ovariectomized rats was inhibited.

Example 16

Determination of Binding Site (Epitope) of Rat Anti-Mouse Siglec-15 Monoclonal Antibody
Expression and Purification of Human Siglec-15 V-Set Domain A DNA encoding a protein in which a His tag and a thrombin recognition sequence were attached to the N-terminal side of a human Siglec-15 V-set domain (a polypeptide comprising 39 to 165 amino acid residues of an amino acid sequence in the NCBI Protein database with the accession number of NP_998767 or an amino acid sequence represented by SEQ ID NO: 2 in the Sequence Listing) was integrated into a vector pDEST14 (Invitrogen, Inc., Cat. No. 11801-016). By using this plasmid, *Escherichia coli* Rosetta-gamiB (DE3) (Novagen, Inc., Cat. No. 71136-4) was transformed, and cultured in TB medium (Invitrogen, Inc., Cat. No. 22711-022). After culturing, the bacterial cells were homogenized by ultrasound, the resulting homogenate was centrifuged, and the supernatant was purified with a HisTrap HP column (GE Healthcare, Co., Ltd., Cat. No. 17-5247-01). Thereafter, the His tag was cleaved with thrombin, and then the human Siglec-15 V-set domain was purified using a Mono S5/50 GL column (GE Healthcare, Co., Ltd., Cat. No. 17-5168-01) and a Superdex 75 10/300 column (GE Healthcare, Co., Ltd., Cat. No. 17-5174-01) until a single band with a molecular weight of 14 kDa was obtained by electrophoresis.

b) Purification of Soluble Human Siglec-15-Fc

The soluble human Siglec-15-Fc was purified by the method described in Example 12.

c) Competitive ELISA of Human V-Set Domain and Rat Anti-Mouse Siglec-15 Monoclonal Antibody #32A1

Figure 14:
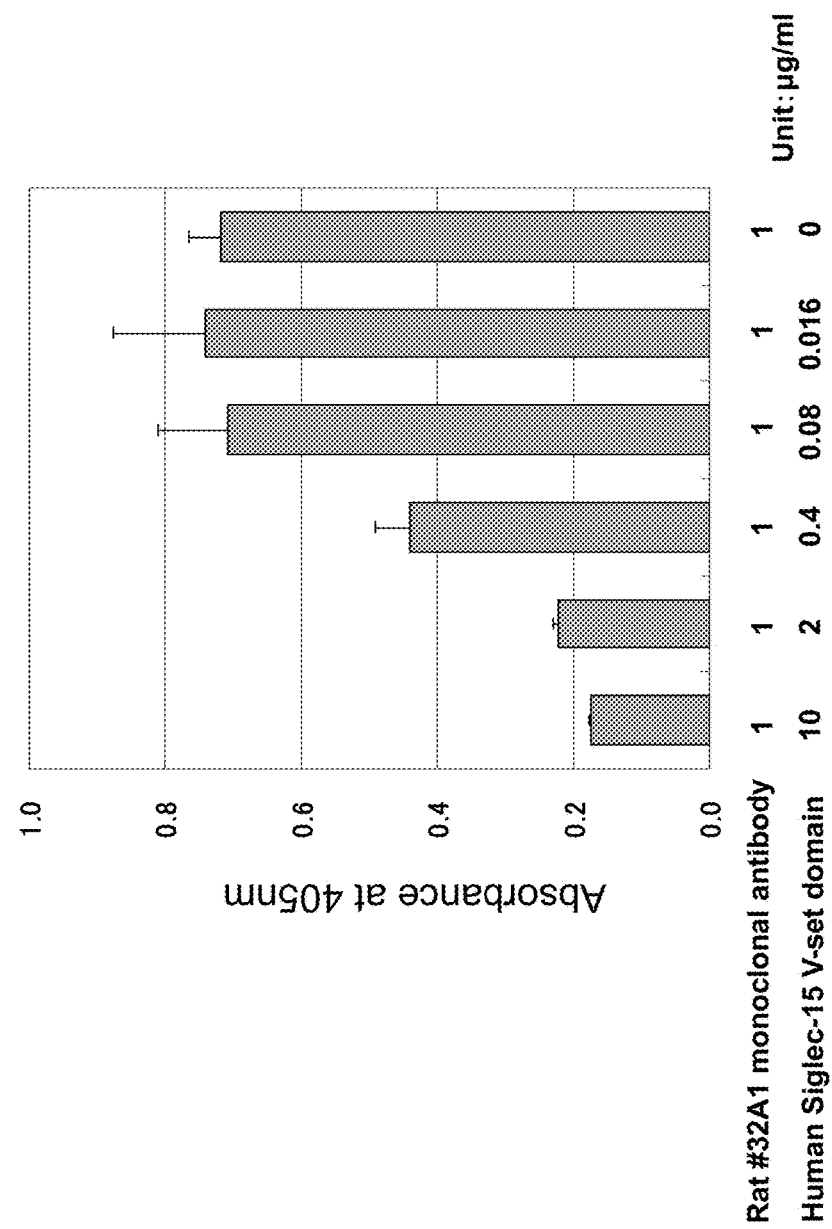
FIG. 14 is a graph showing that a rat anti-mouse Siglec-15 monoclonal antibody #32A1 binds to the V-set domain of human Siglec-15 by competitive ELISA.

In a 96-well maxi-sorp plate (manufactured by Nunc, Inc., model number: 442404), 100 µl of a goat anti-human Fc antibody (Jackson ImmunoResearch, Inc., model number: 109-005-098) (1.25 µg/ml) was added to each well and immobilized overnight at 4° C. After the 96-well maxi-sorp plate was washed twice with PBS, 100 µl of the soluble human Siglec-15-Fc (1 µg/ml) was added to each well and immobilized at room temperature for 1 hour. Thereafter, 300 µl of a 5% skim milk/PBS solution was added to each well, and blocking of the wells was performed at room temperature for 3 hours. In the meantime, 2 µg/ml of the rat anti-mouse Siglec-15 monoclonal antibody #32A1 was mixed with an equivalent amount of 0, 0.032, 0.16, 0.8, 4, or 20 µg/ml of the human Siglec-15 V-set domain, and a reaction was allowed to proceed at room temperature for 1.5 hours. After the 96-well maxi-sorp plate had been washed twice with PBS, 100 µl of the mixed solution of the rat anti-mouse Siglec-15 monoclonal antibody #32A1 and the human Siglec-15 V-set domain was added thereto, and a reaction was allowed to proceed at room temperature for 1 hour. After the 96-well maxi-sorp plate had been washed 5 times with a 0.05% Tween 20 (Bio-Rad Laboratories, Inc., Cat. No. 170-6531)/PBS solution (hereinafter referred to as "PBST solution"), 100 µl of an HRP-labeled goat anti-rat IgG antibody (Beckman Coulter, Inc., Cat. No. 732664, diluted to 2000-fold) was added thereto, and a reaction was allowed to proceed at room temperature for 1 hour. After the plate had been washed 5 times with the PBST solution, 100 µl of a color developing liquid of ELISA POD Substrate ABTS Kit (Nacalai Tesque Co., Ltd., Cat. No. 14351-80) was added thereto, and a reaction was allowed to proceed for 30 minutes. Then, 100 µl of a reaction stopping solution was added thereto, and an absorbance at 405 nm was measured. The results of competitive ELISA showed that the binding of the rat anti-mouse Siglec-15 monoclonal antibody #32A1 to the immobilized human Siglec-15 is inhibited in a human V-set domain concentration-dependent manner. Accordingly, it was shown that the epitope for the rat anti-mouse Siglec-15 monoclonal antibody #32A1 is the human Siglec-15 V-set domain (a domain comprising 39 to 165 amino acid residues of an amino acid sequence in the NCBI Protein database with the accession number of NP_998767 or an amino acid sequence represented by SEQ ID NO: 2 in the Sequence Listing) (FIG. 14).

Example 17

Amplification of cDNA Encoding Variable Region of Rat Anti-Mouse Siglec-15 Monoclonal Antibody #32A1 and Base Sequence Analysis Thereof Preparation of mRNA The hybridoma #32A1 was cultured according to a) of Example 6. From $4 \times 10^7$ cells of the hybridoma #32A1, about 65 µg of mRNA was prepared using a QuickPrep mRNA purification kit (GE Healthcare, Co., Ltd.).

b) Synthesis of cDNA (5'-RACE-Ready cDNA)

The synthesis of cDNA (5'-RACE-Ready cDNA) was performed using 0.3 µg of the mRNA prepared in a) with PrimeScript Reverse Transcriptase (TaKaRa Bio, Inc.) and SMART RACE cDNA Amplification Kit (Clontech Co., Ltd.).

c) Amplification of cDNA of #32A1 Gene Heavy Chain Variable Region by 5'-RACE PCR As primers for amplifying the cDNA of the #32A1 heavy chain gene variable region by PCR, UPM (Universal Primer A Mix, attached to the SMART RACE cDNA Amplification Kit) and an oligonucleotide having a sequence of 5'-GGC-CGGGTGGGCTACGTTGCAGGTGACGGTCTG-3' (RG2AR2: SEQ ID NO: 23 in the Sequence Listing) were used. As the UPM, one attached to the SMART RACE cDNA Amplification Kit (Clontech Co., Ltd.) was used, and the RG2AR2 was designed from the sequence of the rat heavy chain (IgG2a) constant region in the database and synthesized according to a common procedure.

The cDNA of the #32A1 heavy chain gene variable region was amplified by 5'-RACE PCR using this combination of primers and the cDNA synthesized in b) (5'-RACE-Ready cDNA) as a template. The PCR was performed using Advantage 2 PCR Kit (Clontech Co., Ltd.), and the conditions for a thermal cycler were set as follows: after heating at 94° C. for 1 minute, a temperature cycle of "94° C. for 0.5 minutes and 72° C. for 3 minutes" was repeated 5 times, then, a temperature cycle of "94° C. for 0.5 minutes, 70° C. for 0.5 minutes, and 72° C. for 3 minutes" was repeated 5 times, and further, a temperature cycle of "94° C. for 0.5 minutes, 68° C. for 0.5 minutes, and 72° C. for 3 minutes" was repeated 20 times, followed by incubating at 4° C.

d) Amplification of cDNA of #32A1 Light Chain Gene Variable Region by 5'-RACE PCR As primers for amplifying the cDNA of the #32A1 light chain gene variable region by PCR, UPM (Universal Primer A Mix, attached to the SMART RACE cDNA Amplification Kit) and an oligonucleotide having a sequence of 5'-CAT-GCTGTACGTGCTGTCTTTGCTGTCCTGATCAG-3' (RKR2: SEQ ID NO: 24 in the Sequence Listing) were used. As the UPM, one attached to the SMART RACE cDNA Amplification Kit (Clontech Co., Ltd.) was used, and the RKR2 was designed from the sequence of the rat light chain (κ chain) constant region in the database and synthesized according to a common procedure.

The cDNA of the #32A1 light chain gene variable region was amplified by 5'-RACE PCR using this combination of primers and the cDNA synthesized in b) (5'-RACE-Ready cDNA) as a template. The PCR was performed using Advantage 2 PCR Kit (Clontech Co., Ltd.), and the conditions for a thermal cycler were set as follows: after heating at 94° C. for 1 minute, a temperature cycle of "94° C. for 0.5 minutes and 72° C. for 3 minutes" was repeated 5 times, then, a temperature cycle of "94° C. for 0.5 minutes, 70° C. for 0.5 minutes, and 72° C. for 3 minutes" was repeated 5 times, and further, a temperature cycle of "94° C. for 0.5 minutes, 68° C. for 0.5 minutes, and 72° C. for 3 minutes" was repeated 20 times, followed by incubating at 4° C.

e) Determination of Base Sequences of cDNAs of Heavy and Light Chain Variable Regions The cDNA of the heavy chain variable region amplified in c) was purified using MinElute PCR Purification Kit (QIAGEN Inc.), and then the sequence analysis of the DNA sequence was performed. As a sequencing primer, an oliginucleotide having a sequence of 5'-CTCCAGAGTTCCAG-GTCACGGTGACTGGC-3' (RG2AR3: SEQ ID NO: 25 in the Sequence Listing) was designed from the sequence of the rat heavy chain (IgG2a) constant region in the database and synthesized according to a common procedure.

The cDNA of the light chain variable region amplified in d) was purified using MinElute PCR Purification Kit (QIAGEN Inc.), and then the sequence analysis of the DNA sequence was performed. As a sequencing primer, an oligonucleotide having a sequence of 5'-TCCAGTTGCTAACTGTTCCG-3' (sqRK: SEQ ID NO: 26 in the Sequence Listing) was designed from the sequence of the rat light chain (κ chain) constant region in the database and synthesized according to a common procedure.

The cDNA containing the heavy chain variable region obtained by the sequence analysis has a base sequence represented by SEQ ID NO: 27 in the Sequence Listing and encodes the amino acid sequence represented by SEQ ID NO: 28 in the Sequence Listing. The amino acid sequence represented by amino acid numbers 1 to 19 of SEQ ID NO: 28 corresponds to a secretory signal, the amino acid sequence represented by amino acid numbers 20 to 140 thereof corresponds to a heavy chain variable region, and the amino acid sequence represented by amino acid numbers 141 to 167 thereof corresponds to a heavy chain constant region (partial). The above-mentioned heavy chain variable region contains CDRH1 (DYFMN) comprising the amino acid sequence represented by SEQ ID NO: 44, CDRH2 (QIRNKIYTYATFYAESLEG) comprising the amino acid sequence represented by SEQ ID NO: 45, and CDRH3 (SLTGGDYFDY) comprising the amino acid sequence represented by SEQ ID NO: 46. Further, the cDNA containing the light chain variable region has a base sequence represented by SEQ ID NO: 29 in the Sequence Listing and encodes the amino acid sequence represented by SEQ ID NO: 30 in the Sequence Listing. The amino acid sequence represented by amino acid numbers 1 to 20 of SEQ ID NO: 30 corresponds to a secretory signal, the amino acid sequence represented by amino acid numbers 21 to 132 thereof corresponds to a light chain variable region, and the amino acid sequence represented by amino acid numbers 133 to 139 thereof corresponds to a light chain constant region (partial). The above-mentioned light chain variable region contains CDRL1 (RASQSVTISGYSFIH) comprising the amino acid sequence represented by SEQ ID NO: 47, CDRL2 (RASNLAS) comprising the amino acid sequence represented by SEQ ID NO: 48, and CDRL3 (QQSRKSPWT) comprising the amino acid sequence represented by SEQ ID NO: 49.

Example 18

Production of Gene Expression Construct of Human Chimeric Antibody of Rat Anti-Mouse Siglec-15 Monoclonal Antibody #32A1

Production of Universal Expression Vectors pEF1/FCCU-1 and pEF6KCL a)-i) Construction of Human Light Chain Expression Vector pEF6KCL By performing PCR using a plasmid pEF6/V5-HisB (Invitrogen) as a template and also using the following primers, a DNA fragment from immediately downstream of BGHpA (2174) to SmaI (2958) (a DNA fragment containing f1 origin of replication and SV40 promoter and origin, hereinafter referred to as "fragment A") was obtained.

```
5'-CCACGCGCCCTGTAGCGGCGCATTAAGC-3'
(primer EFF1: SEQ ID NO: 31 in the Sequence
Listing)

5'-AAACCCGGGAGCTTTTTGCAAAAGCCTAGG-3'
(primer EFsmaR: SEQ ID NO: 32)
```

The obtained fragment A and a DNA fragment (SEQ ID NO: 33, hereinafter referred to as "fragment B") containing a DNA sequence encoding a human κ chain secretory signal, a human κ chain constant region, and a human poly-A additional signal were ligated by overlapping PCR. The thus obtained DNA fragment in which the fragment A and the fragment B were ligated (hereinafter referred to as "fragment A+B") was digested with the restriction enzymes KpnI and SmaI, which was ligated to a plasmid pEF6/V5-HisB (Invitrogen) which was digested with the restriction enzymes KpnI and SmaI, whereby a human light chain expression vector pEF6KCL having a signal sequence, a cloning site, a human κ chain constant region, and a human poly-A additional signal sequence downstream of the EF1 promoter was constructed.

a)-ii) Construction of pEF1/KCL

A DNA fragment obtained by cleaving the pEF6KCL obtained by the above-mentioned method with the restriction enzymes KpnI and SmaI was ligated to pEF1/myc-HisB (Invitrogen, Inc.) which was digested with KpnI and SmaI, whereby a plasmid pEF1/KCL was constructed.

a)-iii) Construction of Human Heavy Chain Expression Vector pEF1/FCCU-1

A DNA fragment (SEQ ID NO: 34 in the Sequence Listing) containing a DNA sequence encoding a human IgG1 signal sequence and a constant region amino acid sequence was digested with the restriction enzymes NheI and PmeI and was ligated to the plasmid pEF1/KCL which was digested with NheI and PmeI, whereby a human heavy chain expression vector pEF1/FCCU-1 having a signal sequence, a cloning site, a human heavy chain constant region, and a human poly-A additional signal sequence downstream of the EF1 promoter was constructed.

b) Production of #32A1 Human Chimeric Antibody Heavy Chain Expression Construct

As primers for amplifying the cDNA of the #32A1 heavy chain variable region by PCR, an oligonucleotide having a sequence of 5'-aaagctgagcGAGGTGCAAATTTTGGAGACTGGAGGAGGC-3' (32A1HF: SEQ ID NO: 35 in the Sequence Listing) and an oligonucleotide having a sequence of 5'-aaagctgagctGACTGTGACCATGACTCCTTGGCCCCAG-3' (32A1HR: SEQ ID NO: 36 in the Sequence Listing) were synthesized according to a common procedure.

Incidentally, in order to integrate a PCR product into pEF1/FCCU-1, these primers were designed such that a recognition sequence for the restriction enzyme BlpI was added. The PCR was performed according to a common procedure using this combination of primers and the cDNA of the heavy chain variable region purified in e) of Example 17 as a template. The resulting PCR product was purified using MinElute PCR Purification Kit (QIAGEN, Inc.), and then a DNA fragment obtained by digesting the PCR product with the restriction enzyme BlpI (NEW ENGLAND BIOLABS, Inc.) was inserted into the pEF1/FCCU-1 at the site cleaved with the restriction enzyme BlpI, whereby a #32A1 human chimeric antibody heavy chain expression construct was constructed. The sequence of the insert was confirmed by a sequence analysis. As a primer for sequencing, an oligonucleotide having a sequence of 5'-TAATACGACTCACTATAGGG-3' (F11: SEQ ID NO: 37 in the Sequence Listing) was synthesized according to a common procedure. An expression vector in which the insert could be correctly inserted was named "32A1H/pEF1/FCCU".

c) Production of #32A1 Human Chimeric Antibody Light Chain Expression Construct

As primers for amplifying the cDNA of the #32A1 light chain variable region by PCR, an oligonucleotide having a sequence of 5'-aaacatatggcGACATTGTCTTGACCCA-GTCTCCTGCTTTGG-3' (32A1LF: SEQ ID NO: 38 in the Sequence Listing) and an oligonucleotide having a sequence of 5'-aaacgtacgTCTCAATTCCAGCTTGGTGCCTCCA-GCG-3' (32A1LR SEQ ID NO: 39 in the Sequence Listing) were synthesized according to a common procedure.

Incidentally, in order to integrate a PCR product into pEF6KCL, these primers were designed such that a recognition sequence for the restriction enzyme NdeI was added to 32A1LF, and a recognition sequence for the restriction enzyme BsiWI was added to 32A1LR. The PCR was performed according to a common procedure using this combination of primers and the cDNA of the light chain variable region purified in e) of Example 17 as a template. The resulting PCR product was purified using MinElute PCR Purification Kit (QIAGEN, Inc.), and then, a DNA fragment obtained by digesting the PCR product with the restriction enzymes NdeI (TaKaRa Bio, Inc.) and BsiWI (NEW ENGLAND BIOLABS, Inc.) was inserted into the pEF6KCL at the site cleaved with the restriction enzymes NdeI (TaKaRa Bio, Inc.) and BsiWI (NEW ENGLAND BIOLABS, Inc.), whereby a #32A1 human chimeric antibody light chain expression construct was constructed. The sequence of the insert was confirmed by a sequence analysis. As a primer for sequencing, a primer F11 represented by SEQ ID NO: 37 in the Sequence Listing was used. An expression vector in which the insert could be correctly inserted was named "32A1L/pEF6KCL".

The #32A1 human chimeric antibody heavy chain gene produced in b) has the nucleotide sequence represented by SEQ ID NO: 40 in the Sequence Listing and encodes the amino acid sequence represented by SEQ ID NO: 41 in the Sequence Listing. The amino acid sequence represented by amino acid numbers 1 to 19 of SEQ ID NO: 41 corresponds to a secretory signal, the amino acid sequence represented by amino acid numbers 20 to 140 thereof corresponds to a heavy chain variable region, and the amino acid sequence represented by amino acid numbers 141 to 470 thereof corresponds to a heavy chain constant region. Further, the #32A1 human chimeric antibody light chain gene produced in c) has the nucleotide sequence represented by SEQ ID NO: 42 in the Sequence Listing and encodes the amino acid sequence represented by SEQ ID NO: 43 in the Sequence Listing. The amino acid sequence represented by amino acid numbers 1 to 20 of SEQ ID NO: 43 corresponds to a secretory signal, the amino acid sequence represented by amino acid numbers 21 to 132 thereof corresponds to a light chain variable region, and the amino acid sequence represented by amino acid numbers 133 to 237 thereof corresponds to a light chain constant region.

Example 19

Preparation of Human Chimeric Antibody of Rat Anti-Mouse Siglec-15 Monoclonal Antibody #32A1

Production of Human Chimeric Antibody $3 \times 10^7$ cells of 293 FreeStyle cells in logarithmic growth phase were seeded in 30 ml of fresh FreeStyle 293 Expression Medium (Invitrogen, Inc.) (four lots were prepared, in which the 30-ml culture was taken as one lot) and subjected to shaking culture (125 rpm) at 37° C. in an 8% $CO_2$ incubator. 300 μg of polyethyleneimine (manufactured by Polyscience, Inc. #24765) was dissolved in 1 ml of Opti-Pro SFM medium (manufactured by Invitrogen, Inc.), and the resulting solution was left at room temperature for 5 minutes. The #32A1 human chimeric antibody heavy chain expression vector 32A1H/pEF1/FCCU and the #32A1 human chimeric antibody light chain expression vector 32A1L/pEF6KCL produced in Example 18 were prepared using PureLink HiPure Plasmid Kit (Invitrogen, Inc.). The 32A1H/pEF1/FCCU (15 μg) and the 32A1L/pEF6KCL (45 μg) were suspended in 1 ml of Opti-Pro SFM medium (Invitrogen, Inc.), and the resulting suspension was added to 1 ml of the polyethyleneimine/Opti-Pro SFM mixed liquid which had been left at room temperature for 5 minutes, and the resulting mixture was left at room temperature for an additional 5 minutes. Subsequently, 2 ml of the polyethyleneimine/the expression vectors/Opti-Pro SFM mixed liquid was added to each lot of the 293 FreeStyle cell suspension, and the shaking culture was continued. After the cells were cultured for 7 days at 37° C. in 8% $CO_2$, the culture supernatant was collected from each lot.

b) Purification of Human Chimeric Antibody 90 ml of the culture supernatant (for three lots) obtained above was filtered through a filter (manufactured by NALGENE, Inc., #295-4545), and 0.5 ml of MabSelect SuRe (manufactured by GE Healthcare Bio-science Co., Ltd., #17-5438-01) equilibrated with PBS was added to the filtrate, and the resulting mixture was shaken overnight at 80 rpm and 10° C. On the next day, the carrier was collected and washed with PBS, and thereafter, the antibody was eluted with 1 M arginine solution (pH 4.0). The eluate was applied to a PD-10 column (manufactured by GE Healthcare Bio-science Co., Ltd., #17-0851-01) to replace the liquid with PBS, and then concentrated with Amicon Ultra-4 (manufactured by Millipore Co., Ltd., #UFC805008), whereby 1.2 ml of a human chimeric antibody (0.98 mg/ml) was obtained. The concentration of the antibody was calculated from the measurement at 280 nm obtained using Hitachi Diode Array BioPhotometer U-0080D.

Example 20

Figure 15:
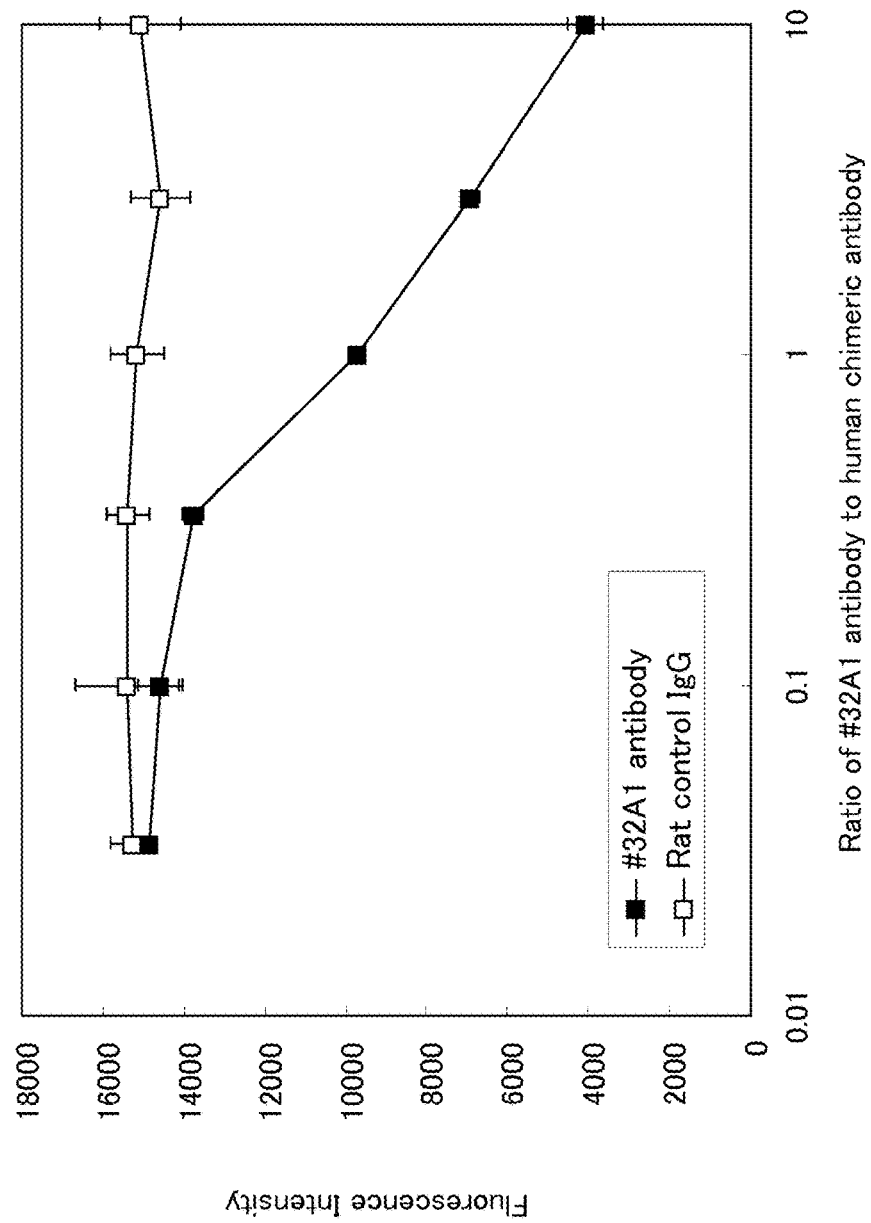
FIG. 15 is a graph showing that a rat #32A1 antibody and a human chimeric antibody thereof have substantially the same affinity for mouse Siglec-15-Fc by competitive ELISA.

Evaluation of Property of Human Chimeric Antibody of Rat Anti-Mouse Siglec-15 Monoclonal Antibody #32A1 Binding to Mouse Siglec-15 Protein The competitive inhibition of the rat #32A1 antibody against the purified human chimeric antibody prepared in Example 19 was determined by the following method. The mouse Siglec-15-Fc purified in Example 4 was diluted to 1 μg/ml with PBS, the diluted solution was dispensed at 100 μl/well onto an immunoplate (manufactured by Nunc, Inc., #437111), and the plate was left to stand overnight at 4° C., whereby the protein was adsorbed to the plate. On the next day, each well was washed twice with a PBS-T solution (PBS, 0.05% (v/v) Tween 20), a solution obtained by diluting skim milk (manufactured by Morinaga Milk Industry Co., Ltd.) to 5% with PBS was dispensed at 350 μl/well, and the plate was left to stand at room temperature for 2 hours. The liquid in each well was removed, and each well was washed 3 times with the PBS-T solution. Thereafter, a mixed solution (a PBS solution containing skim milk at a final concentration of 0.5%) containing the human chimeric antibody at 0.25 μg/ml and the #32A1 antibody or a rat control IgG antibody (manufactured by R&D Systems, Inc., #6-001-A) at a different concentration (0 μg/ml, 0.016 μg/ml, 0.05 μg/ml, 0.16 μg/ml, 0.5 μg/ml, 1.66 μg/ml, or 5 μg/ml) was dispensed at 100 μl/well, and the plate was left to stand at room temperature for 2 hours. After each well was washed 3 times with the PBS-T solution, alkaline phosphatase-conjugated AffiniPure goat anti-human IgG (manufactured by Jackson ImmunoResearch, Inc., #109-055-097) diluted to 2500-fold with a TBS-T solution (TBS, 0.05% (v/v) Tween 20) was added at 100 µl/well, and the plate was left to stand at room temperature for 1 hour. The liquid in each well was removed, and each well was washed 5 times with the TBS-T solution. Thereafter, a fluorescent substrate solution (manufactured by Roche Co., Ltd., #11681982001) was added at 100 µl/well, and a fluorescence reaction was allowed to proceed. At 10 minutes after the addition of the fluorescent substrate solution, the fluorescence intensity was measured using a plate reader. As a result, it was shown that the #32A1 antibody inhibits the binding of the human chimeric antibody to the mouse Siglec-15-Fc in a concentration-dependent manner. Further, when the #32A1 antibody and the human chimeric antibody were mixed at the same concentration (1:1), about 40% competitive inhibition was exhibited. Therefore, it is considered that the #32A1 antibody and the human chimeric antibody have substantially the same affinity for the mouse Siglec-15-Fc. On the other hand, the rat control IgG did not show competitive inhibition (FIG. 15).

Example 21

Figure 16:
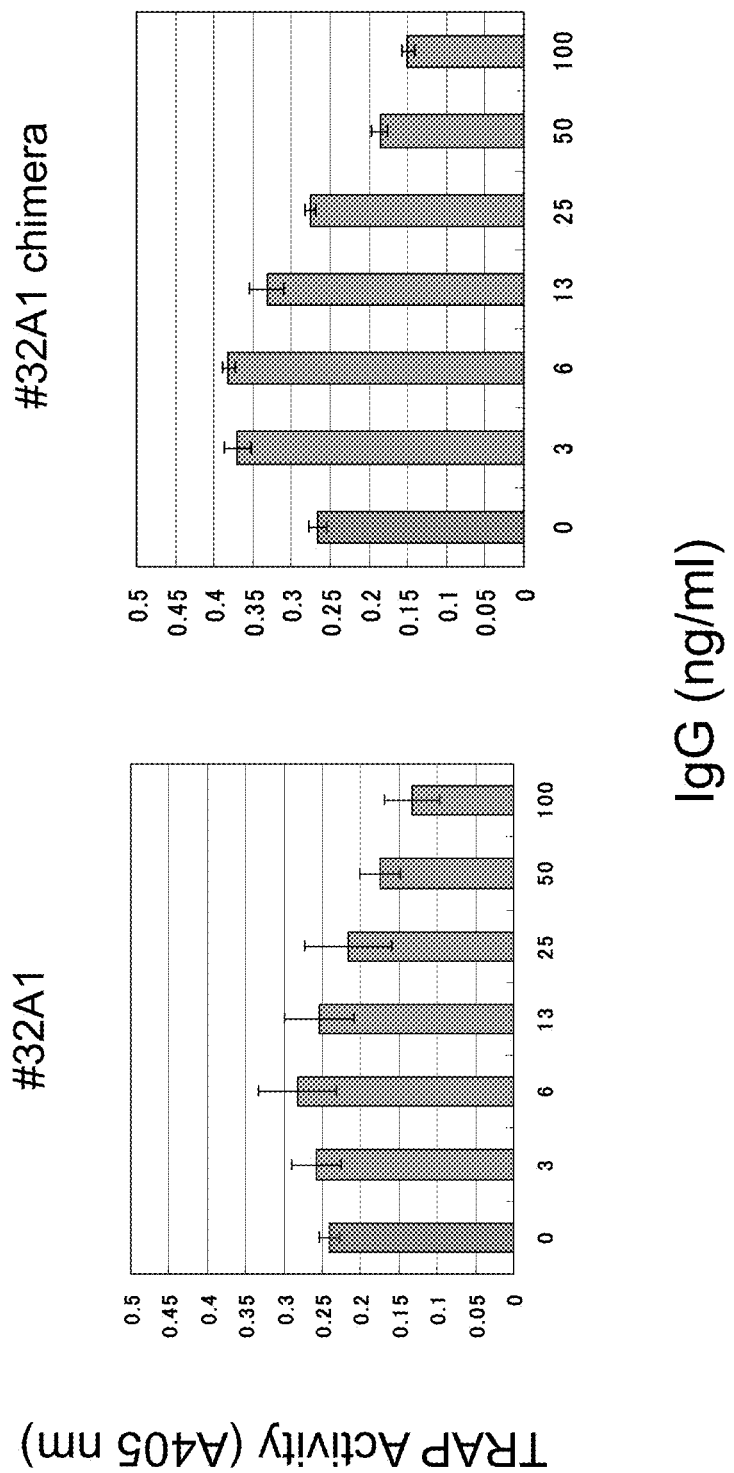
FIG. 16 shows graphs depicting, by the enzymatic activity of TRAP, the inhibition of mouse osteoclast formation by the addition of a rat anti-mouse Siglec-15 monoclonal antibody (#32A1 antibody) and a chimeric antibody thereof (N=3).

Evaluation of Biological Activity of Human Chimeric Antibody of Rat Anti-Mouse Siglec-15 Monoclonal Antibody #32A1 Based on Test for Mouse Osteoclast Formation and Test for Human Osteoclast Formation Test for Mouse Osteoclast Formation By using the human chimeric antibody of the rat anti-mouse Siglec-15 monoclonal antibody #32A1 prepared in Example 19, the effect on osteoclast differentiation of mouse bone marrow nonadherent cells was examined. Mouse bone marrow nonadherent cells prepared by the method of Example 8 were prepared at $1.5 \times 10^5$ cells/ml in α-MEM medium containing 10% FBS and 10 ng/ml of M-CSF (manufactured by R&D Systems, Inc.), the resulting cell preparation was seeded in each well of a 96-well plate in an amount of 200 µl and the cells were cultured for 2 days in a $CO_2$ incubator. The old culture solution in the 96-well plate was removed, and 100 µl of MEM-α medium was added to each well, the 100 µl of MEM-α medium containing 10% FBS to which human RANKL (RANKL, manufactured by Peprotech, Inc.) and M-CSF had been added to give final concentrations of 20 ng/ml and 10 ng/ml, respectively. To the cell culture solution, the rat anti-mouse Siglec-15 monoclonal antibody #32A1 produced in Example 6 or the human chimeric antibody of the rat anti-mouse Siglec-15 monoclonal antibody #32A1 prepared in Example 19 was added at a concentration of from 3 to 100 ng/ml, and the cells were cultured for an additional 3 days in a $CO_2$ incubator. After completion of the culturing, the activity of tartrate-resistant acid phosphatase (TRAP) of the formed osteoclasts was measured by the method described in Example 9. After stopping the enzymatic reaction, an absorbance of each well at 405 nm was measured, and the obtained measurement was used as an index of TRAP activity. The results are shown in FIG. 16. A dose-dependent inhibition of TRAP activity was observed at a concentration of 50 ng/ml or higher in the case of the #32A1 antibody and the human chimeric antibody of the rat anti-mouse Siglec-15 monoclonal antibody #32A1. From this result, it was shown that the human chimeric antibody of the rat anti-mouse Siglec-15 monoclonal antibody #32A1 has an activity of inhibiting osteoclast formation (osteoclast differentiation and maturation) substantially comparable to that of the rat #32A1 antibody.

b) Evaluation Using Normal Human Osteoclast Precursor Cells (TRAP Staining)

Figure 17:
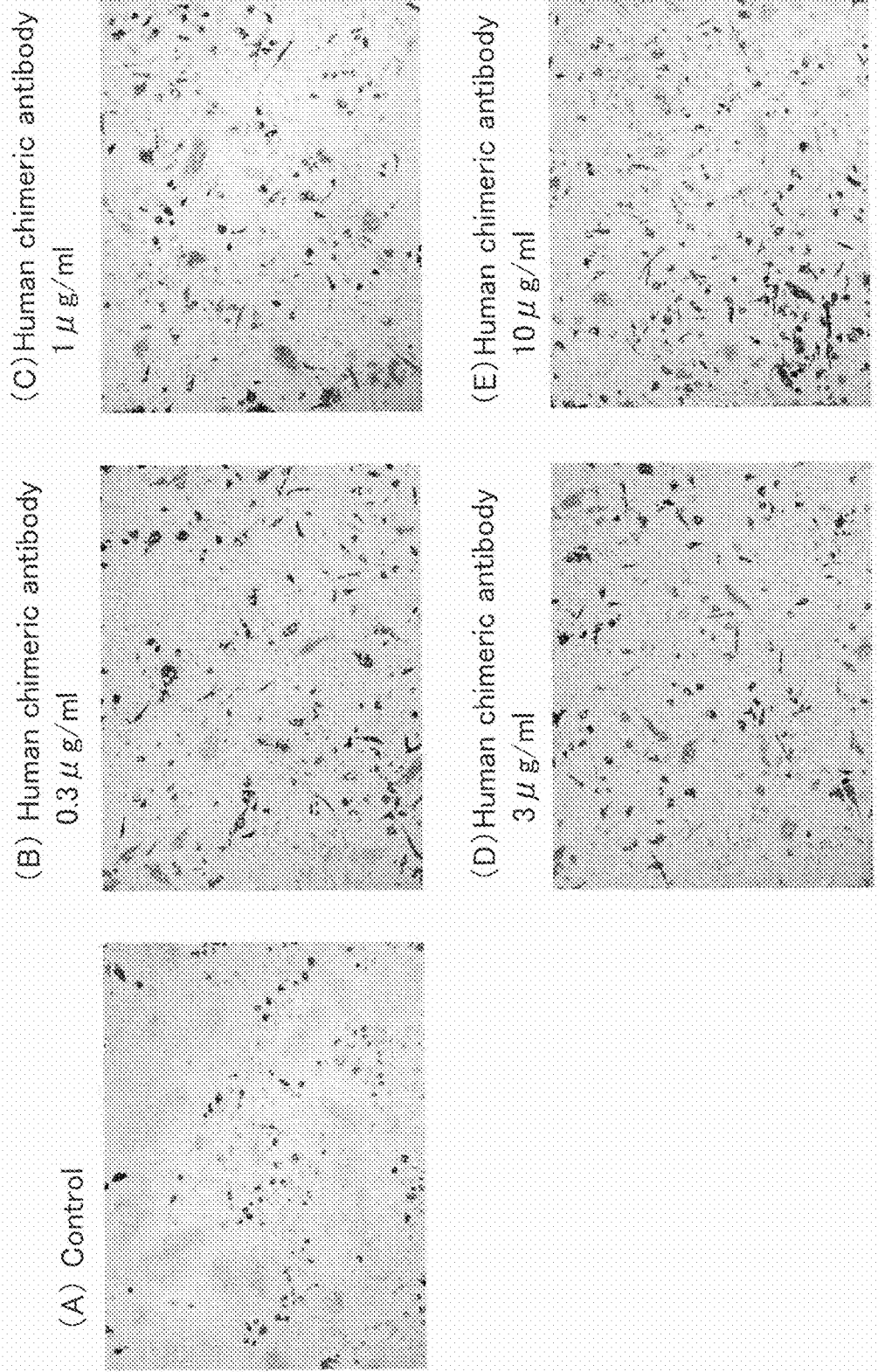
FIG. 17 shows photomicrographs depicting, by TRAP staining, the inhibition of giant osteoclast formation from normal human osteoclast precursor cells by the addition of a human chimeric antibody of a rat anti-mouse Siglec-15 monoclonal antibody #32A1.

Normal human osteoclast precursor cells (Normal Human Natural Osteoclast Precursor Cells, purchased from Sanko Junyaku Co., Ltd., Cat. No. 2T-110) were seeded in a 96-well plate at $1 \times 10^4$ cells/well according to the protocol attached to the cells. As the medium, a minimal essential medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 66 ng/ml), human M-CSF (final concentration: 33 ng/ml), and the like was used. To the resulting culture supernatant, the human chimeric antibody of the rat anti-mouse Siglec-15 monoclonal antibody #32A1 prepared in Example 19 was added at a final concentration of 0.3, 1, 3, or 10 µg/ml, and the cells were cultured for 3 days in a $CO_2$ incubator. After the culturing, the supernatant was removed, and 10% neutral formalin was added to fix the cells. After fixing the cells, the cells were washed twice with distilled water, a TRAP staining solution (0.27 mM naphthol AS-MX phosphate (manufactured by Sigma Co., Ltd.), 1.6 mM fast red violet LB salt (manufactured by Sigma Co., Ltd.), 1% dimethylformamide, 50 mM sodium tartrate, 0.1 M sodium acetate buffer (pH 5.0)) was added at 100 µl/well, and a reaction was allowed to proceed at room temperature for 5 minutes. After the reaction, the cells were washed twice with distilled water, and then observed by microscopy (FIG. 17). As a result, the formation of TRAP-positive multinucleated osteoclasts was inhibited by the addition of the human chimeric antibody of #32A1 within the range of from 0.3 µg/ml to 10 µg/ml.

Example 22

Designing of Humanized Antibody of Rat Anti-Mouse Siglec-15 Monoclonal Antibody #32a1 (1)

Designing of Humanized Version of #32A1 a)-i) Molecular Modeling of Variable Region of #32A1

The molecular modeling of the variable region of #32A1 was performed by a method generally known as homology modeling (Methods in Enzymology, 203, 121-153, (1991)). The primary sequences (three-dimensional structures derived from the X-ray crystal structures are available) of the variable regions of human immunoglobulin registered in Protein Data Bank (Nuc. Acid Res. 35, D301-D303 (2007)) were compared with the variable region of #32A1 determined above. As a result, 1LK3 was selected as having the highest sequence homology with the variable region of the light chain of #32A1 among antibodies having a similar deletion in the framework. Further, 1AD0 was selected as having the highest sequence homology with the variable region of the heavy chain of #32A1. The three-dimensional structure of the framework region was generated by obtaining the "framework model" by combining the coordinates of 1LK3 and 1AD0 corresponding to the light and heavy chains of #32A1. The CDRs of #32A1 were classified according to the classification of Thornton et al. (J. Mol. Biol., 263, 800-815, (1996)) as follows: CDRL1, CDRL2, CDRL3, CDRH1, and CDRH2 were assigned to clusters 15A, 7A, 9A, 10A, and 12B, respectively. CDRH3 was classified into k(8)C according to the H3-rules (FEBS letter 399, 1-8 (1996)). Then, the representative conformations of the respective CDRs were integrated into the framework model.

Finally, in order to obtain a probable molecular model of the variable region of #32A1 in terms of energy, an energy calculation was performed for excluding disadvantageous interatomic contact. The above procedure was performed using the commercially available three-dimensional protein structure prediction program Prime and the coordinate search program MacroModel (Schrodinger, LLC).

a)-ii) Designing of Amino Acid Sequence of Humanized #32A1

A humanized #32A1 antibody was constructed according to a method generally known as CDR grafting (Proc. Natl. Acad. Sci. USA 86, 10029-10033 (1989)). An acceptor antibody was selected in two ways based on the amino acid homology within the framework region. The sequence of the framework region of #32A1 was compared with the sequences of all human frameworks in the Kabat Database (Nuc. Acid Res. 29, 205-206 (2001)) involving antibody amino acid sequences. As a result, an M37G037'CL antibody was selected as an acceptor based on a sequence homology of 73% in the framework region. The amino acid residues in the framework region of M37G037'CL were aligned with the amino acid residues of #32A1, and the positions where different amino acids were used were identified. The positions of these residues were analyzed using the three-dimensional model of #32A1 constructed above. Then, donor residues to be grafted onto the acceptor were selected according to the criteria provided by Queen et al. (Proc. Natl. Acad. Sci. USA 86, 10029-10033 (1989)).

The sequence of the framework region of #32A1 was compared with the sequences of all human frameworks in the IgBLAST (Nuc. Acid Res. 36, D25-D30 (2007)). As a result, for the L-chain, AAB34430 was selected as an acceptor based on a sequence homology of 79% in the framework region. As for the H-chain, CAF31288 was selected as an acceptor based on a sequence homology of 78% in the framework region. In respect of the L-chain, the amino acid residues in the framework region of AAB34430, and in respect of the H-chain, the amino acid residues in the framework region of CAF31288, were aligned with the amino acid residues of #32A1, and the positions where different amino acids were used were identified. The positions of these residues were analyzed using the three-dimensional model of #32A1 constructed above. Then, donor residues to be grafted on the acceptor were selected according to the criteria provided by Queen et al. (Proc. Natl. Acad. Sci. USA 86, 10029-10033 (1989)). In these methods, by transferring some selected donor residues to the acceptor antibody, humanized #32A1 sequences were constructed as described in the following Examples.

b) Humanization of #32A1 Heavy Chain b)-i) h#32A1-T1H-Type Heavy Chain:

A humanized #32A1 heavy chain designed by replacing amino acid numbers 23 (isoleucine), 24 (leucine), 26 (threonine), 32 (lysine), 43 (threonine), 61 (glutamic acid), 89 (valine), 95 (aspartic acid), 96 (serine), 97 (glutamic acid), 98 (serine), 100 (valine), 104 (valine), 105 (serine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, glycine, phenylalanine, asparagine, alanine, lysine, asparagine, leucine, methionine, asparagine, valine, alanine, threonine, leucine, and serine, respectively, was named "h#32A1-T1H-type heavy chain".

The amino acid sequence of the h#32A1-T1H-type heavy chain is represented by SEQ ID NO: 51 in the Sequence Listing. The sequence comprising amino acid residues 1 to 19 of the amino acid sequence of SEQ ID NO: 51, the sequence comprising amino acid residues 20 to 140 thereof, and the sequence comprising amino acid residues 141 to 470 thereof correspond to the signal sequence, the heavy chain variable region, and the heavy chain constant region, respectively. A nucleotide sequence encoding the amino acid sequence of SEQ ID NO: 51 is represented by SEQ ID NO: 50 in the Sequence Listing. The sequence comprising nucleotides 1 to 57 of the nucleotide sequence of SEQ ID NO: 50, the sequence comprising nucleotides 58 to 420 thereof, and the sequence comprising nucleotides 421 to 1410 thereof encode the signal sequence, the heavy chain variable region sequence, and the heavy chain constant region sequence, respectively. The nucleotide sequence of SEQ ID NO: 50 and the amino acid sequence of SEQ ID NO: 51 are also shown in FIG. 27.

b)-ii) h#32A1-T2H-Type Heavy Chain:

A humanized #32A1 heavy chain designed by replacing amino acid numbers 23 (isoleucine), 24 (leucine), 26 (threonine), 32 (lysine), 43 (threonine), 95 (aspartic acid), 96 (serine), 97 (glutamic acid), 98 (serine), 100 (valine), 104 (valine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, asparagine, alanine, lysine, asparagine, leucine, methionine, valine, alanine, threonine, leucine, and serine, respectively, was named "h#32A1-T2H-type heavy chain".

The amino acid sequence of the h#32A1-T2H-type heavy chain is represented by SEQ ID NO: 53 in the Sequence Listing. The sequence comprising amino acid residues 1 to 19 of the amino acid sequence of SEQ ID NO: 53, the sequence comprising amino acid residues 20 to 140 thereof, and the sequence comprising amino acid residues 141 to 470 thereof correspond to the signal sequence, the heavy chain variable region, and the heavy chain constant region, respectively. A nucleotide sequence encoding the amino acid sequence of SEQ ID NO: 53 is represented by SEQ ID NO: 52 in the Sequence Listing. The sequence comprising nucleotides 1 to 57 of the nucleotide sequence of SEQ ID NO: 52, the sequence comprising nucleotides 58 to 420 thereof, and the sequence comprising nucleotides 421 to 1410 thereof encode the signal sequence, the heavy chain variable region sequence, and the heavy chain constant region sequence, respectively. The nucleotide sequence of SEQ ID NO: 52 and the amino acid sequence of SEQ ID NO: 53 are also shown in FIG. 28.

b)-iii) h#32A1-T3H-Type Heavy Chain:

A humanized #32A1 heavy chain designed by replacing amino acid numbers 24 (leucine), 26 (threonine), 32 (lysine), 104 (valine), 114 (isoleucine), 134 (valine), 135 (methionine), and 140 (leucine) of the #32A1 heavy chain represented by SEQ ID NO: 28 in the Sequence Listing with valine, serine, glutamine, methionine, valine, threonine, leucine, and serine, respectively, was named "h#32A1-T3H-type heavy chain".

The amino acid sequence of the h#32A1-T3H-type heavy chain is represented by SEQ ID NO: 55 in the Sequence Listing. The sequence comprising amino acid residues 1 to 19 of the amino acid sequence of SEQ ID NO: 55, the sequence comprising amino acid residues 20 to 140 thereof, and the sequence comprising amino acid residues 141 to 470 thereof correspond to the signal sequence, the heavy chain variable region, and the heavy chain constant region, respectively. The nucleotide sequence encoding the amino acid sequence of SEQ ID NO: 55 is represented by SEQ ID NO: 54 in the Sequence Listing. The sequence comprising nucleotides 1 to 57 of the nucleotide sequence of SEQ ID NO: 54, the sequence comprising nucleotides 58 to 420 thereof, and the sequence comprising nucleotides 421 to 1410 thereof encode the signal sequence, the heavy chain variable region sequence, and the heavy chain constant region sequence, respectively. The nucleotide sequence of SEQ ID NO: 54 and the amino acid sequence of SEQ ID NO: 55 are also shown in FIG. 29.

b)-iv) h#32A1-T5H-Type Heavy Chain:

A humanized #32A1 heavy chain designed by replacing amino acid numbers 23 (isoleucine), 24 (leucine), 26 (threonine), 32 (lysine), 61 (glutamic acid), 89 (valine), 95 (aspartic acid), 97 (glutamic acid), 99 (serine), 104 (valine), 105 (serine), 114 (isoleucine), 134 (valine), 135 (methionine), and 140 (leucine) of the #32A1 heavy chain represented by SEQ ID NO: 28 in the Sequence Listing with valine, valine, serine, glutamine, glycine, phenylalanine, asparagine, lysine, threonine, methionine, asparagine, valine, threonine, leucine, and serine, respectively, was named "h#32A1-T5H-type heavy chain".

The amino acid sequence of the h#32A1-T5H-type heavy chain is represented by SEQ ID NO: 57 in the Sequence Listing. The sequence comprising amino acid residues 1 to 19 of the amino acid sequence of SEQ ID NO: 57, the sequence comprising amino acid residues 20 to 140 thereof, and the sequence comprising amino acid residues 141 to 470 thereof correspond to the signal sequence, the heavy chain variable region, and the heavy chain constant region, respectively. A nucleotide sequence encoding the amino acid sequence of SEQ ID NO: 57 is represented by SEQ ID NO: 56 in the Sequence Listing. The sequence comprising nucleotides 1 to 57 of the nucleotide sequence of SEQ ID NO: 56, the sequence comprising nucleotides 58 to 420 thereof, and the sequence comprising nucleotides 421 to 1410 thereof encode the signal sequence, the heavy chain variable region sequence, and the heavy chain constant region sequence, respectively. The nucleotide sequence of SEQ ID NO: 56 and the amino acid sequence of SEQ ID NO: 57 are also shown in FIG. 30.

b)-v) h#32A1-T6H-Type Heavy Chain:

A humanized #32A1 heavy chain designed by replacing amino acid numbers 23 (isoleucine), 24 (leucine), 26 (threonine), 32 (lysine), 95 (aspartic acid), 97 (glutamic acid), 99 (serine), 104 (valine), 114 (isoleucine), 134 (valine), 135 (methionine), and 140 (leucine) of the #32A1 heavy chain represented by SEQ ID NO: 28 in the Sequence Listing with valine, valine, serine, glutamine, asparagine, lysine, threonine, methionine, valine, threonine, leucine, and serine, respectively, was named "h#32A1-T6H-type heavy chain".

The amino acid sequence of the h#32A1-T6H-type heavy chain is represented by SEQ ID NO: 59 in the Sequence Listing. The sequence comprising amino acid residues 1 to 19 of the amino acid sequence of SEQ ID NO: 59, the sequence comprising amino acid residues 20 to 140 thereof, and the sequence comprising amino acid residues 141 to 470 thereof correspond to the signal sequence, the heavy chain variable region, and the heavy chain constant region, respectively. A nucleotide sequence encoding the amino acid sequence of SEQ ID NO: 59 is represented by SEQ ID NO: 58 in the Sequence Listing. The sequence comprising nucleotides 1 to 57 of the nucleotide sequence of SEQ ID NO: 58, the sequence comprising nucleotides 58 to 420 thereof, and the sequence comprising nucleotides 421 to 1410 thereof encode a signal sequence, the heavy chain variable region sequence, and the heavy chain constant region sequence, respectively. The nucleotide sequence of SEQ ID NO: 58 and the amino acid sequence of SEQ ID NO: 59 are also shown in FIG. 31.

b)-vi) h#32A1-T7H-Type Heavy Chain:

A humanized #32A1 heavy chain designed by replacing amino acid numbers 23 (isoleucine), 24 (leucine), 26 (threonine), 32 (lysine), 43 (threonine), 89 (valine), 95 (aspartic acid), 96 (serine), 97 (glutamic acid), 98 (serine), 100 (valine), 104 (valine), 105 (serine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, phenylalanine, asparagine, alanine, lysine, asparagine, leucine, methionine, asparagine, valine, alanine, threonine, leucine, and serine, respectively, was named "h#32A1-T7H-type heavy chain".

The amino acid sequence of the h#32A1-T7H-type heavy chain is represented by SEQ ID NO: 72 in the Sequence Listing. The sequence comprising amino acid residues 1 to 121 of the amino acid sequence of SEQ ID NO: 72 and the sequence comprising amino acid residues 122 to 451 thereof correspond to the heavy chain variable region and the heavy chain constant region, respectively. The amino acid sequence of SEQ ID NO: 72 is also shown in FIG. 38.

b)-vii) h#32A1-T8H-Type Heavy Chain:

A humanized #32A1 heavy chain designed by replacing amino acid numbers 23 (isoleucine), 24 (leucine), 26 (threonine), 32 (lysine), 43 (threonine), 61 (glutamic acid), 95 (aspartic acid), 96 (serine), 97 (glutamic acid), 98 (serine), 100 (valine), 104 (valine), 105 (serine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, glycine, asparagine, alanine, lysine, asparagine, leucine, methionine, asparagine, valine, alanine, threonine, leucine, and serine, respectively, was named "h#32A1-T8H-type heavy chain".

The amino acid sequence of the h#32A1-T8H-type heavy chain is represented by SEQ ID NO: 73 in the Sequence Listing. The sequence comprising amino acid residues 1 to 121 of the amino acid sequence of SEQ ID NO: 73 and the sequence comprising amino acid residues 122 to 451 thereof correspond to the heavy chain variable region and the heavy chain constant region, respectively. The amino acid sequence of SEQ ID NO: 73 is also shown in FIG. 38.

b-viii) h#32A1-T9H-Type Heavy Chain:

A humanized #32A1 heavy chain designed by replacing amino acid numbers 23 (isoleucine), 24 (leucine), 26 (threonine), 32 (lysine), 43 (threonine), 61 (glutamic acid), 89 (valine), 95 (aspartic acid), 96 (serine), 97 (glutamic acid), 98 (serine), 100 (valine), 104 (valine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, glycine, phenylalanine, asparagine, alanine, lysine, asparagine, leucine, methionine, valine, alanine, threonine, leucine, and serine respectively, was named "h#32A1-T9H-type heavy chain".

The amino acid sequence of the h#32A1-T9H-type heavy chain is represented by SEQ ID NO: 74 in the Sequence Listing. The sequence comprising amino acid residues 1 to 121 of the amino acid sequence of SEQ ID NO: 74 and the sequence comprising amino acid residues 122 to 451 thereof correspond to the heavy chain variable region and the heavy chain constant region, respectively. The amino acid sequence of SEQ ID NO: 74 is also shown in FIG. 38.

b)-ix) h#32A1-T10H-Type Heavy Chain:

A humanized #32A1 heavy chain designed by replacing amino acid numbers 23 (isoleucine), 24 (leucine), 26 (threonine), 32 (lysine), 43 (threonine), 95 (aspartic acid), 96 (serine), 97 (glutamic acid), 98 (serine), 100 (valine), 104

(valine), 105 (serine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, asparagine, alanine, lysine, asparagine, leucine, methionine, asparagine, valine, alanine, threonine, leucine, and serine, respectively, was named "h#32A1-T10H-type heavy chain".

The amino acid sequence of the h#32A1-T10H-type heavy chain is represented by SEQ ID NO: 75 in the Sequence Listing. The sequence comprising amino acid residues 1 to 121 of the amino acid sequence of SEQ ID NO: 75 and the sequence comprising amino acid residues 122 to 451 thereof correspond to the heavy chain variable region and the heavy chain constant region, respectively. The amino acid sequence of SEQ ID NO: 75 is also shown in FIG. 39.

b)-x) h#32A1-T11H-Type Heavy Chain:

A humanized #32A1 heavy chain designed by replacing amino acid numbers 23 (isoleucine), 24 (leucine), 26 (threonine), 32 (lysine), 43 (threonine), 89 (valine), 95 (aspartic acid), 96 (serine), 97 (glutamic acid), 98 (serine), 100 (valine), 104 (valine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, phenylalanine, asparagine, alanine, lysine, asparagine, leucine, methionine, valine, alanine, threonine, leucine, and serine, respectively, was named "h#32A1-T11H-type heavy chain".

The amino acid sequence of the h#32A1-T11H-type heavy chain is represented by SEQ ID NO: 76 in the Sequence Listing. The sequence comprising amino acid residues 1 to 121 of the amino acid sequence of SEQ ID NO: 76 and the sequence comprising amino acid residues 122 to 451 thereof correspond to the heavy chain variable region and the heavy chain constant region, respectively. The amino acid sequence of SEQ ID NO: 76 is also shown in FIG. 39.

b)-xi) h#32A1-T12H-Type Heavy Chain:

A humanized #32A1 heavy chain designed by replacing amino acid residues 23 (isoleucine), 24 (leucine), 26 (threonine), 32 (lysine), 43 (threonine), 61 (glutamic acid), 95 (aspartic acid), 96 (serine), 97 (glutamic acid), 98 (serine), 100 (valine), 104 (valine), 114 (isoleucine), 118 (threonine), 134 (valine), 135 (methionine), and 140 (leucine) of the #32A1 heavy chain represented by SEQ ID NO: 28 in the Sequence Listing with leucine, valine, serine, glutamine, alanine, glycine, asparagine, alanine, lysine, asparagine, leucine, methionine, valine, alanine, threonine, leucine, and serine, respectively, was named "h#32A1-T12H-type heavy chain".

The amino acid sequence of the h#32A1-T12H-type heavy chain is represented by SEQ ID NO: 77 in the Sequence Listing. The sequence comprising amino acid residues 1 to 121 of the amino acid sequence of SEQ ID NO: 77 and the sequence comprising amino acid residues 122 to 451 thereof correspond to the heavy chain variable region and the heavy chain constant region, respectively. The amino acid sequence of SEQ ID NO: 77 is also shown in FIG. 39.

c) Humanization of #32A1 Light Chain c)-i) h#32A1-T1L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 68 (arginine), 81 (isoleucine), 99 (asparagine), 100 (proline), 101 (valine), 104 (aspartic acid), 106 (isoleucine), 108 (threonine), 110 (phenylalanine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, lysine, valine, serine, serine, leucine, glutamic acid, valine, valine, tyrosine, glycine, valine, isoleucine, lysine, and threonine, respectively, was named "h#32A1-T1L-type light chain".

The amino acid sequence of the h#32A1-T1L-type light chain is represented by SEQ ID NO: 61 in the Sequence Listing. The sequence comprising amino acid residues 1 to 20 of the amino acid sequence of SEQ ID NO: 61, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 61 is represented by SEQ ID NO: 60 in the Sequence Listing. The sequence comprising nucleotides 1 to 60 of the nucleotide sequence of SEQ ID NO: 60, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 60 and the amino acid sequence of SEQ ID NO: 61 are also shown in FIG. 32.

c)-ii) h#32A1-T2L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 81 (isoleucine), 99 (asparagine), 100 (proline), 101 (valine), 104 (aspartic acid), 106 (isoleucine), 108 (threonine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, valine, serine, serine, leucine, glutamic acid, valine, valine, valine, isoleucine, lysine, and threonine, respectively, was named "h#32A1-T2L-type light chain".

The amino acid sequence of the h#32A1-T2L-type light chain is represented by SEQ ID NO: 63 in the Sequence Listing. The sequence comprising amino acid residues 1 to 20 of the amino acid sequence of SEQ ID NO: 63, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 63 is represented by SEQ ID NO: 62 in the Sequence Listing. The sequence comprising nucleotides 1 to 60 of the nucleotide sequence of SEQ ID NO: 62, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 62 and the amino acid sequence of SEQ ID NO: 63 are also shown in FIG. 33.

c)-iii) h#32A1-T3L-Type Light Chain:

A humanized #32A1 light chain designed by replacing amino acid numbers 29 (alanine), between 29 and 30 (i.e. inserting a residue missing from the rat framework), 36 (glutamine), 99 (asparagine), 100 (proline), 101 (valine), 104 (aspartic acid), 106 (isoleucine), 127 (leucine), 129 (leucine), 130 (arginine), and 132 (alanine) of the #32A1 light chain represented by SEQ ID NO: 30 in the Sequence Listing with aspartic acid, serine, glutamic acid, serine, serine, leucine, glutamic acid, valine, valine, isoleucine, lysine, and threonine, respectively, was named "h#32A1-T3L-type light chain".

The amino acid sequence of the h#32A1-T3L-type light chain is represented by SEQ ID NO: 65 in the Sequence Listing. The sequence comprising amino acid residues 1 to 20 of the amino acid sequence of SEQ ID NO: 65, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 65 is represented by SEQ ID NO: 64 in the Sequence Listing. The sequence comprising nucleotides 1 to 60 of the nucleotide sequence of SEQ ID NO: 64, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 64 and the amino acid sequence of SEQ ID NO: 65 are also shown in FIG. 34.

c)-iv) h#32A1-T4L-Type Light Chain:

A humanized #32A1 light chain designed by replacing amino acid numbers 36 (glutamine), 99 (asparagine), 100 (proline), 101 (valine), 104 (aspartic acid), 106 (isoleucine), 129 (leucine), 130 (arginine), and 132 (alanine) of the #32A1 light chain represented by SEQ ID NO: 30 in the Sequence Listing with glutamic acid, serine, serine, leucine, glutamic acid, valine, isoleucine, lysine, and threonine, respectively, was named "h#32A1-T4L-type light chain".

The amino acid sequence of the h#32A1-T4L-type light chain is represented by SEQ ID NO: 67 in the Sequence Listing. The sequence comprising amino acid residues 1 to 20 of the amino acid sequence of SEQ ID NO: 67, the sequence comprising amino acid residues 21 to 132 thereof, and the sequence comprising amino acid residues 133 to 237 thereof correspond to the signal sequence, the light chain variable region, and the light chain constant region, respectively. A nucleotide sequence encoding the amino acid sequence of SEQ ID NO: 67 is represented by SEQ ID NO: 66 in the Sequence Listing. The sequence comprising nucleotides 1 to 60 of the nucleotide sequence of SEQ ID NO: 66, the sequence comprising nucleotides 61 to 396 thereof, and the sequence comprising nucleotides 397 to 711 thereof encode the signal sequence, the light chain variable region sequence, and the light chain constant region sequence, respectively. The nucleotide sequence of SEQ ID NO: 66 and the amino acid sequence of SEQ ID NO: 67 are also shown in FIG. 35.

c)-v) h#32A1-T5L-Type Light Chain:

A humanized #32A1 light chain designed by replacing amino acid numbers 29 (alanine), between 29 and 30 (i.e. inserting a residue missing from the rat framework), 36 (glutamine), 41 (serine), 66 (glutamine), 68 (arginine), 99 (asparagine), 100 (proline), 101 (valine), 104 (aspartic acid), 106 (isoleucine), 110 (phenylalanine), 122 (alanine), 123 (glycine), 127 (leucine), 129 (leucine), 130 (arginine), and 132 (alanine) of the #32A1 light chain represented by SEQ ID NO: 30 in the Sequence Listing with aspartic acid, serine, glutamic acid, asparagine, proline, lysine, serine, serine, leucine, glutamic acid, valine, tyrosine, glycine, glutamine, valine, isoleucine, lysine, and threonine, respectively, was named "h#32A1-T5L-type light chain".

The amino acid sequence of the h#32A1-T5L-type light chain is represented by SEQ ID NO: 69 in the Sequence Listing. The sequence comprising amino acid residues 1 to 20 of the amino acid sequence of SEQ ID NO: 69, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 69 is represented by SEQ ID NO: 68 in the Sequence Listing. The sequence comprising nucleotides 1 to 60 of the nucleotide sequence of SEQ ID NO: 68, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 68 and the amino acid sequence of SEQ ID NO: 69 are also shown in FIG. 36.

c)-vi) h#32A1-T6L-Type Light Chain:

A humanized #32A1 light chain designed by replacing amino acid numbers 29 (alanine), between 29 and 30 (i.e. inserting a residue missing from the rat framework), 36 (glutamine), 66 (glutamine), 99 (asparagine), 100 (proline), 101 (valine), 104 (aspartic acid), 106 (isoleucine), 127 (leucine), 129 (leucine), 130 (arginine), and 132 (alanine) of the #32A1 light chain represented by SEQ ID NO: 30 in the Sequence Listing with aspartic acid, serine, glutamic acid, proline, serine, serine, leucine, glutamic acid, valine, valine, isoleucine, lysine, and threonine, respectively, was named "h#32A1-T6L-type light chain".

The amino acid sequence of the h#32A1-T6L-type light chain is represented by SEQ ID NO: 71 in the Sequence Listing. The sequence comprising amino acid residues 1 to 20 of the amino acid sequence of SEQ ID NO: 71, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 71 is represented by SEQ ID NO: 70 in the Sequence Listing. The sequence comprising nucleotides 1 to 60 of the nucleotide sequence of SEQ ID NO: 70, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 70 and the amino acid sequence of SEQ ID NO: 71 are also shown in FIG. 37.

c)-vii) h#32A1-T7L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 68 (arginine), 81 (isoleucine), 99 (asparagine), 100 (proline), 101 (valine), 104 (aspartic acid), 106 (isoleucine), 108 (threonine), 110 (phenylalanine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, lysine, valine, serine, serine, leucine, glutamic acid, valine, valine, tyrosine, glycine, valine, isoleucine, lysine, and threonine, respectively, was named "h#32A1-T7L-type light chain".

The amino acid sequence of the h#32A1-T7L-type light chain is represented by SEQ ID NO: 78 in the Sequence Listing. The sequence comprising amino acid residues 1 to 113 of the amino acid sequence of SEQ ID NO: 78 and the sequence comprising amino acid residues 114 to 218 thereof correspond to the light chain variable region and the light chain constant region, respectively. The amino acid sequence of SEQ ID NO: 78 is also shown in FIG. 40.

c)-viii) h#32A1-T8L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 81 (isoleucine), 99 (asparagine), 100 (proline), 101 (valine), 104 (aspartic acid), 106 (isoleucine), 108 (threonine), 110 (phenylalanine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, valine, serine, serine, leucine, glutamic acid, valine, valine, tyrosine, glycine, valine, isoleucine, lysine, and threonine, respectively, was named "h#32A1-T8L-type light chain".

The amino acid sequence of the h#32A1-T8L-type light chain is represented by SEQ ID NO: 79 in the Sequence Listing. The sequence comprising amino acid residues 1 to 113 of the amino acid sequence of SEQ ID NO: 79 and the sequence comprising amino acid residues 114 to 218 thereof correspond to the light chain variable region and the light chain constant region, respectively. The amino acid sequence of SEQ ID NO: 79 is also shown in FIG. 40.

c)-ix) h#32A1-T9L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 68 (arginine), 81 (isoleucine), 99 (asparagine), 100 (proline), 101 (valine), 104 (aspartic acid), 106 (isoleucine), 108 (threonine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, lysine, valine, serine, serine, leucine, glutamic acid, valine, valine, glycine, valine, isoleucine, lysine, and threonine, respectively, was named "h#32A1-T9L-type light chain".

The amino acid sequence of the h#32A1-T9L-type light chain is represented by SEQ ID NO: 80 in the Sequence Listing. The sequence comprising amino acid residues 1 to 113 of the amino acid sequence of SEQ ID NO: 80 and the sequence comprising amino acid residues 114 to 218 thereof correspond to the light chain variable region and the light chain constant region, respectively. The amino acid sequence of SEQ ID NO: 80 is also shown in FIG. 40.

c)-x) h#32A1-T10L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 68 (arginine), 81 (isoleucine), 99 (asparagine), 100 (proline), 101 (valine), 104 (aspartic acid), 106 (isoleucine), 108 (threonine), 110 (phenylalanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, lysine, valine, serine, serine, leucine, glutamic acid, valine, valine, tyrosine, valine, isoleucine, lysine, and threonine, respectively, was named "h#32A1-T10L-type light chain".

The amino acid sequence of the h#32A1-T10L-type light chain is represented by SEQ ID NO: 81 in the Sequence Listing. The sequence comprising amino acid residues 1 to 113 of the amino acid sequence of SEQ ID NO: 81 and the sequence comprising amino acid residues 114 to 218 thereof correspond to the light chain variable region and the light chain constant region, respectively. The amino acid sequence of SEQ ID NO: 81 is also shown in FIG. 40.

c)-xi) h#32A1-T11L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 81 (isoleucine), 99 (asparagine), 100 (proline), 101 (valine), 104 (aspartic acid), 106 (isoleucine), 108 (threonine), 110 (phenylalanine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, valine, serine, serine, leucine, glutamic acid, valine, valine, tyrosine, glycine, valine, isoleucine, lysine, and threonine, respectively, was named "h#32A1-T11L-type light chain".

The amino acid sequence of the h#32A1-T11L-type light chain is represented by SEQ ID NO: 82 in the Sequence Listing. The sequence comprising amino acid residues 1 to 113 of the amino acid sequence of SEQ ID NO: 82 and the sequence comprising amino acid residues 114 to 218 thereof correspond to the light chain variable region and the light chain constant region, respectively. The amino acid sequence of SEQ ID NO: 82 is also shown in FIG. 40.

c)-xii) h#32A1-T12L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 68 (arginine), 81 (isoleucine), 99 (asparagine), 100 (proline), 101 (valine), 104 (aspartic acid), 106 (isoleucine), 108 (threonine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, lysine, valine, serine, serine, leucine, glutamic acid, valine, valine, glycine, valine, isoleucine, lysine, and threonine, respectively, was named "h#32A1-T12L-type light chain".

The amino acid sequence of the h#32A1-T12L-type light chain is represented by SEQ ID NO: 83 in the Sequence Listing. The sequence comprising amino acid residues 1 to 113 of the amino acid sequence of SEQ ID NO: 83 and the sequence comprising amino acid residues 114 to 218 thereof correspond to the light chain variable region and the light chain constant region, respectively. The amino acid sequence of SEQ ID NO: 83 is also shown in FIG. 41.

c)-xiii) h#32A1-T13L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 68 (arginine), 81 (isoleucine), 99 (asparagine), 100 (proline), 101 (valine), 104 (aspartic acid), 106 (isoleucine), 108 (threonine), 110 (phenylalanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, lysine, valine, serine, serine, leucine, glutamic acid, valine, valine, tyrosine, valine, isoleucine, lysine, and threonine, respectively, was named "h#32A1-T13L-type light chain".

The amino acid sequence of the h#32A1-T13L-type light chain is represented by SEQ ID NO: 84 in the Sequence Listing. The sequence comprising amino acid residues 1 to 113 of the amino acid sequence of SEQ ID NO: 84 and the sequence comprising amino acid residues 114 to 218 thereof correspond to the light chain variable region and the light chain constant region, respectively. The amino acid sequence of SEQ ID NO: 84 is also shown in FIG. 41.

c)-xiv) h#32A1-T14L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 81 (isoleucine), 99 (asparagine), 100 (proline), 101 (valine), 104 (aspartic acid), 106 (isoleucine), 108 (threonine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, valine, serine, serine, leucine, glutamic acid, valine, valine, glycine, valine, isoleucine, lysine, and threonine, respectively, was named "h#32A1-T14L-type light chain".

The amino acid sequence of the h#32A1-T14L-type light chain is represented by SEQ ID NO: 85 in the Sequence Listing. The sequence comprising amino acid residues 1 to 113 of the amino acid sequence of SEQ ID NO: 85 and the sequence comprising amino acid residues 114 to 218 thereof correspond to the light chain variable region and the light chain constant region, respectively. The amino acid sequence of SEQ ID NO: 85 is also shown in FIG. 41.

c)-xv) h#32A1-T15L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 81 (isoleucine), 99 (asparagine), 100 (proline), 101 (valine), 104 (aspartic acid), 106 (isoleucine), 108 (threonine), 110 (phenylalanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, valine, serine, serine, leucine, glutamic acid, valine, valine, tyrosine, valine, isoleucine, lysine, and threonine, respectively, was named "h#32A1-T15L-type light chain".

The amino acid sequence of the h#32A1-T15L-type light chain is represented by SEQ ID NO: 86 in the Sequence Listing. The sequence comprising amino acid residues 1 to 113 of the amino acid sequence of SEQ ID NO: 86 and the sequence comprising amino acid residues 114 to 218 thereof correspond to the light chain variable region and the light chain constant region, respectively. The amino acid sequence of SEQ ID NO: 86 is also shown in FIG. 41.

c)-xvi) h#32A1-T16L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 68 (arginine), 81 (isoleucine), 99 (asparagine), 100 (proline), 101 (valine), 104 (aspartic acid), 106 (isoleucine), 108 (threonine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, lysine, valine, serine, serine, leucine, glutamic acid, valine, valine, valine, isoleucine, lysine, and threonine, respectively, was named "h#32A1-T16L-type light chain".

The amino acid sequence of the h#32A1-T16L-type light chain is represented by SEQ ID NO: 87 in the Sequence Listing. The sequence comprising amino acid residues 1 to 113 of the amino acid sequence of SEQ ID NO: 87 and the sequence comprising amino acid residues 114 to 218 thereof correspond to the light chain variable region and the light chain constant region, respectively. The amino acid sequence of SEQ ID NO: 87 is also shown in FIG. 41.

c)-xvii) h#32A1-T17L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 81 (isoleucine), 99 (asparagine), 100 (proline), 101 (valine), 104 (aspartic acid), 106 (isoleucine), 108 (threonine), 122 (alanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, valine, serine, serine, leucine, glutamic acid, valine, valine, glycine, valine, isoleucine, lysine, and threonine, respectively, was named "h#32A1-T17L-type light chain".

The amino acid sequence of the h#32A1-T17L-type light chain is represented by SEQ ID NO: 88 in the Sequence Listing. The sequence comprising amino acid residues 1 to 113 of the amino acid sequence of SEQ ID NO: 88 and the sequence comprising amino acid residues 114 to 218 thereof correspond to the light chain variable region and the light chain constant region, respectively. The amino acid sequence of SEQ ID NO: 88 is also shown in FIG. 42.

c)-xviii) h#32A1-T18L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 81 (isoleucine), 99 (asparagine), 100 (proline), 101 (valine), 104 (aspartic acid), 106 (isoleucine), 108 (threonine), 110 (phenylalanine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, valine, serine, serine, leucine, glutamic acid, valine, valine, tyrosine, valine, isoleucine, lysine, and threonine, respectively, was named "h#32A1-T18L-type light chain".

The amino acid sequence of the h#32A1-T18L-type light chain is represented by SEQ ID NO: 89 in the Sequence Listing. The sequence comprising amino acid residues 1 to 113 of the amino acid sequence of SEQ ID NO: 89 and the sequence comprising amino acid residues 114 to 218 thereof correspond to the light chain variable region and the light chain constant region, respectively. The amino acid sequence of SEQ ID NO: 89 is also shown in FIG. 42.

c)-xix) h#32A1-T19L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 66 (glutamine), 68 (arginine), 81 (isoleucine), 99 (asparagine), 100 (proline), 101 (valine), 104 (aspartic acid), 106 (isoleucine), 108 (threonine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, proline, lysine, valine, serine, serine, leucine, glutamic acid, valine, valine, valine, isoleucine, lysine, and threonine, respectively, was named "h#32A1-T19L-type light chain".

The amino acid sequence of the h#32A1-T19L-type light chain is represented by SEQ ID NO: 90 in the Sequence Listing. The sequence comprising amino acid residues 1 to 113 of the amino acid sequence of SEQ ID NO: 90 and the sequence comprising amino acid residues 114 to 218 thereof correspond to the light chain variable region and the light chain constant region, respectively. The amino acid sequence of SEQ ID NO: 90 is also shown in FIG. 42.

c)-xx) h#32A1-T20L-Type Light Chain:

A humanized #32A1 light chain designed by replacing amino acid numbers 24 (leucine), 29 (alanine), between 29 and 30 (i.e. inserting a residue missing from the rat framework), 36 (glutamine), 41 (serine), 66 (glutamine), 81 (isoleucine), 99 (asparagine), 100 (proline), 101 (valine), 104 (aspartic acid), 106 (isoleucine), 108 (threonine), 127 (leucine), 129 (leucine), 130 (arginine), and 132 (alanine) of the #32A1 light chain represented by SEQ ID NO: 30 in the Sequence Listing with methionine, aspartic acid, serine, glutamic acid, asparagine, proline, valine, serine, serine, leucine, glutamic acid, valine, valine, valine, isoleucine, lysine, and threonine, respectively, was named "h#32A1-T20L-type light chain".

The amino acid sequence of the h#32A1-T20L-type light chain is represented by SEQ ID NO: 91 in the Sequence Listing. The sequence comprising amino acid residues 1 to 113 of the amino acid sequence of SEQ ID NO: 91 and the sequence comprising amino acid residues 114 to 218 thereof correspond to the light chain variable region and the light chain constant region, respectively. The amino acid sequence of SEQ ID NO: 91 is also shown in FIG. 42.

c)-xxi) h#32A1-T21L-Type Light Chain:

A humanized #32A1 light chain designed by replacing amino acid numbers 21 (aspartic acid), 24 (leucine), between 29 and 30 (i.e. inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 110 (phenylalanine), 122 (alanine), 123 (glycine), 127 (leucine), 129 (leucine), 130 (arginine), and 132 (alanine) of the #32A1 light chain represented by SEQ ID NO: 30 in the Sequence Listing with glutamic acid, methionine, threonine, serine, leucine, proline, glutamic acid, leucine, alanine, serine, serine, leucine, glutamic acid, proline, glutamic acid, phenylalanine, leucine, tyrosine, glycine, glutamine, valine, isoleucine, lysine, and threonine, respectively, was named "h#32A1-T21L-type light chain".

The amino acid sequence of the h#32A1-T21L-type light chain is represented by SEQ ID NO: 92 in the Sequence Listing. The sequence comprising amino acid residues 1 to 113 of the amino acid sequence of SEQ ID NO: 92 and the sequence comprising amino acid residues 114 to 218 thereof correspond to the light chain variable region and the light chain constant region, respectively. The amino acid sequence of SEQ ID NO: 92 is also shown in FIG. 42.

c)-xxii) h#32A1-T22L-Type Light Chain:

A humanized #32A1 light chain designed by replacing amino acid numbers 21 (aspartic acid), 24 (leucine), between 29 and 30 (i.e inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 123 (glycine), 127 (leucine), 129 (leucine), 130 (arginine), and 132 (alanine) of the #32A1 light chain represented by SEQ ID NO: 30 in the Sequence Listing with glutamic acid, methionine, threonine, serine, leucine, proline, gluta-mic acid, leucine, alanine, serine, serine, leucine, glutamic acid, proline, glutamic acid, phenylalanine, leucine, glutamine, valine, isoleucine, lysine, and threonine, respectively, was named "h#32A1-T22L-type light chain".

The amino acid sequence of the h#32A1-T22L-type light chain is represented by SEQ ID NO: 93 in the Sequence Listing. The sequence comprising amino acid residues 1 to 113 of the amino acid sequence of SEQ ID NO: 93 and the sequence comprising amino acid residues 114 to 218 thereof correspond to the light chain variable region and the light chain constant region, respectively. The amino acid sequence of SEQ ID NO: 93 is also shown in FIG. 43.

c)-xxiii) h#32A1-T23L-Type Light Chain:

A humanized #32A1 light chain designed by replacing amino acid numbers 24 (leucine), between 29 and 30 (i.e. inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 127 (leucine), 129 (leucine), 130 (arginine), and 132 (alanine) of the #32A1 light chain represented by SEQ ID NO: 30 in the Sequence Listing with methionine, threonine, serine, leucine, proline, glutamic acid, leucine, alanine, serine, serine, leucine, glutamic acid, proline, glutamic acid, phenylalanine, leucine, valine, isoleucine, lysine, and threonine, respectively, was named "h#32A1-T23L-type light chain".

The amino acid sequence of the h#32A1-T23L-type light chain is represented by SEQ ID NO: 94 in the Sequence Listing. The sequence comprising amino acid residues 1 to 113 of the amino acid sequence of SEQ ID NO: 94 and the sequence comprising amino acid residues 114 to 218 thereof correspond to the light chain variable region and the light chain constant region, respectively. The amino acid sequence of SEQ ID NO: 94 is also shown in FIG. 43.

c)-xxiv) h#32A1-T24L-Type Light Chain:

A humanized #32A1 light chain designed by replacing amino acid numbers 21 (aspartic acid), between 29 and 30 (i.e. inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 110 (phenylalanine), 122 (alanine), 123 (glycine), 127 (leucine), 129 (leucine), 130 (arginine), and 132 (alanine) of the #32A1 light chain represented by SEQ ID NO: 30 in the Sequence Listing with glutamic acid, threonine, serine, leucine, proline, glutamic acid, leucine, alanine, serine, serine, leucine, glutamic acid, proline, glutamic acid, phenylalanine, leucine, tyrosine, glycine, glutamine, valine, isoleucine, lysine, and threonine, respectively, was named "h#32A1-T24L-type light chain".

The amino acid sequence of the h#32A1-T24L-type light chain is represented by SEQ ID NO: 95 in the Sequence Listing. The sequence comprising amino acid residues 1 to 113 of the amino acid sequence of SEQ ID NO: 95 and the sequence comprising amino acid residues 114 to 218 thereof correspond to the light chain variable region and the light chain constant region, respectively. The amino acid sequence of SEQ ID NO: 95 is also shown in FIG. 43.

c)-xxv) h#32A1-T25L-Type Light Chain:

A humanized #32A1 light chain designed by replacing amino acid numbers between 29 and 30 (i.e. inserting a residue missing from the rat framework), 31 (alanine), 32 (valine), 34 (leucine), 36 (glutamine), 40 (isoleucine), 99 (asparagine), 100 (proline), 101 (valine), 102 (glutamine), 103 (alanine), 104 (aspartic acid), 106 (isoleucine), 110

(phenylalanine), 127 (leucine), 129 (leucine), 130 (arginine), and 132 (alanine) of the #32A1 light chain represented by SEQ ID NO: 30 in the Sequence Listing with threonine, serine, leucine, proline, glutamic acid, leucine, serine, serine, leucine, glutamic acid, proline, glutamic acid, phenylalanine, tyrosine, valine, isoleucine, lysine, and threonine, respectively, was named "h#32A1-T25L-type light chain".

The amino acid sequence of the h#32A1-T25L-type light chain is represented by SEQ ID NO: 96 in the Sequence Listing. The sequence comprising amino acid residues 1 to 113 of the amino acid sequence of SEQ ID NO: 96 and the sequence comprising amino acid residues 114 to 218 thereof correspond to the light chain variable region and the light chain constant region, respectively. The amino acid sequence of SEQ ID NO: 96 is also shown in FIG. 43.

Example 23

Production of Gene of Humanized Antibody of Rat Anti-Mouse Siglec-15 Monoclonal Antibody #32A1

Construction of h#32A1-T1L, h#32A1-T2L, h#32A1-T3L, H#32A1-T4L, H#32A1-T5L, and h#32A1-T6L-Type Light Chain Expression Vectors DNAs each containing a gene encoding a h#32A1-T1L, h#32A1-T2L, h#32A1-T3L, h#32A1-T4L, h#32A1-T5L, or h#32A1-T6L-type light chain variable region fused to a secretory signal represented by: amino acid numbers 1 to 133 of SEQ ID NO: 61 in the Sequence Listing; amino acid numbers 1 to 133 of SEQ ID NO: 63; amino acid numbers 1 to 133 of SEQ ID NO: 65; amino acid numbers 1 to 132 of SEQ ID NO: 67; amino acid numbers 1 to 133 of SEQ ID NO: 69; or amino acid numbers 1 to 133 of SEQ ID NO: 71 were synthesized (Medical & Biological Laboratories Co., Ltd., Artificial Gene Synthesis Service). Then, each of the DNA fragments obtained by cleaving the synthesized DNAs with the restriction enzymes NheI and BsiWI was inserted into a universal humanized antibody light chain expression vector (pEF6KCL) at the site cleaved with the restriction enzymes NheI and BsiWI, whereby h#32A1-T1L, h#32A1-T2L, h#32A1-T3L, h#32A1-T4L, h#32A1-T5L, and h#32A1-T6L-type light chain expression vectors were constructed. The thus obtained expression vectors were named "pEF6KCL/h#32A1-T1L", "pEF6KCL/h#32A1-T2L", "pEF6KCL/h#32A1-T3L", "pEF6KCL/h#32A1-T4L", "pEF6KCL/h#32A1-T5L", and "pEF6KCL/h#32A1-T6L", respectively.

b) Construction of h#32A1-T1H, h#32A1-T2H, h#32A1-T3H, h#32A1-T5H, and h#32A1-T6H Heavy Chain Expression Vectors DNAs each containing a gene encoding a h#32A1-T1H, h#32A1-T2H, h#32A1-T3H, h#32A1-T5H, or h#32A1-T6H-type heavy chain variable region fused to a secretory signal represented by amino acid numbers 1 to 140 of SEQ ID NO: 51, 53, 55, 57, or 59 in the Sequence Listing were synthesized (Medical & Biological Laboratories Co., Ltd., Artificial Gene Synthesis Service). Then, each of the DNA fragments obtained by cleaving the synthesized DNAs with the restriction enzyme BlpI was inserted into a universal humanized antibody heavy chain expression vector (pEF1/FCCU-1) at the site cleaved with the restriction enzyme BlpI, whereby h#32A1-T1H, h#32A1-T2H, h#32A1-T3H, h#32A1-T5H, and h#32A1-T6H heavy chain expression vectors were constructed. The thus obtained expression vectors were named "pEF1/FCCU/h#32A1-T1H", "pEF1/FCCU/h#32A1-T2H", "pEF1/FCCU/h#32A1-T3H", "pEF1/FCCU/h#32A1-T5H", and "pEF1/FCCU/h#32A1-T6H", respectively.

Example 24

Preparation of Humanized Antibody of Rat Anti-Mouse Siglec-15 Monoclonal Antibody #32a1

Production of Humanized Antibody $1.5 \times 10^8$ cells of 293 FreeStyle cells in logarithmic growth phase were seeded in 100 ml of fresh FreeStyle 293 Expression Medium (Invitrogen, Inc.) and subjected to shaking culture (125 rpm) at 37° C. in an 8% $CO_2$ incubator. 1 mg of polyethyleneimine (manufactured by Polyscience, Inc. #24765) was dissolved in 4 ml of Opti-Pro SFM medium (manufactured by Invitrogen, Inc.), and the resulting solution was left at room temperature for 5 minutes. A heavy chain expression plasmid (0.05 mg) and a light chain expression plasmid (0.15 mg) prepared using PureLink HiPure Plasmid Kit (Invitrogen, Inc.) were suspended in 4 ml of Opti-Pro SFM medium (Invitrogen, Inc.). Then, 4 ml of the resulting expression plasmids/Opti-Pro SFM mixed liquid was added to 4 ml of the polyethyleneimine/Opti-Pro SFM mixed liquid which had been left at room temperature for 5 minutes, and the resulting mixture was left at room temperature for an additional 5 minutes. Subsequently, 8 ml of the polyethyleneimine/the expression plasmids/Opti-Pro SFM mixed liquid was added to the 293 FreeStyle cell suspension, and the shaking culture was continued. After the cells were cultured for 7 days at 37° C. in 8% $CO_2$, the culture supernatant was collected.

b) Purification of Humanized Antibody

The culture supernatant obtained in the above a) was purified by Protein A affinity chromatography. 100 ml of the culture supernatant was put in a 500-ml stoppered flask, and 1 ml of a suspension (50% slurry) of MabSelect SuRe (manufactured by GE Healthcare Bio-science Co., Ltd.) equilibrated with PBS was added thereto. The resulting mixture was stirred overnight at 100 rpm in an incubator at 10° C. Then, the 293F culture supernatant/MabSelect SuRe suspension was applied to Zeba Spin Column empty 5 mL (PIERCE, Inc.). After all resin was poured into the column, the column was washed with 10 ml of 1 M NaCl. Subsequently, 1 ml of 1 M arginine solution (pH 4.0) was applied to the column, and a fraction containing the antibody was collected. The fraction was added to a centrifugal filter device (Amicon Ultra-4, fractional molecular weight: 50 K, Millipore Co., Ltd.), and liquid replacement with a citrate buffer and condensation were performed. The final volume was made up to 200 µl, which was used as a purified sample.

A humanized antibody of #32A1 obtained by a combination of pEF6KCL/h#32A1-T1L and pEF1/FCCU/h#32A1-T1H was named "h#32A1-T1"; a humanized antibody of #32A1 obtained by a combination of pEF6KCL/h#32A1-T2L and pEF1/FCCU/h#32A1-T2H was named "h#32A1-T2"; a humanized antibody of #32A1 obtained by a combination of pEF6KCL/h#32A1-T3L and pEF1/FCCU/h#32A1-T3H was named "h#32A1-T3"; a humanized antibody of #32A1 obtained by a combination of pEF6KCL/h#32A1-T4L and pEF1/FCCU/h#32A1-T3H was named "h#32A1-T4"; a humanized antibody of #32A1 obtained by a combination of pEF6KCL/h#32A1-T5L and pEF1/FCCU/h#32A1-T5H was named "h#32A1-T5"; and a humanized antibody of #32A1 obtained by a combination of pEF6KCL/h#32A1-T6L and pEF1/FCCU/h#32A1-T6H was named "h#32A1-T6".

81

Example 25

Figure 18:
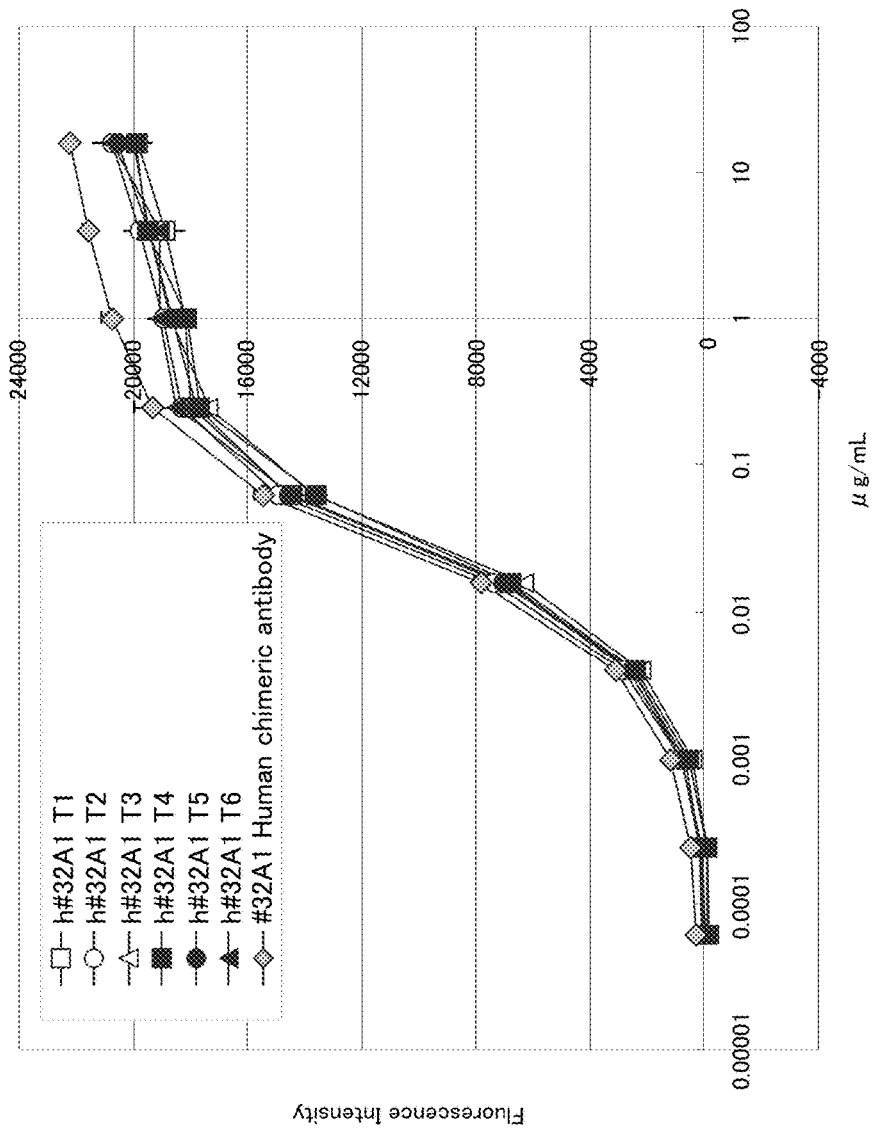
FIG. 18 is a view in which it was confirmed that 6 types of humanized rat anti-mouse Siglec-15 antibodies bind to mouse Siglec-15 protein in an antibody concentration-dependent manner by an ELISA method using a plate having mouse Siglec-15-Fc immobilized thereon.
Figure 19:
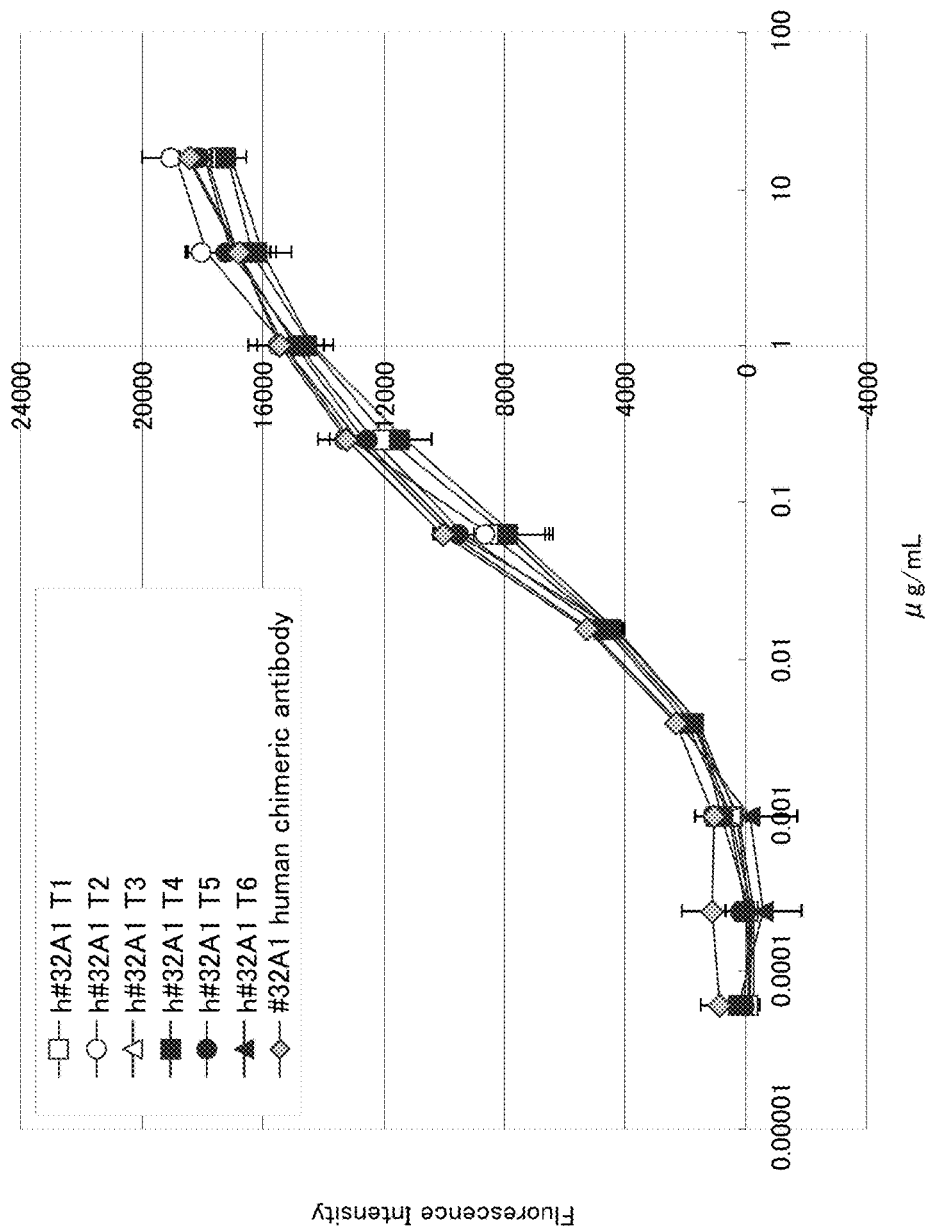
FIG. 19 is a view in which it was confirmed that 6 types of humanized rat anti-mouse Siglec-15 antibodies bind to human Siglec-15 protein in an antibody concentration-dependent manner by an ELISA method using a plate having human Siglec-15-Fc immobilized thereon.

Evaluation of Binding Property of Humanized Antibody of Rat Anti-Mouse Siglec-15 Monoclonal Antibody #32A1 to Mouse Siglec-15 Protein The binding property of the humanized antibodies of the rat anti-mouse Siglec-15 #32A1 T1 to T6 to mouse Siglec-15-Fc and human Siglec-15-Fc was evaluated by the following method. The mouse Siglec-15-Fc purified in Example 4 or the human Siglec-15-Fc purified in Example 12 was diluted to 1 µg/ml with PBS, and the diluted solution was dispensed at 100 µl/well onto an immunoplate (manufactured by Nunc, Inc., #437111), and the plate was left to stand overnight at 4° C., whereby each protein was adsorbed to the plate. On the next day, each well was washed 5 times with a PBS-T solution (PBS, 0.05% (v/v) Tween 20), and a solution obtained by diluting skim milk (manufactured by Morinaga Milk Industry Co., Ltd.) to 5% with PBS was dispensed at 350 µl/well, and the plate was left stand at room temperature for 2 hours. The liquid in each well was removed, and each well was washed 5 times with the PBS-T solution. Thereafter, each of the purified humanized antibodies of the rat anti-mouse Siglec-15 #32A1 T1 to T6 prepared in Example 24 or the human chimeric antibody prepared in Example 19 was diluted to a final concentration of from 1 to 0.004 µg/ml (4-fold dilution series) with a PBS solution containing 0.5% skim milk, the diluted solution was dispensed at 100 µl/well, and the plate was left to stand at room temperature for 2 hours. At this time, the concentration of each antibody was determined by performing measurement at 280 nm using a spectrophotometer DU-7400 (manufactured by Beckman Coulter, Inc.) and performing calculations based on a molar molecular extinction coefficient of each antibody. After each well had been washed 5 times with the PBS-T solution, alkaline phosphatase-conjugated AffiniPure goat anti-human IgG (manufactured by Jackson ImmunoResearch, Inc., #109-055-097) diluted to 2500-fold with a TBS-T solution (TBS, 0.05% (v/v) Tween 20) was added at 100 µl/well, and the plate was left to stand at room temperature for 1 hour. The liquid in each well was removed, and each well was washed 5 times with the TBS-T solution. Thereafter, a fluorescent substrate solution (manufactured by Roche Co., Ltd., #11681982001) was added at 100 µl/well, and a fluorescence reaction was allowed to proceed. After 10 minutes from the addition of the fluorescent substrate solution in the case of the plate having the mouse Siglec-15-Fc adsorbed thereto, and after 15 minutes in the case of the plate having the human Siglec-15-Fc adsorbed thereto, a fluorescence intensity was measured using Spectra Max M5 (manufactured by Molecular Devices, Inc.). As a result, it was confirmed that all of the examined six humanized antibodies of the rat anti-mouse Siglec-15 bind to the mouse Siglec-15 protein (FIG. 18) and the human Siglec-15 protein (FIG. 19) in an antibody concentration-dependent manner.

Example 26

Effect of Addition of Chimeric Antibody of Rat Anti-Mouse Siglec-15 Monoclonal Antibody #32A1 on Osteoclast Differentiation of Mouse Bone Marrow Nonadherent Cells (Stimulation with TNFα)

Figure 20:
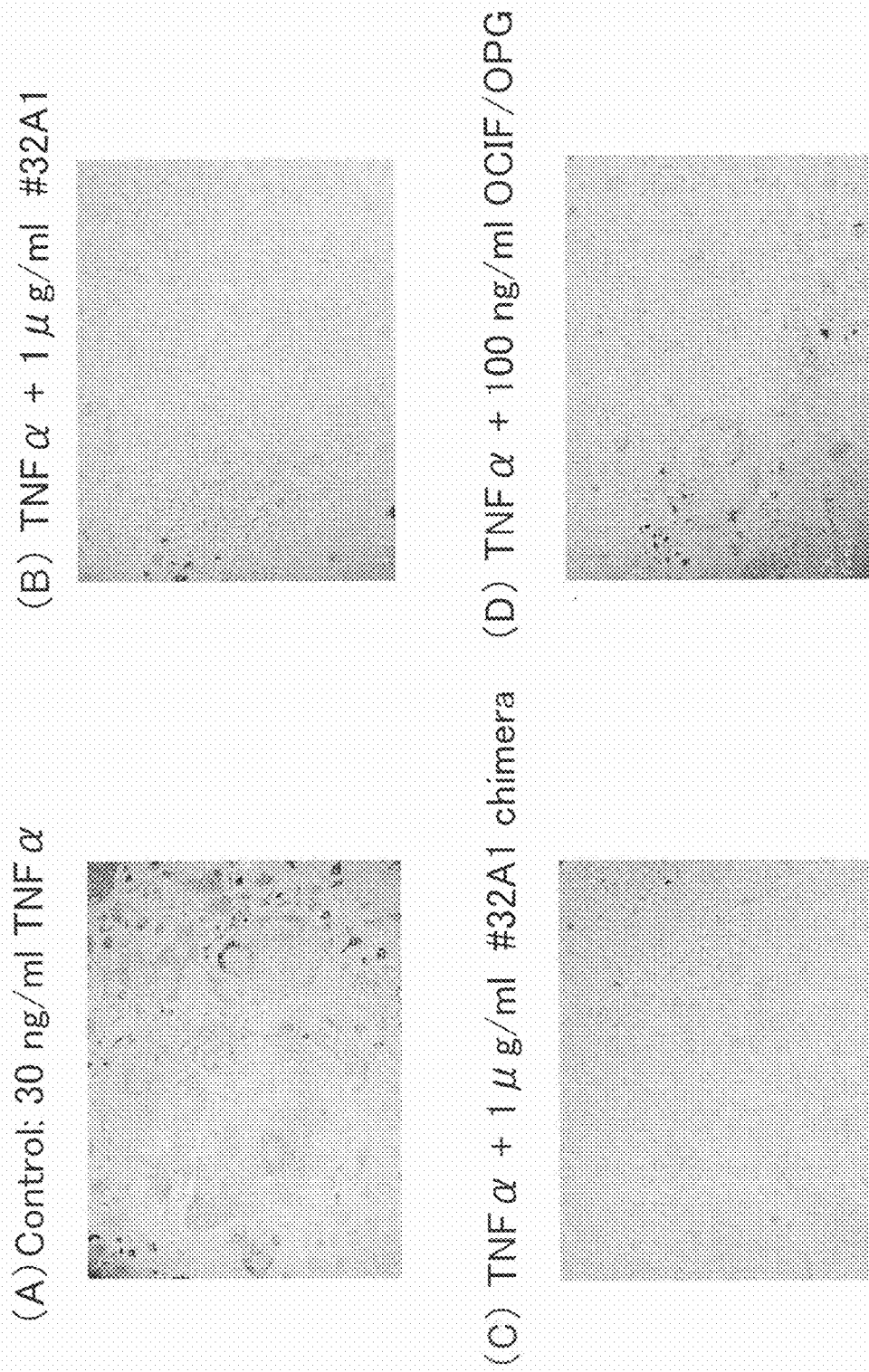
FIG. 20 shows photomicrographs depicting, by TRAP staining, the inhibition of mouse giant osteoclast formation under stimulation with TNFα by the addition of a rat anti-mouse Siglec-15 monoclonal antibody (#32A1 antibody) or a chimeric antibody thereof.
Figure 21:
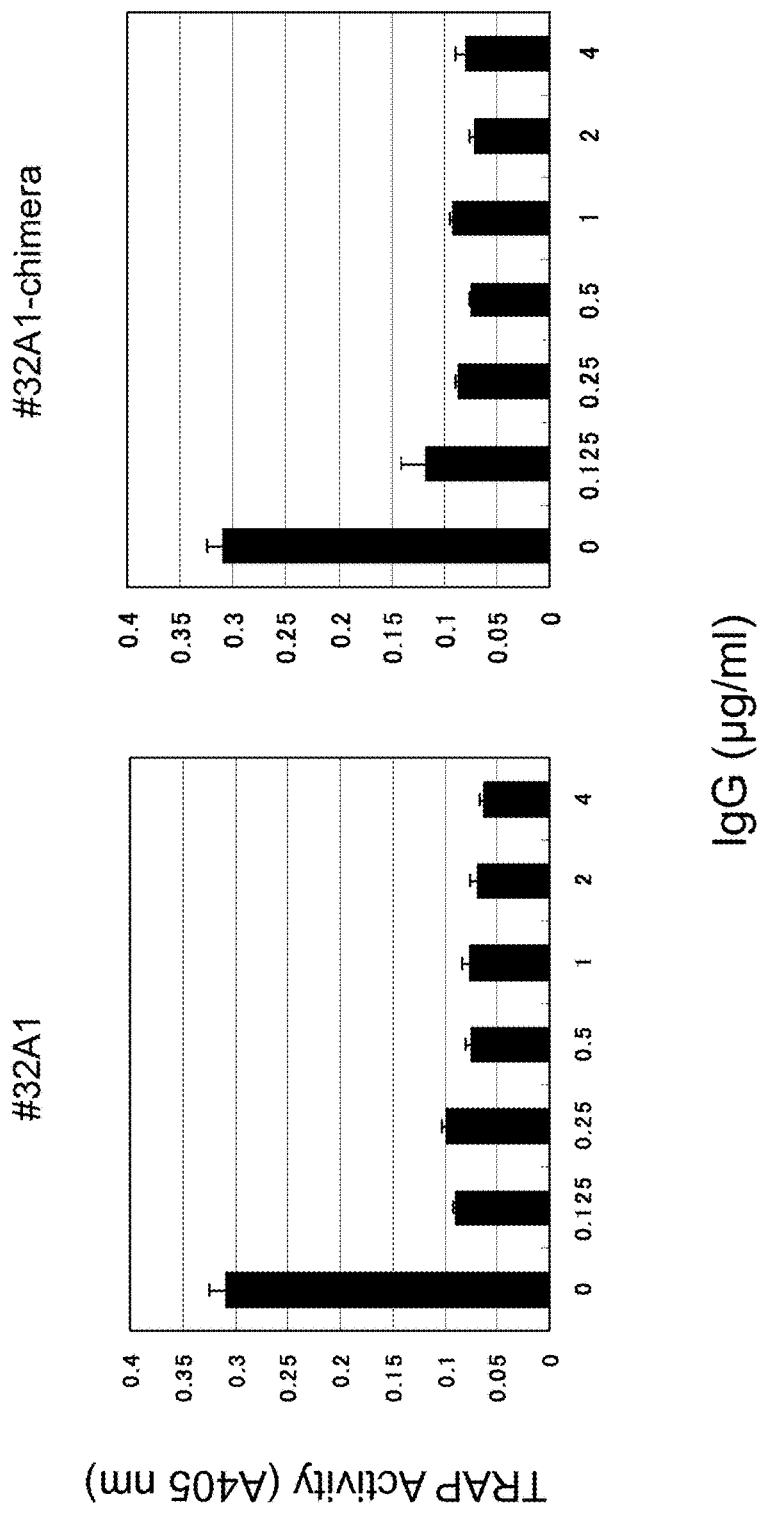
FIG. 21 shows graphs depicting, by the enzymatic activity of TRAP, the inhibition of mouse osteoclast formation under stimulation with TNFα by the addition of a rat anti-mouse Siglec-15 monoclonal antibody (#32A1 antibody) or a chimeric antibody thereof (N=3).

By using the rat anti-mouse Siglec-15 monoclonal antibody #32A1 prepared in Example 6 and the chimeric antibody of the rat anti-mouse Siglec-15 monoclonal antibody #32A1 prepared in Example 19, an effect on osteoclast differentiation of mouse bone marrow nonadherent cells by stimulation with TNFα was examined. Mouse bone marrow nonadherent cells prepared by the method of Example 8 were prepared at $1.5 \times 10^5$ cells/ml in α-MEM medium containing 10% fetal bovine serum (FBS), 10 ng/ml of M-CSF, and 2 ng/ml of TGF-β (manufactured by R&D Systems, Inc.), the resulting cell preparation was seeded in each well of a 96-well plate in an amount of 200 µl and the cells were cultured for 2 days in a $CO_2$ incubator. The old culture solution in the 96-well plate was removed, and 100 µl of MEM-α medium was added to each well, the 100 µl of MEM-α medium containing 10% FBS to which recombinant human TNFα (manufactured by R&D Systems, Inc.) and M-CSF had been added to give final concentrations of 30 ng/ml and 10 ng/ml, respectively. To the cell culture solution, the rat anti-mouse Siglec-15 monoclonal antibody #32A1 prepared in Example 6 or the chimeric antibody of the rat anti-mouse Siglec-15 monoclonal antibody #32A1 prepared in Example 19 was added at a concentration of from 0.125 to 4 µg/ml, and the cells were cultured for an additional 3 days in a $CO_2$ incubator. At the same time, a well in which the cells were cultured by adding recombinant human OCIF/OPG prepared by the method described in the description of Patent Application Publication No. WO 96/26217 at a concentration of 100 ng/ml was also prepared. After completion of the culturing, TRAP staining was performed using a leukocyte acid phosphatase kit (manufactured by Sigma Co., Ltd.) according to the protocol accompanying the kit, and the formation of TRAP-positive multinucleated osteoclasts was observed. As a result, the formation of TRAP-positive giant multinucleated osteoclasts was inhibited by the addition of the anti-mouse Siglec-15 polyclonal antibody (FIG. 20). Although small mononuclear osteoclasts were formed even in the case where the rat anti-mouse Siglec-15 monoclonal antibody #32A1 or the chimeric antibody thereof was added, the formation of large multinucleated osteoclasts induced by TNFα was almost completely inhibited. On the other hand, even when a sufficient amount of OCIF/OPG, which is an RANKL blocker, was added, the formation of large multinucleated osteoclasts was inhibited only a little. Further, in the same manner, the activity of tartrate-resistant acid phosphatase (TRAP) of the formed osteoclasts was measured by the procedure described in Example 9. After stopping the enzymatic reaction, an absorbance of each well at 405 nm was measured, and the obtained measurement was used as an index of TRAP activity. The results are shown in FIG. 21. A significant inhibition of TRAP activity was observed in the case of the #32A1 antibody and the chimeric antibody of #32A1 within the range of from 125 ng/ml to 4 µg/ml. From these results, it was shown that the rat anti-mouse Siglec-15 monoclonal antibody and the chimeric antibody thereof strongly inhibit the process of cell fusion in osteoclast differentiation and maturation induced by TNFα.

Example 27

Evaluation of Biological Activity of Rat Anti-Mouse Siglec-15 Monoclonal Antibodies #8A1 and #32A1 Based on Test for Rat Osteoclast Formation By using the rat anti-mouse Siglec-15 monoclonal antibodies #8A1 and #32A1 prepared in Example 6, an effect on osteoclast differentiation of rat bone marrow nonadherent cells was examined. Rat bone marrow nonadherent cells were prepared by modifying the method of Example 8. That is, the femur was excised from both legs of a female F344 rat at the age of 12 weeks and soft tissues were removed. Both ends of the femur were cut off, and MEM-α medium was injected using a syringe with a 23-gauge injection needle to push out bone marrow cells, which were collected in a centrifugal tube. Centrifugation was performed at room temperature for 5 minutes at 100 g, and the supernatant was removed. To the resulting cell pellet, 1 ml of a hemolytic buffer (Red Blood Cell Lysing Buffer, manufactured by Sigma Co., Ltd.) was added to suspend it, and the resulting suspension was left at room temperature for 5 minutes. 20 ml of D-PBS was added thereto, the suspension was centrifuged at room temperature for 5 minutes at 100 g, and the supernatant was removed. To the resulting cell pellet, 10 ml of MEM-α medium (manufactured by Invitrogen, Inc.) containing 5 ng/ml of M-CSF (manufactured by R&D Systems, Inc.) and 10% fetal bovine serum (FBS) was added to suspend it. Then, the resulting suspension was passed through a cell strainer (40 µm Nylon, manufactured by BD Falcon) to remove aggregates. The resulting cells were transferred to a 75 cm² T-flask (for the attachment of adherent cells) and cultured overnight in a $CO_2$ incubator. After the overnight culture, the cells which did not adhere to the T-flask were recovered and used as rat bone marrow nonadherent cells.

Figure 22:
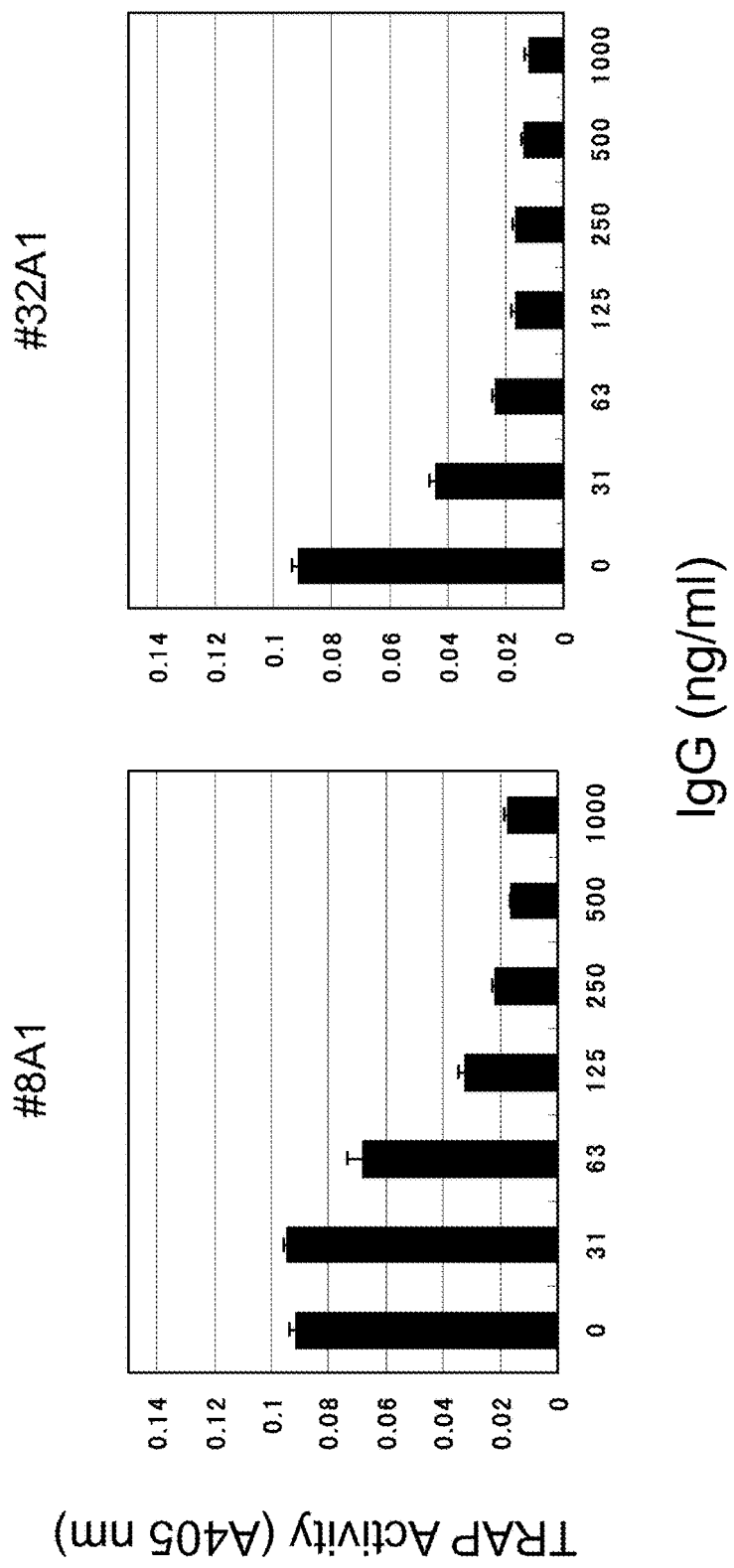
FIG. 22 shows graphs depicting, by the enzymatic activity of TRAP, the inhibition of rat osteoclast formation by the addition of a rat anti-mouse Siglec-15 monoclonal antibody (#8A1 or #32A1 antibody) (N=3).

The rat bone marrow nonadherent cells prepared by this method were cultured and a test for rat osteoclast formation was performed according to the method of Example 9. That is, the thus prepared rat bone marrow nonadherent cells were prepared at $1.5 \times 10^5$ cells/ml in α-MEM medium containing 10% FBS and 10 ng/ml of M-CSF (manufactured by R&D Systems, Inc.), and the resulting cell preparation was seeded in each well of a 96-well plate in an amount of 200 µl and the cells were cultured for 2 days in a $CO_2$ incubator. The old culture solution in the 96-well plate was removed, and 100 µl of MEM-α medium was added to each well, the 100 µl of MEM-α medium containing 10% FBS to which human RANKL (RANKL, manufactured by Peprotech, Inc.) and M-CSF had been added to give final concentrations of 20 ng/ml and 10 ng/ml, respectively. To the cell culture solution, the rat anti-mouse Siglec-15 monoclonal antibody #8A1 or #32A1 produced in Example 6 was added at a concentration of from 31 to 1000 ng/ml, and the cells were cultured for an additional 3 days in a $CO_2$ incubator. After completion of the culturing, the activity of tartrate-resistant acid phosphatase (TRAP) of the formed osteoclasts was measured by the method described in Example 9. After stopping the enzymatic reaction, an absorbance of each well at 405 nm was measured, and the obtained measurement was used as an index of TRAP activity. The results are shown in FIG. 22. In the case of the #8A1 antibody, a dose-dependent inhibition of TRAP activity was observed at a concentration of 63 ng/ml or higher, and in the case of the #32A1 antibody, a dose-dependent inhibition of TRAP activity was observed at a concentration of 31 ng/ml or higher. From these results, it was shown that the rat anti-mouse Siglec-15 monoclonal antibodies #8A1 and #32A1 strongly inhibit the rat osteoclast formation in the same manner as the mouse osteoclast formation, and the in vitro activity of inhibiting rat osteoclast formation of the #32A1 antibody is higher than that of #8A1 antibody.

Example 28

Designing of Humanized Antibody of Rat Anti-Mouse Siglec-15 Monoclonal Antibody #32A1 (2)
Designing of Humanized Version of #32A1
a)-i) Designing of Amino Acid Sequence of Humanized #32A1
A humanized #32A1 antibody was constructed according to a method generally known as CDR grafting (Proc. Natl. Acad. Sci. USA 86, 10029-10033 (1989)). As for the definitions of CDR regions, the Kabat definitions (SEQUENCES OF PROTEINS OF IMMUNOLOGICAL INTEREST VOL. I, FIFTH EDITION (1991)) were used for all except for CDRH2. As for CDRH2, the sequence thereof was made shorter by five residues at the C terminus than the Kabat definition using a definition of its own. In the heavy chain sequence containing the thus defined CDRH2, the CDR sequence derived from a rat is made shorter and more of a human framework sequence is incorporated, and therefore, when it is administered to humans, it is much less likely to be recognized as a heterologous antigen. An acceptor antibody was selected based on the amino acid homology within the framework region. The sequence of the framework region of #32A1 was compared with the sequences of all human frameworks in the Kabat Database (Nuc. Acid Res. 29, 205-206 (2001)) involving antibody amino acid sequences. As a result, for the L-chain, GF4/1.1'CL was selected as an acceptor based on a sequence homology of 71% in the framework region. As for the H-chain, M37G037'CL was selected as an acceptor based on a sequence homology of 73% in the framework region. In respect of the L-chain, the amino acid residues in the framework region of GF4/1.1'CL, and in respect of the H-chain, the amino acid residues in the framework region of M37G037'CL were aligned with the amino acid residues of #32A1, and the positions where different amino acids were used were identified. The positions of these residues were analyzed using the three-dimensional model of #32A1 constructed in a)-i) of Example 22. Then, donor residues to be grafted on the acceptor were selected according to the criteria provided by Queen et al. (Proc. Natl. Acad. Sci. USA 86, 10029-10033 (1989)). By transferring some selected donor residues to the acceptor antibody, humanized #32A1 sequences were constructed as described in the following Examples.

a)-ii) Humanization of #32A1 Heavy Chain
a)-ii)-i) h#32A1-H1-1-Type Heavy Chain:

A humanized 32A1 heavy chain designed by replacing amino acid numbers 23 (isoleucine), 24 (leucine), 26 (threonine), 32 (lysine), 43 (threonine), 61 (glutamic acid), 83 (glutamic acid), 85 (leucine), 86 (glutamic acid), 89 (valine), 95 (aspartic acid), 96 (serine), 97 (glutamic acid), 98 (serine), 100 (valine), 104 (valine), 105 (serine), 114 (isoleucine), 118 (threonine), 134 (valine), 135 (methionine), and 140 (leucine) of 32A1 represented by SEQ ID NO: 28 in the Sequence Listing with leucine, valine, serine, glutamine, alanine, glycine, alanine, valine, lysine, phenylalanine, asparagine, alanine, lysine, asparagine, leucine, methionine, asparagine, valine, alanine, threonine, leucine, and serine, respectively, was named "h#32A1-H1-1-type heavy chain".

The amino acid sequence of the h#32A1-H1-1-type heavy chain is represented by SEQ ID NO: 99 in the Sequence Listing. The sequence comprising amino acid residues 1 to 19 of the amino acid sequence of SEQ ID NO: 99, the sequence comprising amino acid residues 20 to 140 thereof, and the sequence comprising amino acid residues 141 to 466 thereof correspond to the signal sequence, the heavy chain variable region, and the heavy chain constant region, respectively. A nucleotide sequence encoding the amino acid sequence of SEQ ID NO: 99 is represented by SEQ ID NO: 98 in the Sequence Listing. The sequence comprising nucleotides 1 to 57 of the nucleotide sequence of SEQ ID NO: 98, the sequence comprising nucleotides 58 to 420 thereof, and the sequence comprising nucleotides 421 to 1398 thereof encode the signal sequence, the heavy chain variable region sequence, and the heavy chain constant region sequence, respectively. The nucleotide sequence of SEQ ID NO: 98 and the amino acid sequence of SEQ ID NO: 99 are also shown in FIG. 54.

a)-iii) Humanization of #32A1 Light Chain a)-iii)-i) h#32A1-L2-15-Type Light Chain:

A humanized 32A1 light chain designed by replacing amino acid numbers 21 (aspartic acid), 23 (valine), 24 (leucine), between 29 and 30 (i.e. inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 110 (phenylalanine), 122 (alanine), 123 (glycine), 127 (leucine), 129 (leucine), 130 (arginine), and 132 (alanine) of 32A1 represented by SEQ ID NO: 30 in the Sequence Listing with glutamic acid, leucine, methionine, threonine, serine, leucine, proline, glutamic acid, leucine, alanine, serine, serine, leucine, glutamic acid, proline, glutamic acid, phenylalanine, leucine, tyrosine, glycine, glutamine, valine, isoleucine, lysine, and threonine, respectively, was named "h#32A1-L2-15-type light chain".

The amino acid sequence of the h#32A1-L2-15-type light chain is represented by SEQ ID NO: 103 in the Sequence Listing. The sequence comprising amino acid residues 1 to 20 of the amino acid sequence of SEQ ID NO: 103, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 103 is represented by SEQ ID NO: 102 in the Sequence Listing. The sequence comprising nucleotides 1 to 60 of the nucleotide sequence of SEQ ID NO: 102, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 102 and the amino acid sequence of SEQ ID NO: 103 are also shown in FIG. 56.

a)-iii)-ii) h#32A1-L2-16-Type Light Chain:

A humanized 32A1 light chain designed by replacing amino acid numbers 21 (aspartic acid), 23 (valine), 24 (leucine), between 29 and 30 (i.e. inserting a residue missing from the rat framework), 31 (alanine), 32 (valine), 34 (leucine), 36 (glutamine), 40 (isoleucine), 66 (glutamine), 99 (asparagine), 100 (proline), 101 (valine), 102 (glutamine), 103 (alanine), 104 (aspartic acid), 106 (isoleucine), 108 (threonine), 123 (glycine), 127 (leucine), 129 (leucine), 130 (arginine), and 132 (alanine) of 32A1 represented by SEQ ID NO: 30 in the Sequence Listing with glutamic acid, leucine, methionine, threonine, serine, leucine, proline, glutamic acid, leucine, alanine, serine, serine, leucine, glutamic acid, proline, glutamic acid, phenylalanine, leucine, glutamine, valine, isoleucine, lysine, and threonine, respectively, was named "h#32A1-L2-16-type light chain".

The amino acid sequence of the h#32A1-L2-16-type light chain is represented by SEQ ID NO: 105 in the Sequence Listing. The sequence comprising amino acid residues 1 to 20 of the amino acid sequence of SEQ ID NO: 105, the sequence comprising amino acid residues 21 to 133 thereof, and the sequence comprising amino acid residues 134 to 238 thereof correspond to the signal sequence, the light chain variable region, and the light chain constant region, respectively. A nucleotide sequence encoding the amino acid sequence of SEQ ID NO: 105 is represented by SEQ ID NO: 104 in the Sequence Listing. The sequence comprising nucleotides 1 to 60 of the nucleotide sequence of SEQ ID NO: 104, the sequence comprising nucleotides 61 to 399 thereof, and the sequence comprising nucleotides 400 to 714 thereof encode the signal sequence, the light chain variable region sequence, and the light chain constant region sequence, respectively. The nucleotide sequence of SEQ ID NO: 104 and the amino acid sequence of SEQ ID NO: 105 are also shown in FIG. 57.

b) Production of Gene of Humanized Antibody of Rat Anti-Mouse Siglec-15 Monoclonal Antibody #32A1 b)-i) Construction of Universal Human Heavy Chain Expression Vector pEG2

A DNA fragment containing a DNA sequence encoding amino acids of the signal sequence and the constant region of human IgG2 represented by SEQ ID NO: 106 was synthesized (Medical & Biological Laboratories Co., Ltd., Artificial Gene Synthesis Service), and digested with the restriction enzymes NheI and PmeI, whereby a DNA fragment of about 1100 bp was obtained. This DNA fragment was ligated to a DNA fragment of about 6200 bp obtained by digesting pEF1/FCCU-1 with NheI and PmeI and removing a DNA fragment of about 1100 bp, whereby a universal humanized antibody (hIgG2 type) heavy chain expression vector pEG2 was constructed.

b)-ii) Construction of h#32A1-H1-1 Heavy Chain Expression Vector

A DNA fragment obtained by synthesizing a DNA containing a gene encoding the h#32A1-H1-1 heavy chain variable region fused to a secretory signal represented by amino acid numbers 1 to 140 of SEQ ID NO: 99 in the Sequence Listing (Invitrogen), and cleaving the DNA with the restriction enzyme BlpI was inserted into the universal humanized antibody (hIgG2 type) heavy chain expression vector (pEG2) at the site cleaved with the restriction enzyme BlpI, whereby a h#32A1-H1-1 heavy chain expression vector was constructed. The thus obtained expression vector was named "pEG2/h#32A1-H1-1".

b)-iii) Construction of h#32A1-H5 Heavy Chain Expression Vector

A humanized 32A1 heavy chain in which the signal sequence and the constant region of h#32A1-T5H-type heavy chain designed in b)-iv) of Example 22 were changed to those of IgG2 type was named "h#32A1-H5-type heavy chain".

The amino acid sequence of the h#32A1-H5-type heavy chain is represented by SEQ ID NO: 101 in the Sequence Listing. The sequence comprising amino acid residues 1 to 19 of the amino acid sequence of SEQ ID NO: 101, the sequence comprising amino acid residues 20 to 140 thereof, and the sequence comprising amino acid residues 141 to 466 thereof correspond to the signal sequence, the heavy chain variable region, and the heavy chain constant region, respectively. A nucleotide sequence encoding the amino acid sequence of SEQ ID NO: 101 is represented by SEQ ID NO: 100 in the Sequence Listing. The sequence comprising nucleotides 1 to 57 of the nucleotide sequence of SEQ ID NO: 100, the sequence comprising nucleotides 58 to 420 thereof, and the sequence comprising nucleotides 421 to 1398 thereof encode the signal sequence, the heavy chain variable region sequence, and the heavy chain constant region sequence, respectively. The nucleotide sequence of SEQ ID NO: 100 and the amino acid sequence of SEQ ID NO: 101 are also shown in FIG. 55.

A DNA fragment obtained by cleaving the pEF1/FCCU/ h#32A1-T5H produced in Example 23 with the restriction enzyme BlpI was inserted into the universal humanized antibody (hIgG2 type) heavy chain expression vector (pEG2) at the site cleaved with the restriction enzyme BlpI, whereby a h#32A1-H5 heavy chain expression vector was constructed. The thus obtained expression vector was named "pEG2/h#32A1-H5".

b)-iv) Construction of h#32A1-L2-15 and h#32A1-L2-16-Type Light Chain Expression Vectors DNAs each containing a gene encoding a h#32A1-L2-15 or h#32A1-L2-16-type light chain variable region fused to a secretory signal represented by amino acid numbers 1 to 133 of SEQ ID NO: 103 in the Sequence Listing or amino acid numbers 1 to 133 of SEQ ID NO: 105 were synthesized (Invitrogen), and h#32A1-L2-15 and h#32A1-L2-16-type light chain expression vectors were constructed in the same manner as in Example 23. The thus obtained expression vectors were named "pEF6KCL/h#32A1-L2-15" and "pEF6KCL/h#32A1-L2-16", respectively.

c) Preparation of Humanized Antibody of Rat Anti-Mouse Siglec-15 Monoclonal Antibody #32A1 c)-i) Production of Humanized Antibody $1.2 \times 10^9$ cells of FreeStyle 293F cells (Invitrogen) in logarithmic growth phase were seeded in 1.2 L of fresh FreeStyle 293 Expression Medium (Invitrogen) and subjected to shaking culture at 37° C. in an 8% $CO_2$ incubator at 90 rpm for 1 hour. 3.6 mg of polyethyleneimine (Polyscience, #24765) was dissolved in 20 ml of Opti-Pro SFM medium (Invitrogen). Subsequently, an H-chain expression plasmid (0.4 mg) and an L-chain expression plasmid (0.8 mg) prepared using PureLink HiPure Plasmid Kit (Invitrogen, Inc.) were suspended in 20 ml of Opti-Pro SFM medium. Then, 20 ml of the resulting expression plasmids/Opti-Pro SFM mixed liquid was added to 20 ml of the polyethyleneimine/Opti-Pro SFM mixed liquid, and the resulting mixture was gently stirred and then left for 5 minutes. Thereafter, the mixture was added to the FreeStyle 293F cells, and shaking culture was performed for 7 days at 37° C. in an 8% $CO_2$ incubator at 90 rpm. The resulting culture supernatant was filtered through a Disposable Capsule Filter (Advantec #CCS-045-E1H).

A humanized antibody of #32A1 obtained by a combination of pEF6KCL/h#32A1-T5L and pEG2/h#32A1-H5 was named "h#32A1-H5/L5"; a humanized antibody of #32A1 obtained by a combination of pEF6KCL/h#32A1-T5L and pEG2/h#32A1-H1-1 was named "h#32A1-H1-1/L5"; a humanized antibody of #32A1 obtained by a combination of pEF6KCL/h#32A1-L2-15 and pEG2/h#32A1-H1-1 was named "h#32A1-H1-1/L2-15"; and a humanized antibody of #32A1 obtained by a combination of pEF6KCL/h#32A1-L2-16 and pEG2/h#32A1-H1-1 was named "h#32A1-H1-1/L2-16".

c)-ii) Purification of Humanized Antibody

The culture supernatant obtained in the above c)-i) was purified by a two-step process including rProtein A affinity chromatography (at 4 to 6° C.) and ceramic hydroxyapatite (at room temperature). A buffer replacement step after the purification by rProtein A affinity chromatography and after the purification by ceramic hydroxyapatite was performed at room temperature. First, 1100 to 1200 ml of the culture supernatant was applied to MabSelect SuRe (manufactured by GE Healthcare Bioscience Co., Ltd., 2×1 ml HiTrap columns in series) equilibrated with PBS. After all culture solution was poured into the column, the column was washed with 15 to 30 ml of PBS. Subsequently, elution was performed with 2 M arginine hydrochloride solution (pH 4.0), and a fraction containing the antibody was collected. The fraction was applied to a desalting column (manufactured by GE Healthcare Bioscience Co., Ltd., 2×5 ml HiTrap desalting columns in series) and the liquid was replaced with a buffer containing 5 mM sodium phosphate, 50 mM MES, and 20 mM NaCl at pH 6.5. Further, the antibody solution subjected to the replacement with the buffer was applied to a ceramic hydroxyapatite column (Japan Bio-Rad Laboratories, Inc., Bio-Scale CHT2-1 hydroxyapatite column (2 ml volume)) equilibrated with a buffer containing 5 mM NaPi, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bioscience Co., Ltd., 2×5 ml HiTrap desalting columns in series) and the liquid was replaced with CBS (10 mM citrate buffer containing 140 mM sodium chloride, pH 6.0). Finally, the resulting solution was concentrated using Centrifugal UF Filter Device VIVASPIN 20 (fractional molecular weight: 30 K, Sartorius Co., Ltd., at 4° C.), the concentration of IgG was adjusted to 1.0 mg/ml or more, and the thus obtained solution was used as a purified sample. The volumes of the respective purified samples were as follows: h#32A1-H1-1/L5: 2.2 ml, h#32A1-H5/L5: 1.8 ml, h#32A1-H1-1/L2-16: 6.0 ml, and h#32A1-H1-1/L2-15: 2.2 ml.

Example 29

Figure 44:
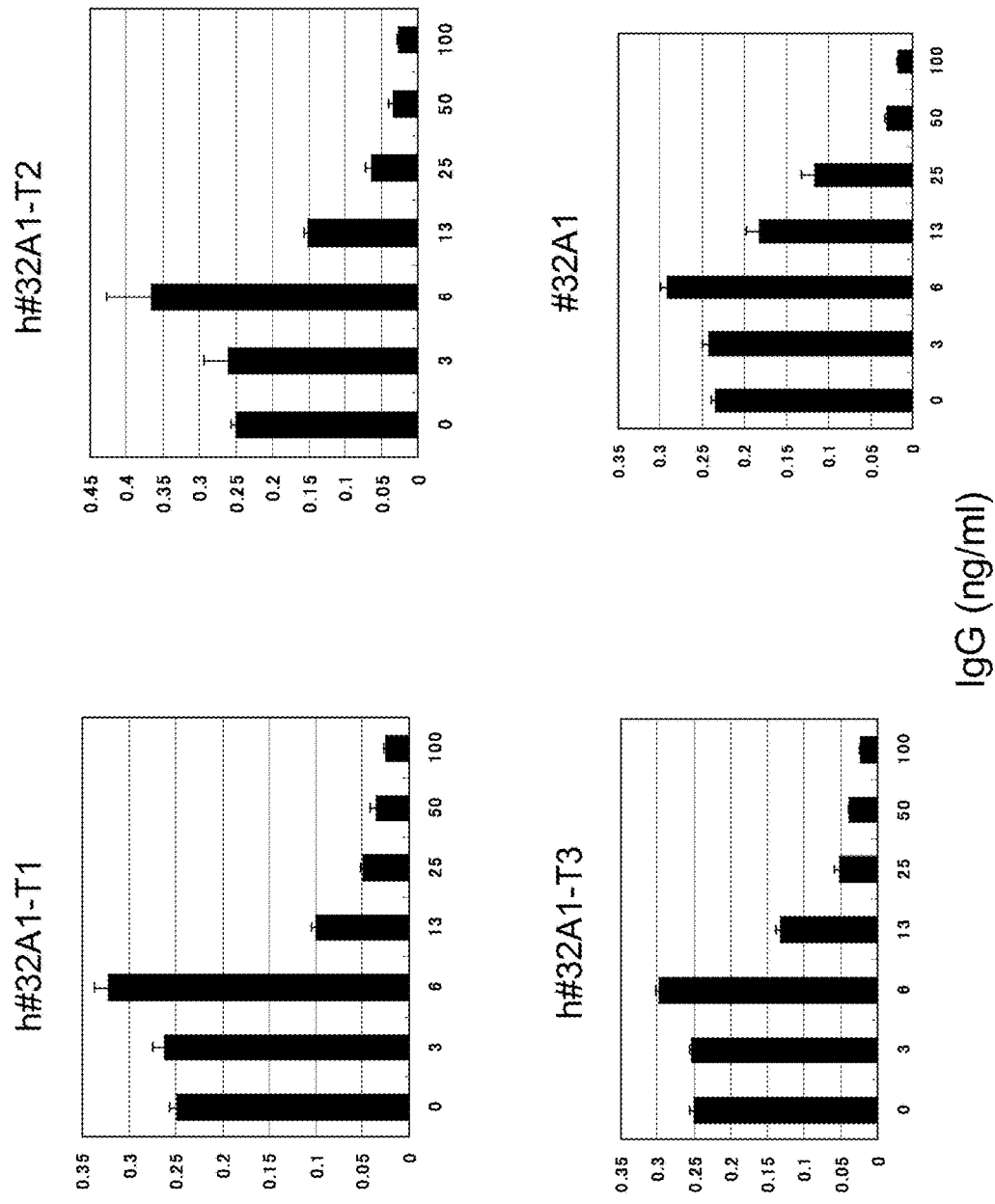
FIG. 44 shows graphs depicting, by the enzymatic activity of TRAP, the inhibition of mouse osteoclast formation by the addition of a humanized rat anti-mouse Siglec-15 antibody (h#32A1-T1, h#32A1-T2, or h#32A1-T3). Incidentally, the rat #32A1 antibody in the drawing is a positive control common to FIGS. 44 and 45.
Figure 45:
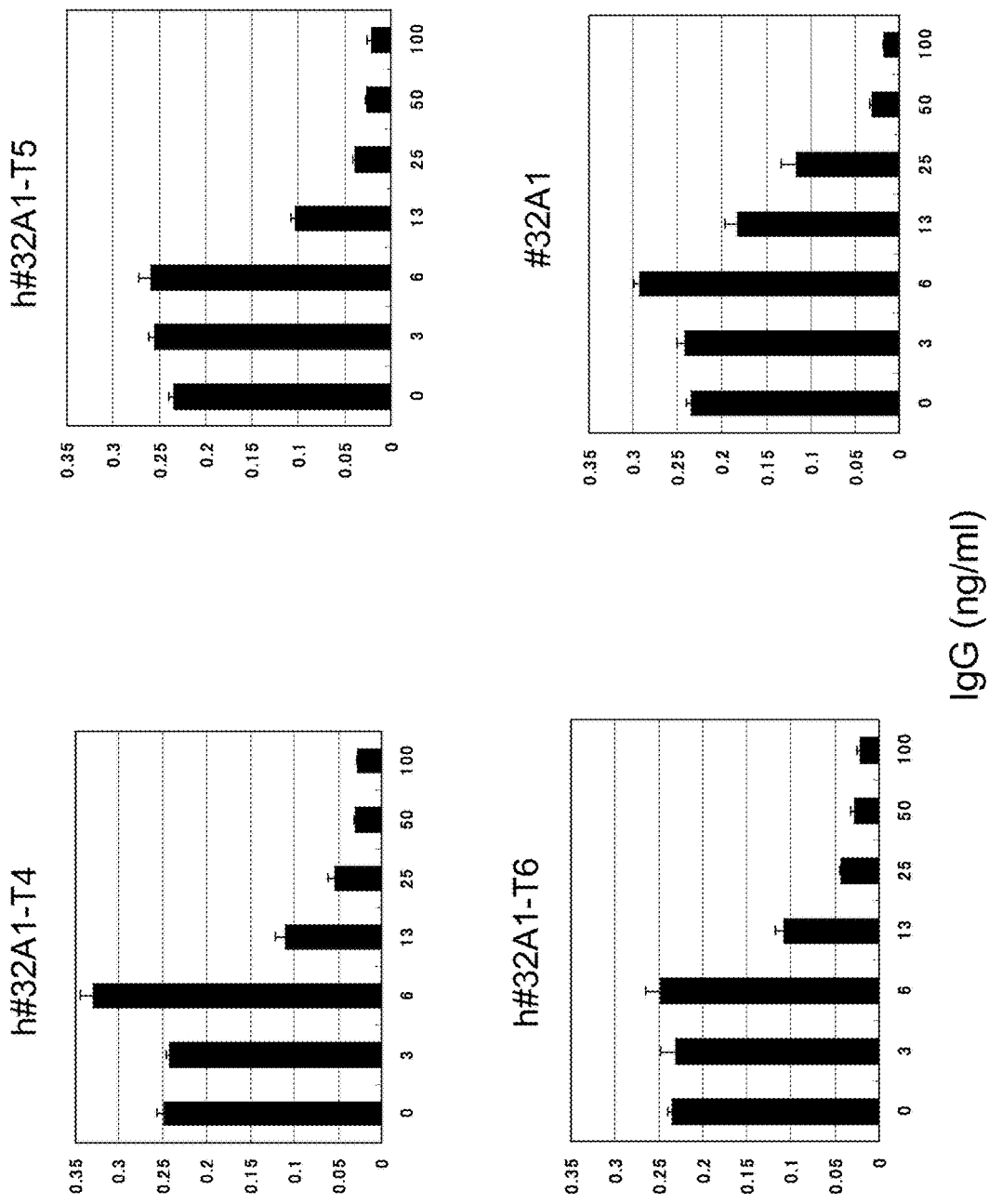
FIG. 45 shows graphs depicting, by the enzymatic activity of TRAP, the inhibition of mouse osteoclast formation by the addition of a humanized rat anti-mouse Siglec-15 antibody (h#32A1-T4, h#32A1-T5, or h#32A1-T6).
Figure 47:
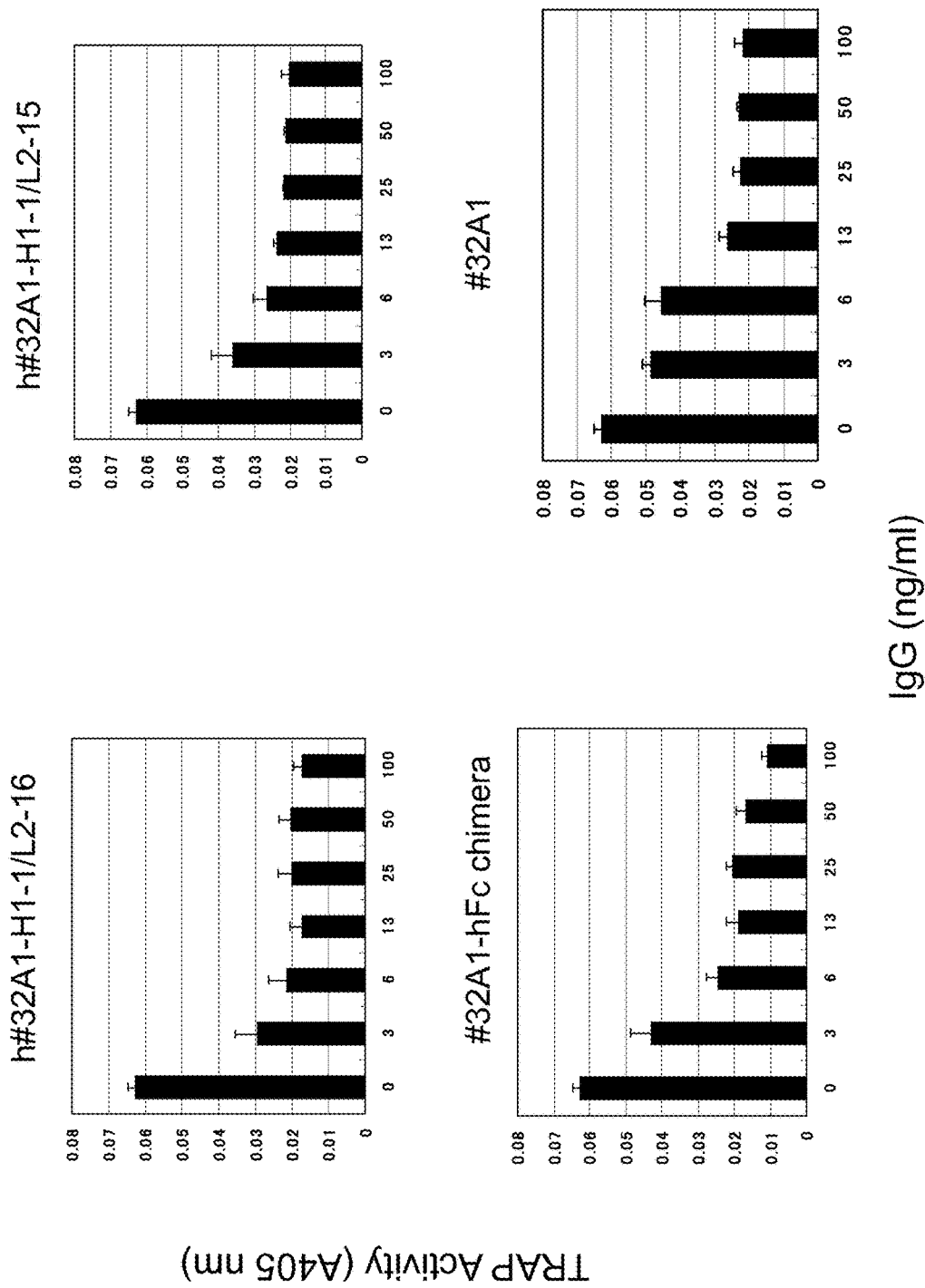
FIG. 47 shows graphs depicting, by the enzymatic activity of TRAP, the inhibition of mouse osteoclast formation by the addition of a humanized rat anti-mouse Siglec-15 antibody (h#32A1-H1-1/L2-16 or h#32A1-H-1/L2-15).

Evaluation of Biological Activity of Humanized Antibody of Rat Anti-Mouse Siglec-15 Monoclonal Antibody #32A1 Based on Test for Mouse Osteoclast Formation An inhibitory effect on mouse osteoclast formation exhibited by the humanized antibodies obtained in Examples 24 and 28 was evaluated by partially modifying the method described in Example 9. Mouse bone marrow nonadherent cells prepared by the method of Example 8 were prepared at $1.5 \times 10^5$ cells/ml in α-MEM medium containing 10% FBS and 10 ng/ml of M-CSF (manufactured by R&D Systems, Inc.), the resulting cell preparation was seeded in each well of a 96-well plate in an amount of 200 μl and the cells were cultured for 2 days in a $CO_2$ incubator. The old culture solution in the 96-well plate was removed, and 100 μl of MEM-α medium was added to each well, the 100 μl of MEM-α medium containing 10% FBS to which human RANKL (RANKL, manufactured by Peprotech, Inc.) and M-CSF had been added to give final concentrations of 20 ng/ml and 10 ng/ml, respectively. To the cell culture solution, the rat anti-mouse Siglec-15 monoclonal antibody (#32A1 antibody) prepared in Example 6 or each of the 6 types of humanized #32A1 antibodies (h#32A1-T1, h#32A1-T2, h#32A1-T3, h#32A1-T4, h#32A1-T5, and h#32A1-T6) prepared in Example 24 was added at a concentration of from 3 to 100 ng/ml, and the cells were cultured for an additional 3 days in a $CO_2$ incubator. After completion of the culturing, the activity of tartrate-resistant acid phosphatase (TRAP) of the formed osteoclasts was measured by the following procedure. The culture solution in each well of the 96-well plate was removed by suction, and 50 μl of 50 mM sodium citrate buffer (pH 6.1) containing 1% Triton X-100 was added to each well. Then, the plate was shaken for 5 minutes on a plate shaker to lyse the cells. To each well, 50 μl of a substrate solution (50 mM sodium citrate buffer (pH 6.1) containing 5 mg/ml p-nitrophenyl phosphate and 0.46% sodium tartrate) was added, and the plate was incubated at room temperature for 10 minutes. After the incubation, 50 μl of a 1 N sodium hydroxide solution was added to each well of the 96-well plate to stop the enzymatic reaction. After stopping the enzymatic reaction, an absorbance of each well at 405 nm was measured, and the obtained measurement was used as an index of TRAP activity. The results are shown in FIGS. 44 and 45. Further, for the rat anti-mouse Siglec-15 monoclonal antibody (#32A1 antibody) prepared in Example 6, the human chimeric antibody of the #32A1 antibody prepared in Example 19, and 4 types of the humanized #32A1 antibodies (h#32A1-H1-1/L5, h#32A1-H5/L5, h#32A1-H1-1/L2-16, and h#32A1-H1-1/L2-15) prepared in Example 28, the biological activity was evaluated by the same method as in this test, and the results are shown in FIGS. 46 and 47. In all cases of the 10 types of humanized #32A1 antibodies (h#32A1-T1, h#32A1-T2, h#32A1-T3, h#32A1-T4, h#32A1-T5, h#32A1-T6, h#32A1-H1-1/L5, h#32A1-H5/L5, h#32A1-H1-1/L2-16, and h#32A1-H1-1/L2-15) for which the activity was evaluated, a strong activity of inhibiting osteoclast formation substantially comparable to that of the rat anti-mouse Siglec-15 monoclonal antibody (#32A1 antibody) or the human chimeric antibody of the #32A1 antibody was observed.

Example 30

Effect of Addition of Humanized Antibody of Rat Anti-Mouse Siglec-15 Monoclonal Antibody #32A1 on Bone Resorption Activity of Normal Human Osteoclast Precursor Cells (Evaluation Using Collagen-Coated Plate)

Figure 48:
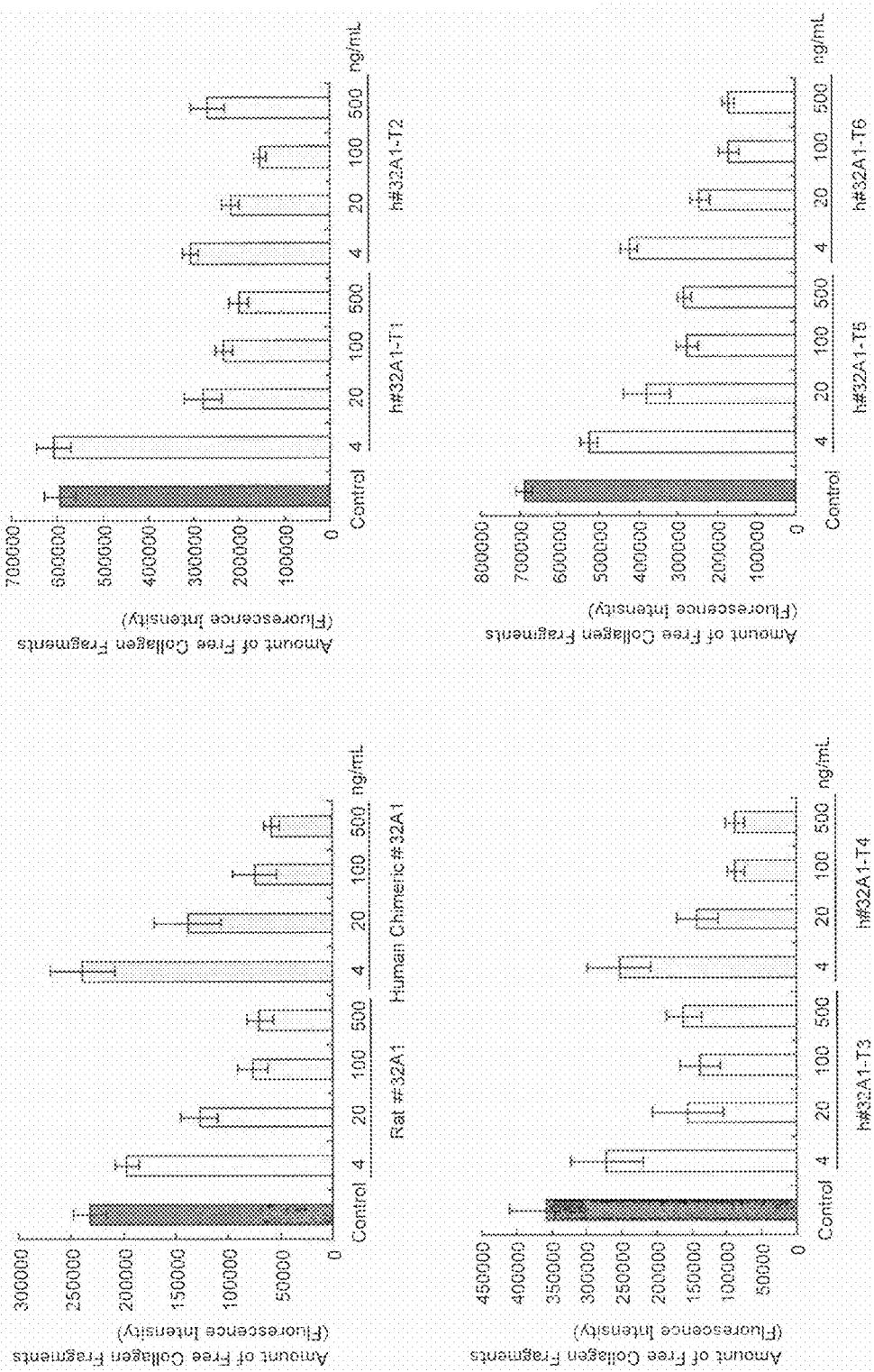
FIG. 48 shows graphs depicting the inhibition of the bone resorption activity of normal human osteoclasts by the addition of a humanized rat anti-mouse Siglec-15 antibody (h#32A1-T1, h#32A1-T2, h#32A1-T3, h#32A1-T4, h#32A1-T5, or h#32A1-T6). Incidentally, the rat #32A1 antibody and #32A1 human chimeric antibody in the drawing are positive controls common to FIGS. 48 and 49.
Figure 49:
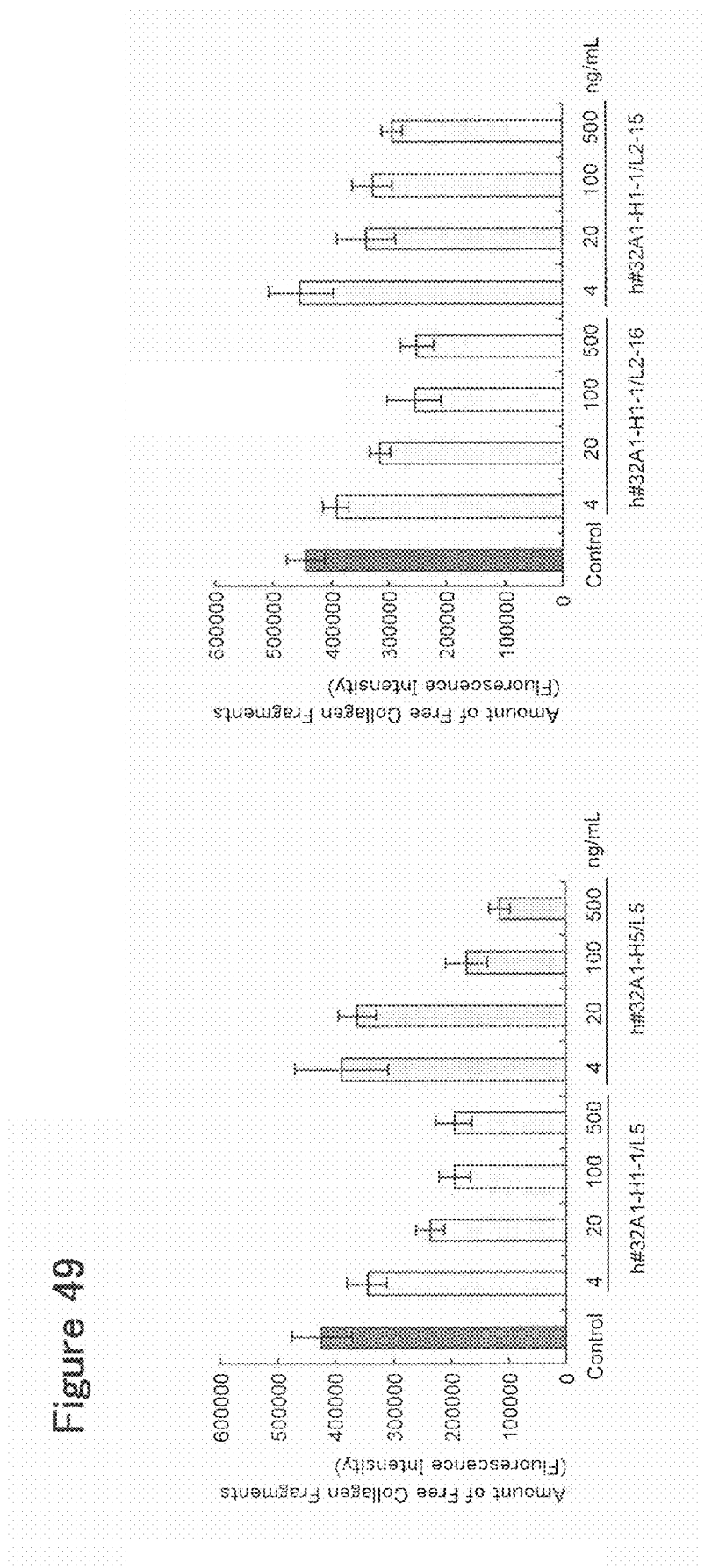
FIG. 49 shows graphs depicting the inhibition of the bone resorption activity of normal human osteoclasts by the addition of a humanized rat anti-mouse Siglec-15 antibody (h#32A1-H1-1/L5, h#32A1-H5/L5, h#32A1-H1-1/L2-16, or h#32A1-H1-1/L2-15).

Normal human osteoclast precursor cells (Normal Human Natural Osteoclast Precursor Cells, purchased from Sanko Junyaku Co., Ltd., Cat. No. 2T-110) were seeded in a 96-well OsteoLyse cell culture plate (purchased from Sanko Junyaku Co., Ltd., Cat. No. PA-1500) at $1 \times 10^4$ cells/well according to the protocol accompanying the cells. As the medium, a minimal essential medium for osteoclast precursor cells (OPBM, purchased from Sanko Junyaku Co., Ltd., Cat. No. PT-8201) supplemented with an OPGM supplement set (purchased from Sanko Junyaku Co., Ltd., Cat. No. PT-9501) containing fetal bovine serum (final concentration: 10%), human RANKL (final concentration: 63.8 ng/ml), human M-CSF (final concentration: 33 ng/ml), and the like was used. To the resulting culture supernatant, each of the rat anti-mouse Siglec-15 monoclonal antibody (#32A1 antibody) prepared in Example 6, the human chimeric antibody of the #32A1 antibody prepared in Example 19, and the 10 types of humanized #32A1 antibodies (h#32A1-T1, h#32A1-T2, h#32A1-T3, h#32A1-T4, h#32A1-T5, h#32A1-T6, h#32A1-H1-1/L5, h#32A1-H5/L5, h#32A1-H1-1/L2-16, and h#32A1-H1-1/L2-15) prepared in Examples 24 and 28 was added at a final concentration of 4, 20, 100, or 500 ng/ml, and the cells were cultured for 5 days in a $CO_2$ incubator. A 10 µl aliquot of the culture supernatant was collected, 200 µl of Fluorophore Releasing Reagent included in the OsteoLyse Assay Kit was added thereto, and by using a fluorescence plate reader (ARVO MX, manufactured by Perkin Elmer Inc.), time-resolved fluorometry (time-resolved fluorescence fluorometer) (Excitation: 340 nm, Emission: 615 nm) suitable for fluorescence measurement using europium was performed, whereby the amount of free fluorescent collagen fragments released in the culture supernatant was determined (FIGS. 48 and 49). As a result, the amount of fluorescent collagen fragments increased by the addition of RANKL was reduced by the addition of the rat #32A1 antibody or the human chimeric #32A1 antibody in a concentration-dependent manner. In the same manner, also by all of the examined 10 types of humanized #32A1 antibodies, a concentration-dependent inhibition was observed. From this result, it was revealed that the bone resorption activity of human osteoclasts is inhibited by the humanized #32A1 antibodies specifically binding to the Siglec-15 protein.

Example 31

Biological Evaluation of Humanized Antibody of Rat Anti-Mouse Siglec-15 Monoclonal Antibody #32A1 Using Ovariectomized Rats An inhibitory effect on a decrease in bone mineral density in ovariectomized rats exhibited by the humanized antibodies obtained in Examples 24 and 28 can be evaluated by the method described in Example 15.

Example 32

Evaluation of biological activity of humanized antibody of rat anti-mouse Siglec-15 monoclonal antibody #32A1 based on test for mouse osteoclast formation by stimulation with TNFα

An inhibitory effect on mouse osteoclast formation by stimulation with TNFα exhibited by the humanized antibodies obtained in Examples 24 and 28 can be evaluated by the method described in Example 26.

Example 33

Determination of Thermal Stability of Humanized Antibody Using Differential Scanning Calorimetry (DSC)

Figure 50:
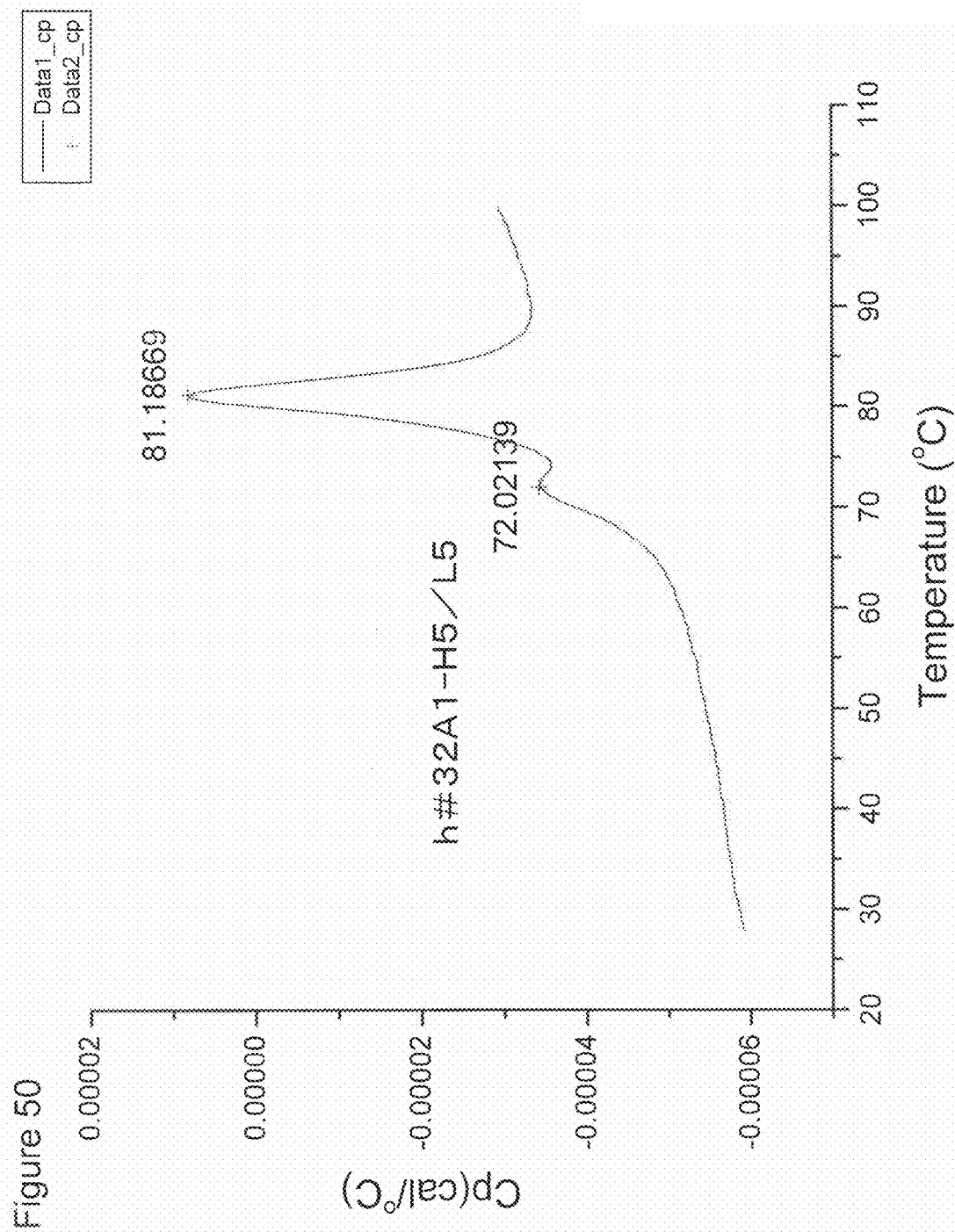
FIG. 50 is a thermogram obtained for determining the thermal stability of the h#32A1-H5/L5 antibody.
Figure 51:
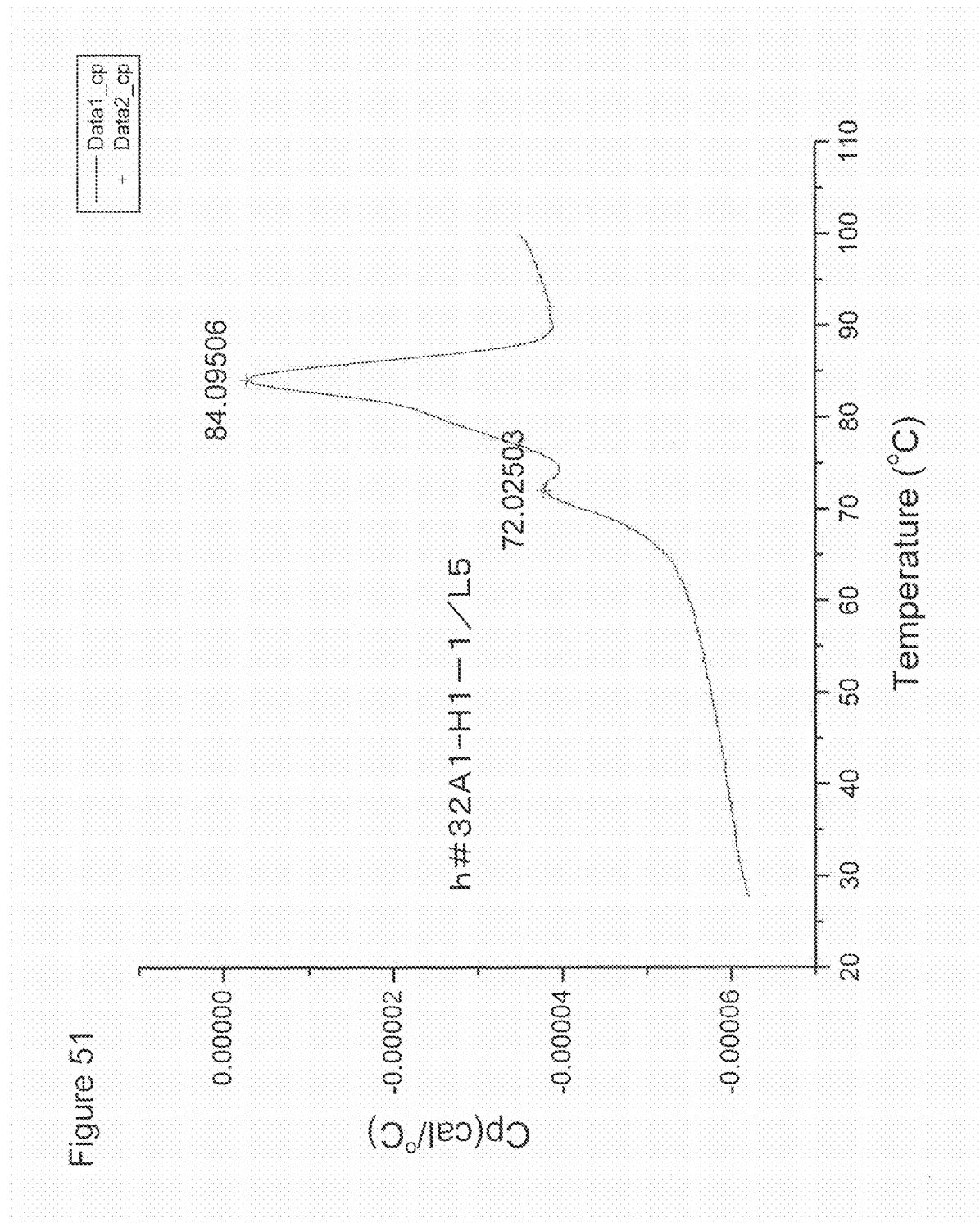
FIG. 51 is a thermogram obtained for determining the thermal stability of the h#32A1-H1-1/L5 antibody.
Figure 52:
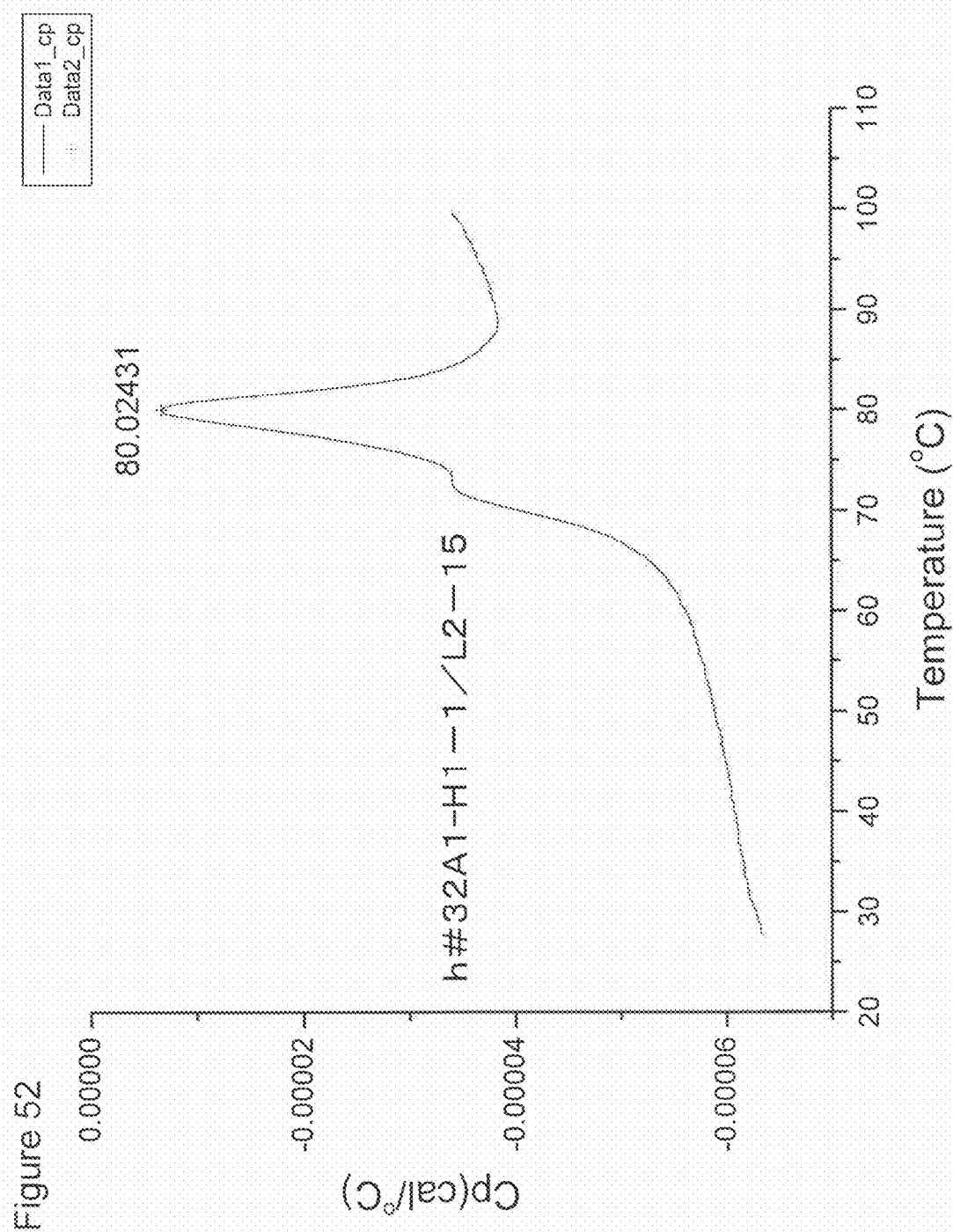
FIG. 52 is a thermogram obtained for determining the thermal stability of the h#32A1-H1-1/L2-15 antibody.
Figure 53:
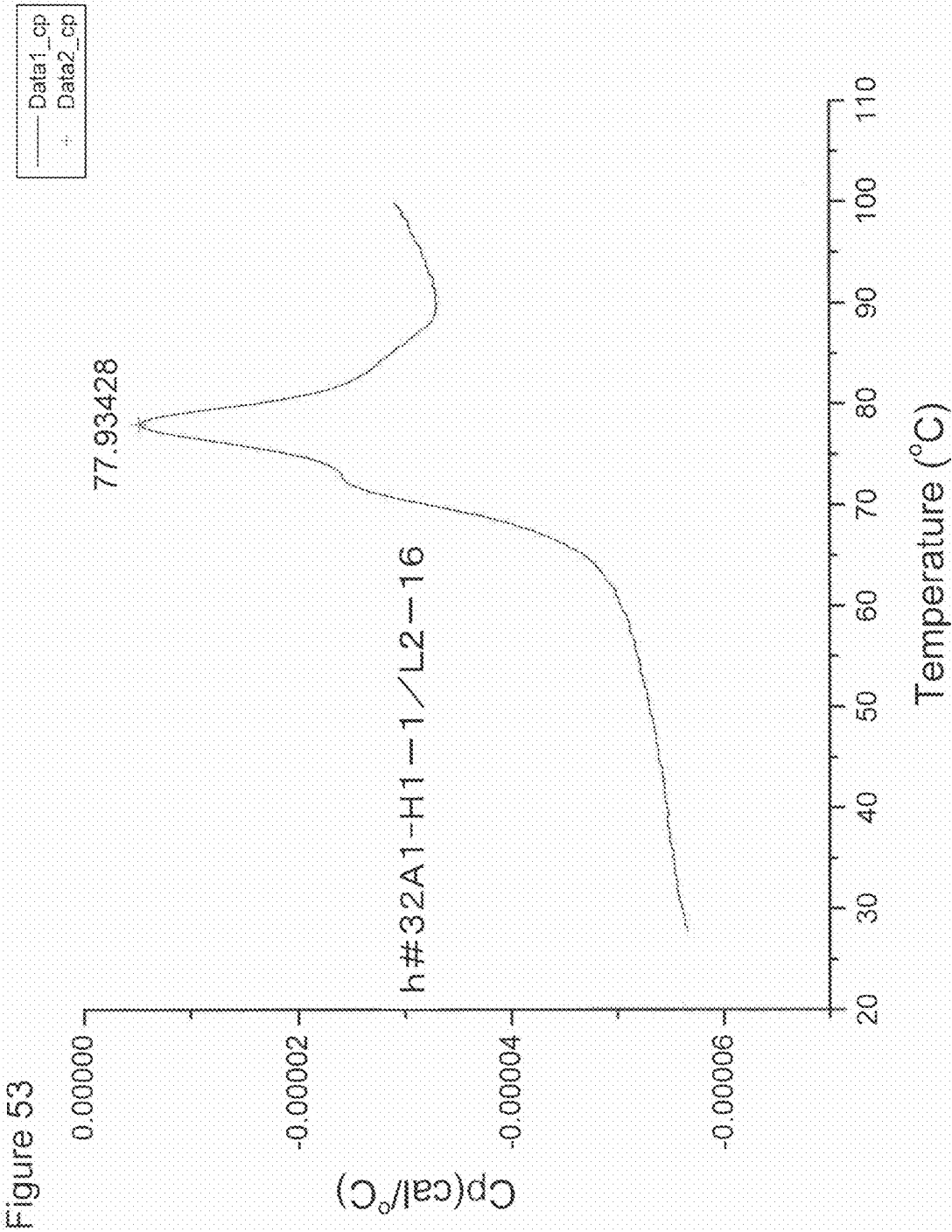
FIG. 53 is a thermogram obtained for determining the thermal stability of the h#32A1-H1-1/L2-16 antibody.

For h#32A1-H5/L5, h#32A1-H1-1/L5, h#32A1-H1-1/L2-15, and h#32A1-H1-1/L2-16, thermal stability was determined. Each of these samples was prepared at a concentration of 0.5 mg/ml (in a CBS solution), and a 400 µl aliquot thereof was used as a sample solution for the DSC measurement. The conditions for the DSC measurement were set as follows. That is, the initial temperature was set to 20° C., the final temperature was set to 100° C., the temperature increase rate was set to 60° C./hour, and the filter time was set to 10 seconds. As a reference solution, CBS was used. As an instrument for the DSC measurement, VP-Capillary DSC platform manufactured by MicroCal Inc. USA was used. The baseline (a scanning curve obtained by filling the reference solution also in a sample cell) was subtracted from a scanning curve obtained for each sample solution, whereby baseline correction was performed. FIG. 50 shows a thermogram for h#32A1-H5/L5, FIG. 51 shows a thermogram for h#32A1-H1-1/L5, FIG. 52 shows a thermogram for h#32A1-H1-1/L2-15, and FIG. 53 shows a thermogram for h#32A1-H1-1/L2-16. When a peak top value in each thermogram was taken as a thermal denaturation midpoint temperature (Tm) in the Fab region, the Tm value of h#32A1-H5/L5 was 81.2° C., the Tm value of h#32A1-H1-1/L5 was 84.1° C., the Tm value of h#32A1-H1-1/L2-15 was 80.0° C. and the Tm value of h#32A1-H1-1/L2-16 (IgG2) was 77.9° C.

INDUSTRIAL APPLICABILITY

The chimeric or humanized anti-Siglec-15 antibody of the invention has an ability to inhibit osteoclast differentiation or bone resorption activity, and a pharmaceutical composition containing the anti-Siglec-15 antibody can be a therapeutic or preventive agent for a disease of abnormal bone metabolism.

Accession Number
FERM BP-10999

---

The invention claimed is:

1. A pharmaceutical composition comprising an antibody or antigen binding fragment thereof in an amount effective to inhibit osteoclast differentiation, wherein the antibody or antigen binding fragment comprises: a light chain sequence that comprises a light chain variable region having CDRL1, CDRL2, and CDRL3, wherein CDRL1, comprises the amino acid sequence of SEQ ID NO: 47, CDRL2, comprises the amino acid sequence of SEQ ID NO: 48, and CDRL3, comprises the amino acid sequence of SEQ ID NO: 49, and a heavy chain sequence that comprises a heavy chain variable region having CDRH1, CDRH2, and CDRH3, wherein CDRH1 comprises the amino acid sequence of SEQ ID NO: 44, CDRH2 comprises the amino acid sequence selected from the group consisting of SEQ ID NO: 45 and SEQ ID NO: 97, and CDRH3 comprises the amino acid sequence of SEQ ID NO: 46, wherein the antibody or antigen binding fragment thereof binds a Siglec-15 protein comprising the amino acid sequence of SEQ ID NO: 2 or 4, and a pharmaceutically acceptable excipient.

2. The pharmaceutical composition of claim 1, wherein the antigen binding fragment is an scFv.

3. The pharmaceutical composition of claim 1, wherein the antibody is a chimeric antibody.

4. The pharmaceutical composition of claim 1, wherein the antibody or antigen binding fragment is humanized.

5. The pharmaceutical composition of claim 1, wherein CDRH2 comprises the amino acid sequence of SEQ ID NO: 45.

6. The pharmaceutical composition of claim 1, wherein CDRH2 comprises the amino acid sequence of SEQ ID NO: 97.

7. The pharmaceutical composition of claim 1, wherein the excipient comprises a liquid or a solid.

8. The pharmaceutical composition of claim 1, wherein the excipient comprises one or more of water, physiological saline, artificial cerebrospinal fluid, and albumin.

9. The pharmaceutical composition of claim 1, wherein the composition is formulated for oral or parenteral administration.

10. The pharmaceutical composition of claim 1, wherein the dosage form of the composition is an infusion, a suppository, a transnasal agent, a sublingual agent, or a percutaneous absorbent.

* * * * *

UNITED STATES PATENT AND TRADEMARK OFFICE
CERTIFICATE OF CORRECTION

PATENT NO. : 9,751,944 B2
APPLICATION NO. : 14/731519
DATED : September 5, 2017
INVENTOR(S) : Yoshiharu Hiruma et al.

It is certified that error appears in the above-identified patent and that said Letters Patent is hereby corrected as shown below:

On the Title Page

Item [60], delete "14/401,479" and insert --14/041,479--.

Signed and Sealed this
Second Day of January, 2018

Joseph Matal
*Performing the Functions and Duties of the*
*Under Secretary of Commerce for Intellectual Property and*
*Director of the United States Patent and Trademark Office*